United States Patent [19]

Doll et al.

[11] Patent Number: 5,714,609
[45] Date of Patent: Feb. 3, 1998

[54] TRICYCLIC AMIDE AND UREA COMPOUNDS USEFUL FOR INHIBITION OF G-PROTEIN FUNCTION AND FOR TREATMENT OF PROLIFERATIVE DISEASES

[75] Inventors: Ronald J. Doll, Maplewood; F. George Njoroge, Union; Stacy W. Remiszewski, Township of Washington, all of N.J.

[73] Assignee: Schering Corporation, Kenilworth, N.J.

[21] Appl. No.: 450,064

[22] Filed: May 25, 1995

Related U.S. Application Data

[63] Continuation of Ser. No. 410,187, Jan. 24, 1995, which is a continuation-in-part of Ser. No. 312,028, Sep. 26, 1994, abandoned, which is a continuation-in-part of Ser. No. 137,862, Oct. 15, 1993, abandoned.

[51] Int. Cl.$^6$ .................. C07D 401/08; C07D 403/08
[52] U.S. Cl. ................................ 546/93; 544/361
[58] Field of Search .......................... 546/93; 544/361

[56] References Cited

U.S. PATENT DOCUMENTS

| | | | |
|---|---|---|---|
| 4,282,233 | 8/1981 | Villani | 435/267 |
| 4,826,853 | 5/1989 | Piwinski et al. | 514/290 |
| 4,831,042 | 5/1989 | Villani | 514/316 |
| 4,863,931 | 9/1989 | Schumacher et al. | 514/290 |
| 5,089,496 | 2/1992 | Piwinski et al. | 514/253 |
| 5,104,876 | 4/1992 | Piwinski et al. | 514/254 |
| 5,141,851 | 8/1992 | Brown et al. | 435/15 |
| 5,151,423 | 9/1992 | Piwinski et al. | 514/254 |

FOREIGN PATENT DOCUMENTS

| | | |
|---|---|---|
| 0042544 | 12/1981 | European Pat. Off. |
| 0270818 | 6/1988 | European Pat. Off. |
| 0396083 | 11/1990 | European Pat. Off. |
| 0495484 | 7/1992 | European Pat. Off. |
| 0535730 | 4/1993 | European Pat. Off. |
| WO88/03138 | 5/1988 | WIPO |
| WO89/10363 | 11/1989 | WIPO |
| WO90/13548 | 11/1990 | WIPO |
| WO92/00293 | 1/1992 | WIPO |
| WO92/11034 | 7/1992 | WIPO |
| WO94/04561 | 3/1994 | WIPO |
| WO94/24107 | 10/1994 | WIPO |

OTHER PUBLICATIONS

Cell, 65, 1–4 (1991)month of publication not provided.
J. Biol. Chem.,266, (24) 15575–15578 (1991)month of publication not provided.
Proc. Natl. Acad. Sci. USA, 87, 3042–3046 (190)month of publication not provided.
Proc. Natl. Acad. Sci. USA, 88, 8631–8635 (1991)month of publication not provided.
Nature, 356, 713–715 (1992)month of publication not provided.
Proc. Natl. Acad. Sci. USA, 87, 7541–7545 (1990)month of publication not provided.
J. Biol. Chem., 265, (25) 14701–14704 (1990)month of publication not provided.
Proc. Natl. Acad. Sci. USA, 87, 7926–7929 (1990)month of publication not provided.
Cell, 62, 81–88 (1990)month of publication not provided.
Biochemistry, 31, 3800–3807 month of publication not provided.
Science, 260, 1934–1937 month of publication not provided.
Science, 260 1937–1942 month of publication not provided.
Piwinski, et al., J. Med. Chem., 34, (1) 457–461 (1991)month of publication not provided.
Chem. Abstracts No. 121:53129x (1994) for WO94/04561 month of publication not provided.
Masci, J. Chem. Soc., Chem. Commun., 1262–1263 (1982)month of publication not provided.
Masci, J. Org. Chem., 50, 4081–4087 (1985)month of publication not provided.
Sebti, et al., Proc. Ann. Meeting AM Assoc. Cancer Res., 33:A2217 (1992)month of publication not provided.
Villani, et al., J. Med. Chem., 15 (7) 750–754 (1972)month of publication not provided.
Billah, et al., Lipids, 26, (12) 1172–1174 (1991)month of publication not provided.
Villani, et al., Arzneim.–Forsch./Drug Res., 36(II), 1311–1314 (1986)month of publication not provided.
Bakke et al., Dinitrogen Pentoxide–Sulfer Dioxide, a New Nitration System, Acta Chemica Scandinavica 48 (1994) ; pp. 181–182.
Carey, F.A. et al. Advanced Organic Chemistry. Part B: Reactions and Synthesis (Plenum Press, New York), pp. 571–573 (1990).
Sarges, R. et al. J. Med. Chem. 33, 1859–1865 (1990).

Primary Examiner—Matthew V. Grumbling
Assistant Examiner—King Lit Wong
Attorney, Agent, or Firm—Henry C. Jeanette; Paul A. Thompson

[57] ABSTRACT

A method of inhibiting Ras function and therefore inhibiting the abnormal growth of cells is disclosed. The method comprises the administration of a compound of Formula 1.0:

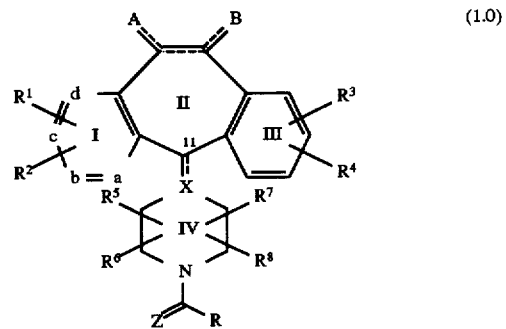

(1.0)

to a biological system. In particular, the method inhibits the abnormal growth of cells in a mammal such as a human being. Novel compounds of formulas 5.0, 5.1 and 5.2, wherein R is —$C(R^{20})(R^{21})(R^{46})$, and 5.3, 5.3A and 5.3B, wherein R is —$N(R^{25})(R^{48})$, are disclosed. Also disclosed are processes for making 3-substituted compounds of Formulas 5.0, 5.1, 5.2 and 5.3. Further disclosed are novel compounds which are intermediates in the process for making 3-substituted compounds of Formulas 5.0, 5.1, 5.2 and 5.3.

22 Claims, No Drawings

TRICYCLIC AMIDE AND UREA COMPOUNDS USEFUL FOR INHIBITION OF G-PROTEIN FUNCTION AND FOR TREATMENT OF PROLIFERATIVE DISEASES

This is a continuation of application Ser. No. 08/410,187, filed Mar. 24, 1995, which in turn is a continuation-in-part of U.S. application Ser. No. 08/312,028, filed Sep. 26, 1994 (now abandoned), which in turn is a continuation-in-part of U.S. Ser. No. 08/137,862, filed Oct. 15, 1993 (now abandoned).

BACKGROUND

International Publication Number WO92/11034, published Jul. 9, 1992, discloses a method of increasing the sensitivity of a tumor to an antineoplastic agent, which tumor is resistant to the antineoplastic agent, by the concurrent administration of the antineoplastic agent and a potentiating agent of the formula:

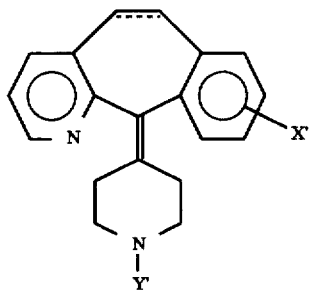

wherein the dotted line represents an optional double bond, X' is hydrogen or halo, and Y' is hydrogen, substituted carboxylate or substituted sulfonyl. For example, Y' can be, amongst others, —COOR' wherein R' is C1 to C6 alkyl or substituted alkyl, phenyl, substituted phenyl, C7 to C12 aralkyl or substituted aralkyl or -2, -3, or -4 piperidyl or N-substituted piperidyl. Y' can also be, amongst others, $SO_2R'$ wherein R' is C1 to C6 alkyl, phenyl, substituted phenyl, C7 to C12 aralkyl or substituted aralkyl. Examples of such potentiating agents include 11-(4-piperidylidene)-5H-benzo[5,6]cyclohepta[1,2-b]pyridines such as Loratadine.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras. Several compounds of this invention have been demonstrated to have anti-tumor activity in animal models.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds useful in the claimed methods are represented by Formula 1.0:

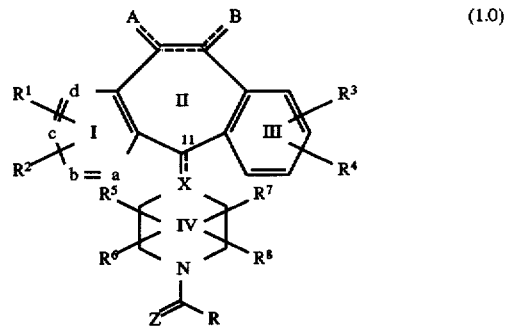

(1.0)

or a pharmaceutically acceptable salt or solvate thereof, wherein:

one of a, b, c and d represents N or $NR^9$ wherein $R^9$ is $O^-$, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, —$NR^{10}COOR^{11}$,

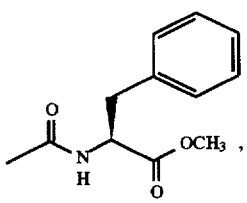

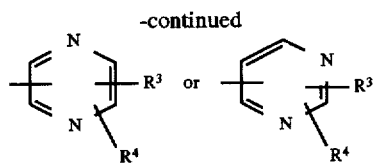

—SR$^{11}$C(O)OR$^{11}$ (e.g., —SCH$_2$CO$_2$CH$_3$), —SR$^{11}$N(R$^{75}$)$_2$ wherein each R$^{75}$ is independently selected from H and —C(O)OR$^{11}$ (e.g., —S(CH$_2$)$_2$NHC(O)O-t-butyl and —S(CH$_2$)$_2$NH$_2$), benzotriazol-1-yloxy, tetrazol-5-ylthio, or substituted tetrazol-5-ylthio (e.g., alkyl substituted tetrazol5-ylthio such as 1-methyl-tetrazol-5-ylthio), alkynyl, alkenyl or alkyl, said alkyl or alkenyl group optionally being substituted with halo, —OR$^{10}$ or —CO$_2$R$^{10}$;

R$^3$ and R$^4$ are the same or different and each independently represents H, any of the substituents of R$^1$ and R$^2$, or R$^3$ and R$^4$ taken together represent a saturated or unsaturated C$_5$–C$_7$ fused ring to the benzene ring (Ring III);

R$^5$, R$^6$, R$^7$ and R$^8$ each independently represents H, —CF$_3$, —COR$^{10}$, alkyl or aryl, said alkyl or aryl optionally being substituted with —OR$^{10}$, —SR$^{10}$, —S(O)$_t$R$^{11}$, —NR$^{10}$COOR$^{11}$, —N(R$^{10}$)$_2$, —NO$_2$, —COR$^{10}$, —OCOR$^{10}$, —OCO$_2$R$^{11}$, —CO$_2$R$^{10}$, OPO$_3$R$^{10}$ or one of R$^5$, R$^6$, R$^7$ and R$^8$ can be taken in combination with R$^{40}$ as defined below to represent —(CH$_2$)$_r$— wherein r is 1 to 4 which can be substituted with lower alkyl, lower alkoxy, —CF$_3$ or aryl, or R$^5$ is combined with R$^6$ to represent =O or =S and/or R$^7$ is combined with R$^8$ to represent =O or =S;

R$^{10}$ represents H, alkyl, aryl, or aralkyl (e.g., benzyl);

R$^{11}$ represents alkyl or aryl;

X represents N, CH or C, which C may contain an optional double bond (represented by the dotted line) to carbon atom 11;

the dotted line between carbon atoms 5 and 6 represents an optional double bond, such that when a double bond is present, A and B independently represent —R$^{10}$, halo, —OR$^{11}$, —OCO$_2$R$^{11}$ or —OC(O)R$^{10}$, and when no double bond is present between carbon atoms 5 and 6, A and B each independently represent H$_2$, —(OR$^{11}$)$_2$; H and halo, dihalo, alkyl and H, (alkyl)$_2$, —H and —OC(O)R$^{10}$, H and —OR$^{10}$, =O, aryl and H, =NOR$^{10}$ or —O—(CH$_2$)$_p$—O— wherein p is 2, 3 or 4;

R represents R$^{40}$, R$^{42}$, R$^{44}$, or R$^{54}$, as defined below;

R$^{40}$ represents H, aryl, alkyl, cycloalkyl, alkenyl, alkynyl or —D wherein —D represents

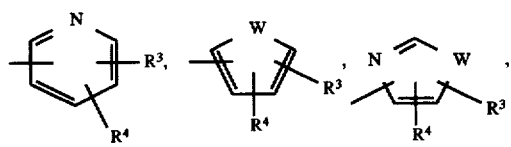

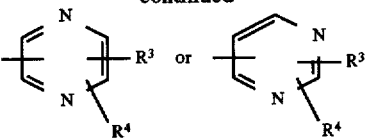

wherein R$^3$ and R$^4$ are as previously defined and W is O, S or NR$^{10}$ wherein R$^{10}$ is as defined above; said R$^{40}$ cycloalkyl, alkenyl and alkynyl groups being optionally substituted with from 1–3 groups selected from halo, —CON(R$^{10}$)$_2$, aryl, —CO$_2$R$^{10}$, —OR$^{12}$, —SR$^{12}$, —N(R$^{10}$)$_2$, —N(R$^{10}$)CO$_2$R$^{11}$, —COR$^{12}$, —NO$_2$ or D, wherein —D, R$^{10}$ and R$^{11}$ are as defined above and R$^{12}$ represents R$^{10}$, —(CH$_2$)$_m$OR$^{10}$ or —(CH$_2$)$_q$CO$_2$R$^{10}$ wherein R$^{10}$ is as previously defined, m is 1 to 4 and q is 0 to 4; said alkenyl and alkynyl R$^{40}$ groups not containing —OH, —SH or —N(R$^{10}$)$_2$ on a carbon containing a double or triple bond respectively; or R$^{40}$ represents phenyl substituted with a group selected from —SO$_2$NH$_2$, —NHSO$_2$CH$_3$, —SO$_2$NHCH$_3$, —SO$_2$CH$_3$, —SOCH$_3$, —SCH$_3$, or —NHSO$_2$CF$_3$, preferably, said group is located in the para (p-) position of the phenyl ring; or R$^{40}$ represents a group selected from

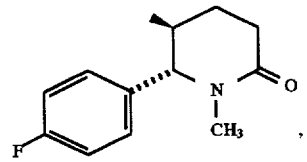

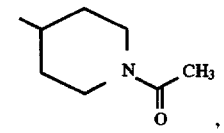

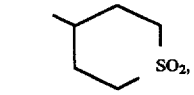

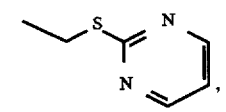

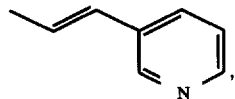

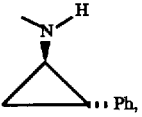

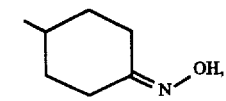

5,714,609

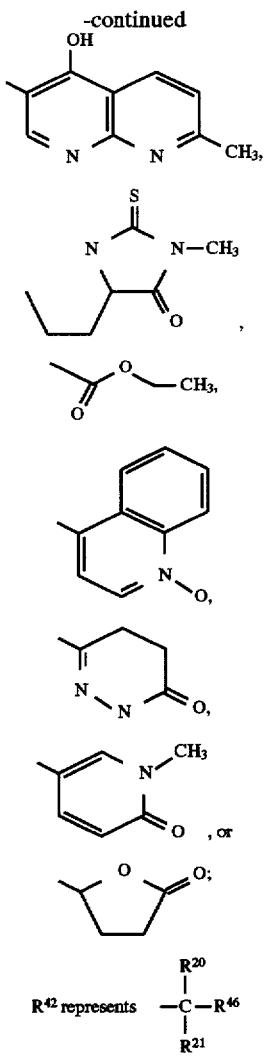

wherein $R^{20}$, $R^{21}$ and $R^{46}$ are each independently selected from the group consisting of:

(1) H;
(2) —(CH$_2$)$_q$SC(O)CH$_3$ wherein q is 1 to 3 (e.g., —CH$_2$SC(O)CH$_3$);
(3) —(CH$_2$)$_q$OSO$_2$CH$_3$ wherein q is 1 to 3 (e.g., —CH$_2$OSO$_2$CH$_3$);
(4) —OH;
(5) —CS(CH$_2$)$_w$(substituted phenyl) wherein w is 1 to 3 and the substitutents on said substituted phenyl group are the same substitutents as described below for said substituted phenyl (e.g., —C—S—CH$_2$-4-methoxyphenyl);
(6) —NH$_2$;
(7) —NHCBZ (wherein CBZ stands for carbonylbenzyloxy—i.e., CBZ represents —C(O)OCH$_2$C$_6$H$_5$);
(8) —NHC(O)OR$^{22}$ wherein R$^{22}$ is an alkyl group having from 1 to 5 carbon atoms (e.g., R$^{22}$ is t-butyl thus forming —NHBOC wherein BOC stands for tert-butyloxycarbonyl—i.e., BOC represents —C(O)OC(CH$_3$)$_3$), or R$^{22}$ represents phenyl substituted with 1 to 3 alkyl groups (e.g., 4-methylphenyl);
(9) alkyl (e.g., ethyl);
(10) —(CH$_2$)$_k$phenyl wherein k is 1 to 6, usually 1 to 4 and preferably 1 (e.g., benzyl);
(11) phenyl;
(12) substituted phenyl (i.e., phenyl substituted with from 1 to 3 substituents, preferably one) wherein the substituents are selected from the group consisting of: halo (e.g., Br, Cl, or I, with Br being preferred); NO$_2$; —OH; —OCH$_3$; —NH$_2$; —NHR$^{22}$; —N(R$^{22}$)$_2$; alkyl (e.g., alkyl having from 1 to 3 carbons with methyl being preferred); —O(CH$_2$)$_t$phenyl (wherein t is from 1 to 3 with 1 being preferred); and —O(CH$_2$)$_t$substituted phenyl (wherein t is from 1 to 3 with 1 being preferred); examples of substituted phenyls include, but are not limited to, p-bromophenyl, m-nitrophenyl, o-nitrophenyl, m-hydroxy-phenyl, o-hydroxyphenyl, methoxyphenyl, p-methylphenyl, m-methyl-phenyl, and —OCH$_2$C$_6$H$_5$;
(13) naphthyl;
(14) substituted naphthyl, wherein the substituents are as defined for substituted phenyl above;
(15) bridged polycyclic hydrocarbons having from 5 to 10 carbon atoms (e.g., adamantyl and norbornyl);
(16) cycloalkyl having from 5 to 7 carbon atoms (e.g., cyclopentyl, and cyclohexyl);
(17) heteroaryl (e.g., pyridyl, and pyridyl N-oxide);
(18) hydroxyalkyl (e.g., —(CH$_2$)$_v$OH wherein v is 1 to 3, such as, for example, —CH$_2$OH);
(19) substituted pyridyl or substituted pyridyl N-oxide wherein the substituents are selected from methylpyridyl, morpholinyl, imidazolyl, 1-piperidinyl, 1-(4-methylpiperazinyl), —S(O)$_t$R$^{11}$, or any of the substituents given above for said substituted phenyl, and said substitutents are bound to a ring carbon by replacement of the hydrogen bound to said carbon;

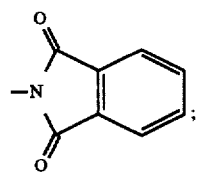
(20)

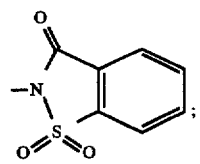
(21)

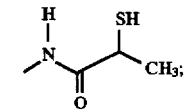
(22)

(23) —NHC(O)—(CH$_2$)$_k$-phenyl or —NH(O)—(CH$_2$)$_k$-substituted phenyl, wherein said k is as defined above (i.e., 1–6, usually 1–4 and preferably 1);
(24) piperidine Ring V:

wherein R$^{50}$ represents H, alkyl (e.g., methyl), alkylcarbonyl (e.g., CH$_3$C(O)—), alkyloxycarbonyl (e.g., —C(O)O-t-C$_4$H$_9$, —C(O)OC$_2$H$_5$, and —C(O)OCH$_3$), haloalkyl (e.g., trifluromethyl), or —C(O)NH(R$^{10}$) wherein R$^{10}$ is H or alkyl; Ring V includes

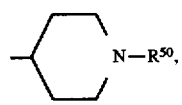

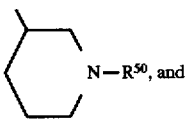

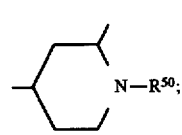

examples of Ring V include:

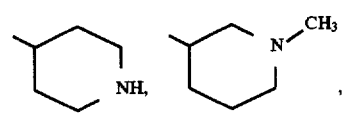

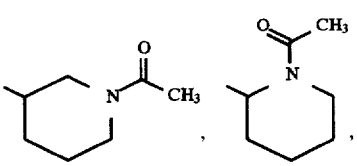

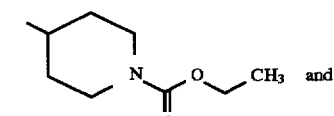

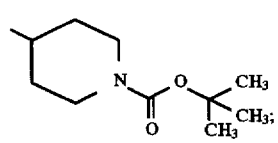

(25) —NHC(O)CH$_2$C$_6$H$_5$ or —NHC(O)CH$_2$-substituted-C$_6$H$_5$, for example —NHC(O)CH$_2$-p-hydroxyphenyl, —NHC(O)CH$_2$-m-hydroxyphenyl, and —NHC(O)CH$_2$-o-hydroxyphenyl;

(26) —NHC(O)OC$_6$H$_5$;

(27) 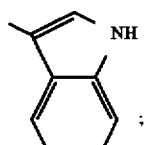

(28) 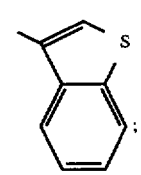

(29) 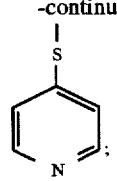

(30) —OC(O)-heteroaryl, for example

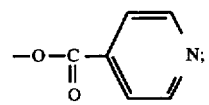

(31) —O-alkyl (e.g., —OCH$_3$);

(32) —CF$_3$;

(33) —CN;

(34) a heterocycloalkyl group of the formula

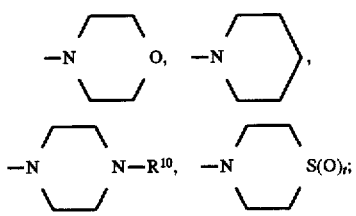

and

(35) a piperidinyl group of the formula

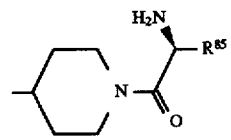

wherein R$^{85}$ is H, alkyl, or alkyl substituted by —OH or —SCH$_3$; or

R$^{20}$ and R$^{21}$ taken together form a =O group and the remaining R$^{46}$ is as defined above; or Two of R$^{20}$, R$^{21}$ and R$^{46}$ taken together form piperidine Ring V

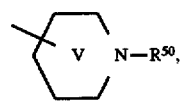

wherein R$^{50}$ represents H, alkyl (e.g., methyl), alkylcarbonyl (e.g., CH$_3$C(O)—), alkyloxycarbonyl (e.g., —C(O)O-t-C$_4$H$_9$, —C(O)OC$_2$H$_5$, and —C(O)OCH$_3$), haloalkyl (e.g., trifluro-methyl), or —C(O)NH(R$^{10}$) wherein R$^{10}$ is H or alkyl; Ring V includes

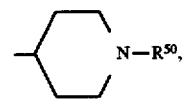

-continued

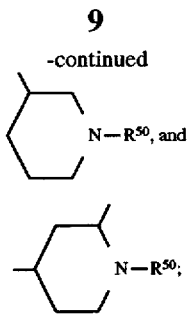

examples of Ring V include:

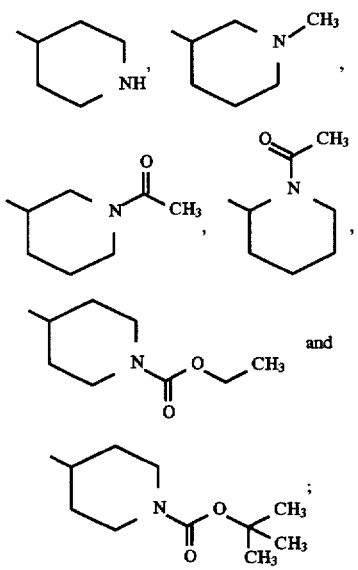

with the proviso $R^{46}$, $R^{20}$, and $R^{21}$ are selected such that the carbon atom to which they are bound does not contain more than one heteroatom (i.e., $R^{46}$, $R^{20}$, and $R^{21}$ are selected such that the carbon atom to which they are bound contains 0 or 1 heteroatom);

$R^{44}$ represents

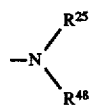

wherein $R^{25}$ represents heteroaryl (e.g., pyridyl or pyridyl N-oxide), N-methylpiperidinyl or aryl (e.g., phenyl and substituted phenyl); and $R^{48}$ represents H or alkyl (e.g., methyl);

$R^{54}$ represents an N-oxide heterocyclic group of the formula (i), (ii), (iii) or (iv):

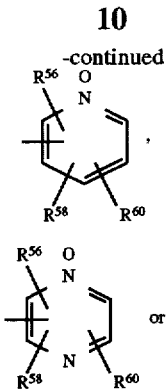

(i)

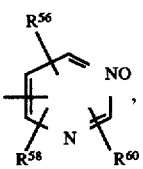

(ii)

(iii)

(iv)

wherein $R^{56}$, $R^{58}$, and $R^{60}$ are the same or different and each is independently selected from H, halo, —$CF_3$, —$OR^{10}$, —$C(O)R^{10}$, —$SR^{10}$, —$S(O)_eR^{11}$ (wherein e is 1 or 2), —$N(R^{10})_2$, —$NO_2$, —$CO_2R^{10}$, —$OCO_2R^{11}$, —$OCOR^{10}$, alkyl, aryl, alkenyl or alkynyl, which alkyl may be substituted with —$OR^{10}$, —$SR^{10}$ or —$N(R^{10})_2$ and which alkenyl may be substituted with $OR^{11}$ or $SR^{11}$; or $R^{54}$ represents an N-oxide heterocyclic group of the formula (ia), (iia), (iiia) or (iva):

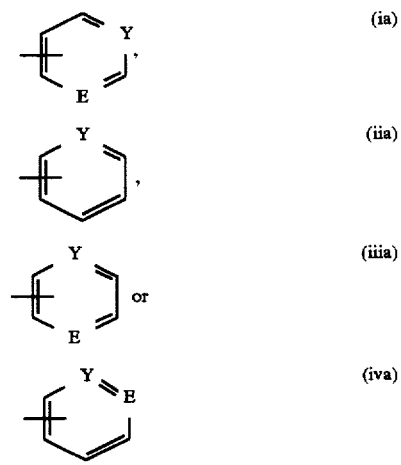

(ia)

(iia)

(iiia)

(iva)

wherein Y represents $N^+$-$O^-$ and E represents N; or $R^{54}$ represents an alkyl group substituted with one of said N-oxide heterocyclic groups (i), (ii), (iii), (iv), (ia), (iia), (iiia) or (iva);

Z represents O or S such that R can be taken in combination with $R^5$, $R^6$, $R^7$ or $R^8$ as defined above, or R represents $R^{40}$, $R^{42}$, $R^{44}$ or $R^{54}$.

Examples of $R^{20}$, $R^{21}$, and $R^{46}$ for the above formulas include:

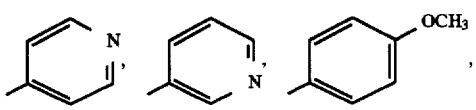

-continued

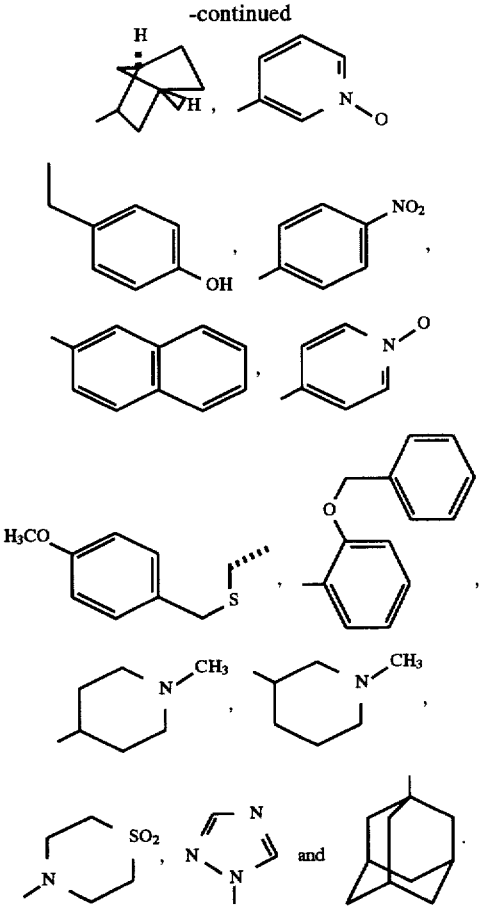

Examples of R²⁵ groups include:

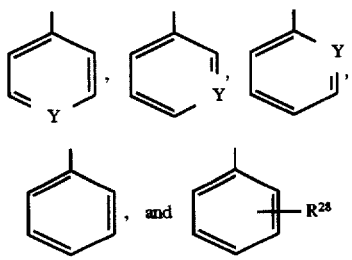

wherein Y represents N or NO, $R^{28}$ is selected from the group consisting of: $C_1$ to $C_4$ alkyl, halo, hydroxy, $NO_2$, amino (—$NH_2$), —$NHR^{30}$, and —$N(R^{30})_2$ wherein $R^{30}$ represents $C_1$ to $C_6$ alkyl.

Tricyclic compounds useful in the methods of this invention are described in: (1) U.S. Pat. No. 5,151,423; (2) U.S. Pat. No. 4,826,853; (3) U.S. Pat. No. 5,089,496; (4) WO 88/03138 published on May 5, 1988 (PCT/US87/02777); and (5) U.S. Pat. No. 5,104,876; the disclosures of each being incorporated herein by reference thereto. Those compounds within the scope of this invention which are not described in these documents are described herein.

This invention also provides novel compounds of Formula 1.0 having the formula:

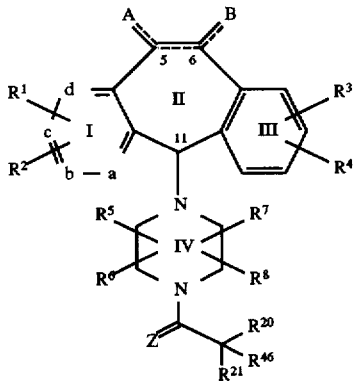
(5.0)

wherein all substituents are as defined for Formula 1.0

This invention further provides novel compounds of Formula 1.0 having the formula:

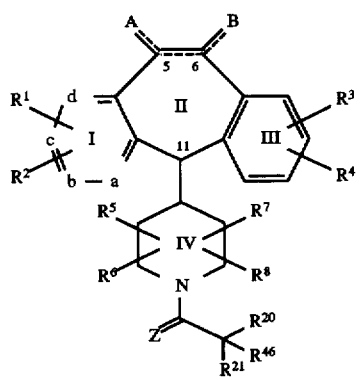
(5.1)

wherein all substituents are as defined for Formula 1.0

Additionally, this invention provides novel compounds of Formula 1.0 having the formula:

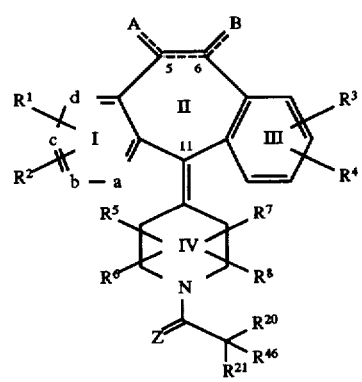
(5.2)

wherein all substituents are as defined for Formula 1.0.

Compounds of Formula 5.2 include compounds wherein the substituents $R^{20}$, $R^{21}$, and $R^{46}$ are selected such that when one of said substituents $R^{20}$, $R^{21}$, and $R^{46}$ (e.g., $R^{46}$) is selected from the group consisting of: (1) H, (2) —OH, (3) —$NH_2$, (4) —$NHC(O)OR^{22}$, (5) alkyl, (6) phenyl, (7) heteroaryl, (8) hydroxyalkyl, (9) substituted pyridyl, (10) substituted phenyl and (11) —O-alkyl, then the remaining two of said substituents $R^{20}$, $R^{21}$ and $R^{46}$ (e.g., $R^{20}$ and $R^{21}$) cannot both be H when: (a) $R^1$ and $R^2$ are both H, and (b) the double bond between C-5 and C-6 is absent, and (c) both A and B are $H_2$, and (d) $R^4$ is H, and (e) $R^3$ is H or Cl at C-8. Compounds of Formula 5.2 also include compounds wherein when $R^{46}$ is a group (1) to (11) defined above then $R^{20}$ and $R^{21}$ cannot both be H when: $R^1$ and $R^2$ are both H, and both A and B are H or $H_2$. Compounds of Formula 5.2 further include compounds wherein when $R^{46}$ is a group (1) to (11) defined above then $R^{20}$ and $R^{21}$ cannot both be H when $R^1$ and $R^2$ are both H. Compounds of Formula 5.2 also include compounds wherein two of $R^{20}$, $R^{21}$ and $R^{46}$ are not H when $R^1$ and $R^2$ are both H.

This invention further provides novel compounds of Formula 1.0 having the formula:

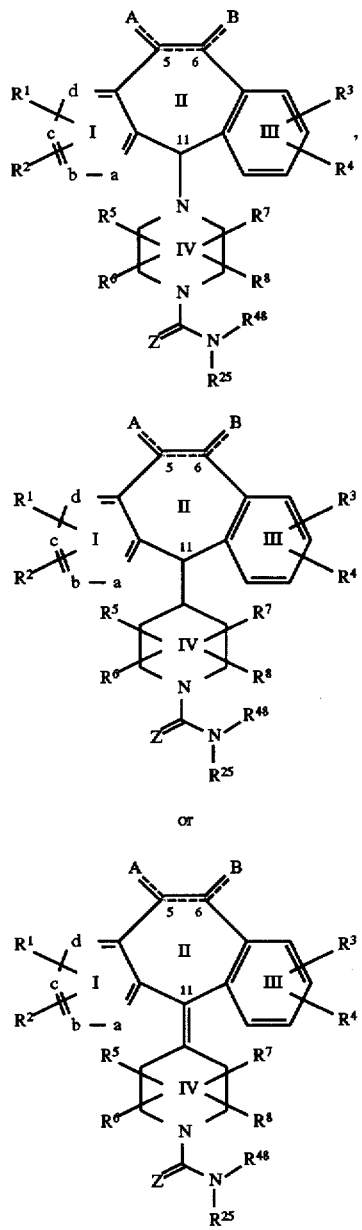

wherein all the substituents are as defined for Formula 1.0. Preferably $R^{25}$ represents heteroaryl.

This invention also provides novel compounds of the formula 7.0 having the formula:

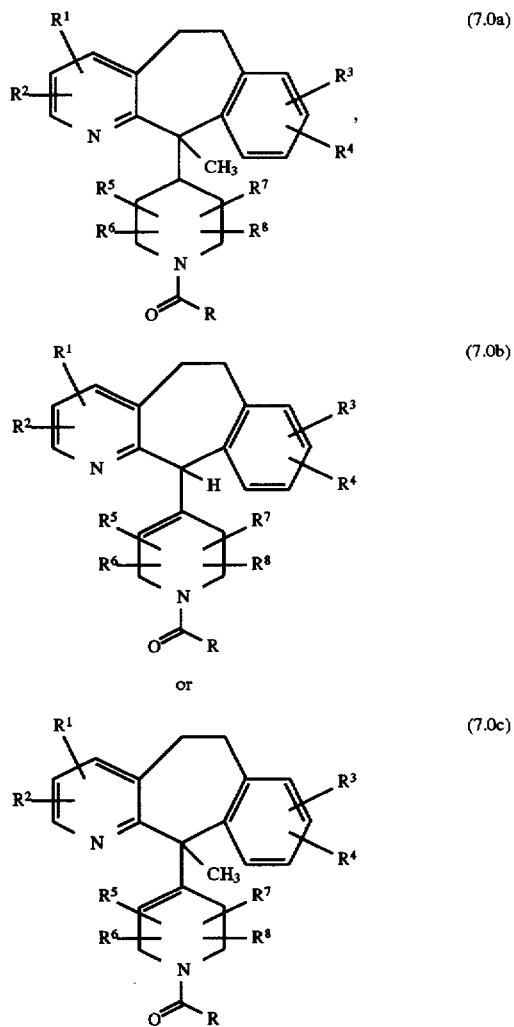

wherein R, $R^1$, $R^2$, $R^3$, $R^4$, $R^5$, $R^6$, $R^7$ and $R^8$ are as defined above for compounds of the formula 1.0, which compounds are useful in the methods claimed herein.

This invention also provides a method for inhibiting tumor growth by administering an effective amount of the tricyclic compounds, described herein, to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

The tricyclic compounds useful in the methods of this invention inhibit the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

This invention also provides a process for producing 3-nitro substituted compounds. The process comprises reacting one molar equivalent of a compound:

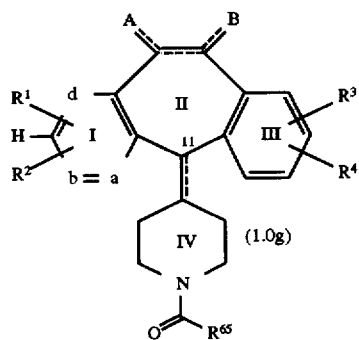

(1.0g)

wherein $R^1$, $R^2$, $R^3$, $R^4$, A, B, a, b, d, and the dotted lines are as defined for Formula 1.0; and $R^{65}$ represents H or —$OR^{66}$ wherein $R^{66}$ represents alkyl (e.g., $C_1$ to $C_4$ alkyl, preferably ethyl); with one molar equivalent of a nitrating reagent, said nitrating reagent being preformed (i.e., prepared first) by mixing, at cold temperature (e.g., at 0° C.) equimolar amounts of tetrabutyl ammonium nitrate with TFAA; the reaction of the nitrating reagent with the compound of Formula 1.0g taking place in a suitable aprotic solvent (e.g., $CH_2Cl_2$, $CHCl_3$, toluene or THF); said reaction with said nitrating reagent being conducted at a temperature and for a period of time sufficient to allow the reaction to proceed at a reasonable rate to produce the desired final 3-nitro compound of Formula 1.0h (described below)—i.e., the reaction of the compound of Formula 1.0g with said nitrating reagent is conducted at an intial temperature of 0° C., and said reaction temperature is thereafter allowed to rise to about 25° C. during the reaction time period. The reaction usually proceeds overnight to completion, i.e., the reaction usually proceeds for about 16 hours. The reaction can be conducted within a temperature of 0° C. to about 25° C. during a time period of about 10 to about 24 hours. Preferably the reaction is initially conducted at 0° C. and the temperature is allowed to warm up to 25° C. The reaction produces the 3-nitro compound (1.0h):

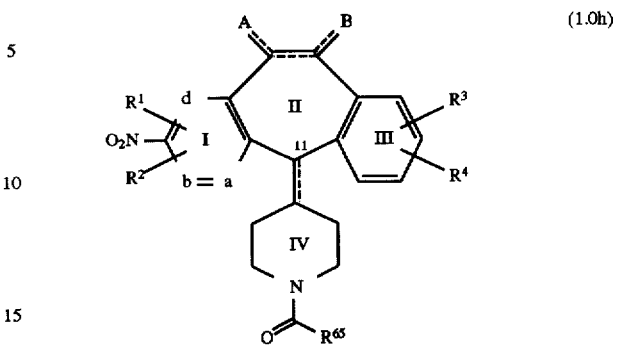

The compound of Formula 1.0h can then be converted to other 3-substituted products by methods well known to those skilled in the art. For example, the 3-nitro compounds can be convened to 3-amino, 3-halo, 3-cyano, 3-alkyl, 3-aryl, 3-thio, 3-arylalkyl, 3-hydroxyl, and 3-$OR^{67}$ wherein $R^{67}$ is alkyl or aryl. The 3-substituted compounds can then be converted to final products (wherein $R^{65}$ is $R^{42}$ or $R^{44}$) by the procedures described herein.

This invention also provides a process for producing 3-nitro compounds of the formula (1.0i):

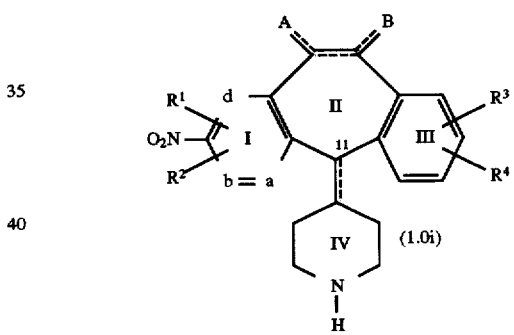

by producing a compound of Formula 1.0h from 1.0g as described above; and then hydrolyzing the compound of Formula 1.0h by dissolving the compound of Formula 1.0h in a sufficient amount of concentrated acid (e.g., concentrated HCl or aqueous sulfuric acid), and heating the resulting mixture to a temperature sufficient to remove (hydrolyze) the —$C(O)R^{65}$ substituent, for example, heating to reflux or to a temperature of about 100° C. This hydrolysis process is exemplified in Preparative Example 28.

The compound of Formula 1.0i can then be converted to other 3-substituted compounds as discussed above for the compounds of Formula 1.0h. The compounds of Formula 1.0i can then be converted to compounds of this invention by the methods described herein.

This invention also provides a process for producing compounds of the formula (1.0j):

by reacting one molar equivalent a compound of formula (1.0k):

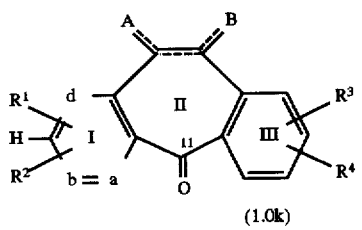

with one molar equivalent of a nitrating reagent, said nitrating reagent being preformed (i.e., prepared first) by mixing, at cold temperature (e.g., at 0° C.) equimolar amounts of tetrabutyl ammonium nitrate with TFAA; the reaction of the nitrating reagent with the compound of Formula 1.0k taking place in a suitable aprotic solvent (e.g., $CH_2Cl_2$, $CHCl_3$, toluene or THF); said reaction with said nitrating reagent being conducted at a temperature and for a period of time sufficient to allow the reaction to proceed at a reasonable rate to produce the desired final 3-nitro compound of Formula 1.0j—i.e., the reaction of the compound of Formula 1.0k with said nitrating reagent is conducted at an intial temperature of 0° C., and said reaction temperature is thereafter allowed to rise to about 25° C. during the reaction time period. The reaction usually proceeds overnight to completion, i.e., the reaction usually proceeds for about 16 hours. The reaction can be conducted within a temperature of 0° C. to about 25° C. during a time period of about 10 to about 24 hours. Preferably the reaction is initially conducted at 0° C. and the temperature is allowed to warm up to 25° C. In Formulas 1.0j and 1.0k, $R^1$, $R^2$, $R^3$, $R^4$, A, B, a, b, d, and the dotted lines are as defined for Formula 1.0

The compounds of Formula 1.0j can be converted to compounds of Formula 1.0h by methods described below. Also, as discussed above for the compounds of Formula 1.0h, the compounds of Formula 1.0j can be converted to other 3-substituted compounds wherein the substituents are those discussed above for Formula 1.0h.

The compounds of Formula 1.0j can be converted to compounds of Formula 1.0m:

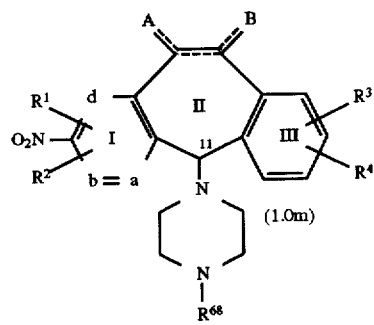

wherein $R^{68}$ is H or $—COOR^a$ wherein $R^a$ is a $C_1$ to $C_3$ alkyl group (preferably $R^{68}$ is H), by reducing a compound of Formula 1.0j with a suitable reducing agent (such as sodium borohydride) in a suitable solvent (such as EtOH or MeOH) at a suitable temperature to allow the reaction to proceed at a reasonable rate (e.g., 0° to about 25° C.); reacting the resulting product (Formula 1.0j wherein the =O has been reduced to a —OH) with a chlorinating agent (e.g., thionyl chloride) in an suitable organic solvent (e.g., benzene, toluene or pyridine) at a suitable temperature to allow the reaction to proceed at a reasonable rate (e.g., about −20° to about 20° C., preferably at −15° C., see, for example Preparative Example 7) to produce a compound of Formula 1.0n:

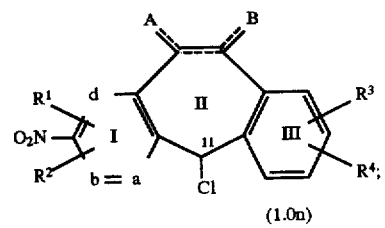

and reacting a compound of Formula 1.0n with a compound of the formula:

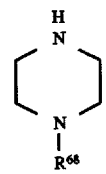

wherein $R^{68}$ is as previously defined, and is preferably H, in a suitable organic solvent (such as THF or toluene) containing a suitable base (such as $Et_3N$ or N-methylmorpholine) at a suitable temperature to allow the reaction to proceed at a reasonable rate (e.g., 25° to about 120° C.).

Compounds of Formula 1.0m can be convened to compounds of this invention by the methods disclosed herein. Also, as discussed above for the compounds of Formula 1.0h, the compounds of Formula 1.0m can be converted to other 3-substituted compounds wherein the substituents are those discussed above for Formula 1.0h.

This invention also provides novel compounds (produced in the above described processes as intermediates to the compounds of this invention) having the formulas:

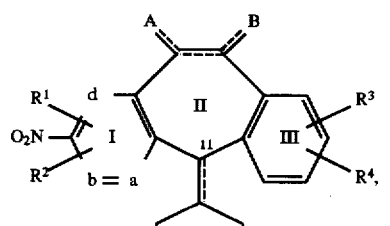
(1.0h)

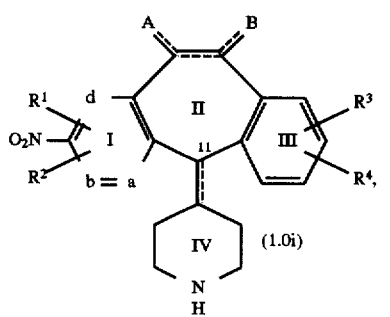
(1.0i)

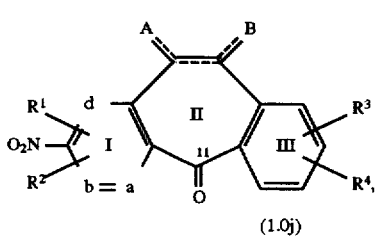
(1.0j)

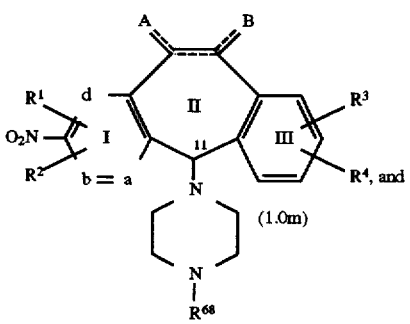
(1.0m)

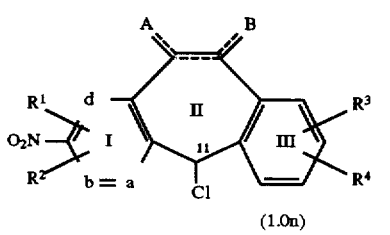
(1.0n)

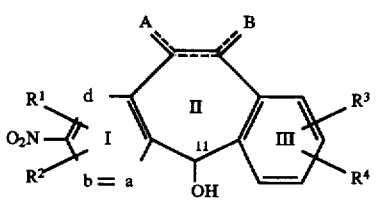

wherein all substituents are as defined herein.

Preferably, for the intermediate compounds of the processes of this invention, $R^1$ and $R^2$ are H; $R^3$ is halo, most preferably Cl, in the C-8 position; $R^4$ is H; and A and B are H when the double between C-5 and C-6 is present, and A and B are $H_2$ when the bond between C-5 and C-6 is a single bond (most preferably the bond between C-5 and C-6 is a single bond). Those skilled in the art will appreciate that Rings I, II, and/or III can be further substituted, as described herein, to produce the desired compounds of the invention.

Examples of such novel intermediate compounds include:

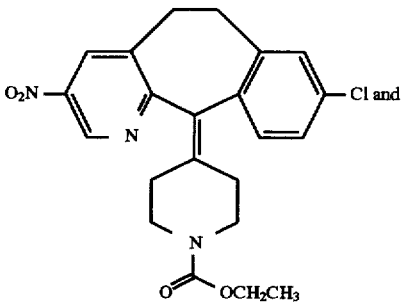

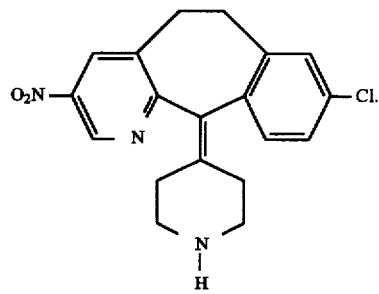

DETAILED DESCRIPTION OF THE INVENTION

As used herein, the following terms are used as defined below unless otherwise indicated:

$M^+$-represents the molecular ion of the molecule in the mass spectrum;

$MH^+$-represents the molecular ion plus hydrogen of the molecule in the mass spectrum;

Bu-represents butyl;

Et-represents ethyl;

Me-represents methyl;

Ph-represents phenyl;

benzotriazol-1-yloxy represents

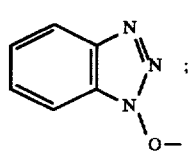

1-methyl-tetrazol-5-ylthio represents

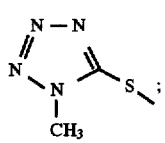

alkyl-(including the alkyl portions of alkoxy, alkylamino and dialkylamino)-represents straight and branched carbon chains and contains from one to twenty carbon atoms, preferably one to six carbon atoms;

alkanediyl-represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, —CH$_2$CH$_2$CH$_2$—, —CH$_2$CHCH$_3$, —CHCH$_2$CH$_3$, etc.

cycloalkyl-represents saturated carbocyclic rings branched or unbranched of from 3 to 20 carbon atoms, preferably 3 to 7 carbon atoms;

heterocycloalkyl-represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —NR$^{10}$- (suitable heterocycloalkyl groups including 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.);

alkenyl-represents straight and branched carbon chains having at least one carbon to carbon double bond and containing from 2 to 12 carbon atoms, preferably from 2 to 6 carbon atoms and most preferably from 3 to 6 carbon atoms;

alkynyl-represents straight and branched carbon chains having at least one carbon to carbon triple bond and containing from 2 to 12 carbon atoms, preferably from 2 to 6 carbon atoms;

aryl (including the aryl portion of aryloxy and aralkyl)- represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, CF$_3$, amino, alkylamino, dialkylamino, —COOR$^{10}$ or —NO$_2$; and halo-represents fluoro, chloro, bromo and iodo; and heteroaryl-represents cyclic groups, optionally substituted with R$^3$ and R$^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, 2-, 3- or 4-pyridyl or pyridyl N-oxide (optionally substituted with R$^3$ and R$^4$), wherein pyridyl N-oxide can be represented as:

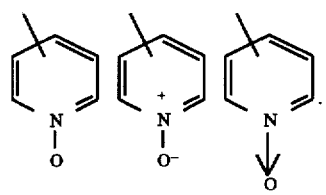

The following solvents and reagents are referred to herein by the abbreviations indicated: tetrehydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine (Et$_3$N); diethyl ether (Et$_2$O); ethyl chloroformate (ClCO$_2$Et); 1-(3-dimethylaminopropyl)-3-ethyl carbodiimde hydrochloride (DEC)

Reference to the position of the substituents R$^1$, R$^2$, R$^3$, and R$^4$ is based on the numbered ring structure:

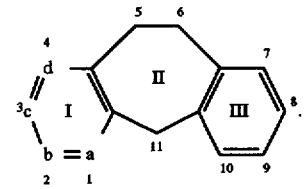

For example, R$^1$ can be at the C-4 position and R$^2$ can be at the C-2 or C-3 position. Also, for example, R$^3$ can be at the C-8 position and R$^4$ can be at the C-9 position.

Representative structures of Formula 1.0 include but are not limited to:

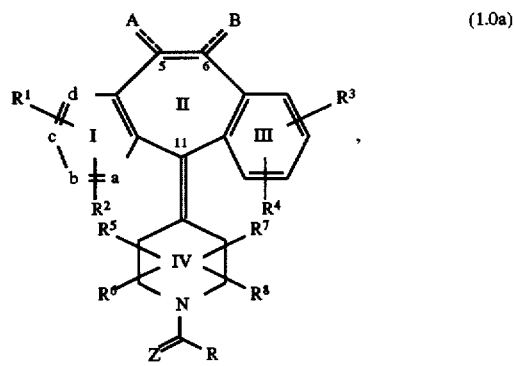

(1.0a)

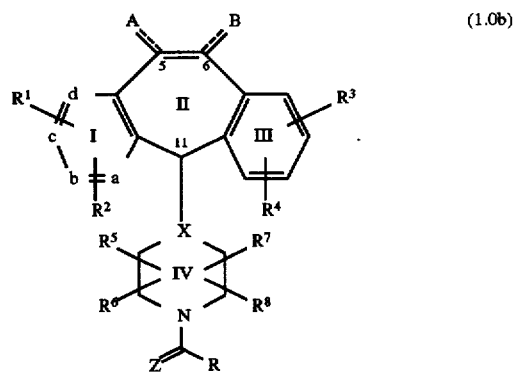

(1.0b)

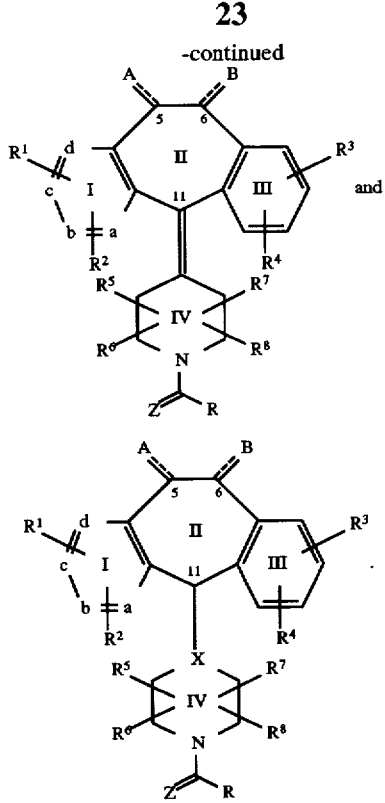

(1.0c)

(1.0d)

Preferably, for the compounds of Formula 1.0 (including 1.0a to 1.0d):

each of a, b, c, and d are C (carbon); or one of a, b, c and d (most preferably a) represents N or NO, most preferably N, and the remaining a, b, c and d groups represent $CR^1$ or $CR^2$;

each $R^1$ and each $R^2$ is independently selected from H, halo (e.g., Cl, Br and F), —$CF_3$, —$OR^{10}$ (e.g., hydroxy and alkoxy (e.g., —$OCH_3$)), alkyl (e.g., methyl and t-butyl, said alkyl group being optionally substituted with halo), benzotriazol-1-yloxy, —$S(O)_tR^{11}$ (e.g., —$SCH_2CH_3$), —$SR^{11}C(O)OR^{11}$ (e.g., —$SCH_2CO_2CH_3$), —$SR^{10}$ (e.g., $R^{10}$ represents —$CH_2C_6H_5$) and 1-methyl-tetrazol-5-ylthio; most preferably $R^1$ and $R^2$ are independently H, halo, —$CF_3$, lower alkyl (e.g., $C_1$ to $C_4$, more preferably methyl) or benzotriazol-1-yloxy; more preferably $R^1$ is Cl or H, and $R^2$ is H, Cl or Br; still more preferably $R^1$ is at the C-4 position, and $R^2$ is at the C-3 position; even more preferably $R^2$ is Br, Cl or I;

$R^3$ and $R^4$ are the same or different and each independently represents H, halo, —$CF_3$, —$OR^{10}$, —$COR^{10}$, —$SR^{10}$, —$S(O)_tR^{11}$ (wherein t is 0, 1 or 2), —$N(R^{10})_2$, —$NO_2$, —$OC(O)R^{10}$, —$CO_2R^{10}$, —$OCO_2R^{11}$, —$C(O)NHR^{10}$, —CN, —$NR^{10}COOR^{11}$, alkynyl, alkenyl or alkyl, said alkyl or alkenyl group optionally being substituted with halo, —$OR^{10}$ or —$CO_2R^{10}$; most preferably $R^3$ and $R^4$ independently represent H, halo, —$CF_3$, —$OR^{10}$ or alkyl (said alkyl group being optionally substituted with halo); more preferably $R^3$ and $R^4$ independently represent H or halo (e.g., Cl, Br, or F); even more preferably $R^3$ is at the C-8 position and $R^4$ is at the C-9 position; still more preferably $R^3$ is Cl at the C-8 position and $R^4$ is H at the C-9 position; $R^5$, $R^6$, $R^7$ and $R^8$ each independently represents H, —$CF_3$ or alkyl (said alkyl optionally being substituted with —$OR^{10}$); most preferably $R^5$, $R^6$, $R^7$ and $R^8$ independently represent H and alkyl, and more preferably H;

when the optional double bond between carbon atoms 5 and 6 is present, A and B independently represent H, —$R^{10}$ or —$OR^{10}$, most preferably H, lower alkyl ($C_1$ to $C_4$) and alkyloxy (i.e., $R^{10}$ represents alkyl), more preferably H and —OH, and still more preferably H; and when no double bond is present between carbon atoms 5 and 6, A and B each independently represent $H_2$, —$(OR^{10})_2$, alkyl and H, (alkyl)$_2$, —H and —$OR^{10}$ or =O, most preferably $H_2$, —H and —OH, or =O, and more preferably A represents $H_2$ and B represents $H_2$ or =O;

R represents $R^{42}$ or $R^{44}$; and

Z represents O or S, and most preferably O.

Compounds of Formula 5.0 include:

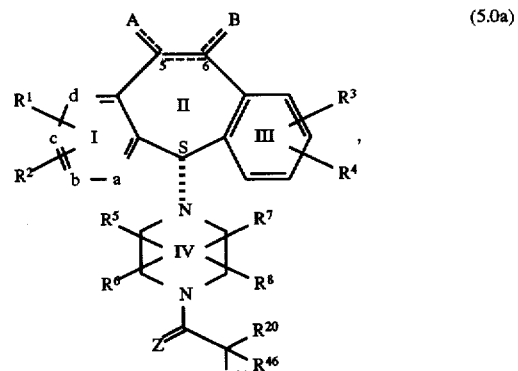

(5.0a)

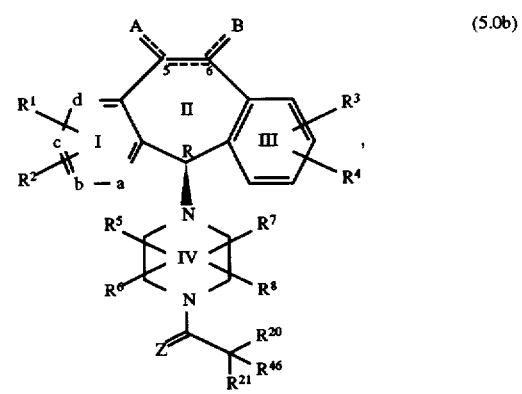

(5.0b)

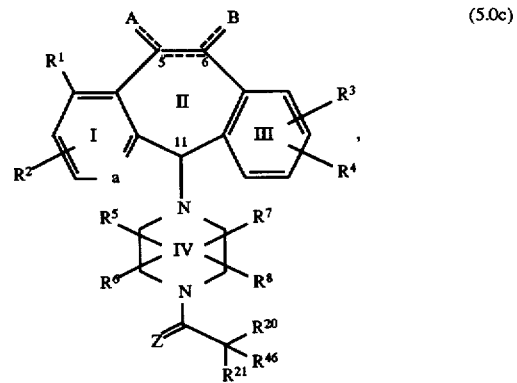

(5.0c)

-continued
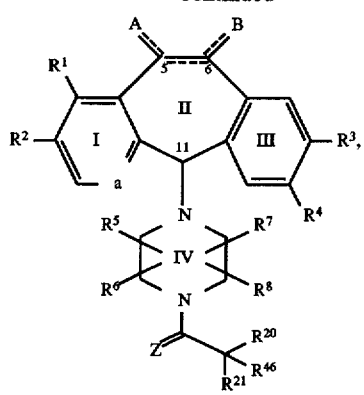
(5.0d)
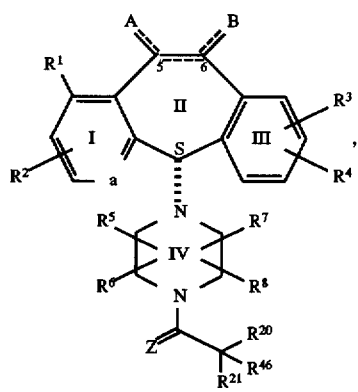
(5.0e)
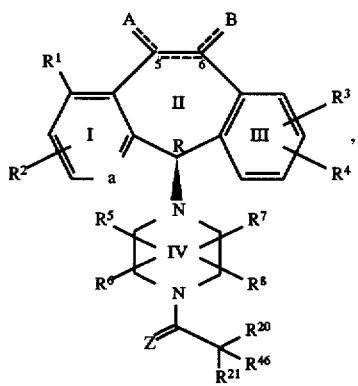
(5.0f)
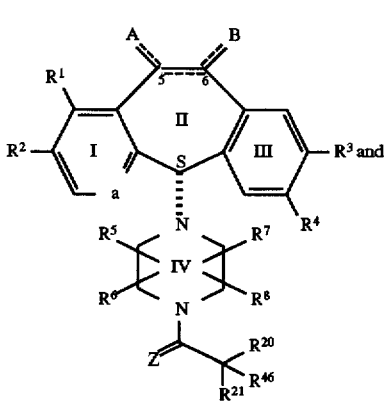
(5.0g)
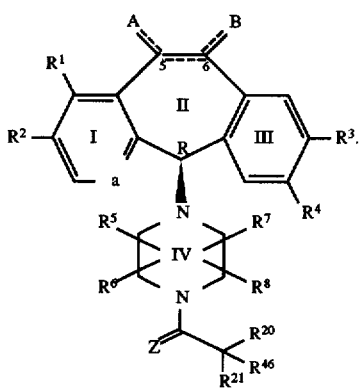
(5.0h)
Compounds of Formula 5.1 include:
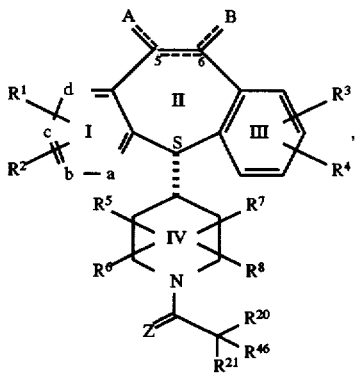
(5.1a)
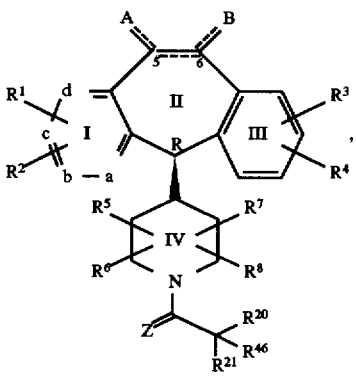
(5.1b)
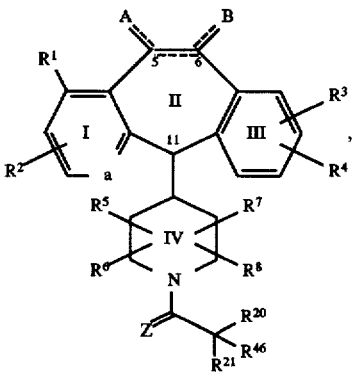
(5.1c)

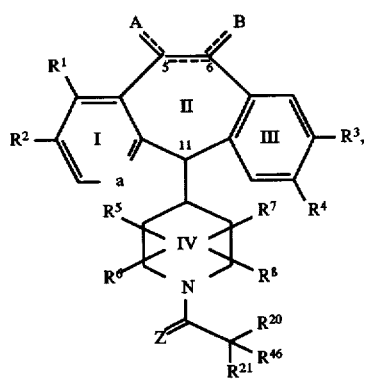
(5.1d)
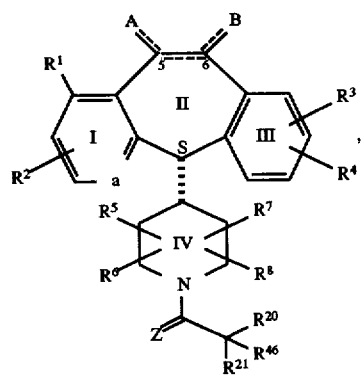
(5.1d)
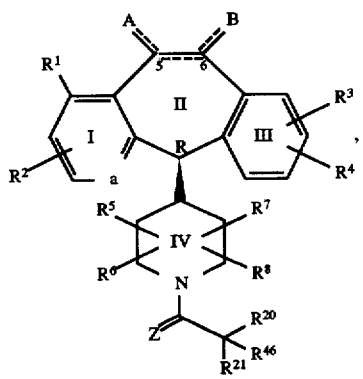
(5.1e)
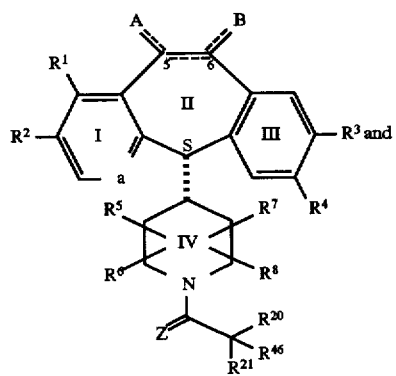
(5.1g)
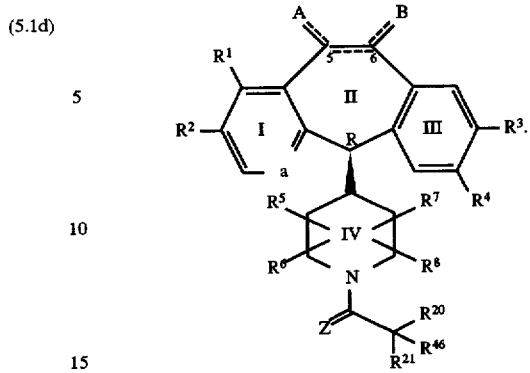
(5.1h)
Compounds of Formula 5.2 additionally include:
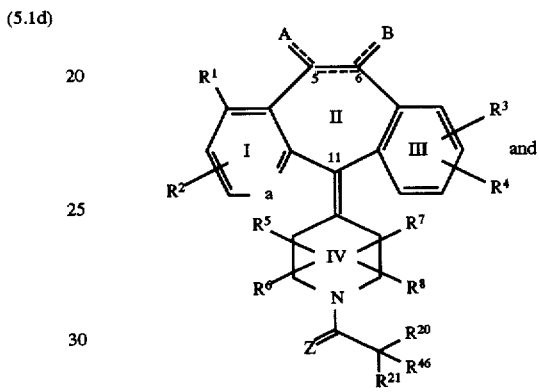
(5.2a)
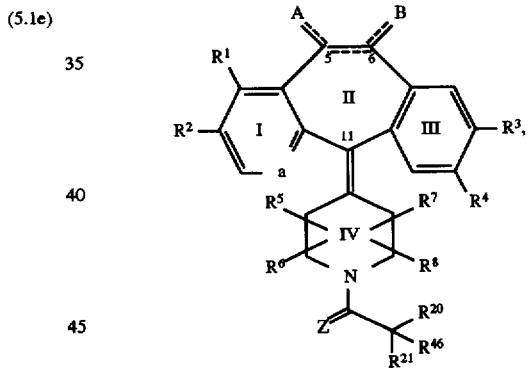
(5.2b)
Compounds of Formula 5.3 include:
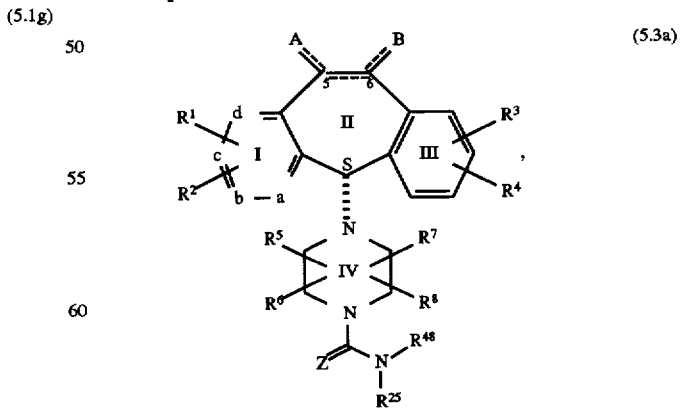
(5.3a)

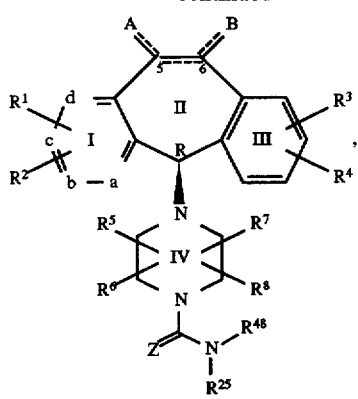
(5.3b)
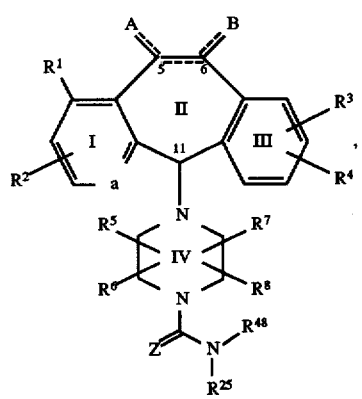
(5.3c)
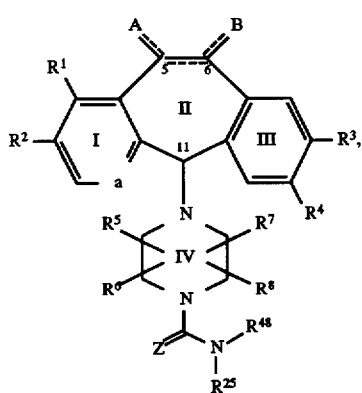
(5.3d)
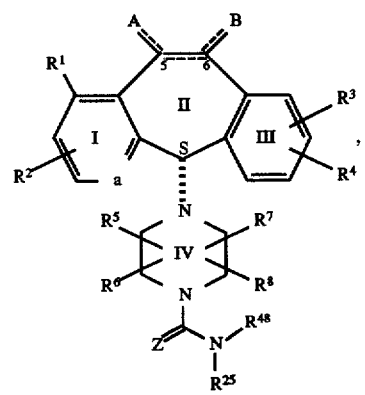
(5.3e)
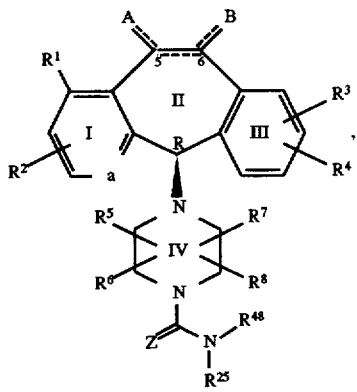
(5.3f)
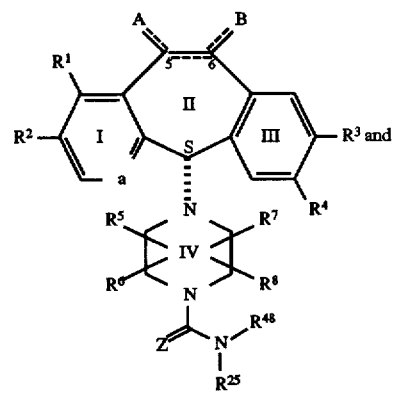
(5.3g)
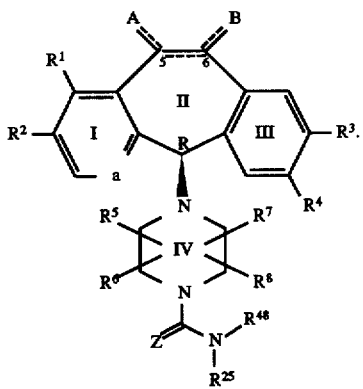
(5.3h)
Compounds of Formula 5.3A include:
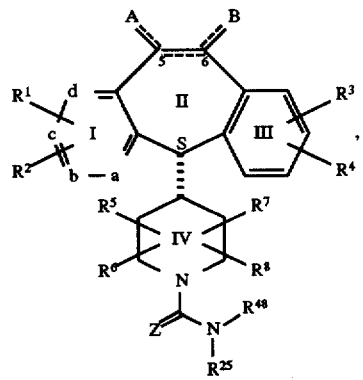
(5.3Aa)

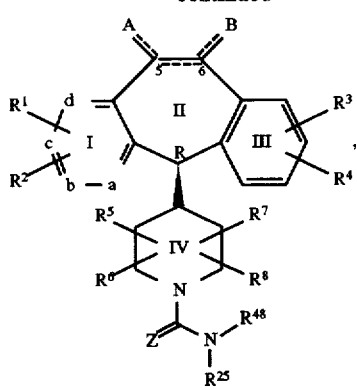 (5.3Ab)

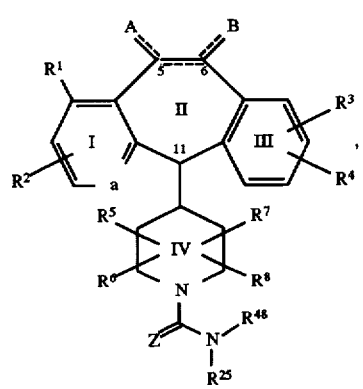 (5.3Ac)

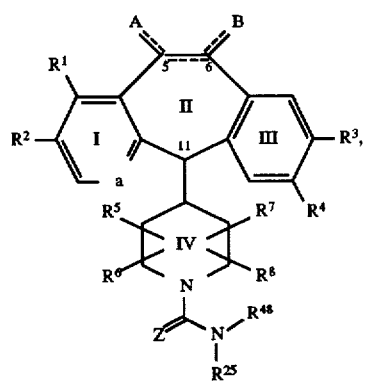 (5.3Ad)

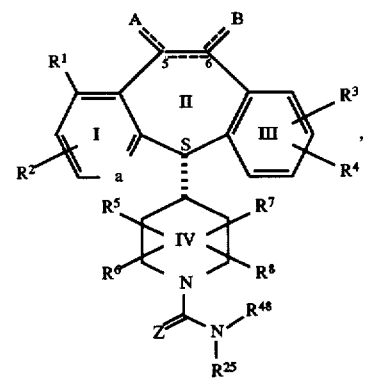 (5.3Ae)

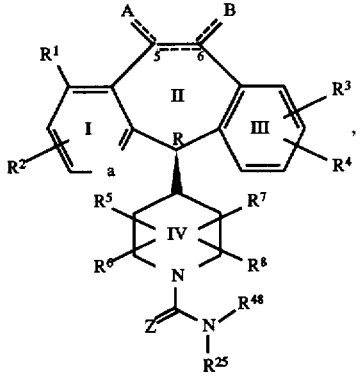 (5.3Af)

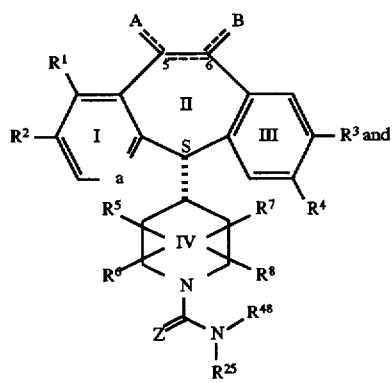 (5.3Ag)

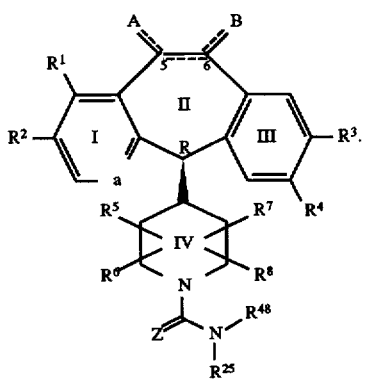 (5.3Ah)

For the compounds of Formulas 5.0, 5.0a–5.0g, 5.1, 5.1a–5.1g, 5.2, 5.2a–5.2b, 5.3, 5.3a–5.3g, 5.3A, 5.3Aa–5.3Ag, and 5.3B, the definitions of the substituents are as defined for Formula 1.0.

Preferably, for compounds of Formulas 5.0, 5.0a–5.0g, 5.1, 5.1a–5.1g, 5.2, and 5.2a–5.2b, $R^{46}$ is selected from piperidine Ring V, heteroaryl, phenyl, substituted phenyl, substituted pyridyl or substituted pyridyl N-oxide, and $R^{20}$ and $R^{21}$ are independently selected from H or alkyl. Most preferably, $R^{46}$ is pyridyl, pyridyl N-oxide or piperidine Ring V. More preferably, $R^{46}$ is pyridyl, pyridyl N-oxide or piperidine Ring V and both $R^{20}$ and $R^{21}$ are hydrogen or both $R^{20}$ and $R^{21}$ are alkyl (still more preferably methyl).

Even more preferably, $R^{46}$ is selected from 3-pyridyl, 4-pyridyl, 3-pyridyl N-oxide, 4-pyridyl N-oxide, 4-N-methylpiperidinyl, 3-N-methylpiperidinyl, 4-N-acetylpiperidinyl or 3-N-acetylpiperidinyl, and both $R^{20}$ and $R^{21}$ are hydrogen or both $R^{20}$ and $R^{21}$ are alkyl (still even more preferably methyl). Even still more preferably, $R^{46}$ is selected from 3-pyridyl, 3-pyridyl N-oxide, 4-pyridyl, and 4-pyridyl N-oxide, and both $R^{20}$ and $R^{21}$ are hydrogen or both $R^{20}$ and $R^{21}$ are methyl.

Examples of the $R^{42}$ groups include:

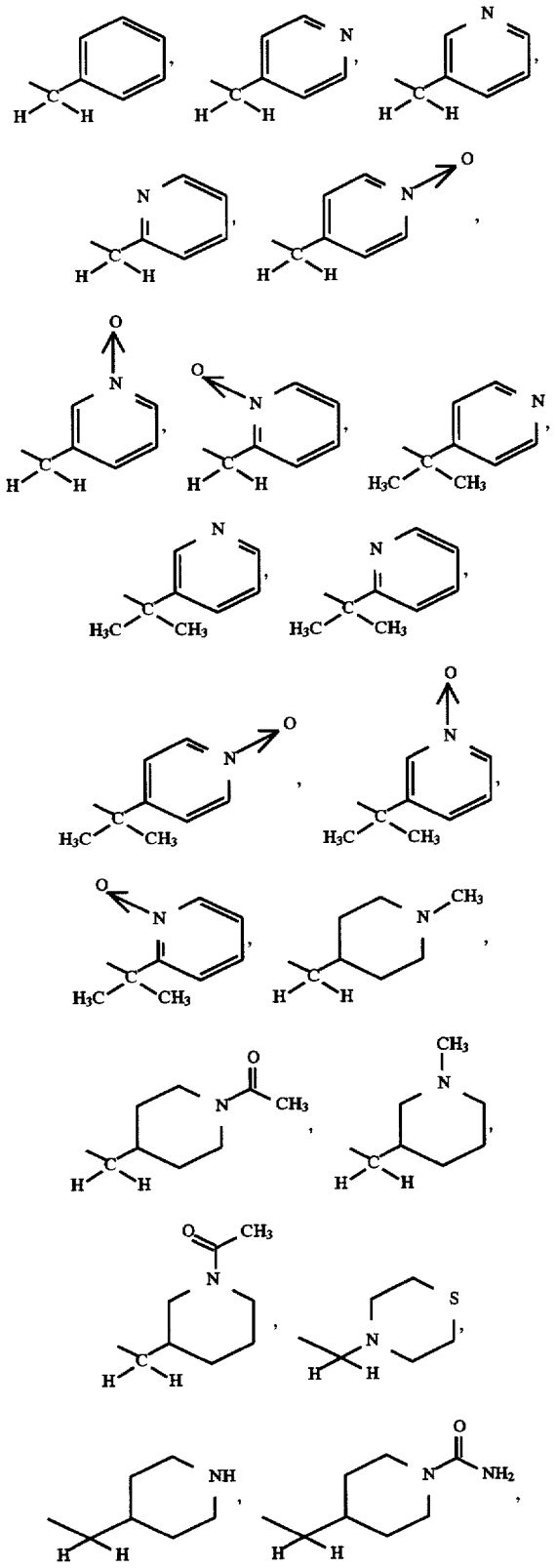

Preferably for the compounds of Formulas 5.3, 5.3a–5.3g, 5.3A, 5.3Aa–5.3Ag, and 5.3B, $R^{25}$ represents phenyl, 2-pyridyl, 3-pyridyl, 4-pyridyl, or 2-, 3- or 4-pyridyl N-oxide, and most preferably 4-pyridyl or 4-pyridyl N-oxide. More prefereably, $R^{48}$ represents H or methyl and still more preferably H.

Compounds of the formula 7.0c include compounds of the formula:

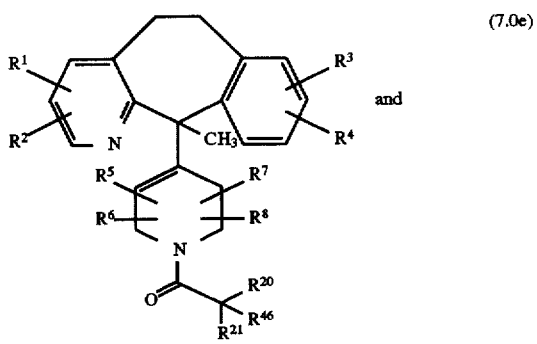
(7.0e)

and

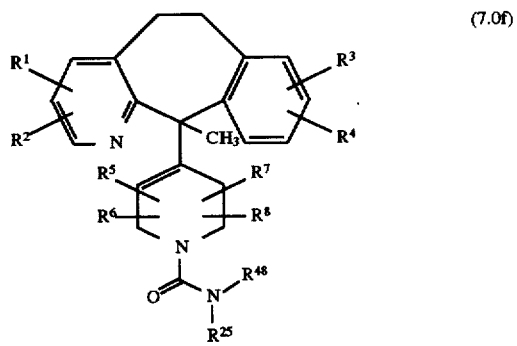
(7.0f)

wherein $R^{21}$, $R^{20}$, $R^{46}$, $R^{25}$ and $R^{48}$ are as defined above for compounds of the formula 1.0.

Compounds of the formula 7.0b include compounds of the formula:

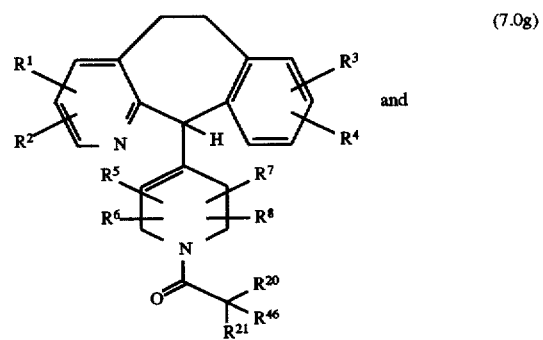
(7.0g)

and

-continued (7.0h)

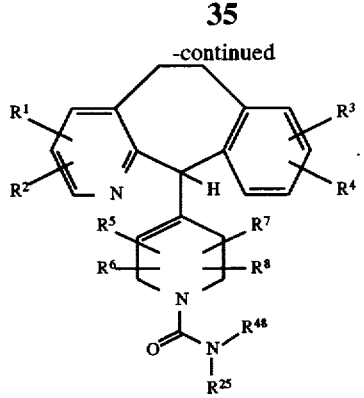

wherein $R^{21}$, $R^{20}$, $R^{46}$, $R^{25}$ and $R^{48}$ are as defined above for compounds of the formula 1.0.

Compounds of the formula 7.0a include compounds of the formula:

(7.0j)

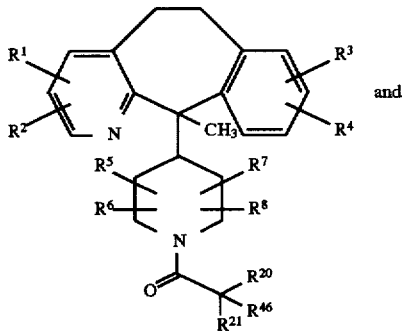

and (7.0k)

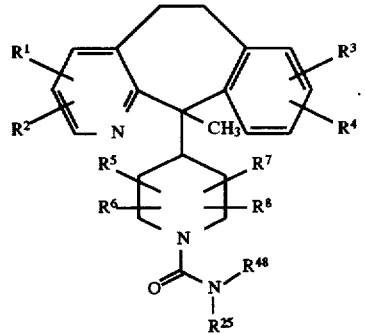

wherein $R^{21}$, $R^{20}$, $R^{46}$, $R^{25}$ and $R^{48}$ are as defined above for compounds of the formula 1.0.

Preferably for compounds of the formula 7.0e, 7.0g and 7.0j the group $R^{46}$ is selected from piperidine ring V, heteroaryl, phenyl, substituted phenyl, substituted pyridyl or substituted pyridyl N-oxide, and $R^{20}$ and $R^{21}$ are independently selected from H or alkyl. Most preferably R is pyridyl, pyridyl N-oxide or piperidine ring V. It is also preferred that $R^{20}$ and $R^{21}$ are both H or are both alkyl, preferably methyl.

Preferably for compounds of the formula 7.0f, 7.0h and 7.0k, the group $R^{25}$ is phenyl, 3-pyridyl, 4-pyridyl, 3-pyridyl N-oxide, 4-pyridyl N-oxide or piperidine ring V. More preferably $R^{48}$ is H or methyl, with H being most preferred.

Preferably for the compounds of formula 7.0a, 7.0b, 7.0c, 7.0e, 7.0f, 7.0g, 7.0h, 7.0j and 7.0k the groups $R^5$, $R^6$, $R^7$ and $R^8$ are H, and $R^1$, $R^2$, $R^3$ and $R^4$ are independently selected from H, halo, —$NO_2$, —$N(R^{10})_2$, alkyl, alkenyl, alkynyl, —$COR^{10}$, —$CO_2R^{10}$, —$CF_3$, —$OR^{10}$, and —CN, wherein $R^{10}$ is as defined above for compounds of the formula 1.0.

Representative compounds of the invention include:

(5.4)

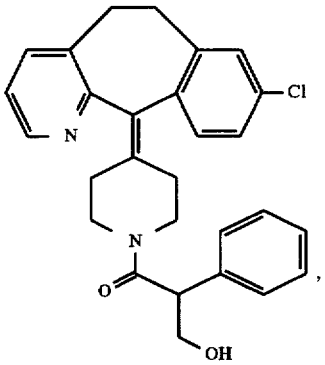

, (5.5)

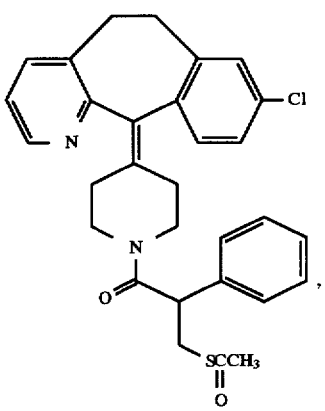

, (5.6)

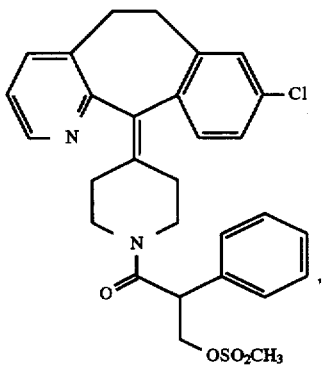

, (5.7)

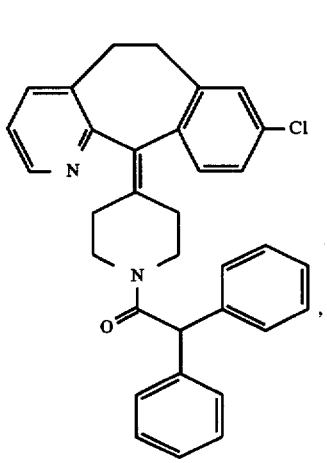

,

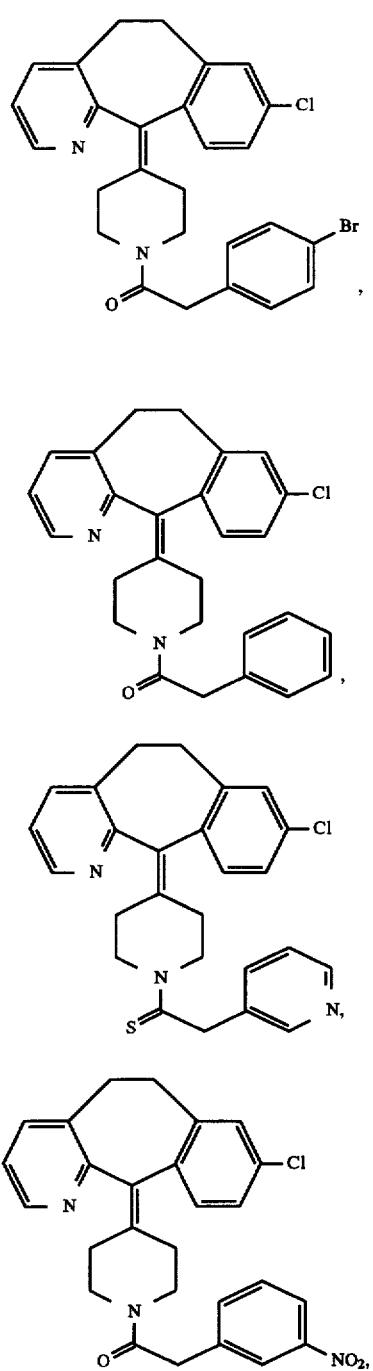
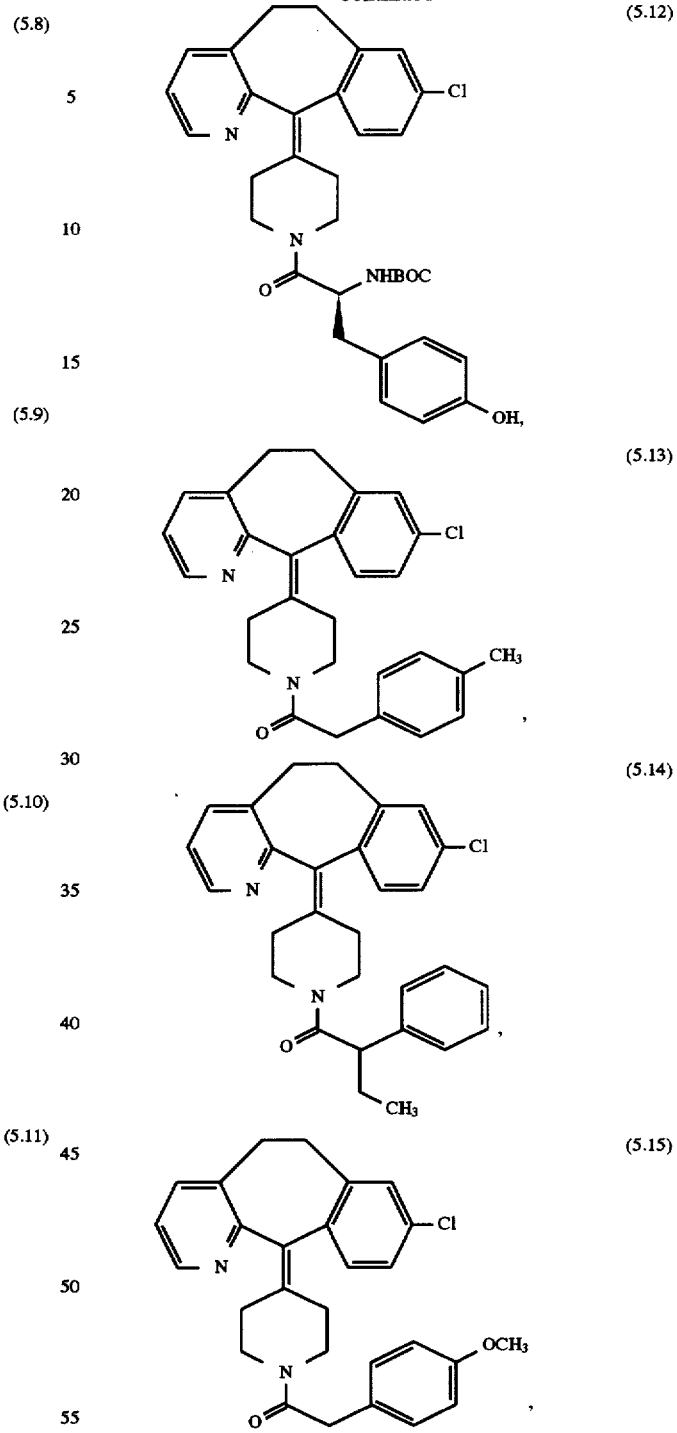

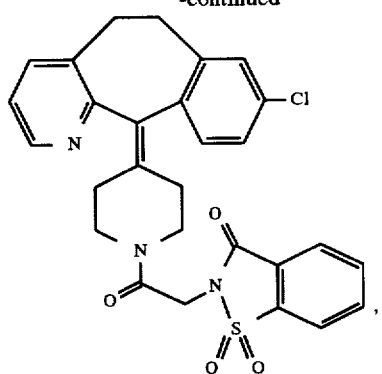 (5.16)
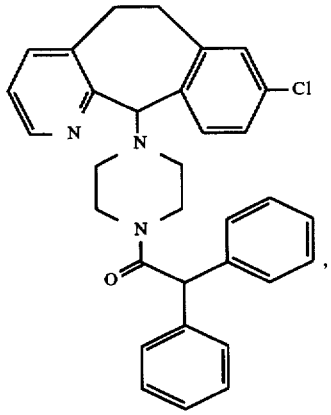 (5.21)
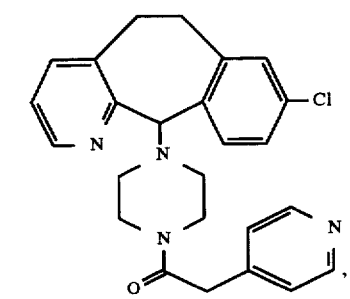 (5.17)
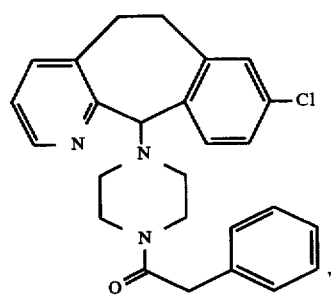 (5.22)
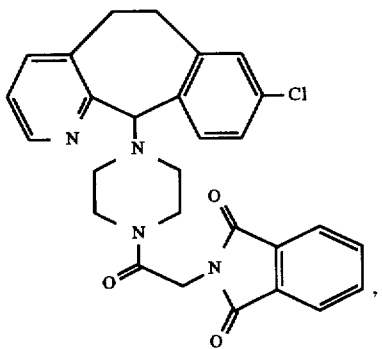 (5.18)
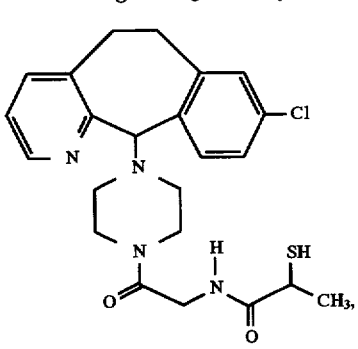 (5.23)
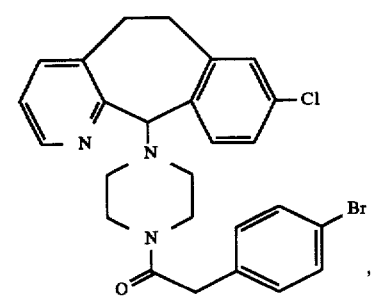 (5.19)
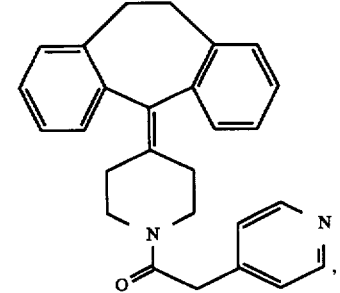 (5.24)
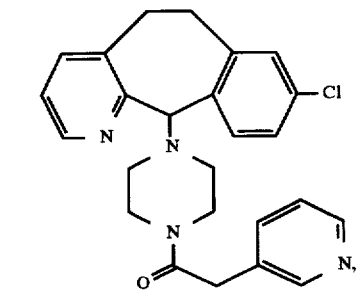 (5.20)
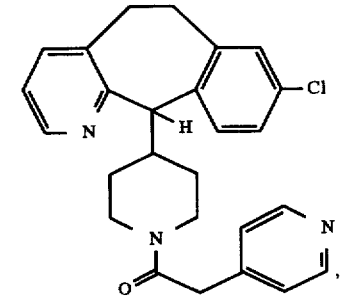 (5.25)

-continued
(5.26)
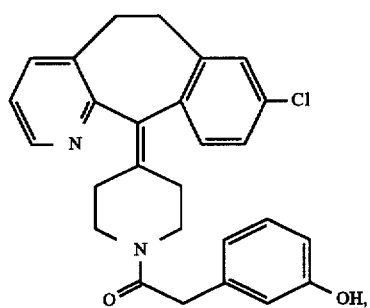
(5.27)
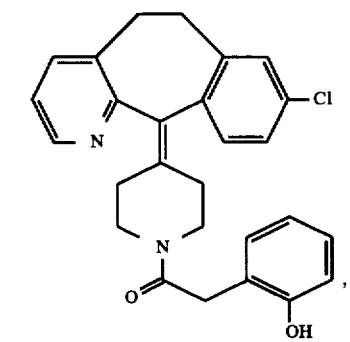
(5.28)
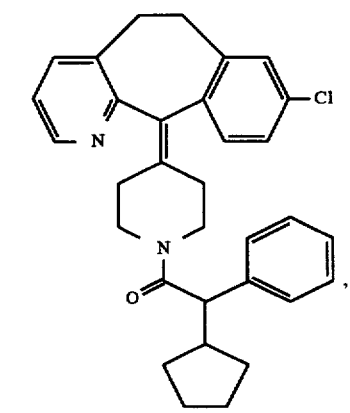
(5.29)
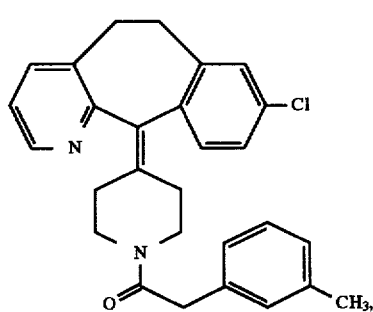
-continued
(5.30)
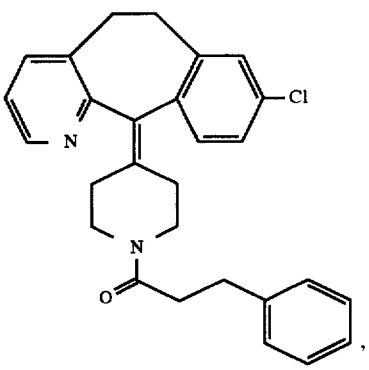
(5.31)
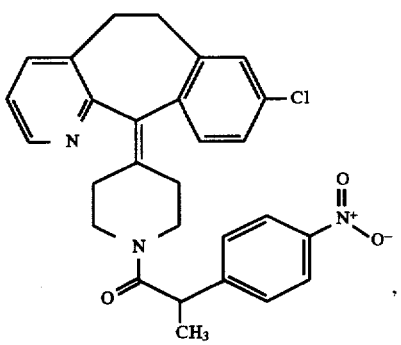
(5.32)
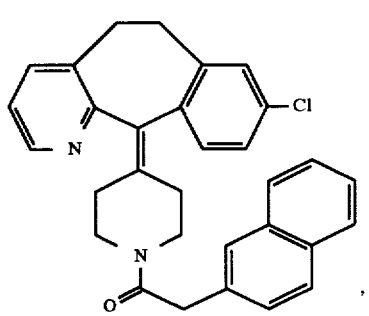
(5.33)
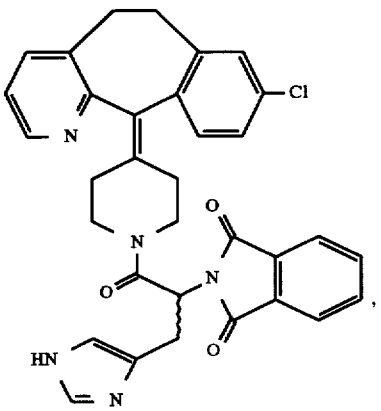

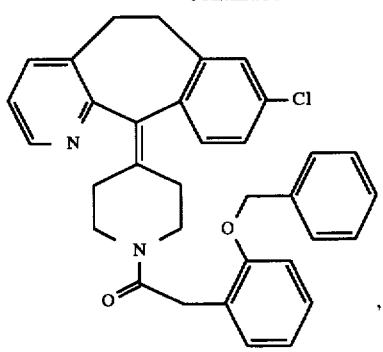
(5.34)
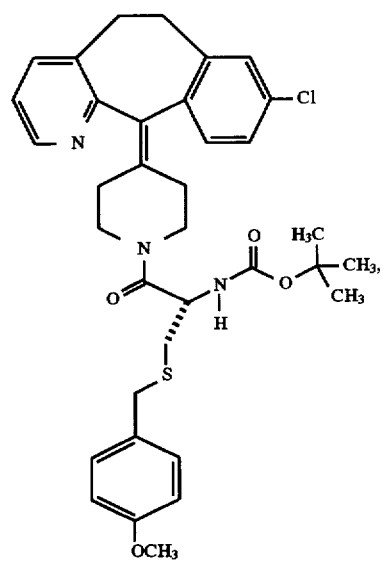
(5.35)
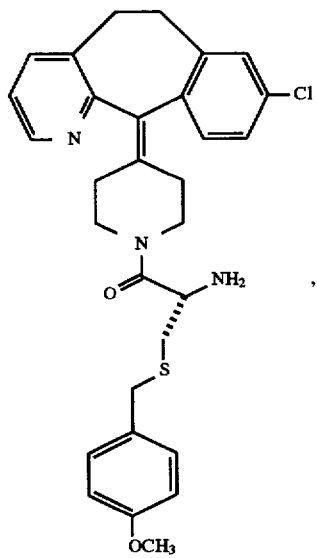
(5.36)
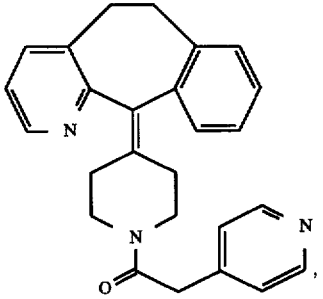
(5.37)
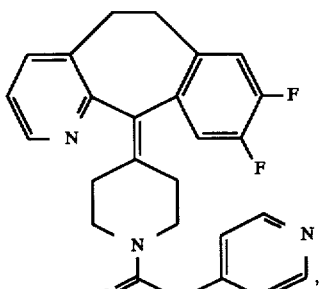
(5.38)
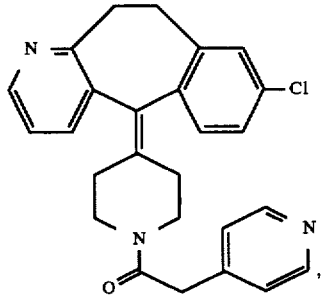
(5.39)
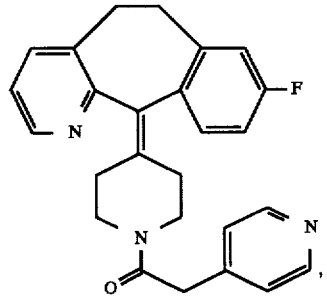
(5.40)
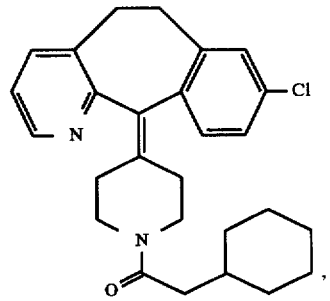
(5.42)

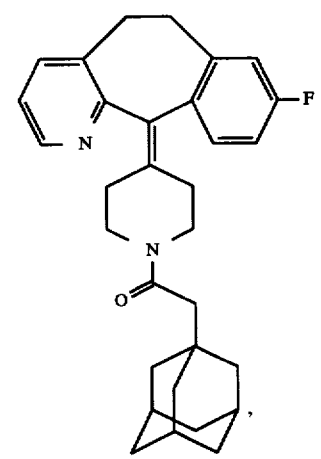
(5.43)
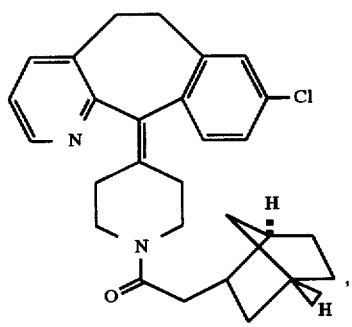
(5.44)
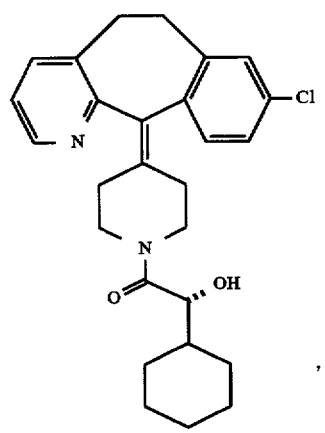
(5.45)
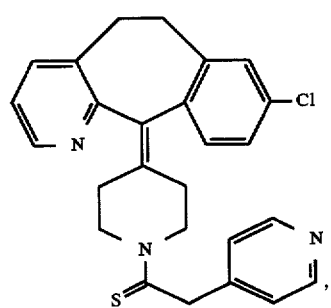
(5.46)
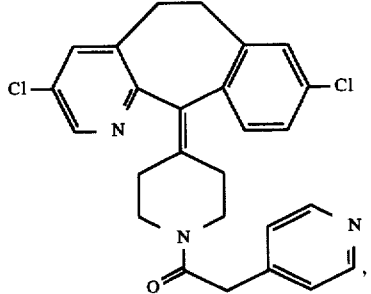
(5.47)
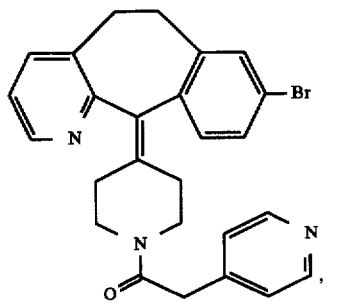
(5.48)
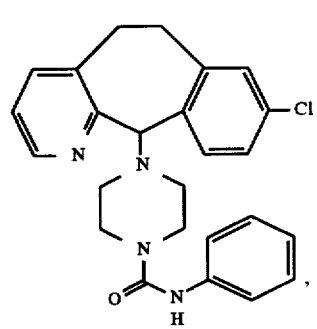
(6.4)
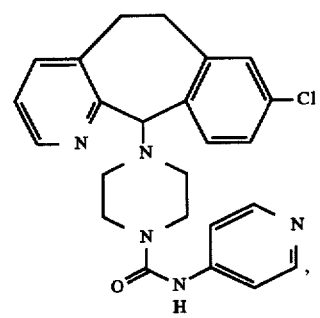
(6.5)
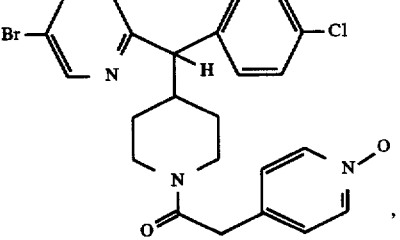
(5.200)

(5.201)
(5.202)
(5.203)
(5.204)
(5.205)
(5.206)
(5.207)
(5.208)
(5.209)
(5.210)

-continued
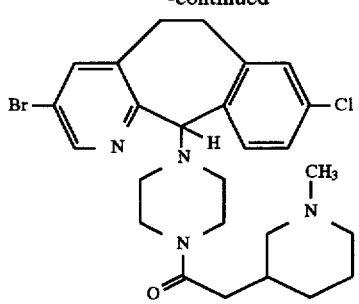
(5.211)
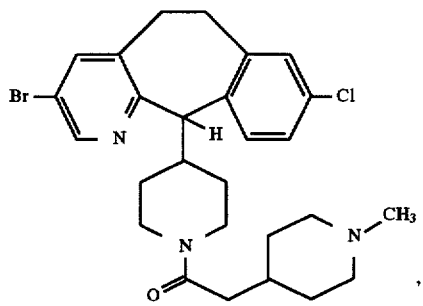
(5.212)
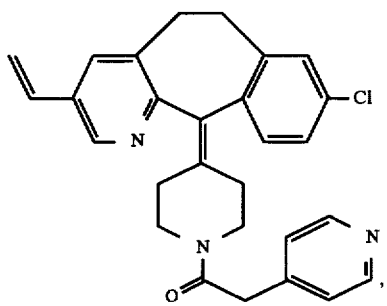
(5.214)
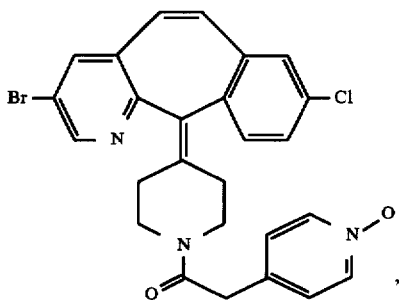
(5.213)
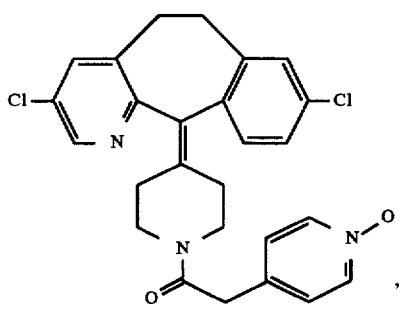
(5.215)
-continued
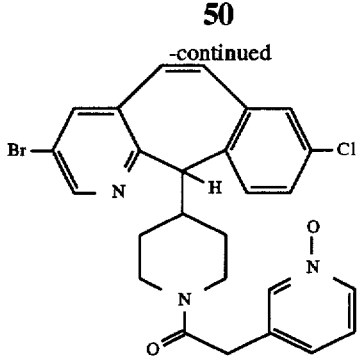
(5.217)
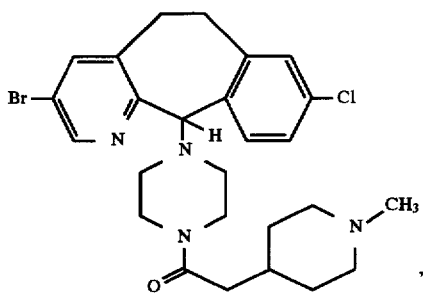
(5.216)
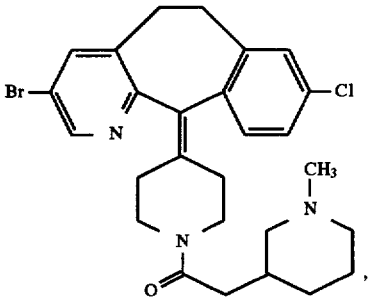
(5.218)
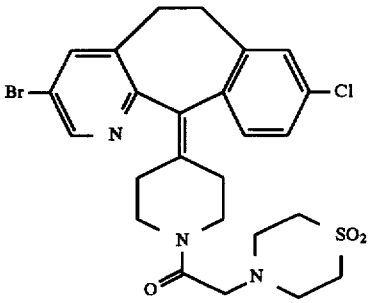
(5.219)
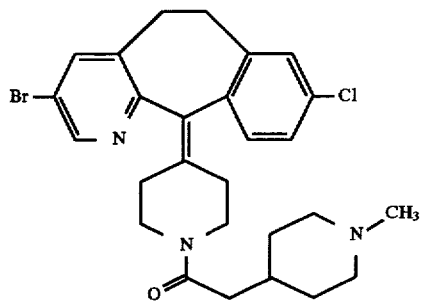
(5.220)
Preferred compounds of this invention are selected from the group consisting of compounds of Examples: 1, 2, 3, 4, 5, 6, 19, 42, 43, 44, 45, 46, 47, 48, 49, 75, 76, 78, 82, 83, 84, 85, 89, 121, 180, 182, 183, 184, 187 (6.7 and 6.8), 192, 196, 197, 198, 200, 201, 206, 222, 223, 224, 225, 226, 227, 233, 234, 236, 239, 246, 247, 248, 249, 250, 251, 261, 262, 266, 267, 269, 273, 276, 283, 285, 286, 287, 288, 289, 291, 292, 293, 299, 300, 301, 303, 307, 309, 311, 312, 313, 314, 316, 350, 351, 352, 354 and 356.

More preferred compounds of this invention are selected from the group consisting of compounds of Examples: 1, 2, 42, 43, 75, 78, 82, 180, 183, 187 (6.7 and 6.8), 196, 197, 198, 200, 222, 223, 224, 227, 233, 234, 246, 247, 248, 249, 250, 251, 266, 269, 273, 283, 285, 286, 291, 292, 300, 301, 303, 307, 311, 312, 313, 314, 350, 351, 352, 354 and 356.

Even more preferred compounds of this invention are selected from the group consisting of compounds of Examples: 82, 197, 233, 246, 266, 312, 351, 352, 354 and 356.

Also more preferred are the compounds of Examples: 426, 400-G, 400-C, 400-F, 400-E, 425-H, 401, 400-B, 400, 400-L, 425-U, 413, 400-J, 417-B, 438, 411-W, 425-O, 400-D, 400-K, 410-G and 400-H.

Lines drawn into the ring systems indicate that the indicated bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of Formula 1.0 wherein R is —N(R$^{10}$)$_2$, and compounds of Formulas 5.3, 5.3A and 5.3B can be prepared by reacting compound 405.00 (described below) with an isocyanate (R$^{10}$—N=C=O) in a solvent such as DMF, CH$_2$Cl$_2$ or THF in accordance with methods known in the art.

The following processes may be employed to produce compounds of the invention—i.e., compounds of Formula 1.0 represented by compounds of Formulas 5.0, 5.1, 5.2 and 5.3. For purposes of describing the processes, the compounds are represented by Formula 400.00:

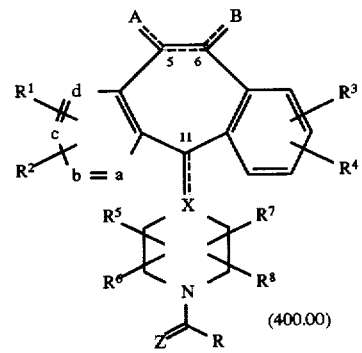

wherein R represents R$^{42}$ or R$^{44}$, and all other substitutents are as described herein.

A. A compound of Formula 405.00 may be coupled with a compound of the formula RCOOH in the presence of coupling agent such as DEC, N,N'-dicyclohexylcarbodiimide (DCC) or N,N'-carbonyldiimidazole (CDI) to produce compounds of Formula 400.00:

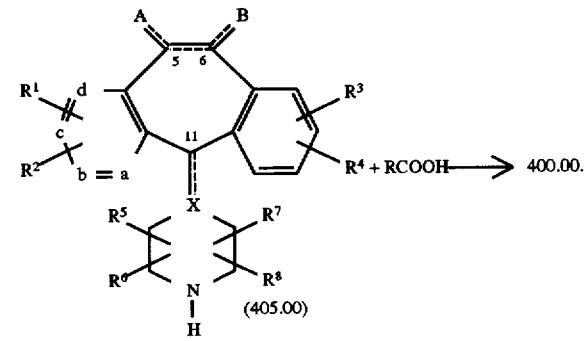

The reaction is usually conducted in an inert solvent such as THF, DMF or CH$_2$Cl$_2$ at a temperature between about 0° C. and reflux, preferably at about room temperature. When the coupling agent is DCC or DEC, the reaction is preferably run in the presence of HOBT. Method A is the method of choice for preparing compounds of this invention.

B. A compound of Formula 405.00 may also be reacted with a compound of Formula 410.00 in the presence of base to produce compounds of Formula 400.00:

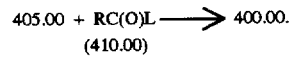

Representative examples of appropriate bases are pyridine and Et$_3$N. L designates a suitable leaving group. For example, a compound of compound 410.00 may be an acyl halide (e.g., L represents halo) or an acyl anhydride, (e.g., L is —O—C(O)—R). The leaving group may also be alkoxy, in which case the compounds of Formula 400.00 may be produced by refluxing a compound of Formula 405.00 with an excess of a compound of Formula 410.00.

Compounds of Formula 405.00 may be prepared by cleaving the group COOR$^a$ from the corresponding carbamates 415.00, for example, via acid hydrolysis (e.g., HCl) or base hydrolysis (e.g., KOH):

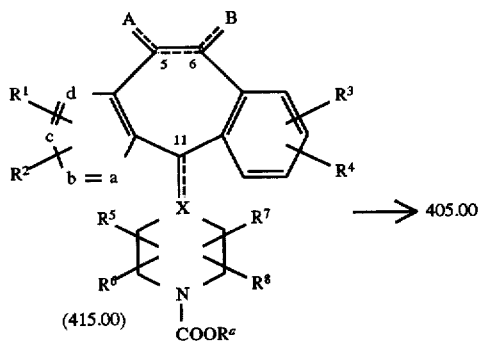

→ 405.00 wherein $R^a$ is a group which does not prevent the cleavage reaction, e.g., $R^a$ is an optionally substituted alkyl such as ethyl.

Alternatively, depending upon the nature of $R^a$, as determined by one skilled in the art, Compound 415.00 may be treated with an organometallic reagent (e.g., $CH_3Li$), a inductive reagent (e.g., Zn in acid), etc., to form compounds of Formula 405.00.

Compound 415.00 may be prepared from the N-alkyl compound shown as Formula 420.00 below, in the manner disclosed in U.S. Pat. Nos. 4,282,233 and 4,335,036.

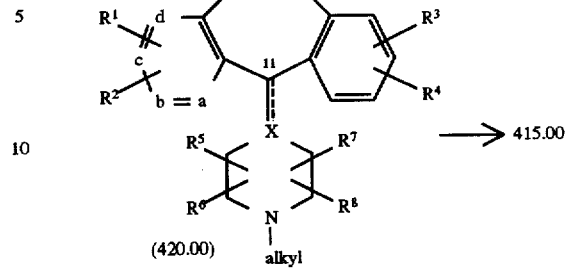

→ 415.00

It also will be apparent to one skilled in the art that there are other methods for converting Compound 420.00 to Compound 405.00. For example, treatment of Compound 420.00 with BrCN via von Braun reaction conditions would provide nitrile 420.00a. Subsequent hydrolysis of the nitrile under either aqueous basic or acidic conditions would produce Compound 405.00. This method is preferable when there is substitution on the piperidine or piperazine ring.

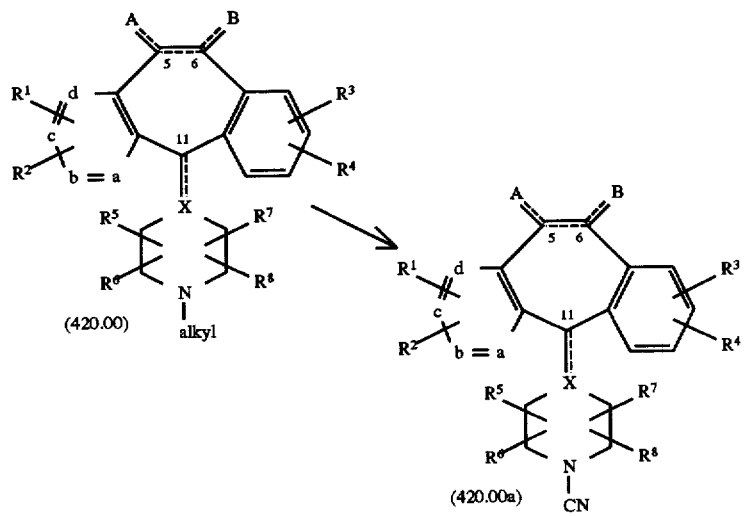

C. The compounds of Formula 400.00 wherein Z is O or S may be made by an alternative process using direct conversion of the N-alkyl compound 420.00 with an appropriate compound of Formula 410.00 such as an acyl halide or acyl anhydride. Preferably the reaction is run in the presence of an appropriate nucleophile (e.g. LiI, etc.) and solvent (e.g., toluene, dioxane or xylenes). An appropriate base, may be added, and heating may be required. Typically, a temperature ranging from 50°–150° C. (preferably 100°–120° C.) is utilized.

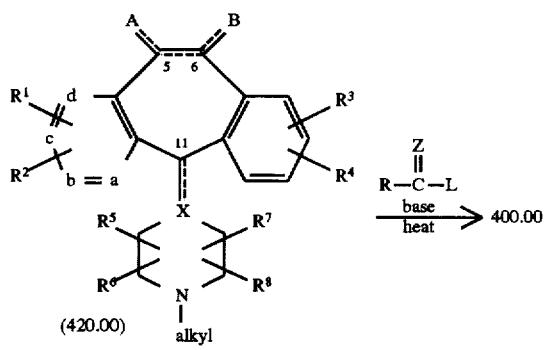

PREPARATION OF DOUBLE BOND COMPOUNDS

Compounds of Formula 400.00, wherein X is a carbon atom having an exocyclic double bond to carbon 11, may be prepared from compound 420.00 as described above. Compounds of Formula 420.00 may be produced by the methods disclosed generally in U.S. Pat. No. 3,326,924 or alternatively may be prepared by a ring closure reaction, wherein the desired cycloheptene ring is formed by treating compound 425.00 with a super acid. Suitable super acids for this purpose include, for example, $HF/BF_3$, $CF_3SO_3H$ (triflic acid), $CH_3SO_3H/BF_3$, etc. The reaction can be performed in the absence of, or with, an inert co-solvent such as $CH_2Cl_2$. The temperature and time of the reaction vary with the acid employed. For example, with $HF/BF_3$ as the super acid system the temperature may be controlled so as to minimize side reactions, such as HF addition to the exocyclic double bond. For this purpose, the temperature is generally in the range of from about +5° C. to –50° C. With $CF_3SO_3H$ as the super acid system, the reaction may be run at elevated temperatures, e.g., from about 25° C. to about 150° C. and at lower temperatures but the reaction then takes longer to complete.

Generally the super acid is employed in excess, preferably in amounts of from about 1.5 to about 30 equivalents.

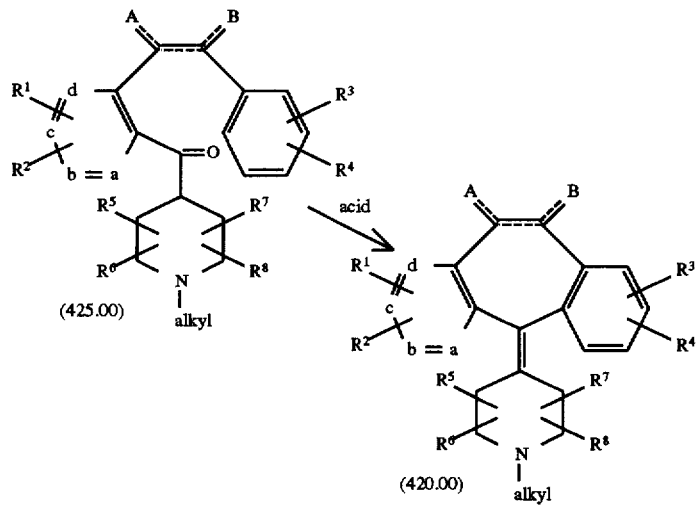

Compound 420.00 is prepared as described in part B above.

PREPARATION OF SINGLE BOND COMPOUNDS

Compounds of Formula 400.00, wherein X is carbon and the bond to carbon 11 (C-11) is a single bond, can be prepared by reducing compounds of Formula 405.00, wherein X is carbon and the bond to C-11 is a double bond, with lithium aluminum hydride in THF. Conversion to final products can be done following the process described above for conversion of compounds of Formula 405.00 to compounds of Formula 400.00.

A ketone compound of Formula 425.00 may be formed by hydrolysis of 430.00, e.g., such as by reacting a Grignard intermediate of Formula 430.00 with an aqueous acid (e.g., aqueous HCl). I² in Formula 430.00 represents chloro, bromo or iodo.

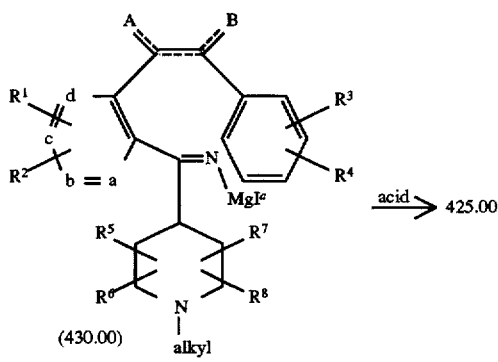

(430.00)

The Grignard intermediate 430.00 is formed by the reaction of the cyano compound 435.00 with an appropriate Grignard reagent 440.00 prepared from 1-alkyl-4halopiperidine. The reaction is generally performed in an inert solvent, such as ether, toluene, or THF, under general Grignard conditions e.g., temperature of from about 0° C. to about 75° C. Alternatively, other organometallic derivatives of the 1alkyl-4-halo piperidine can be employed.

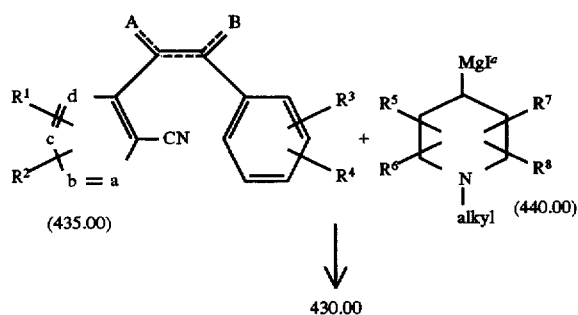

The cyano compound of Formula 435.00 is produced by converting the tertiary butyl amide of Formula 445.00 with a suitable dehydrating agent, such as $POCl_3$, $SOCl_2$, $P_2O_5$, toluene sulfonyl chloride in pyridine, oxalyl chloride in pyridine, etc. This reaction can be performed in the absence of or with a co-solvent, such as xylene.

The dehydrating agent such as $POCl_3$ is employed in equivalent amounts or greater and preferably in amounts of from about 2 to about 15 equivalents. Any suitable temperature and time can be employed for performing the reaction, but generally heat is added to accelerate the reaction. Preferably the reaction is performed at or near reflux.

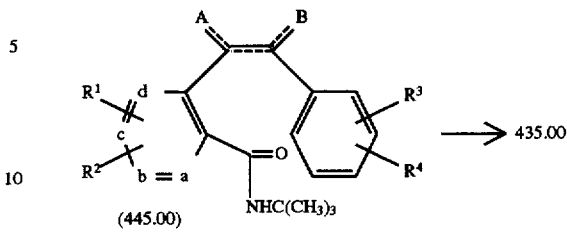

(445.00)

The tert-butylamide of Formula 445.00 may be produced by reaction of a compound of Formula 450.00a and 450.00b. in the presence of base, wherein G is chloro, bromo or iodo.

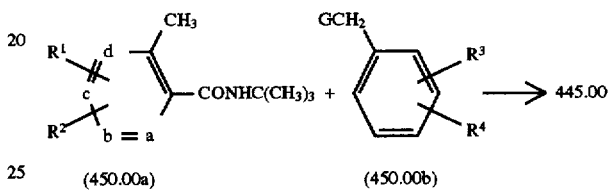

(450.00a)    (450.00b)

The compound of Formula 450.00a may be formed by hydrolysis of the corresponding nitrile wherein the appropriate cyanomethyl pyridine, such as 2-cyano-3-methylpyridine, is reacted with a tertiary butyl compound in acid, such as concentrated sulfuric acid or concentrated sulfuric acid in glacial acetic acid. Suitable tertiary butyl compounds include, but am not limited to, t-butyl alcohol, t-butyl chloride, t-butyl bromide, t-butyl iodide, isobutylene or any other compound which under hydrolytic conditions forms t-butyl carboxamides with cyano compounds. The temperature of the reaction will vary depending upon the reactants, but generally the reaction is conducted in the range of from about 50° C. to about 100° C. with t-butyl alcohol. The reaction may be performed with inert solvents, but is usually run neat.

An alternative process for the formation of compounds of Formula 400.00a may involve direct cyclization of Compound 455.00 as shown below.

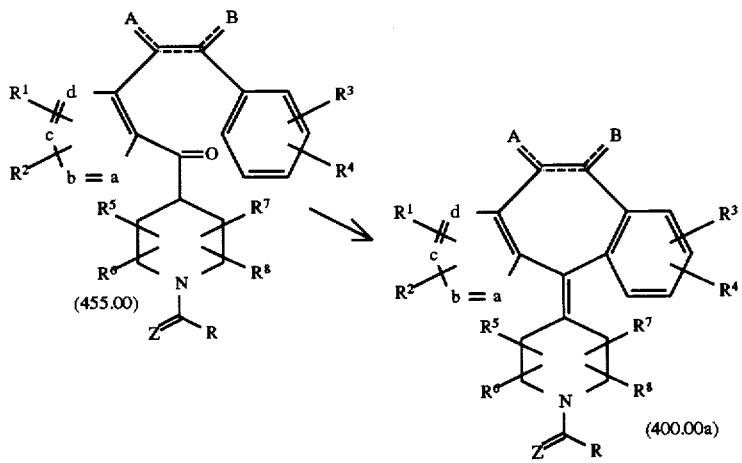

Cyclization to form the cycloheptene ring may be accomplished with a strong acid (e.g., triflic, polyphosphoric, HF/BF$_3$), and may be performed in an inert solvent, such as ether, toluene or THF. The temperature and time may vary with the acid employed, as described in process A above.

Compounds of Formula 455.00 wherein Z=O or S may be prepared by treating a compound of Formula 425.00 with an appropriate acyl halide or acyl anhydride of formula 410.00. Most preferably this reaction is run in the presence of a good nucleophile, such as LiI, in the appropriate solvent, such as toluene, dioxane or xylene, and at a temperature ranging from 50°–150° C., preferably 100°–120° C.

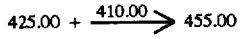

A second method of preparing compounds of Formula 455.00 involves reacting an unsubstituted piperidylidene compound of Formula 460.00 with the appropriate acyl halide or acyl anhydride of Formula 410.00 in the presence of base, such as pyridine or Et$_3$N. Alternatively, if L=OH in compound 410.00, then coupling of compound 460.00 with compound 410.00 may require use of a conventional coupling reagent, such as DCC or CDI.

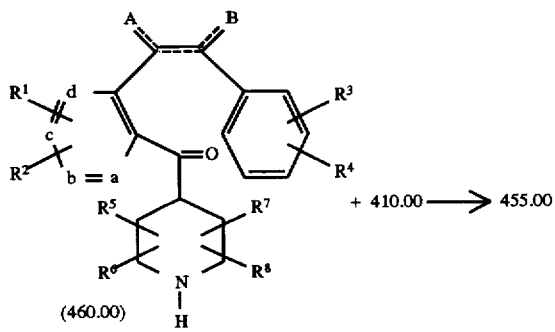

Compounds of Formula 460.00 may be produced from the corresponding carbamates of Formula 465.00, via acid hydrolysis, using for example, aqueous HCl, or base hydrolysis using for example, KOH. Alternatively, some compounds can be prepared by treating the carbamate, Formula 465.00, with an organometallic reagent, such as methyl lithium or a reductive reagent, such as zinc in acid, etc., depending upon the nature of the R$^a$ group. For example, if R$^a$ is a simple alkyl group, CO$_2$R$^a$ may be cleaved by alkaline hydrolysis at 100° C.

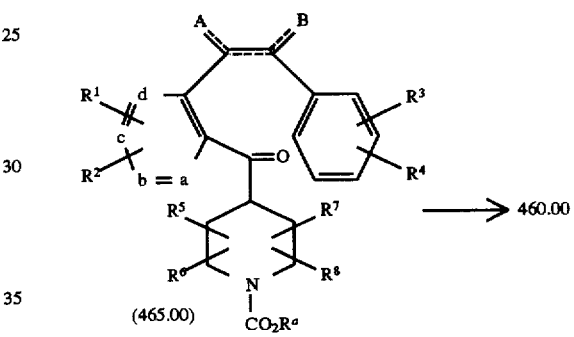

The carbamate compounds of Formula 465.00 may be prepared from the appropriate alkyl compound of Formula 425.00 by treatment with a chloroformate, preferably in an inert solvent, such as toluene, with warming to approximately 80° C. Other alternative methods are available for the conversion of 425.00 to 455.00 as previously described (e.g. Von Braun reaction conditions). Compounds of Formula 425.00 may be prepared as described above.

SUBSTITUTION ON THE PYRIDINE RING

Various methods can be used as described in WO 88/03138 to provide compounds which are substituted on the pyridine ring, i.e., in positions 2-, 3- and or 4- positions of the tricyclic ring system. For example, the cyclization methods described on pages 20–30 of WO 88/03138 can already have the appropriate substituents on the pyridine ring in place. A variety of substituted pyridines are known in the literature and can be employed in these syntheses. Alternatively, the azaketone of Formula XIX (from page 27 of WO 88/03138)

61

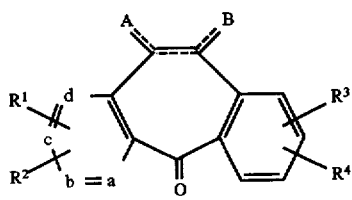

(XIX) p.27 WO88/03138 wherein $R^1$ and $R^2$ are both H can be converted to the appropriately substituted azaketone wherein $R^1$ and $R^2$ are non-H substitutents. If both $R^1$ and $R^2$ are desired to be non-H substitutents the procedure would be repeated.

The azaketone is thus reacted with an oxidizing agent such as meta-chloroperoxybenzoic acid (MCPBA) or hydrogen peroxide to produce the corresponding compound in which the nitrogen of the pyridine ring is as an N-oxide:

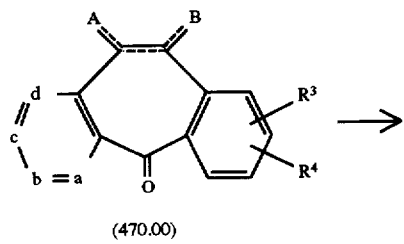

wherein one of a', b', c' or d' is N→O and the others are CH or $CR^1$ or $CR^2$. This reaction is normally run at temperatures from −15° C. to reflux, more typically at about 0° C. The reaction is preferably conducted in an inert solvent such as $CH_2Cl_2$ for MCPBA or acetic acid for hydrogen peroxide.

The azaketone N-oxide of Formula 470.00a can then be reacted with a chlorinating agent such as $SO_2Cl_2$ or $SOCl_2$ to form a compound of Formula 470.00b. Typically, this reaction results in monosubstitution of Cl in the ortho or para-position relative to the N atom of the ring.

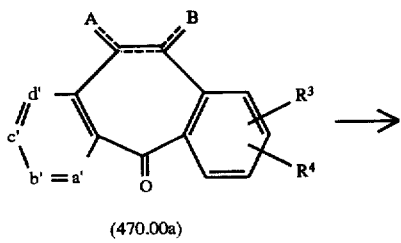

62

-continued

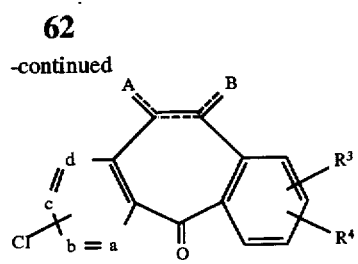

To provide the disubstituted products, steps 1 and 2 above are repeated.

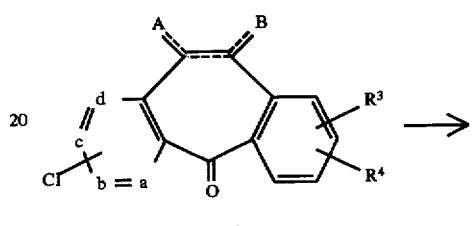

Typically, the resulting disubstituted compounds have Cl ortho and para relative to the N atom of the pyridine ring.

The mono or disubstituted compounds of Formulas 470.00b and 470.00c above can be reacted with various nucleophiles such as alkoxides, amines, thiols, etc. This will result in compounds where one or both of the Cl substituents are replaced by the nucleophile to provide a compound of Formula 470.00d or a compound easily converted to Formula 470.00d.

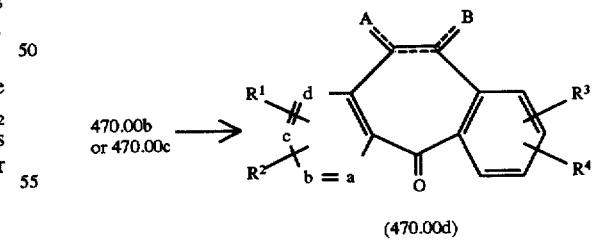

The substituted ketone of Formula 470.00 can then be converted to the desired compound by the methods described above and in WO 88/03138 and in U.S. Pat. No. 3,326,924.

Formula 405.00, wherein $R^1$ or $R^2$ are chlorine, can be made by the following alternate process.

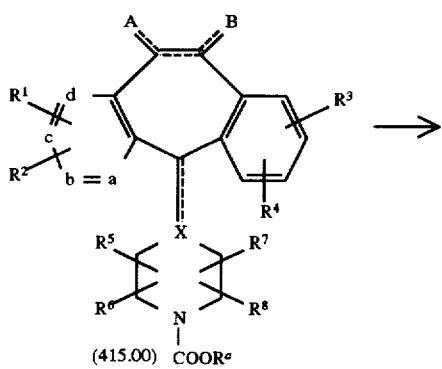

(415.00)

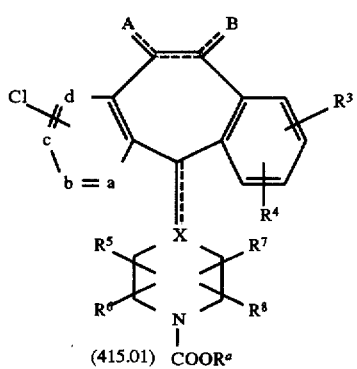

(415.01)

The N-oxide of Formula 415.00 can be treated with POCl₃ to form a compound of Formula 415.01. Typically, this reaction results in mono-substitution of Cl in the ortho or para position relative to the N atom of the ring.

Alternatively, the Cl substituted azaketones of Formula 470.00b or 470.00c above can be converted to the corresponding derivatives of Formula 405.00 above wherein $R^1$ and/or $R^2$ is Cl by methods analogous to those described above. At this point the Cl substituent(s) can be displaced by an appropriate nucleophile to provide the desired substituent. Suitable nucleophiles include alkoxide, amines, thiols, etc. This reaction usually requires higher tempertures (e.g., from about 100° to about 200° C.) than the displacement reaction to produce ketone 470.00d above. It is also usually conducted in a sealed vessel in an inert solvent. The compound of Formula 405.00 is then converted to a compound of Formula 400.00 as described above.

Various electrophilic species can also be added to the pyridine ring from the corresponding halo-substituted pyridine (Formula 405.00 wherein $R^1$ is halo, preferably bromo or iodo). Transmetallation of the halo derivative using an alkyl lithium (e.g. n-BuLi) provides the lithio derivative, which can then be quenched with the appropriate electrophile (e.g. $R^1L$, etc.).

An alternative process for introducing substituents at the C-3 position of pyridine Ring I of Formula 1.0, involves nitrating a compound of Formula 415.00 (except wherein X is nitrogen) or a compound of Formula 470.00d with tetrbutylammonium nitrate—TFAA in $CH_2Cl_2$ at a temperature of 0° C. to room temperature (about 25° C.). The nitro group may then be reduced to the corresponding amine using iron filings in EtOH, or powdered zinc—acetic acid in aqueous THF, or powdered Zn and either $CuCl_2$ or CuBr2 in aqueous EtOH. By methods know to those skilled in the art, the amine group can be converted to a variety of substituents, such as, halo, cyano, thio, hydroxyl, alkyl, alkenyl, alkynyl and haloalkyl.

Wherein Z represents sulfur, a compound of Formula 400.00 wherein Z is oxygen is reacted with $P_2S_5$, Lawesson's reagent, or another reagent capable of introducing sulfur in place of oxygen. The reaction may take place at elevated temperature in pyridine, toluene or other suitable solvents. In this and other reactions, numerous conversions of a compound of Formula 400.00 (Z=O) to another compound of Formula 400.00 (Z=S) are possible.

PREPARATION OF C5-C6-ENE DERIVATIVES

Compounds of formula 400.00 with a double bond between C-5 and C-6 can be prepared by heating a compound of Formula 470.00h in acetic acid with $SeO_2$ to produce a compound of Formula 470.00i. Compounds of Formula 470.00i can be converted to final products according to methods already described.

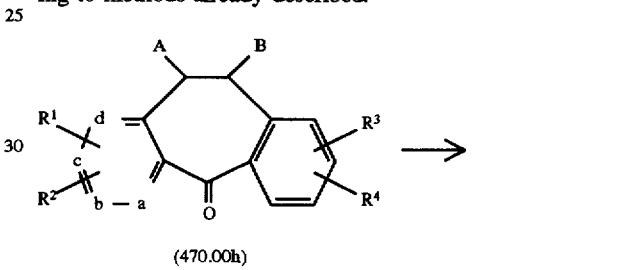

(470.00h)

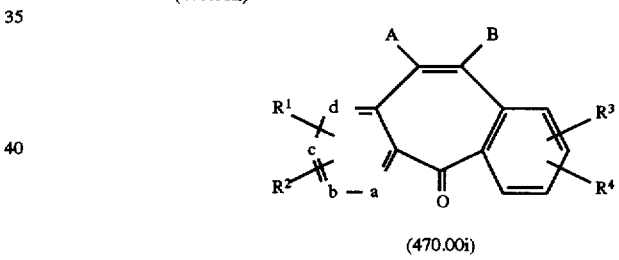

(470.00i)

PREPARATION OF PIPERAZINE ANALOGS

Compounds having a piperazine ring bound to the C-11 of the tricyclic nucleus, i.e., Formula 1.0 wherein X is N, are best prepared via alkylation of the appropriately substituted piperazine compound of Formula 700.00 with a compound of Formula 705.00. Compounds of Formula 705.00 contain the appropriately substituted halide (such as Cl, Br, or I) or other similar leaving group (e.g., tosyloxy or mesyloxy). The reaction is usually conducted in an inert solvent, such as THF or toluene, optionally with a base such as $Et_3N$ or potassium carbonate, and typically at a temperature range of ambient to reflux to produce a compound of Formula 710.00.

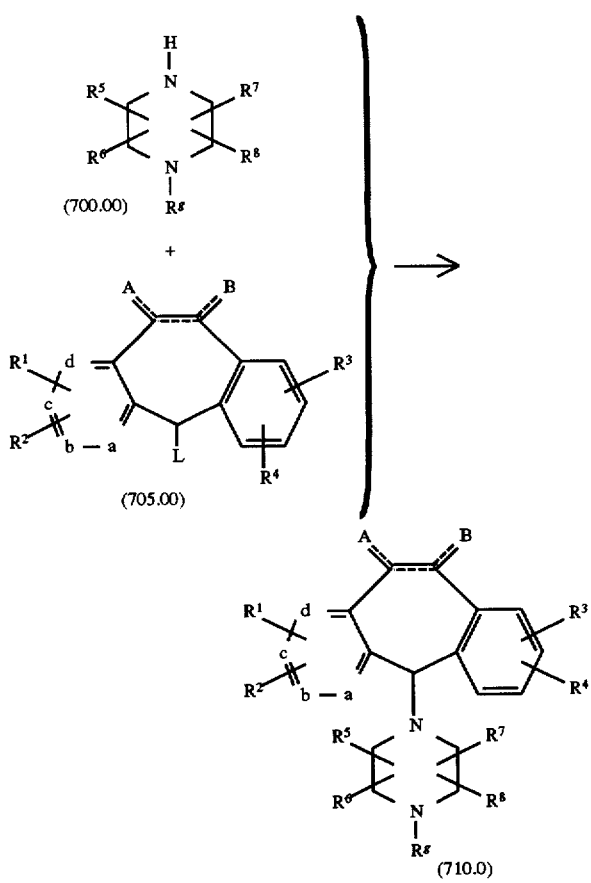

(700.00)

+

(705.00)

→

(710.0)

In this reaction $R^g$ is H, $CO_2R^a$ (wherein $R^a$ is a $C_1$ to $C_4$ alkyl group) or C(Z)R. The preparation of compound 705.00 wherein L is Cl is analogous to the procedure described in U.S. Pat. No. 3,409,621. One skilled in the art can prepare other derivatives of 705.00 (e.g., L is Br, I, mesyloxy, or tosyloxy). When $R^g$ is H, C(Z)R or $CO_2R^a$, these are converted to compounds of the invention by processes known in the art.

An alternate route for generating the compound of Formula 710.00 is by reductive amination of the aza ketone 715.00 with the piperazine 700.00

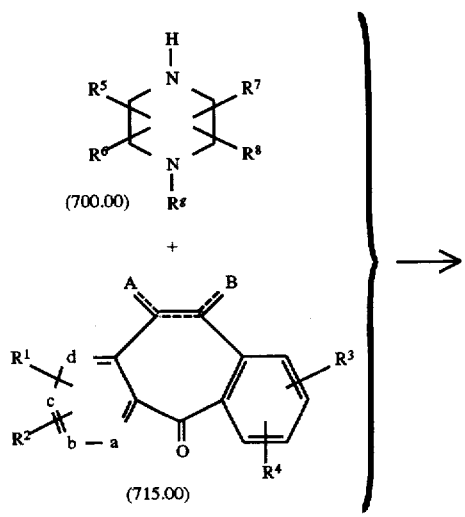

(700.00)

+

(715.00)

→

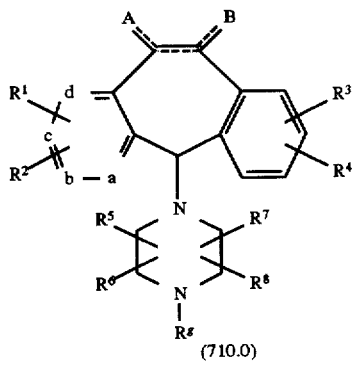

(710.0)

The reaction is typically carried out in a polar solvent, such as MeOH or EtOH, optionally in the presence of a dehydrating agent, such as 3 Å molecular sieves. The intermediate Schiff base can be reduced to the compound of Formula 710.00 by employing a variety of reducing agents, such as $NaCNBH_3$, or catalytic hydrogenation, for example, hydrogen over Pd/C.

When $R^g$ is C(Z)R, these are the compounds of the invention. When $R^g$ is H or $CO_2R^a$, these are converted to compounds of the invention as described herein.

Compounds of Formulas 5.3A and 5.3B, wherein $R^{25}$ represents a pyridyl N-oxide, can be produced by reacting compounds of Formulas 5.3A and 5.3B, wherein $R^{25}$ is pyridyl, with a one molar equivalent of an oxidizing agent (such as oxone).

Compounds of Formulas 5.3, 5.3A and 5.3B, wherein $R^{25}$ represents a pyridyl N-oxide, can be produced by reacting the product of Preparative Example 12 with a peroxyacid (such as MCPBA) to give the corresponding N-oxide intermediate. The desired N-oxide product may be obtained from the N-oxide intermediate by following the procedure of Example 183.

Compounds of the formula 7.0a, 7.0b and 7.0c can be prepared from amines of the formula 7.1a, 7.1b and 7.1c, respectively, by coupling a compound of the formula 7.0a, 7.0b or 7.0c with a carboxylic acid of the formula RCOOH via the method described above for reacting compounds of the formula 405.00.

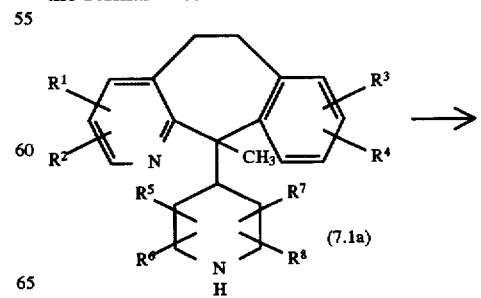

(7.1a)

→

-continued

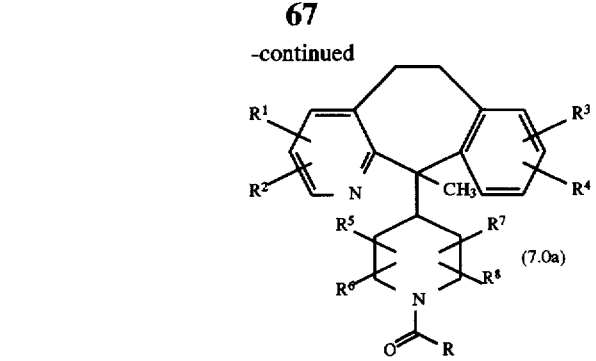
(7.0a)

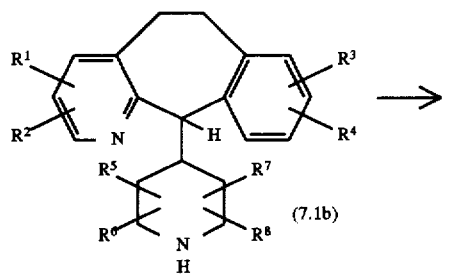
(7.1b)

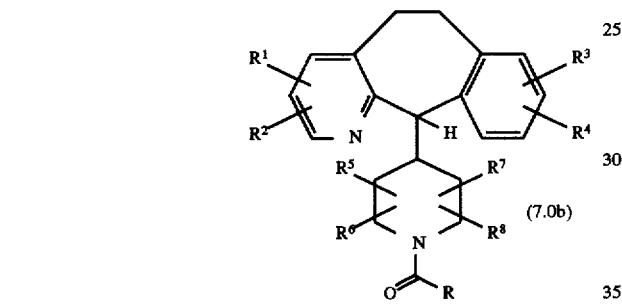
(7.0b)

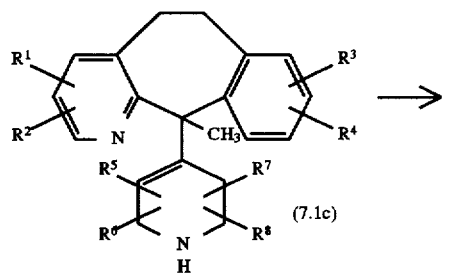
(7.1c)

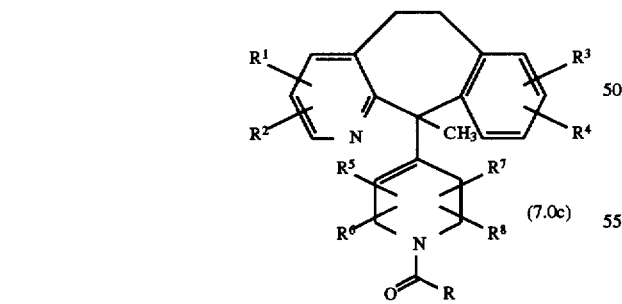
(7.0c)

Alternatively, a compound of the formula 7.0a, 7.0b or 7.0c is treated with a compound of the formula RC(O)L, where L is a suitable leaving group, via the procedure described above for compounds of the formula 405.00.

Compounds of the formula 7.1a can be prepared from a compound of the formula 420.50, (i.e., a compound of the formula 420.00 wherein A and B are both H, no double bond is present between carbons 5 and 6, or between carbon 11 and X, X is CH, and the N-alkyl group is a methyl group) as shown in Reaction Scheme 1.

Reaction Scheme 1

Step A:

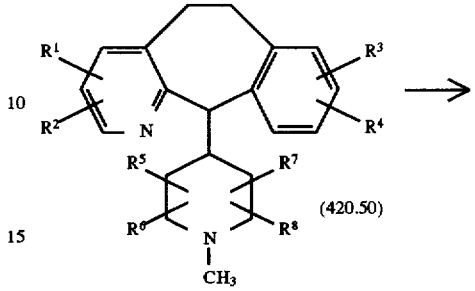
(420.50)

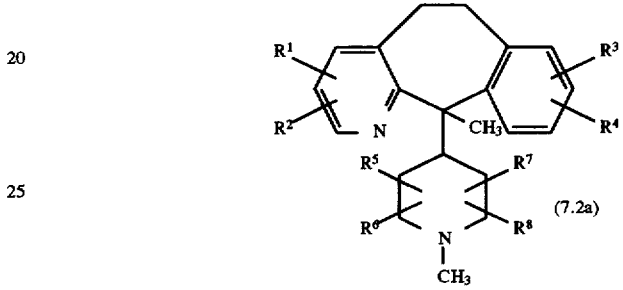
(7.2a)

Step B:

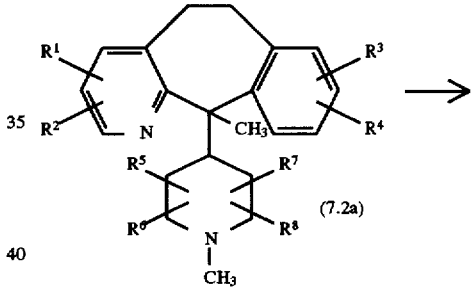
(7.2a)

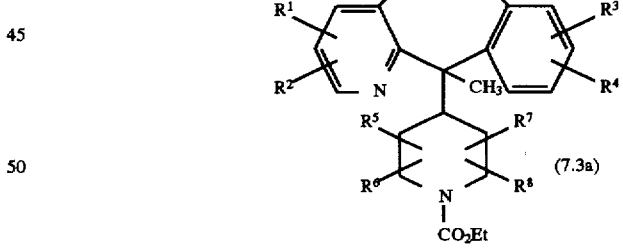
(7.3a)

Step C:

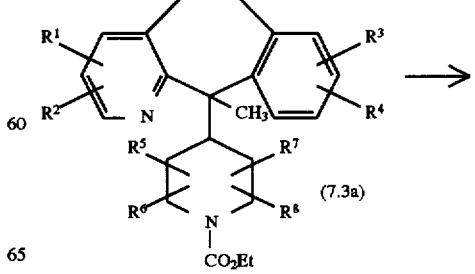
(7.3a)

-continued
Reaction Scheme 1

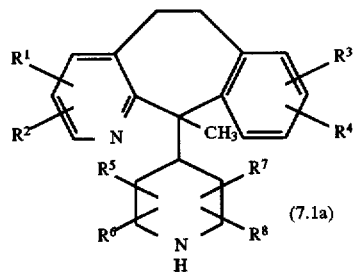

(7.1a)

In Step A of Reaction Scheme 1, a compound of the formula 420.50 is reacted with a strong base, such as an lithium diisopropylamide or an alkyllithium reagent (e.g., n-butyllithium), at −100° to −10° C., preferably at −80° to −20° C., then treated with methyl iodide to form a compound of formula 7.2a.

In Step B of Reaction Scheme 1, a compound of the formula 7.2a is converted to a compound of the formula 7.3a via substantially the same procedure as described above for formation of compounds of the formula 415.00.

In Step C of Reaction Scheme 1, a compound of the formula 7.3a is hydrolyzed via essentially the same procedure as described above for formation of compounds of formula 405.00, to form a compound of the formula 7.1a.

Compounds of the formula 7.1b can be prepared from a compound of the 420.51 (i.e., a compound of the formula 420.00 wherein A and B are both H, no double bond is present between carbons 5 and 6, a double bond is present between carbon 11 and X, X is C, and the N-alkyl group is a methyl group) via the process shown in Reaction Scheme 2.

Reaction Scheme 2

Step A:

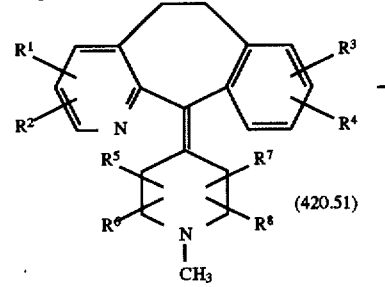

(420.51)

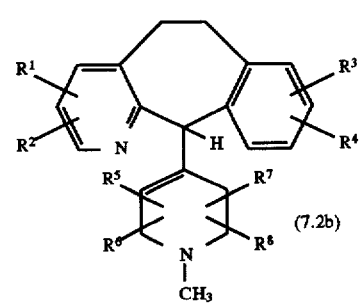

(7.2b)

-continued
Reaction Scheme 2

Step B:

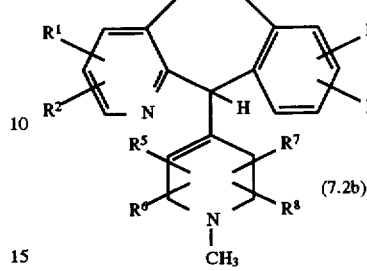

(7.2b)

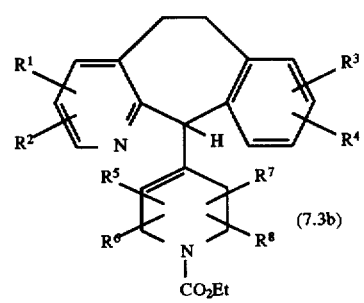

(7.3b)

Step C:

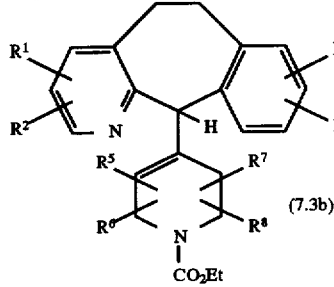

(7.3b)

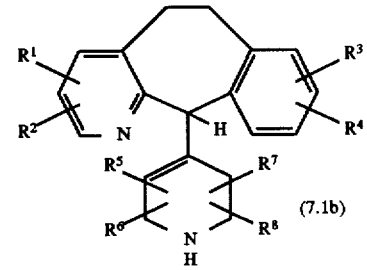

(7.1b)

In Step A of Reaction Scheme 2, a compound of the formula 420.51 is reacted with a strong base, such as an lithium diisopropylamide or an alkyllithium reagent (e.g., n-butyllithium), at −100° to −10° C., preferably at −80° to −20° C., then treated with a protic solvent, such as an alcohol, preferably MeOH, to form a compound of formula 7.2b.

In Step B of Reaction Scheme 2, a compound of the formula 7.2b is convened to a compound of the formula 7.3b via substantially the same procedure as described above for formation of compounds of the formula 415.00.

In Step C of Reaction Scheme 2, a compound of the formula 7.3b is hydrolyzed via essentially the same procedure as described above for formation of compounds of formula 405.00, to form a compound of the formula 7.1b.

Compounds of the formula 7.1c can be prepared from a compound of the 420.51 via the process shown in Reaction Scheme 3.

Reaction Scheme 3

Step A:

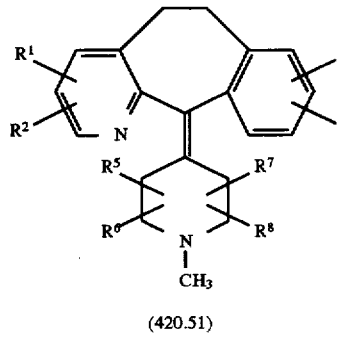

(420.51)

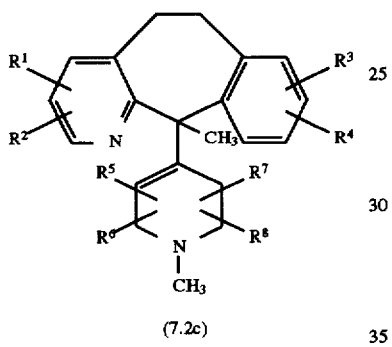

(7.2c)

Step B:

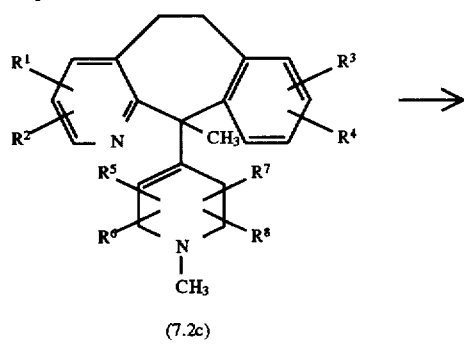

(7.2c)

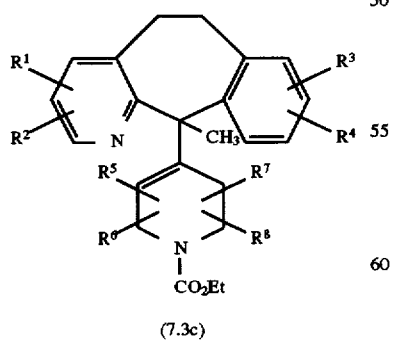

(7.3c)

-continued
Reaction Scheme 3

Step C:

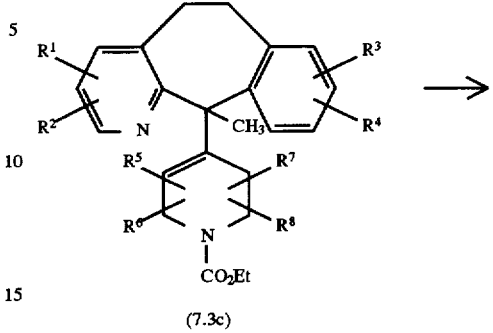

(7.3c)

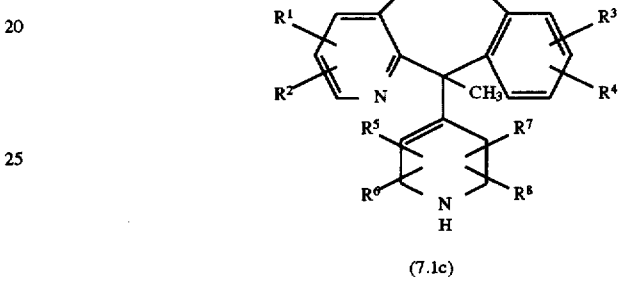

(7.1c)

In Step A of Reaction Scheme 3, a compound of the formula 420.51 is reacted with a strong base, such as an lithium diisopropylamide or an alkyllithium reagent (e.g., n-butyllithium), at −100° to −10° C., preferably at −80° to −20° C., then treated with methyl iodide to form a compound of formula 7.2c.

In Step B of Reaction Scheme 3, a compound of the formula 7.2c is converted to a compound of the formula 7.3c via substantially the same procedure as described above for formation of compounds of the formula 415.00.

In Step C of Reaction Scheme 1, a compound of the formula 7.3c is hydrolyzed via essentially the same procedure as described above for formation of compounds of formula 405.00, to form a compound of the formula 7.1c.

In the above processes, it is sometimes desirable and/or necessary to protect certain $R^1$, $R^2$, $R^3$ and $R^4$ etc., groups during the reactions. Conventional protecting groups are operable as described in Greene, T. W., "Protective Groups In Organic Synthesis," John Wiley & Sons, New York, 1981. For example, the groups listed in column 1 of Table 1 may be protected as indicated in column 2 of the table:

TABLE 1

PROTECTED GROUPS

| 1. GROUP TO BE PROTECTED | 2. PROTECTED GROUP |
|---|---|
| —COOH | —COOalkyl, COObenzyl, —COOphenyl, —C(OCH₂)₃CH₃ |

TABLE 1-continued

PROTECTED GROUPS

| 1. GROUP TO BE PROTECTED | 2. PROTECTED GROUP |
|---|---|
| \NH/ | \NCOalkyl/, \NCObenzyl/, \NCOphenyl/ |
| \CO/ | structures with dioxolane/dioxane |
| —OH | —O-(tetrahydropyranyl), —OCH₂phenyl, —OCH₃, OSi(CH₃)₂(t-Bu), |
| —NHR, wherein R is any substituent on an amino group within the scope of the claims | —N(R)-(tetrahydropyranyl), —NR—CO—CF₃, —NRCOCH₃, —NRCH₂phenyl |
| —NH₂ | —N(succinimide), —NH—C(O)—O(t-Bu) |

Other protecting groups well known in the art also may be used. After the reaction or reactions, the protecting groups may be removed by standard procedures.

Compounds useful in this invention are exemplified by the following preparative examples, which should not be construed to limit the scope of the disclosure. Alternative mechanistic pathways and analogous structures within the scope of the invention may be apparent to those skilled in the art.

PREPARATIVE EXAMPLE 1

A. N-(1,1-DIMETHYLETHYL)-3-METHYL-2-PYRIDINE CARBOXAMIDE

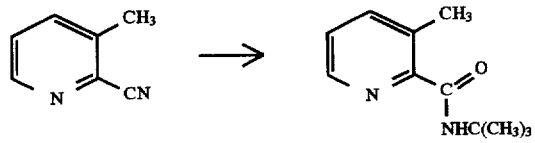

Suspend 2-cyano-3-methyl pyridine (400 g) in t-butanol (800 mL) and heat to 70° C. Add concentrated sulphuric acid (400 mL) dropwise over 45 minutes. Maintain the temperature at 75° C., until the reaction is complete, and for an additional 30 minutes. Dilute the mixture with water (400 mL), charge with toluene (600 mL) and bring to pH 10 with concentrated aqueous ammonia. Maintain the temperature at 50°–55° C. during the work up. Separate the toluene phase, and reextract the aqueous layer. Combine toluene phases and wash with water. Remove the toluene to yield the title compound N-(1,1-dimethylethyl)-3-methyl-2-pyridine carboxamide, as an oil, from which solid product is crystallized. (Yield 97%, as determined by an internal standard assay with gas chromatography).

B. 3-[2-(3-CHLOROPHENYL)ETHYL]-N-(1,1-DIMETHYLETHYL)-2-PYRIDINE CARBOXAMIDE

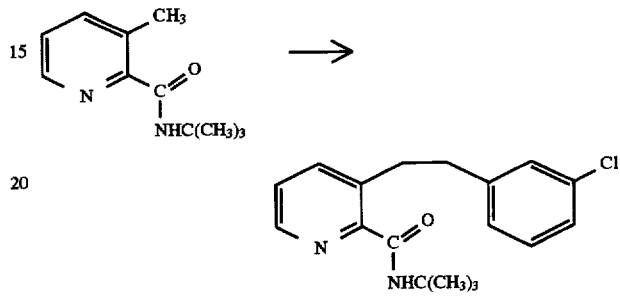

Dissolve the title compound of Preparative Example 1A, N-(1,1-dimethylethyl)-3-methyl-2-pyridine carboxamide (31.5 g.) in THF (600 mL) and cool the resulting solution to −40° C. Add n-butyllithium (2 eq.) in hexane while maintaining the temperature at −40° C. The solution turns deep purple-red. Add sodium bromide (1.6 g) and stir the mixture. Add solution of m-chlorobenzylchloride (26.5 g., 0.174 mole) in THF (125 mL) while maintaining the temperature at −40° C. Stir the reaction mixture until the reaction is complete as determined by thin layer chromatography. Add water to the reaction until the color is dissipated. Extract the reaction mixture with EtOAc, wash with water, and concentrate to a residue which is the title compound. (Yield 92% as shown by chromatography).

C. 3-[2-(3-CHLOROPHENYL)ETHYL]-2-PYRIDINE-CARBONITRILE

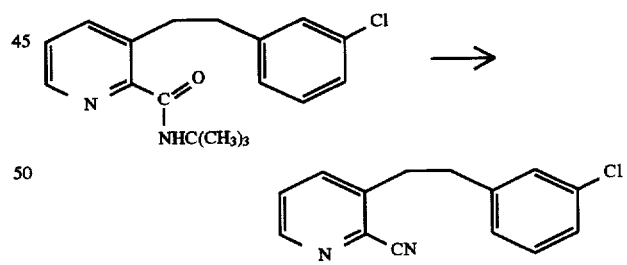

Heat a solution of the title compound of Preparative Example 1B, 3-[2-(3-chlorophenyl)ethyl]-N-(1,1-dimethylethyl)-2-pyridine carboxamide (175 g, 0.554 mole) in phosphorous oxychloride (525 mL, 863 g, 5.63 mole) and reflux for 3 hours. Determine completion of the reaction by thin layer chromatography. Remove any excess phosphorous oxychloride by distillation at reduced pressure and quench the reaction in a mixture of water and isopropanol. Bring to pH 5–7 by adding 50% aqueous NaOH solution while maintaining the temperature below 30° C. Filter the crystalline slurry of crude product and wash with water. Purify the crude product by slurrying the wet cake in hot isopropanol, and cool to 0°–5° C. Filter the product, wash with hexane and dry at a temperature below 50° C. to yield the title compound. (Yield: 118 g (HPLC purity 95.7%), m.p. 72° C.–73° C., 89.4% of theory).

D. 1-(METHYL-4-PIPERIDINYL)[3-(2-(3-CHLOROPHENYL)ETHYL)-2-PYRIDINYL] METHANONE HYDROCHLORIDE

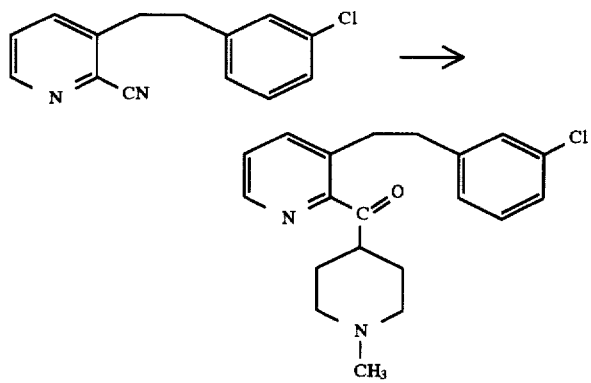

Dissolve the title compound of Preparative Example 1C, (118 g, 0.487 mole) in dry THF (1.2 L) and add N-methylpiperidyl magnesium chloride (395 mL, 2.48 mole/liter, 0.585 mole, 1.2 eq.) over 15 minutes. Maintain the temperature at 40° C.–50° C. by cooling with water as necessary, for 30 minutes. Determine completion of the reaction by thin layer chromatography. Quench the reaction by reducing the pH to below 2 with 2N HCl and stir the resulting solution at 25° C. for 1 hour. Remove the bulk of the THF by distillation and adjust the resulting solution to pH 3.5 by addition of aqueous NaOH. Cool to 0° to 5° C. and filter off the crystalline hydrochloride salt product. Wash with ice cold water and dry to constant weight at 60° C. to yield the title compound. (Yield: 168.2 g (HPLC purity 94%), m.p. 183°–185° C., 89% of theory).

E. 8-CHLORO-11-(1-METHYL-4-PIPERIDYLIDENE)-6,11-DIHYDRO-5H-BENZO [5,6]CYCLOHEPTA[1,2-b]PYRIDINE

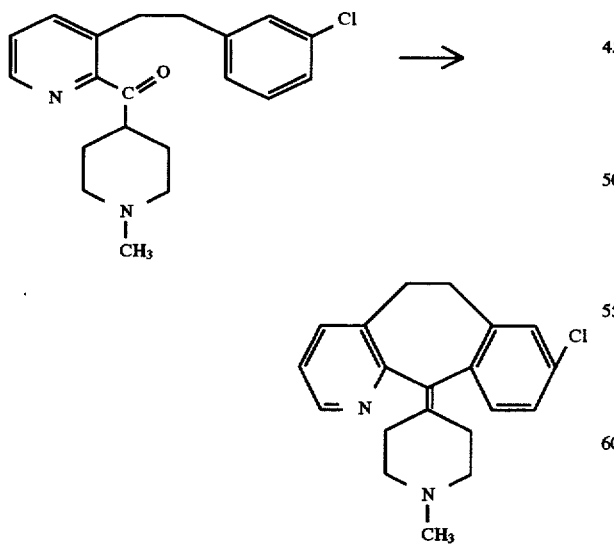

Dissolve the title compound of Preparative Example 1D above (59 g, 0.15 mole) in hydrofluoric acid (120 mL, 120 g, 6.0 mole) at –35° C. and add boron trifluoride (44.3 g, 0.66 mole) over 1 hour. Determine completeness of the reaction by thin layer chromatography. Quench the reaction using ice, water and KOH bringing the solution to a final pH of 10. Extract the product with toluene and wash with water and brine. Concentrate the toluene solution to a residue, and dissolve in hot hexane. Remove the insolubles by filtration and concentrate the filtrate to yield the title compound as an off-white powder. (Yield: 45.7 g (HPLC purity: 95%), 92% of theory).

Alternative Step E:

8-CHLORO-11-(1-METHYL-4-PIPERIDYLIDENE)-6,11-DIHYDRO-5H-BENZO [5,6]CYCLOHEPTA[1,2-b]PYRIDINE

React the title compound of Preparative Example 1D above (177 g, 0.49 mole) in trifluoromethanesulfonic acid (480 ml, 814.1 g, 5.31 mole) at 90°–95° C. for 18 hours under nitrogen. Determine the completeness of the reaction by thin layer chromatography. Cool the reaction and quench the reaction with ice-water and adjust the pH to 6 with barium carbonate. Extract the product with $CH_2Cl_2$, and concentrate under reduced pressure to about 1 liter. Wash with water, and extract the product into 1N HCl which is treated with 30 g of activated charcoal, and filter through celite. Adjust the pH of the filtrate to 10 with aqueous NaOH (50%), extract the product into $CH_2Cl_2$, and remove under reduced pressure to form a residue. Dissolve the residue in hot hexane, and filter to remove insolubles. Concentrate the filtrate to yield the title compound as a beige powder. (Yield: 126 g (HPLC purity 80%), 65% of theory).

F. 8-CHLORO-11-(1-ETHOXYCARBONYL-4-PIPERIDYLIDENE)-6,11-DIHYDRO-5H-BENZO [5,6]CYCLOHEPTA[1,2-b]PYRIDINE

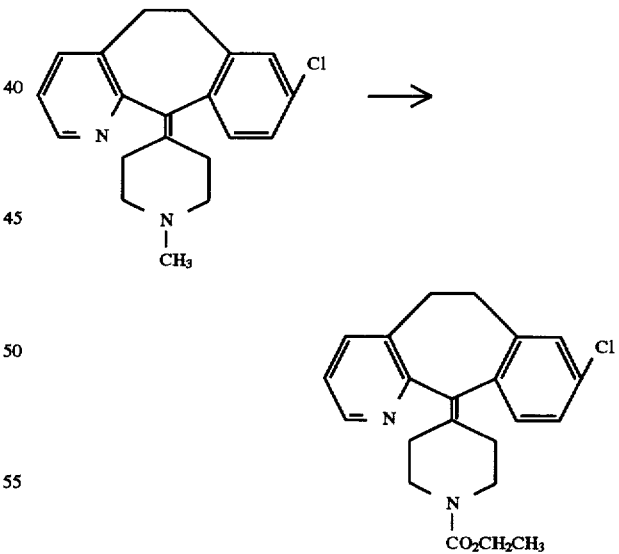

Dissolve the title compound of Preparative Example 1E above (45.6 g, 0.141 mole) in toluene (320 mL) at 80° C. and to it gradually add ethyl chloroformate (40.4 mL, 45.9 g, 0.423 mole). Following complete addition, maintain the temperature at 80° C. for 1 hour, then add diisopropylethylamine (2.7 mL, 2.00 g, 0.016 mole) and additional ethyl chloroformate (4.1 mL, 4.65 g, 0.0429 mole). Monitor completeness of the reaction by thin layer chromatography.

Upon completion, cool the reaction mixture to ambient temperature, and wash the toluene solution with water. Concentrate the organic layer to a residue and dissolve in hot acetonitrile (320 mL). Decolorize the solution with 14 g of activated charcoal. Remove the activated charcoal by filtration and concentrate the filtrate to a crystalline slurry. Cool the mixture to 0°–5° C., and isolate the product by filtration. Wash with cold acetonitrile and dry the product at below 70° C. to yield the title compound. (Yield: 42.4 g (HPLC purity 97.4%), 80% of theory).

G. 8-CHLORO-11-(4-PIPERIDYLIDENE)-6,11-DIHYDRO-5H-BENZO[5,6[CYCLOHEPTA[1,2-b]PYRIDINE

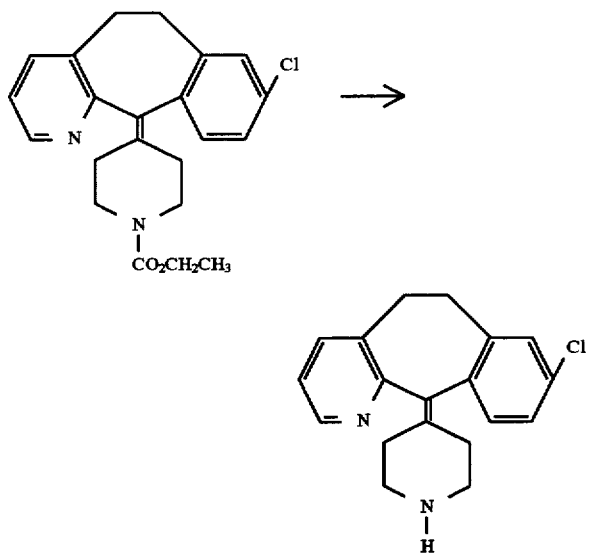

Hydrolize the title compound of Preparative Example 1F, 8-chloro-11-(1-ethoxycarbonyl-4-piperidylidene)-6,11-dihydro-5H-benzo[5,6]cyclohepta[1,2-b]pyridine (39 g, 0.101 mole) with KOH (50 g) in EtOH (305 mL) and water (270 mL) at reflux under an argon atmosphere for 64 hours. Partially distill off the EtOH and dilute the residue with brine, and extract with EtOAc (3×). Wash the combined organic phases with water and dry with $Na_2SO_4$. Remove the solvent to give a solid which can be recrystallized from toluene to give the title compound as a white solid. (Yield: 24.5 g, 77%, melting point 154°–155° C.).

H. By substituting in step 1B above, the benzylic halide:

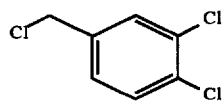

for meta-chlorobenzylchloride, and employing basically the same methods as steps C through G, the compound

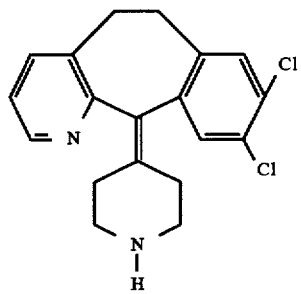

is prepared. Dichloro compound (I) is recrystallized from toluene and has a melting point of 150°–152° C. Reaction times are determined by TLC or HPLC. In some instances purification of the product by chromatography is necessary.

PREPARATIVE EXAMPLE 2

A. N-(1,1-DIMETHYLETHYL)-3-2-(4-FLUOROPHENYL)ETHYL]-2-PYRIDINE CARBOXAMIDE

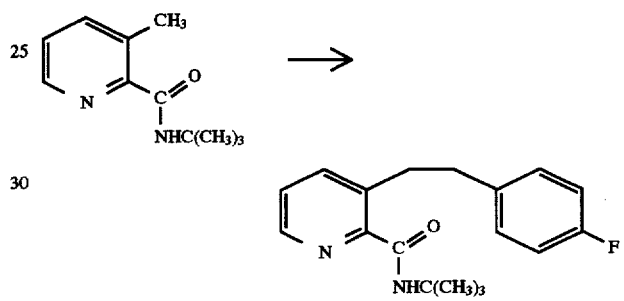

Cool a solution of N-(1,1-dimethylethyl)-3-methyl-2-pyridine-carboxamide (38.4 g, 0.2 mole) in dry THF (250 mL) to −40° C. and add n-butyl lithium (185 mL, 0.44 mole). Add sodium bromide (1.9 g, 18 mmol.) and stir for 15 minutes. Add 4-fluorobenzylchloride (31.8 g, 0.22 mole) and stir for 2.5 hours while warming to −5° C. Quench the reaction with water and extract the product twice with EtOAc, then wash with brine (2×). Dry the organic phase over $Na_2SO_4$, filter and remove the solvent to give the title compound. (60.0 g, Yield 99%, m.p. 59°–61° C.)

B. 3-[2-(4-FLUOROPHENYL)ETHYL]-2-PYRIDINE CARBONITRILE

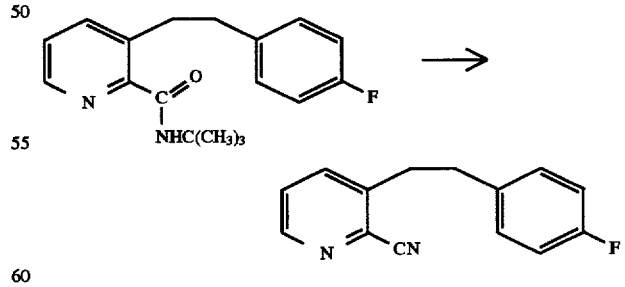

Heat the title compound of Preparative Example 2A above (60.0 g, 0.2 mole) in $POCl_3$ (200 mL) to 110° C. under an argon atmosphere for 3.5 hours. Pour the reaction mixture onto ice and basify with NaOH (50%) solution. Extract the mixture with EtOAc (3×) and wash with water. Wash with brine and dry over $Na_2SO_4$. Remove the solvent and pass the residue through a coarse SiO$_2$ (60–200 mesh) column to give the title compound as a white solid (40 g, Yield 88%, m.p. 48°–49° C.).

C. 9-FLUORO-5,6-DIHYDRO-11H-BENZO[5,6] CYCLOHEPTA[1,2-b]PYRIDIN-11-ONE

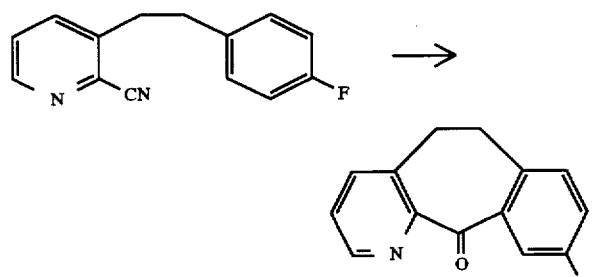

Cyclize the title compound of Preparative Example 2B above (31.5 g, 139 mmol) in polyphosphoric acid (1.24 kg) at 200° C. for 5.5 hours. Pour onto ice and basify with NaOH solution (50%). Extract the product with chloroform (3×) and wash with brine. Dry the organic phase with Na$_2$SO$_4$, filter and remove the solvent to give the title compound (20.4 g, yield 64%, m.p. 78°–81° C. after recrystallization from diisopropyl ether).

D. 9-FLUORO-11-(1-METHYL-4-PIPERIDINYL)-6,11-DIHYDRO-5H-BENZO[5,6]CYCLOPHEPTA[1,2-b]PYRIDIN-11-OL

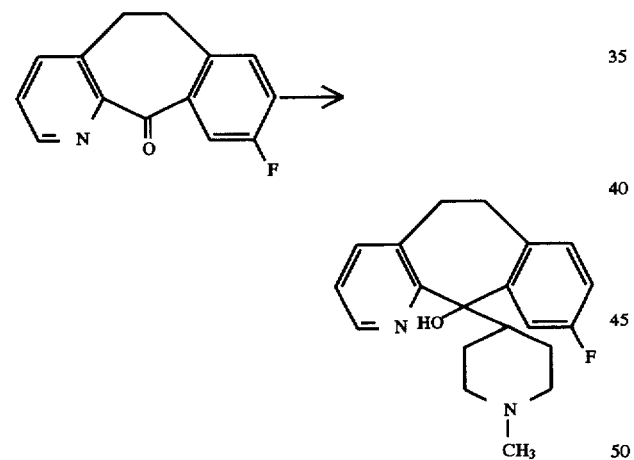

Dissolve the title compound of Preparative Example 2C above (10.0 g, 44 mmol) in THF (100 mL) and add slowly to a cooled (–40° C.) solution of the Grignard reagent prepared from N-methyl-4-chloropiperidine (57.9 mL, 88 mmol) and magnesium in THF (70 mL). Stir the mixture for about 1 hour while warming up to 0° C. Quench the reaction with NH$_4$Cl solution and extract with EtOAc (2×). Wash the organic phase with brine and dry over Na$_2$SO$_4$, filter and remove the solvent. Purify the residue with flash chromatography and elute with MeOH (5%) in CHCl$_3$ to give the title compound as white granular crystals. (10.1 g, Yield 70%, m.p. 126°–127° C. after recrystallization from diisopropyl ether.)

E. 9-FLUORO-11-(1-METHYL-4-PIPERIDYLENE)-6,11-DIHYDRO-5H-BENZO[5,6]CYCLOHEPTA[1,2-b]PYRIDINE

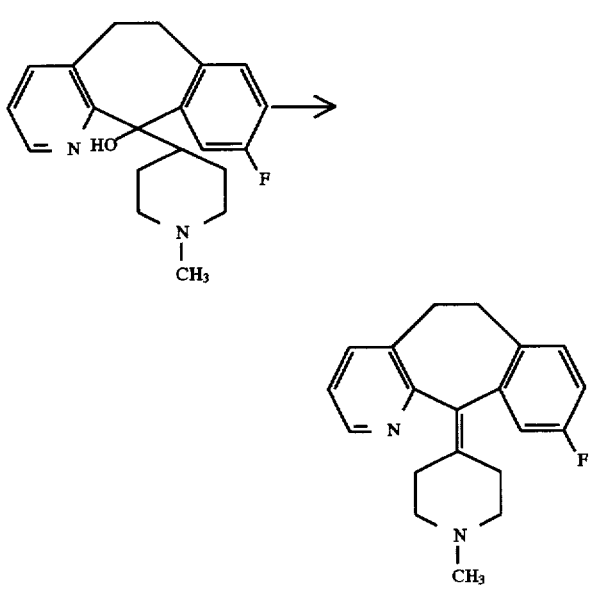

Add the title compound of Preparative Example 2D above (7.3 g, 22.3 mmol) to a mixture of cooled H$_2$SO$_4$ and CF$_3$SO$_3$H (1:1), (146 mL). Stir the reaction mixture for 0.5 hours at ice bath temperature and then at room temperature for 1.5 hours. Pour the reaction mixture onto ice and basify with NaOH (50%) solution. Extract the product with EtOAc (3×) and wash with brine. Dry the organic phase over Na$_2$SO$_4$, filter and remove the solvent to give a crude oil. Charcoal the oil and recrystallize from EtOAc and isopropyl ether to give the title compound. (5.6 g, Yield 82%, m.p. 134.5°–135.5° C.).

F. 9-FLUORO-11-(1-ETHOXYCARBONYL-4-PIPERIDYLIDENE)-6,11-DIHYDRO-5H-BENZO[5,6]CYCLOHEPTA[1,2-b]PYRIDINE

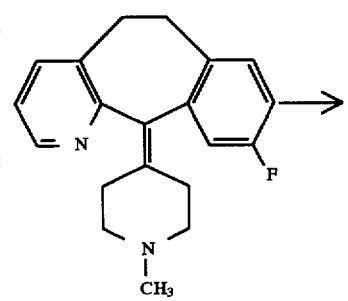

81
-continued

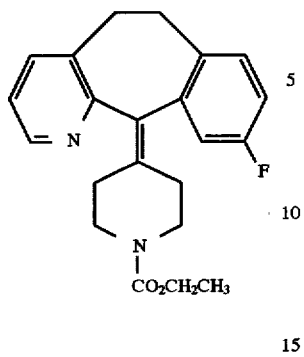

Stir a solution of the title compound of Preparative Example 2E above (5.0 g, 16.2 mmol) and Et₃N (2.6 g, 26 mmol) in dry toluene (60 mL) at 80° C. under an argon atmosphere, and add ethyl chloroformate (9.8 g, 90 mmol) via a syringe. Stir the reaction at this temperature for 30 minutes and at room temperature for one hour. Filter the reaction and remove the solvent. Pass the residue through a coarse SiO₂ column (60–200 mesh), and elute with CHCl₃ to yield the title compound as a white solid. (4.5 g, Yield 76%, m.p. 112°–114° C. after trituration with pentane).

G. 9-FLUORO-11-(4-PIPERIDYLIDENE-6,11-DIHYDRO-5H-BENZO[5,6]CYCLOHEPTA[1,2-b]PYRIDINE

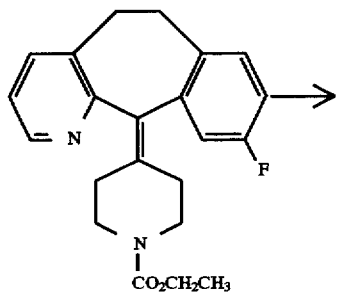

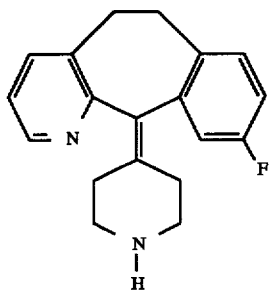

Reflux the title compound of Preparative Example 2F above (3.83 g, 10.4 mmol) with KOH (4.6 g) in 50 mL of EtOH/H₂O (1:1) for 4 hours under an argon atmosphere. Pour the reaction mixture into a brine solution and extract with EtOAc (2×), dry over Na₂SO₄ and filter. Remove the solvent to give the title compound (2.86 g, Yield 90%, m.p. 138°–140° C.).

82

H. By employing the benzyl halide

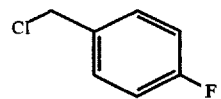

in place of 4-fluorobenzyl chloride in step 2A above, the product

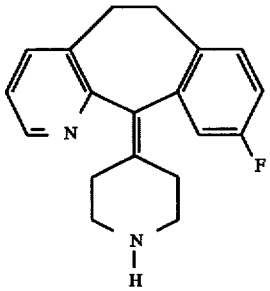

is prepared (m.p. 138°–140° C., triturated with pentane) by employing basically the same process as described in steps 2A–2G. Workup time is determined by either TLC or HPLC. In some instances purification of the product by chromatography is necessary.

PREPARATIVE EXAMPLE 3

A. 3,5-DIMETHYLPYRIDINIUM N-OXIDE

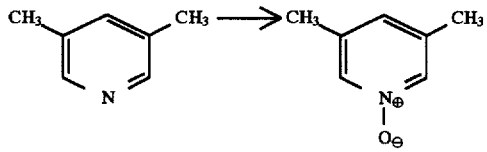

A solution of 285 mL (1.31 mol) of 35% peracetic acid was slowly added to a stirred solution of 149 g (1.39 mol) of 3,5-dimethylpyridine during which the temperature rose to 85° C. and was maintained at this temperature during addition. After the temperature of the mixture dropped to about 35° C. the reaction was stored at 5° C. overnight.

After partial removal of 185 ml of acetic acid via distillation under vacuum, the reaction was washed with NaHSO₄ solution and then neutralized with 10% NaOH solution to pH of about 7. The product was extracted with CH₂Cl₂ to give the title compound as a white solid (yield 142 g, 83%).

B. 1-METHOXY-3,5-DIMETHYLPYRIDINIUM METHYL SULFATE

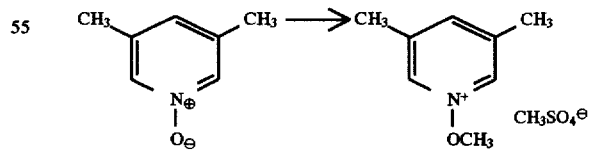

Dimethylsulfate (42.0 g, 0.33 mol) was slowly added to 41.0 g (0.33 mol) of 3,5-dimethylpyridinium N-oxide with mechanical stirring. The mixture was then heated on a steam bath for 1 hr. Then vacuum was applied while cooling to give a brownish solid of the title compound in quantitative yield.

C. 2-CYANO-3,5-DIMETHYLPYRIDINE

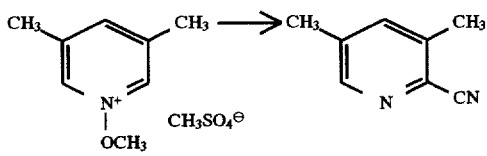

To a cooled (0° C.) solution of sodium cyanide (49.0 g, 0.999 mol, 3.0 eq.) in 135 mL of water (air free) was dripped 1-methoxy-3,5-dimethyl pyridinium methyl sulfate (83.0g, 0.33 mol) in 100 mL water (air free) in 1.25 hr., keeping the temperature below 3° C. The reaction mixture was stored at about 3° C. overnight. The mixture was filtered and washed with water to give 40 g of the title compound. An analytical sample was recrystallized from isopropyl ether and pentane (4:1) (m.p.: 61°–62° C.).

D. N-(1,1-DIMETHYLETHYL)-3,5-DIMETHYL-2-PYRIDINE CARBOXAMIDE

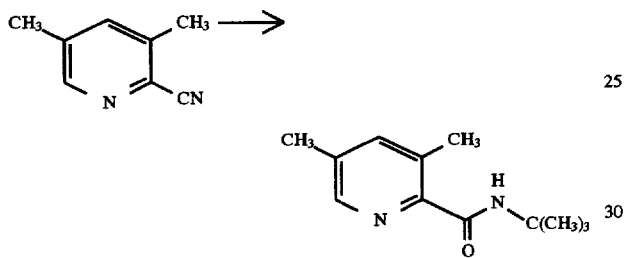

To a stirred solution of 20.3 g (0.153 mol) of 2-cyano-3,5-dimethylpyridine in 100 mL of 20 mL of conc. sulfuric acid within 10 minutes, followed by 20 mL of t-butanol over an additional 15 minutes. The solution was warmed at 75° C. for 30 minutes after which it was cooled to room temperature and basified with 25% NaOH. The product was extracted 3× with EtOAc (600 mL), which was combined and washed 1× with brine, dried (Na₂SO₄), filtered and concentrated in vacuo to give the title compound (31.26 g) as a yellowish oil.

E. 8-CHLORO-3-METHYL-11-(4-PIPERIDYLIDENE)-6,11-DIHYDRO-5H-BENZO [5,6]CYCLOHEPTA[1,2-b]PYRIDINE

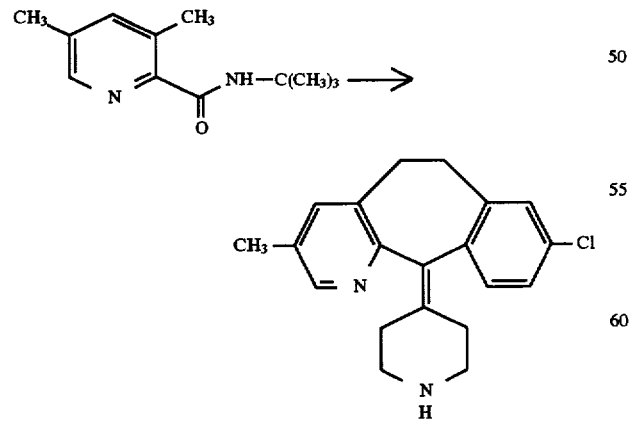

By substituting in step 1B above N-(1,1-dimethylethyl)-3,5-dimethyl-2-pyridine carboxamide for N-(1,1-dimethylethyl)-3-methyl-2-pyridine carboxamide and employing basically the same methods as steps B through G of Preparative Example 1, one obtains 8-chloro-3-methyl-11-(4-piperidylidene)-6,11-dihydro-5H-benzo[5,6] cyclohepta[1,2-b]pyridine. Reaction times are determined by TLC or HPLC.

PREPARATIVE EXAMPLE 4

By substituting

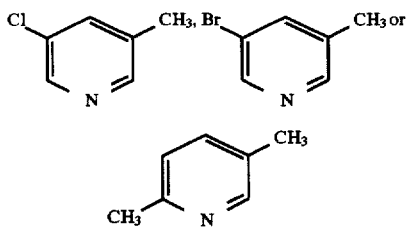

for 3,5-dimethylpyridine in Preparative Example 3 above and following basically the same procedure (steps A–E), the compounds

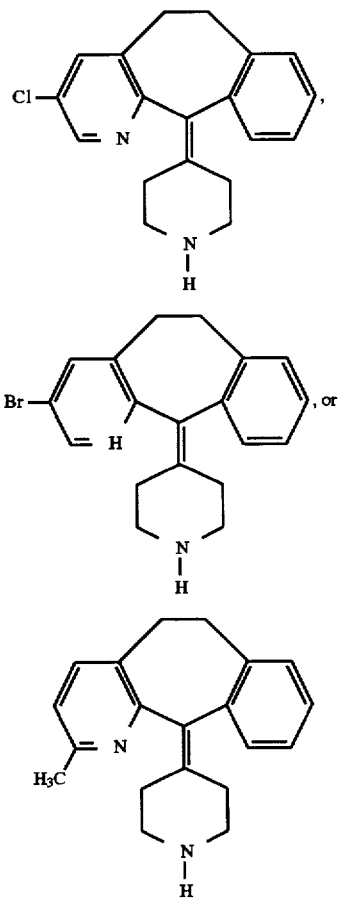

respectively, can be prepared. Note that the addition of the nitrile group to the pyridine in Step C of Preparative Example 3 can result in the formation of other undesirable isomers which can be removed via flash chromatography.

PREPARATIVE EXAMPLE 5

A. 8-CHLORO-5,6-DIHYDRO-11H-BENZO[5,6]CYCLOHEPTA[1,2-b]PYRIDIN-11-ONE N-OXIDE

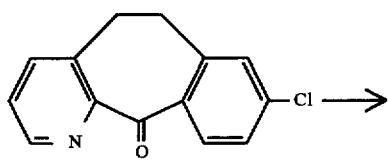

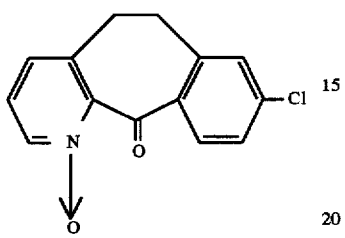

To a mixture of 25.1 grams (0.103 mole) of 8-chloro-5,6-dihydro-11H-benzo[5,6]cyclohepta[1,2-b]pyridin-11-one in 175 ml of dry $CH_2Cl_2$ at 0° C. under an argon atmosphere was added dropwise over 70 minutes a solution of 24.12 grams of 3-chloroperoxy-benzoic acid in 150 ml of $CH_2Cl_2$. After the addition the solution was stirred for ½ hour after which the ice bath was removed. After two days the reaction was poured into 1.0N aqueous NaOH and extracted with $CH_2Cl_2$. The organic portions were combined, washed once with water, dried over $MgSO_4$, filtered and concentrated in vacuo. The resultant product was triturated with isopropyl ether and filtered to provide 25.8 grams (96%) yield of the title compound.

B. 2,8-DICHLORO-5,6-DIHYDRO-11H-BENZO[5,6]-CYCLOHEPTA[1,2-b]PYRIDIN-11-ONE AND 4,8-DICHLORO-5,6-DIHYDRO-11H-BENZO[5,6]CYCLOHEPTA[1,2-b]PYRIDIN-11-ONE

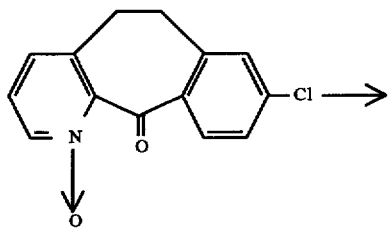

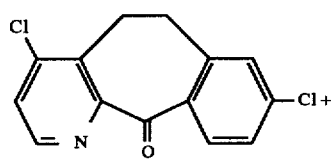

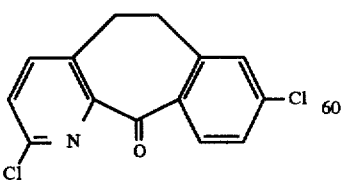

To a mixture of 29.13 grams (112.2 mmol) of the title compound from Preparative Example 5A above, in 40 ml of dry $CH_2Cl_2$ at 0° C. and under argon atmosphere was added 500 ml of 1.0M $SO_2Cl_2$ dropwise over 1 hour. The ice bath was then removed and the reaction stirred at room temperature for 1 hr and then refluxed for seven hours. The mixture was poured into 1.0N aqueous NaOH and extracted three times with $CH_2Cl_2$. The organic portions were combined, dried over $MgSO_4$, filtered and concentrated in vacuo to yield a product which was purified and separated via flash chromatography to yield the two title compounds.

C. 4-(2,8-DICHLORO-5,6-DIHYDRO-11H-BENZO[5,6]-CYCLOHEPTA[1,2-b]PYRIDIN-11-YLIDENE)PIPERIDINE AND 4-(4,8-DICHLORO-5,6-DIHYDRO-11H-BENZO[5,6]CYCLOHEPTA-[1,2-b]PYRIDIN-11-YLIDENE)PIPERIDINE

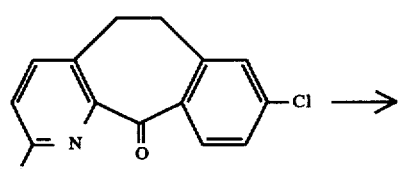

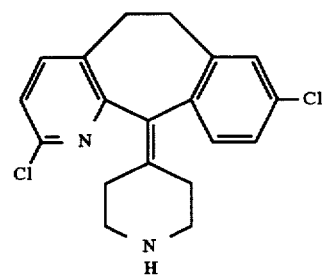

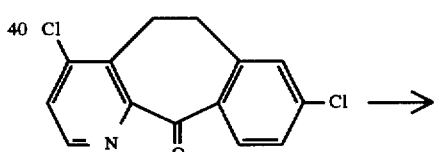

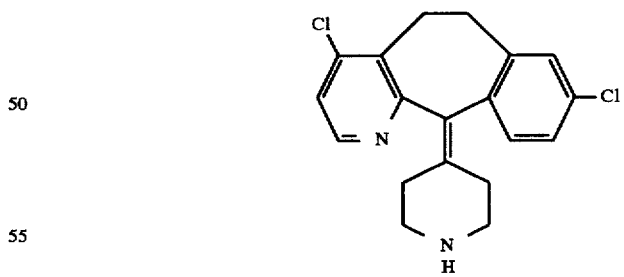

By following essentially the same procedure as that described in parts D–G of Preparative Example 2 above, the 2,8-dichloro and 4,8-dichloro products of Preparative Example 5B above were converted to the corresponding title compounds.

PREPARATIVE EXAMPLE 6

A. 3-(1,1-DIMETHYL-1-ETHYL)-8-CHLORO-5,6-DIHYDRO-11H-BENZO[5,6]CYCLOHEPTA[1,2-b]PYRIDIN-11-ONE

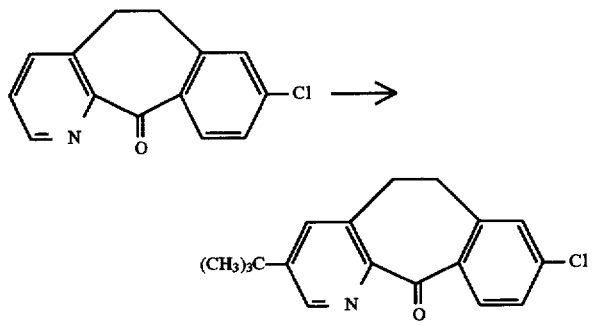

To a mixture of 20.05 grams (82.28 mmol) of 8-chloro-5,6-dihydro-11H-benzo[5,6]cyclohepta[1,2-b]pyridin-11-one in 400 ml of dry THF at –72° C. and under an atmosphere of nitrogen was added dropwise over 40 minutes 66.0 ml of 2.7M t-butyl magnesium chloride in THF. The reaction mixture was slowly warmed to room temperature and stirred overnight. The mixture was then poured into 10% aqueous ammonium chloride and extracted four times with CH$_2$Cl$_2$. The combined organic portions were dried over MgSO$_4$, filtered, and concentrated in vacuo to give the title tom pound, along with 8-chloro-11-(1,1-dimethyl-1-ethyl)-6,11-dihydro-5H-benzo[5,6]cyclohepta[1,2-b]pyridin-11-ol. These compounds were separated via flash chromatography to give the title compound, which was recrystallized from isopropyl ether to give 4.37 grams (18%) of the title compound as a white solid.

B. 4-[3-(1,1-DIMETHYL-1-ETHYL)-8-CHLORO-5,6-DIHYDRO-11H-BENZO[5,6]CYCLOHEPTA[1,2-b]PYRIDIN-11-YLIDENE]PIPERIDINE

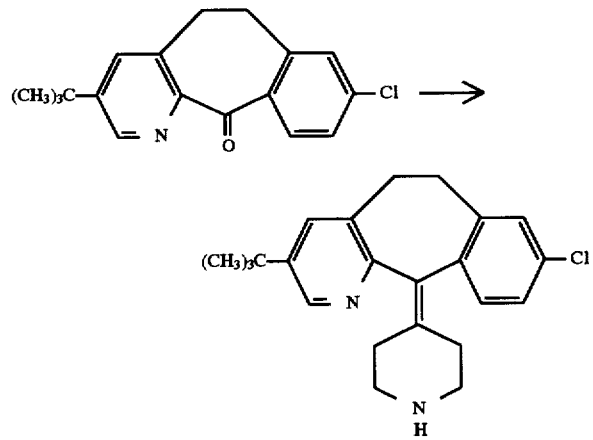

By using the title compound of Part A above and applying essentially the same procedure described in parts D–G of Preparative Example 2 above, one can obtain the title compound.

PREPARATIVE EXAMPLE 7

A. 8-CHLORO-6,11-DIHYDRO-11-HYDROXY-5H-BENZO[5,6]-CYCLOHEPTA[1,2-b]PYRIDINE

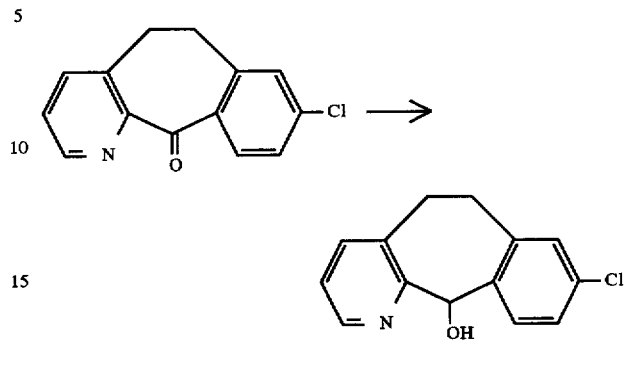

To a mixture of 25.03 g (103 mmol) of 8-chloro-5,6-dihydro-11H-benzo[5,6]cyclohepta[1,2-b]pyridin-11-one in 200 mL of MeOH at room temperature and under a nitrogen atmosphere was added portionwise over a period of about 1 hour 4.82 g (124 mmol) of sodium borohydride. Occasional cooling with an ice bath was necessary at times during the addition in order to avoid excessive reflux. After 1.6 hours the mixture was poured into ice cold water and then extracted with EtOAc (3×). The combined organic portions were washed with brine, dried over MgSO$_4$, filtered, and concentrated in vacuo. The residue was recrystallized from hot isopropyl ether. The remaining filtrate was purified via flash chromatography (20% EtOAc in hexanes) to yield more product which solidified on standing. Both batches were combined to yield 20.41 g of the title compound as a white solid.

B. 8,11-DICHLORO-6,11-DIHYDRO-5H-BENZO[5,6]CYCLOHEPTA[1,2-b]PYRIDINE

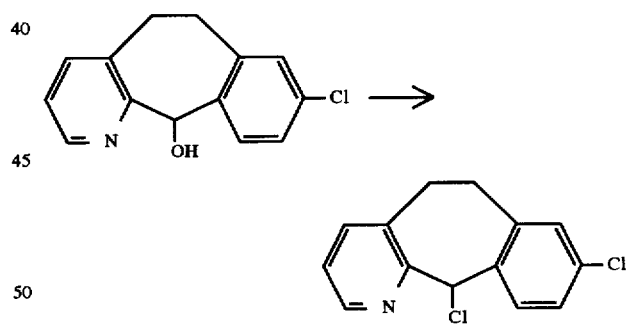

To a mixture of 13.3 g (54 mmol) of 8-chloro-6,11-dihydro-11-hydroxy-5H-benzo[5,6]cyclohepta[1,2-b]pyridine in 290 mL of toluene at –15° C. and under an atmosphere of nitrogen was added via syringe pump over a period of 1 hour 6.20 mL (85.7 mmol) of thionyl chloride. The extent of reaction was monitored by TLC (50% EtOAc in hexanes). When completed the mixture was poured into 300 mL of 1.0N aqueous NaOH and extracted with EtOAc (5×). The combined organic portions were washed with brine, dried over sodium sulfate, filtered, and concentrated in vacuo. The residue was taken up in EtOAc, quickly filtered through basic alumina, and concentrated again to yield a product which was triturated with pentane to yield 10.22 g of the title compound as a tan solid.

C. 8-CHLORO-11-(1PIPERAZINYL)-6,11-DIHYDRO-5H-BENZO[5,6]CYCLOHEPTA[1,2-b]PYRIDINE

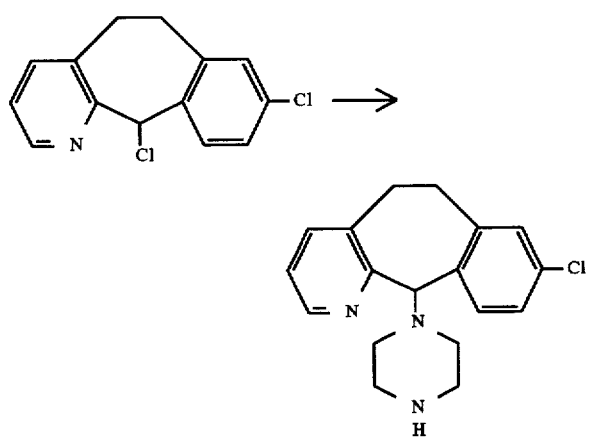

To a mixture of 10.0 g (37.9 mmol) of 8,11-dichloro-6,11-dihydro-5H-benzo[5,6]cyclohepta[1,2-b]pyridine and 1.0 ml of Et$_3$N in 200 mL of dry THF at room temperature and under a nitrogen atmosphere was added 33.0 g of piperazine. The mixture was stirred at room temperature for 22.5 hours and then refluxed for 5.5 hours. It was then cooled to room temperature, poured into 250 mL of 5% aqueous NaOH, and extracted with CH$_2$Cl$_2$ (3×). The combined organic portions were washed with brine, dried over MgSO$_4$, filtered, and concentrated in vacuo. The residue was purified via flash chromatography (2→5% MeOH saturated with ammonia in CH$_2$Cl$_2$) to yield the title compound as a glass.

PREPARATIVE EXAMPLE 8

A. ETHYL 3-PYRIDYLACETIC ACID 1-N-OXIDE

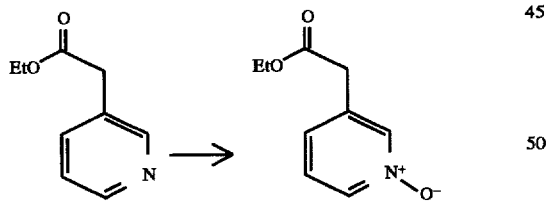

Ethyl 3-pyridylacetic acid (10 grams) (60.6 mmoles) was dissolved in dry CH$_2$Cl$_2$ (120 ml) and the solution was stirred at −18° C. for 30 minutes. MCPBA (31.34 grams) (181.6 mmoles) was added and the mixture was stirred at −18° C. for 1 hour and then at 25° C. for 87 hours. The reaction mixture was diluted with CH$_2$Cl$_2$ and washed with saturated aqueous sodium bicarbonate and then water. The CH$_2$Cl$_2$ was then dried (magnesium sulphate), filtered and evaporated to dryness. The residue was chromatographed on silica gel using 3% (10% concentrated ammonium hydroxide in MeOH)—CH$_2$Cl$_2$ as the eluant to give the title compound (Yield: 8.45 grams, 77%, MH$^+$ 182).

B. 3-PYRIDYLACETIC ACID 1-N-OXIDE

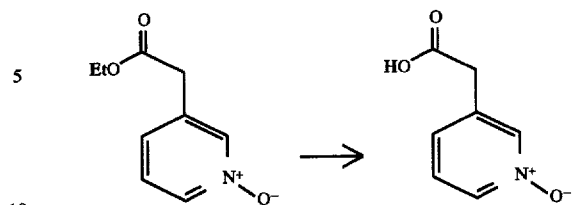

3-Pyridylacetic acid (0.2747 grams) (1.5 mmoles) was dissolved in EtOH (200 proof) (1.22 ml.) and a 1M solution of LiOH in water (3.64 ml.) (3.0 mmoles) was added and the mixture was stirred at 25° C. for 4 hours. 1N HCl (4.28 ml.) was added and the mixture was pumped down to dryness on a rotary evaporator to give the title compound (Yield: 0.2931 grams, 100%).

PREPARATIVE EXAMPLE 9

A. ETHYL α-METHYL-3-PYRIDYLACETIC ACID

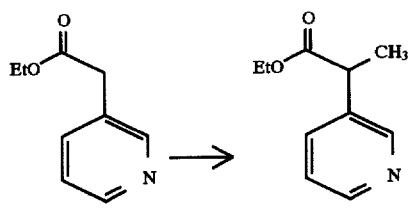

To ethyl 3-pyridylacetic acid (10.86 grams) (65.7 mmoles) was added a 2.0M solution of lithium diisopropylamide in THF/heptane/ethyl benzene (32.87 ml.) (65.8 mmoles) at −30° C. The semi-solid mixture was agitated and sonicated for 1 hour. The mixture was allowed to remain at 25° C. for 1 hour, whereupon methyl iodide (4.09 ml.) (65.7 mmoles) was added. After 1 hour at 25° C. the mixture was taken up in CH$_2$Cl$_2$ and washed with saturated aqueous sodium bicarbonate and water. The CH$_2$Cl$_2$ was dried (magnesium sulphate), filtered and evaporated to dryness. The residue was chromatographed on silica gel using 10% EtOAc in hexane as the eluant to give the title compound (Yield: 3.48 grams, 30%, MH$^+$ 180).

B. α-METHYL-3-PYRIDYLACETIC ACID

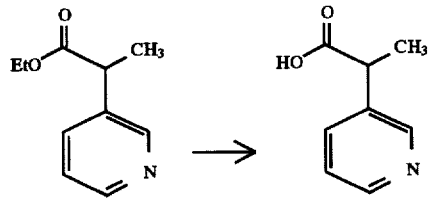

The title compound from Preparative Example 9A above (2.16 grams) (12.05 mmoles) was dissolved in EtOH (10 ml.) and 1.0M LiOH in water (29.15 ml.) (29.2 mmoles) was added. The mixture was stirred at 25° C. for 4 hours, whereupon 1N HCl (34.27 ml.) (34.2 mmoles) was added and the solution was evaporated to dryness to give the title compound (Yield 2.33 grams, 100%).

PREPARATIVE EXAMPLE 10

α,α-DIMETHYL-3-PYRIDYLACETIC ACID

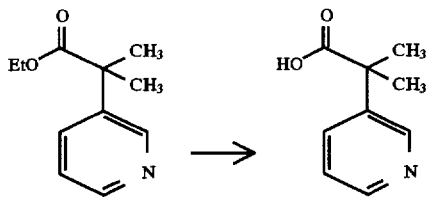

Ethyl α,α-dimethyl -3-pyridylacetate (disclosed in EP Application 0 288 279, published Oct. 26, 1988) (2.67 grams, 13.8 mmoles) was dissolved in EtOH (11.1 ml.) and a 1.0M LiOH in water (33.3 ml.) (33.4 mmoles) was added. The mixture was stirred at 25° C. for 4 hours. 1N HCl (38.73 ml.) was added and after 5 minutes the mixture was evaporated to dryness to give the title compound (Yield: 100%).

PREPARATIVE EXAMPLE 11

A. 8-CHLORO-6,11-DIHYDRO-11-(1-PIPERAZINYL)-5H-BENZO[5,6]CYCLOHEPTA[1,2-b]PYRIDINE 1-N-OXIDE

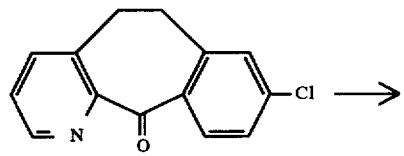

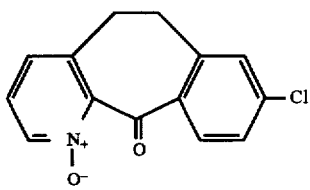

To a mixture of 8-chloro-5,6-dihydro-11H-benzo[5,6]cyclohepta[1,2-b]pyridin-11-one (5 grams) (20.6 mmoles) in dry CH$_2$Cl$_2$ (35 ml) was added dropwise MCPBA (4.7 grams) (27.3 mmoles) in dry CH$_2$Cl$_2$ (75 ml) at 0°–25° C. over 1 hour. The mixture was diluted with CH$_2$Cl$_2$ and washed with saturated aqueous sodium bicarbonate and water. The CH$_2$Cl$_2$ was dried (magnesium sulphate), filtered and evaporated to dryness. The residue was chromatographed on silica gel using 1% (10% saturated ammonium hydroxide in MeOH)—CH$_2$Cl$_2$ as the eluant to give the title compound (Yield: 2.81 grams, 53%, MH$^+$ 260).

B. 8-CHLORO-6,11-DIHYDRO-5H-BENZO[5,6]CYCLOHEPTA[1,2-b]PYRIDIN-11-OL 1-N-OXIDE

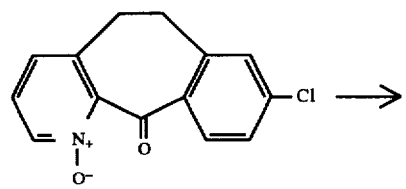

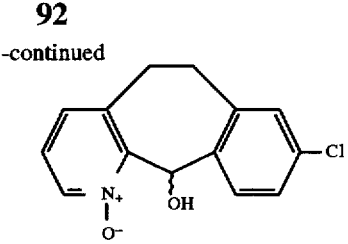

By using the title compound (8.6 grams) from Preparative Example 11A and reducing it by the procedure described in Preparative Example 7A above the title alcohol was obtained (Yield: 7.03 grams, 81%, MH$^+$ 262).

C. 8,11-DICHLORO-6,11-DIHYDRO-5H-BENZO[5,6]CYCLOHEPTA[1,2-b]PYRIDINE 1-N-OXIDE

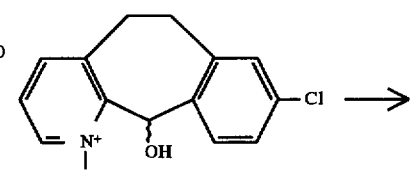

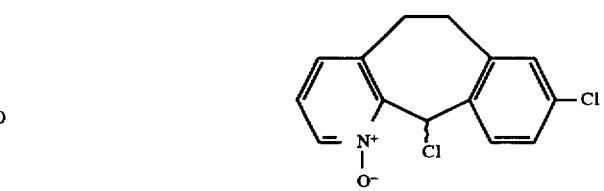

The title compound from Preparative Example 11B (6.2 grams) (23.7 mmoles) was reacted with thionyl chloride as described in Preparative Example 7B to give the title compound.

D. 8-CHLORO-6,11-DIHYDRO-11-(1-PIPERAZINYL)-5H-BENZO[5,6]CYCLOHEPTA[1,2-b]PYRIDINE 1-N-OXIDE

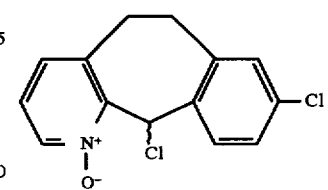

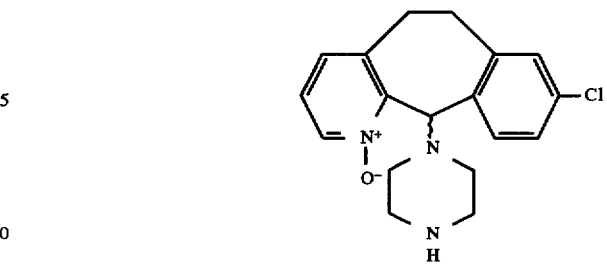

The title compound from Preparative Example 11C above was reacted with piperazine (9.9 grams) (115.0 mmoles) as described in Preparative Example 7C to give the title compound (Yield: 6.78 grams, 87%, MH$^+$ 330).

PREPARATIVE EXAMPLE 12

4-ETHOXYCARBONYLAMINOPYRIDINE

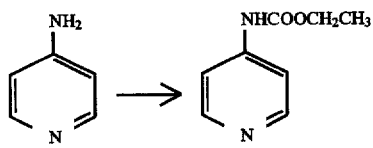

4-Aminopyridine (17.34 grams) (184.3) was dissolved in dry pyridine (217 ml.) and cooled to 0° C. over 30 minutes. Ethyl chloroformate (17.2 ml.) (180.7 mmoles) was added and the solution was stirred at 0° C. for 1 hour and then at 25° C. for 40 hours. The mixture was diluted with $CH_2Cl_2$ and washed with saturated aqueous $NaHCO_3$ and water. The $CH_2Cl_2$ was dried ($MgSO_4$), filtered and evaporated to dryness. The residue was chromatographed on silica gel using 2% (10% saturated $NH_4OH$ in MeOH)—$CH_2Cl_2$ to give the title compound (Yield: 10 grams, 33% $M^+$ 166).

By using essentially the same procedure, with the exception that

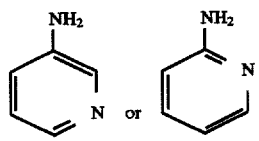

was used instead of 4-aminopyridine, the compound

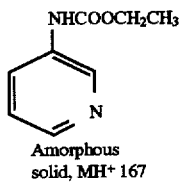

Amorphous solid, $MH^+$ 167 or

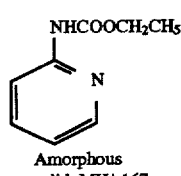

Amorphous solid, $MH^+$ 167 was obtained, respectively.

PREPARATIVE EXAMPLE 13

A. N-ACETYLISONIPECOTIC ACID

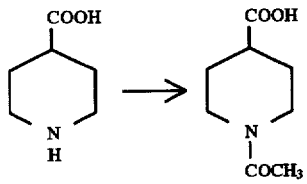

Isonipecotic acid (10 grams) (77.5 mmoles) and acetic anhydride (23.7 grams) (232.5 mmoles) were dissolved in MeOH (100 ml.) and the mixture was stirred at 25° C. for 24 hours. The mixture was evaporated to dryness and the residue was azeotroped with toluene to give the title compound (Yield: 12.8 grams, 97%, $MH^+$ 172).

B. 1-N-tert-BUTOXYCARBONYLISONIPECOTIC ACID

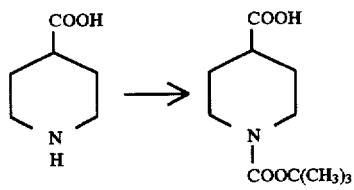

Isonipecotic acid (20 grams) (155.0 mmoles) was dissolved in THF-water (1:1) (400 ml) and NaOH (6.2 grams) (155.0 mmoles) and di-tert-butyldicarbonate (37.2 grams) (170.5 mmoles) were added. The mixture was stirred at 25° C. for 72 hours. The solution was then eluted through a bed of washed BioRad 50WX4 (RSO3H resin) (150 ml bed) and the resin was eluted with a 1:1 mixture of THF and water. The eluate was evaporated to dryness to give the title compound (yield: 33.78 grams, 90%).

PREPARATIVE EXAMPLE 14

1-N-ACETYLNIPECOTIC ACID

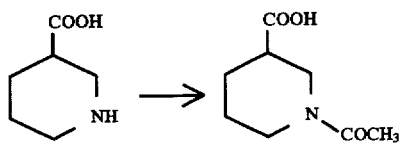

Nipecotic acid (3.87 grams) (30.0 mmoles) was reacted with acetic anhydride (9.17 grams) (90 mmoles) as described in Preparative Example 13A to give the title compound (Yield: 5.0 grams, 97%, $MH^+$ 172).

PREPARATIVE EXAMPLE 15

1-N-METHYLNIPECOTIC ACID

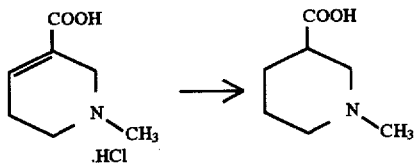

Arecaidine hydrochloride (4 grams) (22.6 mmoles) was hydrogenated in water (100 ml) using 10% Pd—C at 40 psi at 25° C. for 24 hours. The catalyst was filtered off and washed with water. The aqueous solution was shaken with BioRad AG1X8 resin ($OH^-$ form) (23 ml bed) and after 5 minutes the resin was filtered off and washed with water. The aqueous solution was evaporated to give the title compound (Yield: 2.95 grams, 92%).

PREPARATIVE EXAMPLE 16

1-N-ACETYL D,L-PIPECOLINIC ACID

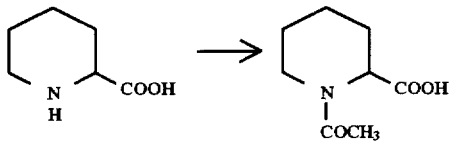

D,L-Pipecolinic acid (10 grams) (77.5 mmoles) and acetic anhydride (23.7 grams) (232.5 mmoles) were reacted as described in Preparative Example 13A above to give the title compound (Yield: 12.94 grams, 98%, MH⁺ 172).

PREPARATIVE EXAMPLE 17

A. PIPERIDINE-4-ACETIC ACID

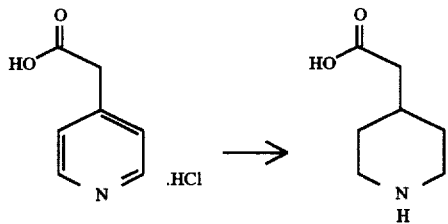

4-Pyridylacetic acid (7 grams) (40.4 mmoles) was hydrogenated as described in Preparative Example 15 to give the title compound (Yield: 5.2 grams, 90%, MH⁺ 144).

B. 1-N-ACETYL-4-PIPERIDINYLACETIC ACID

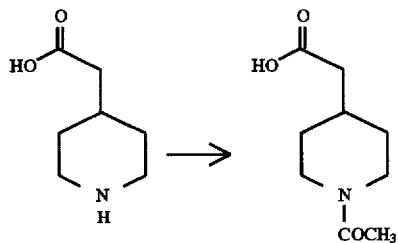

4-Piperidinylacetic acid (5 grams) (35.0 mmoles) was reacted with acetic anhydride (10.7 grams) (105.0 mmoles) as described in Preparative Example 13A to give the title compound (Yield: 6.4 grams, 99%, MH⁺ 185).

C. 1-N-METHYL-4-PIPERIDINYLACETIC ACID

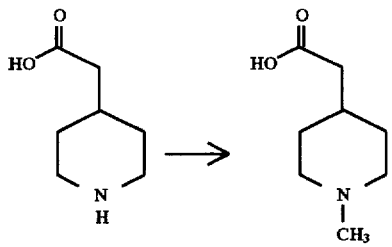

4-Piperidinylacetic acid (4 grams) (28.0 mmoles) from Preparative Example 17A was dissolved in water (50 ml) and 37% formalin (2.72 ml) (33.6 mmoles) was added. The mixture was hydrogenated over 10% Pd—C at 55 psi at 25° C. for 68 hours. The catalyst was filtered off and washed with water. The combined filtrates were evaporated to dryness to give the title compound (MH⁺158).

D. 1-N-tert-BUTOXYCARBONYLPIPERIDINYL-4-ACETIC ACID

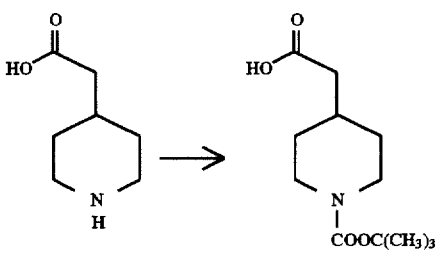

4-Piperidinylacetic acid (41.24 grams) (288.4 mmoles) from Preparative Example 17A was reacted with di-tert-butyldicarbonate (69.14 grams) (317.3 mmoles) and NaOH (11.52 grams) (288.4 mmoles) as described in Preparative Example 13B above to give the title compound (Yield: 53.0 grams, 76%).

PREPARATIVE EXAMPLE 18

A. 3-PIPERIDINYLACETIC ACID

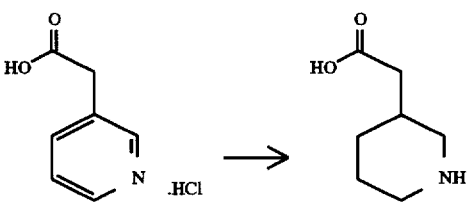

3-Pyridylacetic acid hydrochloride (13 grams) (74.9 mmoles) was hydrogenated as described in Preparative Example 15 to give a mixture of unreacted 3-pyridylacetic acid and the title compound (76:24) (8.63 grams, MH⁺ 144).

B. 1-N-ACETYL-3-PIPERIDINYLACETIC ACID

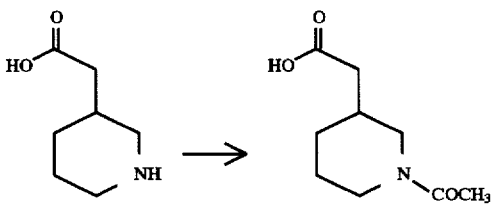

The mixture of compounds from Preparative Example 18A (8.56 grams) were reacted with acetic anhydride (8.56 grams) as described in Preparative Example 13A and the crude mixture of products was taken up in MeOH (60 ml) and passed over a bed of BioRad AG50WX4 resin (RSO₃H) and the latter was eluted with MeOH. The eluates were evaporated to dryness to give the title compound (Yield: 1.23 grams, MH⁺ 186).

C. 1-N-METHYL-3-PIPERIDINYLACETIC ACID

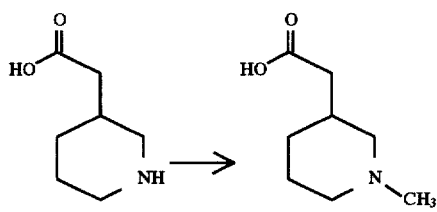

The mixture of compounds from Preparative Example 18A (4 grams) and 37% formalin (2.72 mL) were hydrogenated as described in Preparative Example 17C to give the title compound (MH⁺ 158).

PREPARATIVE EXAMPLE 19

PREPARATION OF THE R(+) AND S(−) DIASTEREOISOMERS

The racemic 8-chloro-11-(1-piperazinyl)-6,11-dihydro-5H-benzo[5,6]cyclohepta[1,2-b]pyridine prepared in Preparative Example 7C above was resolved by the method described in Preparative Example 15 A–C, pages 116–118, of WO 92/00293, published Jan. 9, 1992, to give the R(+) and S(−) diastereoisomers:

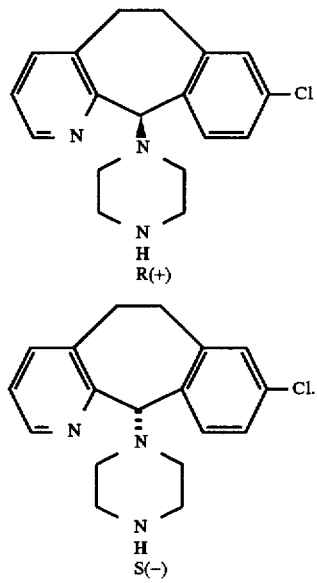

PREPARATIVE EXAMPLE 20

A. 3-BROMO-8-CHLORO-5,6-DIHYDRO-11H-BENZO[5,6]CYCLOHEPTA[1,2-b]PYRIDIN-11-ONE

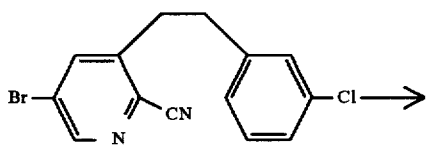

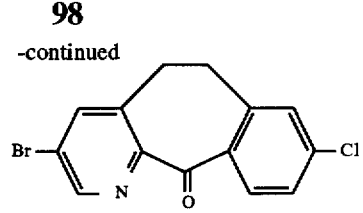

Cyclize 3-[2-(3-chlorophenyl)ethyl]-4-bromo-2-pyridine carbonitrile (10.7 g, 32.8 mmol) in triflic acid (82 mL) at 60° C. for 2 hours and then at room temperature for 2 hours. Add 80 mL of 5N HCl carefully, then reflux in an oil bath (120° C.) for 30 minutes. Cool the solution and pour into ice and basify with 25% NaOH solution. Extract the product with CH₂Cl₂ and wash with brine. Dry the organic layer with Na₂SO₄, filter and remove the solvent to give crude product (10.4 g). Purify the crude product with flash chromatography on silica gel and elute with 15% EtOAc-hexane to give the title compound as a white solid (9 g ,27.95 mmol. Yield 85.2% MH⁺ 322).

B. 8-CHLORO-3-METHOXY-5,6-DIHYDRO-11H-BENZO[5,6]CYCLOHEPTA[1,2-b]PYRIDIN-11-ONE

Dissolve the title compound of Preparative Example 20A (2.37g, 7.4 mmol) in dry MeOH and add Na metal (3.37g, 180 mmol). the reaction is stirred overnight at room temperature. Reflux the reaction for 3 hours, cool to room temperature and extract with CH₂Cl₂-water. Dry the CH₂Cl₂ fraction and chromatograph on silica gel eluting with 50% EtOAc-hexanes to give the title compound as a light yellow solid (1.5 g, Yield 72% MH⁺ 274).

C. 8-CHLORO-3-METHOXY-11-(-4-PIPERIDYLIDENE)-6,11-DIHYDRO-5H-BENZO [5,6]-CYCLOHEPTA[1,2-b]PYRIDINE

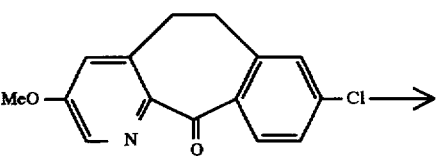

-continued

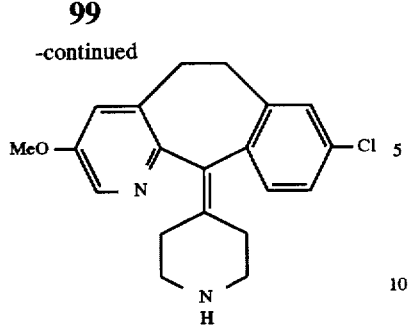

By substituting in Preparative Example 2 step D, 8-chloro-3-methoxy-5,6-dihydro-11H-benzo[5,6]-cyclohepta[1,2-b]pyridin-11-one for 9-fluoro-5,6-dihydro-11H-benzo[5,6]-cyclohepta[1,2-b]pyridin-11-one and employing basically the same methods as steps D through H of Preparative Example 2, one obtains 8-chloro-3-methoxy-11-(4-piperidylidene)-6,11-dihydro-5H-benzo[5,6]-cyclohepta[1,2-b]pyridine as a white solid ( $MH^+$ 340).

PREPARATIVE EXAMPLE 25

A. ETHYL α-METHYL-4-PYRIDYL ACETIC ACID

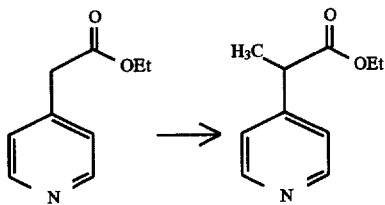

To dry THF at −78° C. was added diisopropylamine (5.05 g 48 mmol, 7 mL) and then n-butyl lithium. The reaction mixture was stirred for 0.5 h and then ethyl 4-pyridyl acetic acid (7.85g, 46 mmol) was added, and after stirring for 0.5 h at that −78° C. the reaction temperature was raised to room temperature. DMF (20 mL was added and the reaction mixture cooled to −78° C. again. Methyl iodide (7.07 g, 50.2 mmol, 3.15 mL) was added and the reaction mixture stirred at that temperature for 1 h and then at room temperature overnight. All the volatiles were then stripped off and the reaction mixture was partitioned between water-$CH_2Cl_2$. The aqueous phase was washed twice with $CH_2Cl_2$. The combined $CH_2Cl_2$ phases were dried and evaporated. The crude product was chromatographed on silica gel eluting with 80% EtOAc hexane to give the title compound (7.88g, $MH^+$ 179).

B. α-METHYL-4-PYRIDYL ACETIC ACID

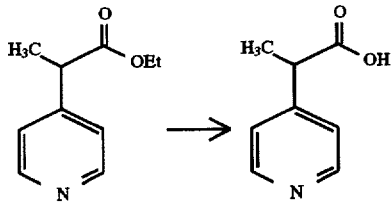

The compound from Preparative Example 25A was hydrolysed in a similar manner to Preparative Example 9B to give the title compound ($MH^+$ 152).

PREPARATIVE EXAMPLE 26

A.–B. α,α-DIMETHYL-4-PYRIDYL ACETIC ACID

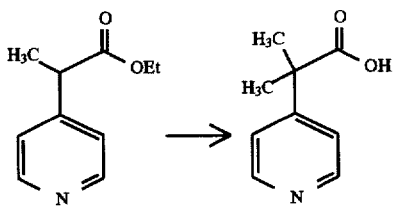

By essentialy the same procedure as set forth in Preparative Example 10A–B, but using ethyl α-methyl-4-pyridylacetic acid (from Preparative Example 25) instead of ethyl pyridyl acetic acid the title compound was obtained as an oil ( $MH^+$ 166).

PREPARATIVE EXAMPLE 27

ETHYL 4-[4,8-DICHLORO-5,6-DIHYDRO-11H-BENZO[5,6]CYCLOHEPTA[1,2-b]PYRIDIN-11-YLIDENE]-1-PIPERIDINECARBOXYLATE and ETHYL 4-[2,8-DICHLORO-5,6-DIHYDRO-11H-BENZO[5,6]CYCLOHEPTA[1,2-b]PYRIDIN-11-YLIDENE]-1-PIPERIDINECARBOXYLATE

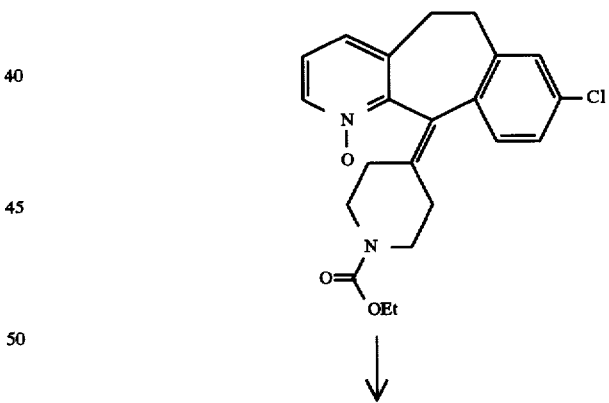

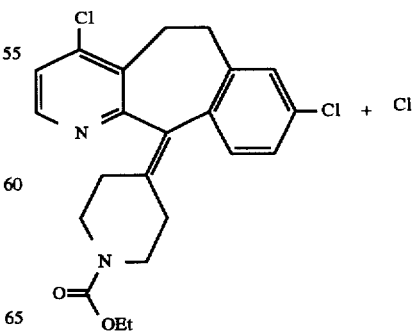

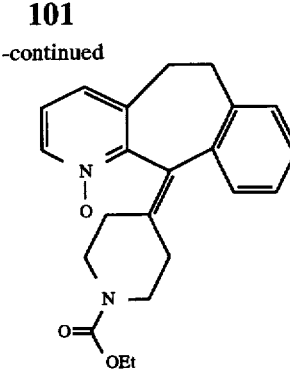

To phosphorous oxychloride (256 mL) stirring at reflux was added dropwise a solution of the title compound (109 grams) from Example 231A dissolved in CHCl₃ (850 mL). After stirring the resulting solution for an additional 20 minutes at reflux, the reaction mixture was cooled to room temperature and the chloroform removed in vacuo. The resulting solution was cooled in an ice-water bath and to it was slowly added 1N aqueous NaOH (850 mL) followed by 50% aqueous NaOH until the resulting mixture was slightly basic. Extraction with EtOAc, drying of the organic phase over anhydrous MgSO₄, concentration in vacuo, and purification by flash column chromatography provided the 4,8-dichloro product (27 grams, 23% yield, mp 141.6°–145.6° C.) and the 2,8-dichloro product (9 grams, 8% yield, 176.5°–177.9° C.).

PREPARATIVE EXAMPLE 28

4,8-DICHLORO-11-(4-PIPERIDYLIDENE)-6,11-5H-BENZO[5,6]CYCLOHEPTA[1,2-b]PYRIDINE

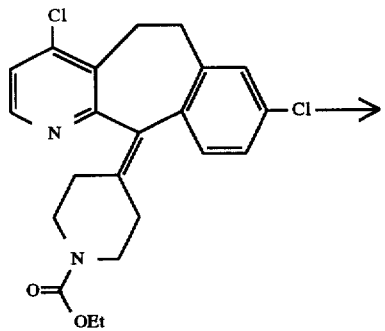

A solution of the 4,8-dichloro compound from Preparative Example 27 (2.6 grams) dissolved in absolute EtOH (50 mL) and concentrated HCl (100 mL) was stirred at reflux for 48 hours. The reaction mixture was cooled in an ice-water bath and was made basic by addition of solid KOH. Concentration in vacuo afforded a solid which was diluted with CH₂Cl₂ and water. The organic phase was dried over anhydrous MgSO₄ and concentrated in vacuo to provide the title compound (2.0 grams, 93% yield, mp=181.1°–183.2° C.).

PREPARATIVE EXAMPLE 29

ETHYL 4-[4,8-DICHLORO-5,6-DIHYDRO-11H-BENZO[5,6]CYCLOHEPTA[1,2-b]PYRIDIN-11-YLIDENE]-1-PIPERIDINE CARBOXYLATE, N-OXIDE

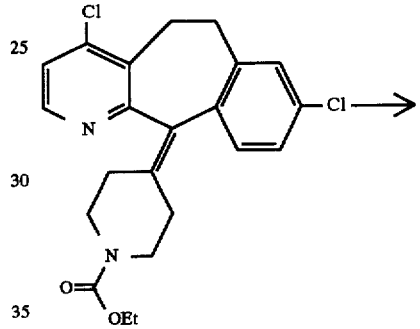

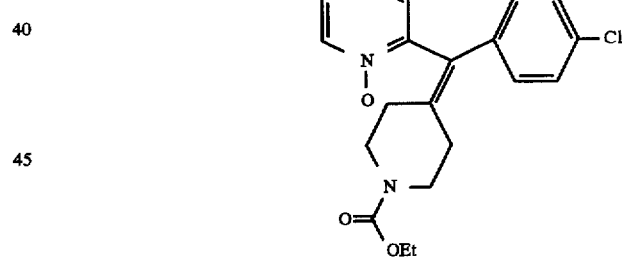

To a cooled (0° C.) solution of the 4,8-dichloro compound from Preparative Example 27 (9.5 grams) dissolved in CH₂Cl₂ (300 mL) under N₂ was added dropwise a solution of MCPBA (6.8 grams) dissolved in EtOAc (200 mL). The resulting mixture was washed with 1N aqueous NaOH, dried over anhydrous MgSO₄ and concentrated in vacuo. The residue was purified by flash column chromatography (silica gel) using 100% EtOAc then 10% MeOH-CH₂Cl₂ to afford the title compound (4.9 grams, 50%, MH⁺ 433).

PREPARATIVE EXAMPLE 30

ETHYL 4-[4-(2-AMINOETHYLTHIO)-8-CHLORO-5,6-DIHYDRO-11H-BENZO[5,6]CYCLOHEPTA[1,2-b]PYRIDIN-11-YLIDENE]-1-PIPERIDINE CARBOXYLATE

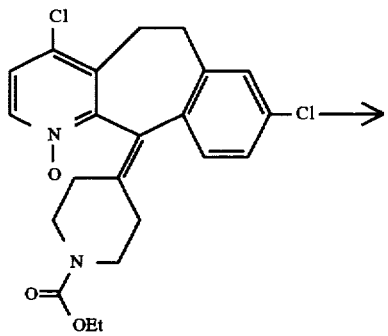

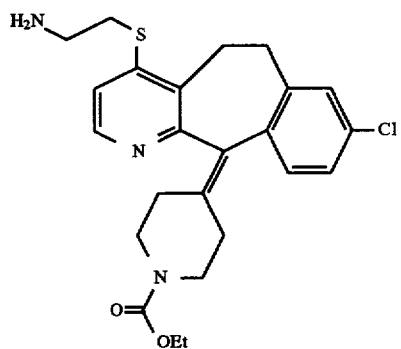

A mixture of the title compound from Preparative Example 29 (0.53 grams), 2-aminoethanethiol hydrochloride (0.74 grams) and absolute EtOH(15 mL) was stirred at reflux for 48 hours. The mixture was cooled to 25° C., diluted with CH$_2$Cl$_2$ and washed with 1N aqueous NaOH. The organic phase was dried over anhydrous MgSO$_4$ and concentrated in vacuo to provide the title compound (0.5 grams, 88%, MH$^+$ 458).

PREPARATIVE EXAMPLE 31

1,1-DIMETHYLETHYL[2-[[8-CHLORO-6,11-DIHYDRO-11-(1-ETHOXYCARBONYL)-4-PIPERIDINYLIDENE]-5H-BENZO[5,6]CYCLOHEPTA[HEPTA[1,2-b]PYRIDIN-4-YL]THIO]ETHYL]CARBAMATE

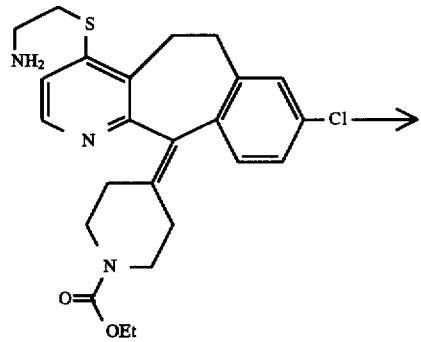

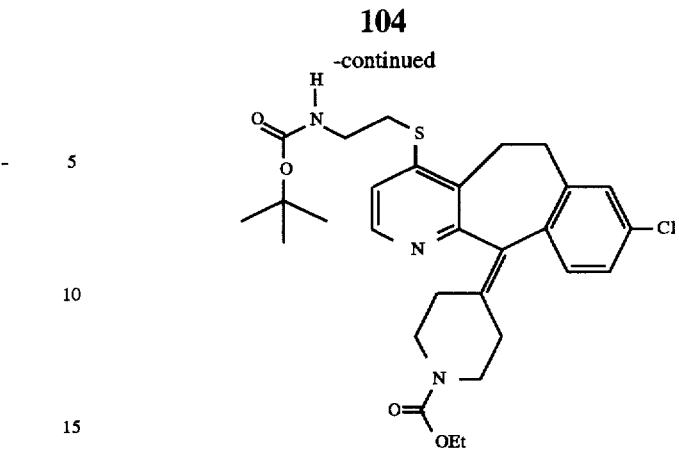

To the title compound from Preparative Example 30 (0.33 grams) dissolved in CH$_2$Cl$_2$ (60 mL) was added di-tert-butyldicarbonate (0.17 grams). The solution was stirred at 25° C. under N$_2$ overnight. An additional 0.1 grams of di-tert-butyldicarbonate was added and after 4 hours the reaction mixture was diluted with CH$_2$Cl$_2$, washed with 1N aqueous NaOH and concentrated in vacuo to afford the title compound (0.5 grams, 100%, MH$^+$ 558).

PREPARATIVE EXAMPLE 32

1,1-DIMETHYLETHYL[2-[[8-CHLORO-6,11-DIHYDRO-11-[4-PIPERIDINYLIDENE]-5H-BENZO[5,6]CYCLOHEPTA[1,2-b]PYRIDIN-4-YL]THIO]ETHYL]CARBAMATE

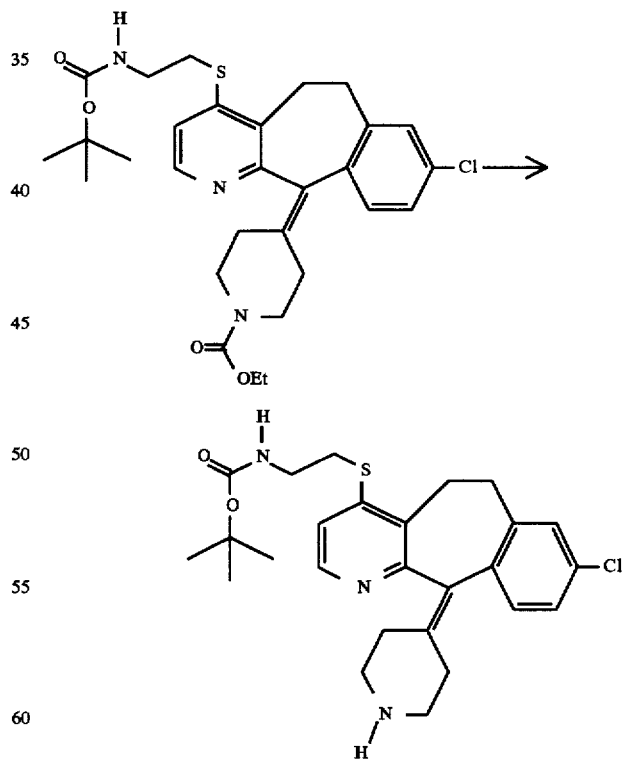

To the title compound from Preparative Example 31 (0.22 grams) dissolved in absolute EtOH (5 mL) was added water (5 mL) and solid KOH (0.33 grams). The solution was stirred at reflux for 4 days, then cooled to 25° C., diluted with CH$_2$Cl$_2$ and washed with water. The organic phase was concentrated in vacuo and the residue purified by flash column chromatography (silica gel) using 5% MeOH-CH$_2$Cl$_2$ saturated with NH$_4$OH to afford the title compound (0.04 grams, 19%, MH$^+$ 486).

PREPARATIVE EXAMPLE 33

3-PYRIDYLISOCYANATE, HYDROCHLORIDE

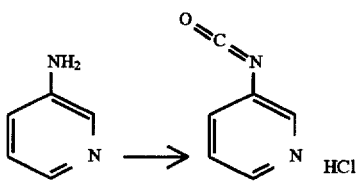

A 1.93 solution of phosgene in toluene (20%) (584 mL) was diluted with dry CH$_2$Cl$_2$ (1 L) and the mixture was stirred at 0° C. under nitrogen atmosphere. A solution of 3-aminopyridine (21.1 grams) and dry pyridine (19 mL) dissolved in dry CH$_2$Cl$_2$ (600 mL) was added dropwise to the stirred solution at 0° C. over a period of 5.5 hours. The mixture was stirred at 0°–25° C. for an additional 48 hours. A stream of nitrogen was passed through the solution to remove most of the phosgene and the solution was then evaporated until almost all of the solvent was removed to give the title compound which was then taken up in dry pyridine (850 mL) to give a stock solution of the title compound.

PREPARATIVE EXAMPLE 34

A. 8-CHLORO-11-(1-ETHOXYCARBONYL-4-PIPERIDINYL)-11H-BENZO[5,6]CYCLOHEPTA(1,2-b)PYRIDINE

B. 8-CHLORO-11-(1-ETHOXYCARBONYL-4-PIPERIDINYL)-9-ETHYL-11H-BENZO[5,6]CYCLOHEPTA(1,2-b)PYRIDINE

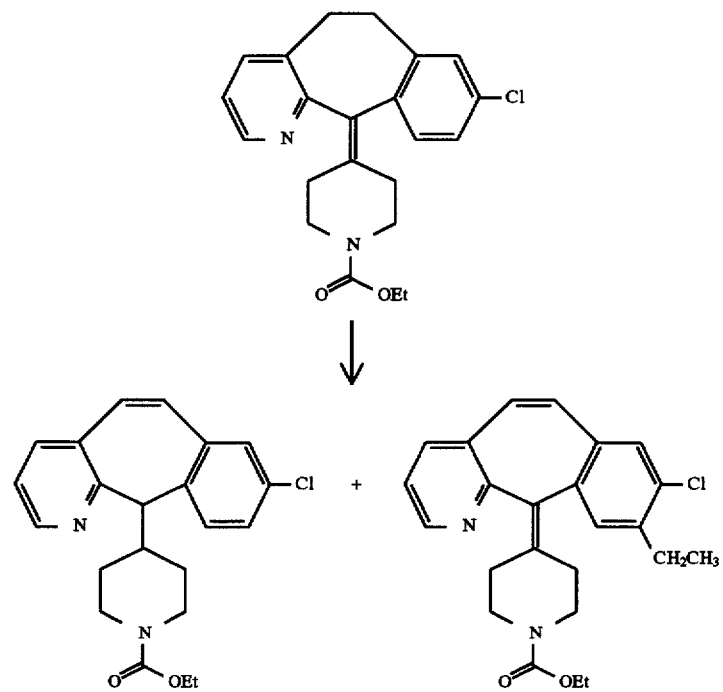

The title compound of Preparative Example 1F above (51.15 grams, 0.1336 mole) was dissolved in trifluoromethanesulfonic acid (170 mL). The dark mixture was heated to reflux for 70 h. The solution was cooled to room temperature and was then poured into 800 mL of an ice/water slurry and the resulting mixture stirred. Concentrated NH₄OH solution (175 mL) was added to the mixture in small portions so that the temperature of the mixture was below 20° C. The resulting basic mixture was extracted with CH₂Cl₂. The CH₂Cl₂ extract was washed with brine and was then evaporated to give a brown residue. This residue was dissolved in CH₂Cl₂ (750 mL) and the solution cooled to 0° C. Ethyl chloroformate (14.8 grams, 0.136 mole) was added over 5 minutes and the resulting mixture stirred at 0° C. for 15 minutes. Saturated NaHCO₃ solution (150 mL) was added and the cooling bath was removed. The resulting biphasic mixture was stirred rapidly for 3 h. The layers were separated and the CH₂Cl₂ layer was filtered through silica gel. The filtrate was evaporated to dryness and the residue chromatographed on silica gel using a gradient of hexane-CH₂Cl₂-acetone 16:2.5:1.5 to hexane-CH₂Cl₂-acetone 28:7.5:4.5 as eluent to give title compound A (25.02 g 49% MH⁺ 383) and title compound B (4.85 g, 9%, MH⁺ 411).

C. 8-CHLORO-11H-(4-PIPERIDINYL)-11H-BENZO[5,6]-CYCLOHEPTA(1,2-b)PYRIDINE

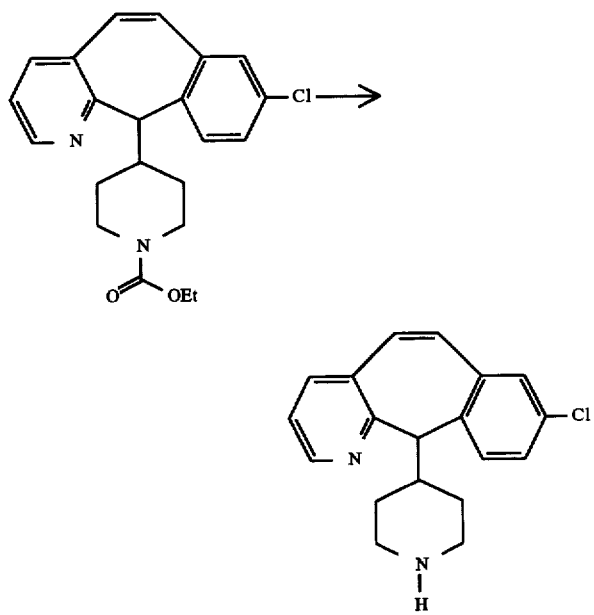

Hydrolyze the title compound of Preparative Example 34A by dissolving in 50% aqueous H₂SO₄ (v/v) and heating to 90° to 100° C. for 16 h. The cooled acidic mixture was neutralized with 25% NaOH solution (w/v). The resulting mixture was extracted with EtOAc and the EtOAc extract was dried with Na₂SO₄. Filtration and evaporation of the EtOAc afforded the title compound (MH⁺ 311).

PREPARATIVE EXAMPLE 35

8-CHLORO-9-ETHYL-11-(4-PIPERIDINYL)-11H-BENZO[5,6]CYCLOHEPTA[1,2-b]PYRIDINE

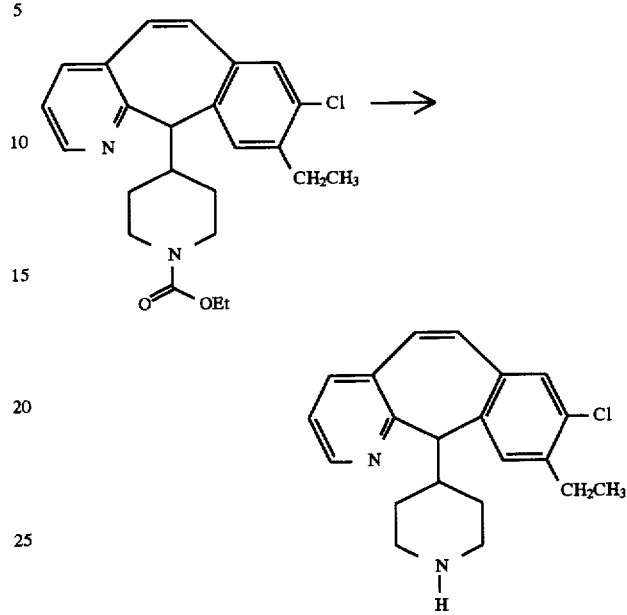

Hydrolyze the title compound of Preparative Example 34B following the procedure described in Preparative Example 34C to provide the title compound. Decomposes between 205.7°–215.4° C., heating 2°–3° C. per minute.

PREPARATIVE EXAMPLE 36

A. 8-CHLORO-11-(1-ETHOXYCARBONYL-4-PIPERIDINYL)-11H-BENZO[5,6]CYCLOHEPTA[1,2-b]PYRIDINE-1-OXIDE

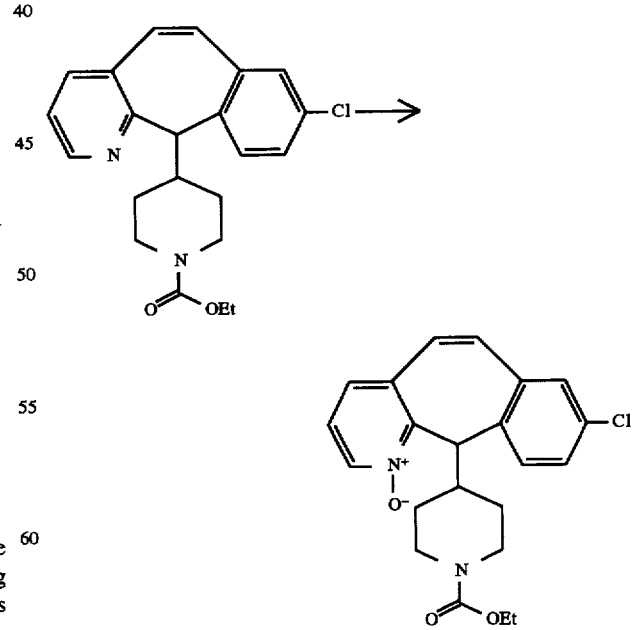

The title compound from Preparative Example 34A above (20.23 grams, 52.84 mmoles) was dissolved in CH₂Cl₂ (250 mL). MCPBA (1.25 equivalents) was added in one portion and this solution was stirred for 45 minutes. Sodium bisulfite solution (20% w/v) was added and the biphasic mixture rapidly stirred for 30 minutes. The layers were separated and the organic layer was washed with saturated $Na_2CO_3$ solution and dried with $Na_2SO_4$. Filtration and evaporation afforded the title compound (21 g, 99%, mp 78.6°–89.4° C., $MH^+$ 399).

B. 4,8-DICHLORO-11-(1-ETHOXYCARBONYL-4-PIPERIDINYL)-11H-BENZO[5,6]CYCLOHEPTA[1,2-b]PYRIDINE (A) and 2,8-DICHLORO-11-(1-ETHOXYCARBONYL-4-PIPERIDINYL)-11H-BENZO[5,6]CYCLOHEPTA[1,2-B]PYRIDINE (B)

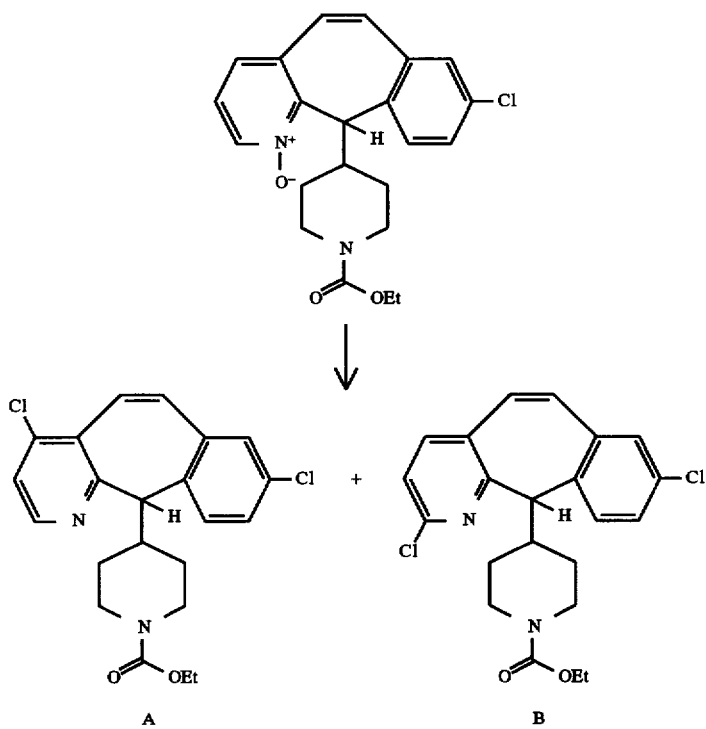

The title compound from Preparative Example 36A (21 grams, 53 mmoles) above was dissolved in anhydrous dichloroethane (250 mL) and the solution cooled to 0° C. $POCl_3$ (49.4 grams, 0.322 mole) was added dropwise to the dichloroethane solution over 15 minutes. After the $POCl_3$ was added the reaction mixture was warmed to 45°–50° C. and stirred for 18 h. Additional $POCl_3$ (8.2 grams) was added and the mixture heated to reflux for 9 h. The mixture was cooled and added to an ice cooled, stirred solution of NaOH (15% w/v). The resulting biphasic mixture was stirred rapidly for 18 h. The layers were separated and the aqueous layer was 15 extracted with $CH_2Cl_2$. The combined organic layers were washed with water followed by brine and dried ($Na_2SO_4$). The mixture was filtered and evaporated, and the residue chromatographed on silica gel using a gradient of 25% EtOAc in hexane to 45% EtOAc in hexane as eluent. The title compound A was obtained as a yellow solid (5.98 g $M^+$ 417), and title compound B was obtained as a yellow solid (1.0 g, mp 84.4°–90.6° C.).

C. 4,8-DICHLORO-11-(4-PIPERIDINYL)-11H-BENZO[5,6]CYCLOHEPTA[1,2-b]PYRIDINE

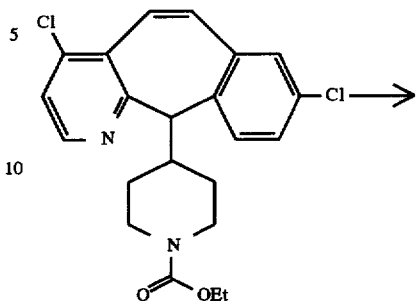

-continued

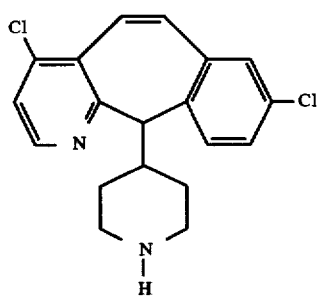

The title compound A from Preparative Example 36B was hydrolyzed under the conditions described in Preparative Example 34C to give the title compound ($M^+$ 345).

PREPARATIVE EXAMPLE 37

A. 4-(8-CHLORO-11H-BENZO[5,6]CYCLOHEPTA[1,2-b]PYRIDIN-11-YLIDENE)-1-(ETHOXYCARBONYL)-PIPERIDINE

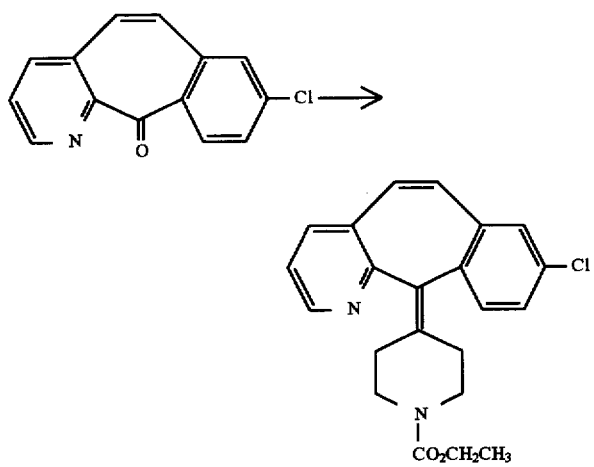

The preparation of the starting material for this reaction was described in *The Journal of Organic Chemistry*, 1990, 55, pp. 3341-3350 by Piwinski, et al. By substituting in Preparative Example 2, 8-chloro-11H-benzo[5,6]-cyclohepta[1,2-b]pyridin-11-one for 9-fluoro-5,6-dihydro-11 H-benzo[5,6]-cyclohepta[1,2-b]pyridin-11-one and employing basically the same methods as steps D through F of Preparative Example 2, one obtains the title compound (mp 154.7°–155.5° C.).

B. 8-CHLORO-11-(4-PIPERIDINYL)-BENZO[5,6]CYCLOHEPTA[1,2-b]PYRIDINE

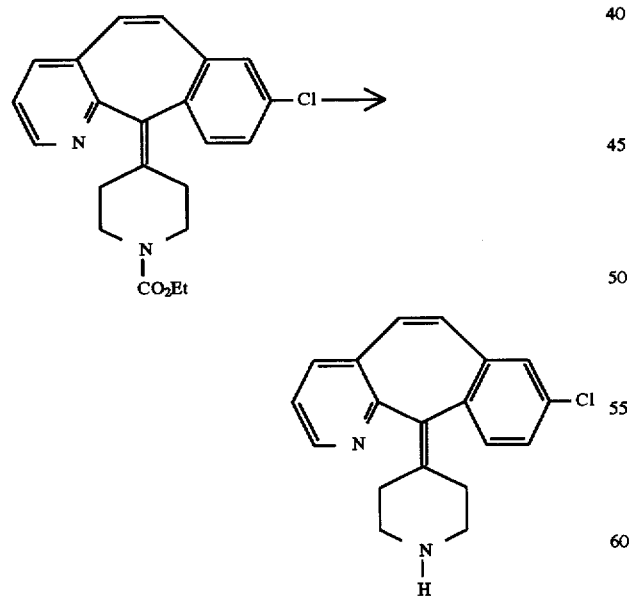

Hydrolyze the title compound of Preparative Example 37A following the procedure described in Preparative Example 334C (mp 168.5°–171.2° C., decomposition).

PREPARATIVE EXAMPLE 38

8-CHLORO-11-(1-PIPERAZINYL)-11H-BENZO[5,6]CYCLOHEPTA[1,2b]PYRIDINE

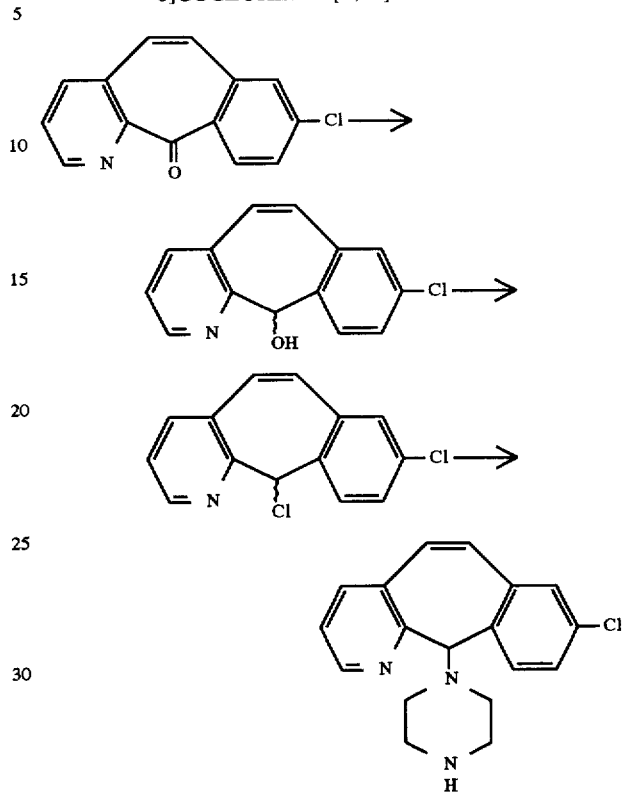

The preparation of the starting material for this reaction was described in *The Journal of Organic Chemistry*, 1990, 55, pp. 3341-3350 by Piwinski, J. J., et al. By substituting in Preparative Example 7A, 8-chloro-11H-benzo[5,6]cyclohepta[1,2-b]pyridin-11-one (11.53 g) (47.71 mmoles) for 8-chloro-5,6-dihydro-11H-benzo[5,6]cyclohepta[1,2-b]pyridin-11-one and employing basically the same methods as steps A through C of Preparative Example 7, one obtains 11.53 g (36%) of the title compound (MH$^+$ 312).

PREPARATIVE EXAMPLE 39

A. ETHYL α,α-DIMETHYL-3-PYRIDYLACETIC ACID N-OXIDE

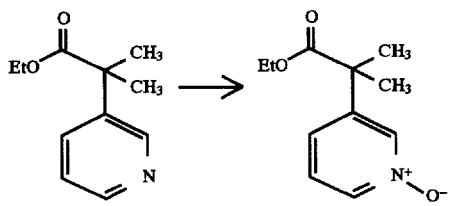

By substituting in Preparative Example 8A, ethyl α,α-dimethyl-3-pyridylacetic acid (4.0 g, 20.7 mmoles) for ethyl 3-pyridylacetic acid and using the same method as described in Preparative Example 8A, one obtains the title compound (3.2 g, 74%, MH$^+$ 210).

113

B. α,α-DIMETHYL-3-PYRIDYLACETIC ACID N-OXIDE

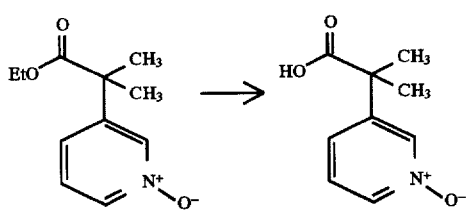

By substituting in Preparative Example 8B, ethyl α,α-dimethyl-3-pyridylacetic acid N-oxide (0.142 g, 0.68 mmoles) (Preparative Example 39A) for ethyl 3-pyridylacetic acid N-oxide and using the same method as described in Preparative Example 8B, one obtains the title compound.

PREPARATIVE EXAMPLE 40

4-BROMO-8-CHLORO-11-(1-PIPERAZINYL)-6,11-DIHYDRO-5H-BENZO[5,6]CYCLOHEPTA[1,2-b]PYRIDINE

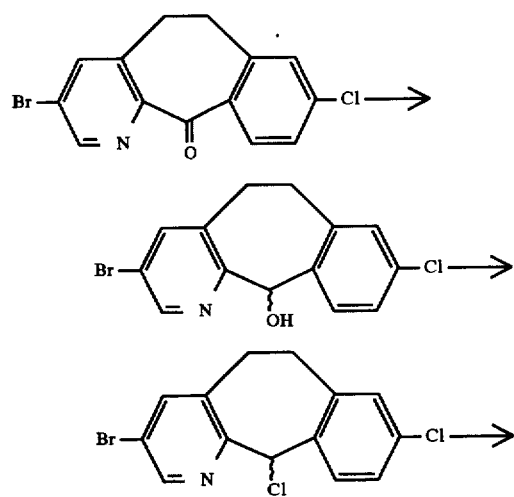

By substituting in Preparative Example 7A, 4-bromo-8-chloro-11-(1-piperazinyl)-5,6-dihydro-11H-benzo[5,6]cyclohepta[1,2-b]pyridin-11-one (1.5 g, 4.65 mmoles) (Preparative Example 20A) for 8-chloro-5,6-dihydro-11H-benzo[5,6]cyclohepta[1,2-b]pyridin-11-one and using the same methods as described in steps A through C of Preparative Example 7, one obtains the title compound (1.31 g, 72%, MH$^+$ 392).

114

PREPARATIVE EXAMPLE 41

4,8-DICHLORO-11-(1-PIPERAZINYL)-6,11-DIHYDRO-5H-BENZO[5,6]CYCLOHEPTA[1,2-b]PYRIDINE

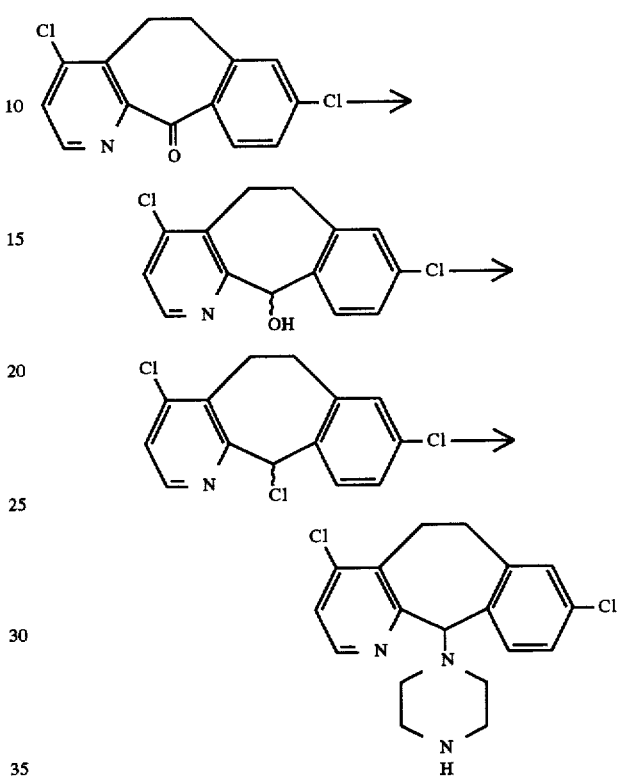

By substituting in Preparative Example 7A 4,8-Dichloro-5,6-dihydro-11H-benzo[5,6]cyclohepta[1,2-b]pyridin-11-one (6.64 g, 28.37 mmoles) (Preparative Example 5B) for 8-chloro-5,6-dihydro-11H-benzo[5,6]cyclohepta[1,2-b]pyridin-11-one and using the same methods as described in steps A through C of Preparative Example 7, one obtains the title compound (2.59 g, 26%, MH$^+$ 348).

PREPARATIVE EXAMPLE 42

ETHYL 4-[4-[(1H-BENZOTRIAZOL-1-YL)OXY]-8-CHLORO-5,6-DIHYDRO-11H-BENZO[5,6]CYCLOHEPTA[1,2-b]PYRIDIN-11-YLIDENE]-1-PIPERIDINE CARBOXYLATE

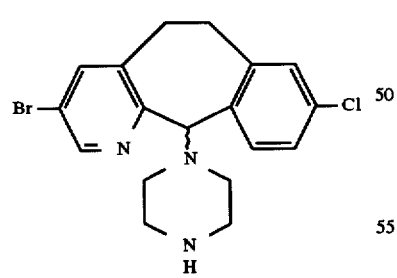

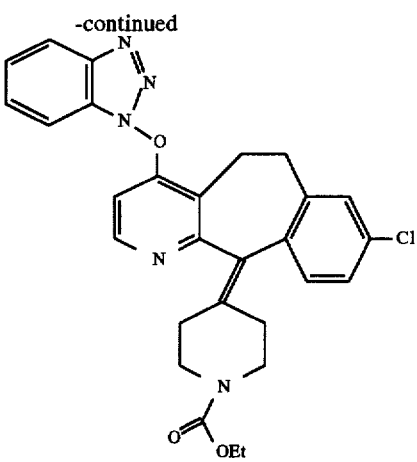

To a solution of the 4,8-dichloro compound from Preparative Example 27 (1.5 grams) in dry DMF (20 mL) was added HOBT (1.5 grams). After stirring for 14 days at 25° C., NaH (0.84 grams, 60% in mineral oil) was added and after an additional 24 hours, the mixture was poured into water. Filtration provided the title compound (Yield: 1.7 grams, 89%, mp=181.5°–183.9° C., $MH^+$ 516).

PREPARATIVE EXAMPLE 43

ETHYL 4-[4-HYDROXY-8-CHLORO-5,6-DIHYDRO-11H-BENZO[5,6]CYCLOHEPTA[1,2-b]PYRIDIN-11YLIDENE]-1-PIPERIDINE CARBOXYLATE

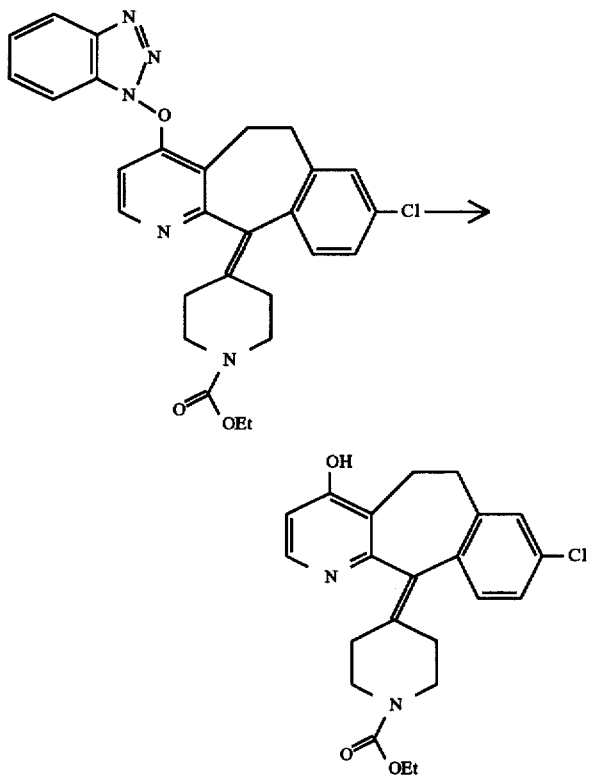

To a solution of the title compound from Preparative Example 42 (0.15 grams) and glacial HOAc (5 mL) was added Zn dust (0.2 grams). After stirring at 25° C. for 1 hour, the mixture was filtered through celite and the filtrate concentrated in vacuo. The residue was diluted with EtOAc, washed with saturated aqueous $NaHCO_3$ and brine. The organic layer was separated, added over $MgSO_4$ and concentrated in vacuo to give the title compound (Yield: 0.11 grams, 95%, $MH^+$ 399).

PREPARATIVE EXAMPLE 44

ETHYL 4-[3-BROMO-4-HYDROXY-8-CHLORO-5,6-DIHYDRO-11H-BENZO[5,6]CYCLOHEPTA[1,2-b]PYRIDIN-11-YLIDENE]-1-PIPERIDINE CARBOXYLATE

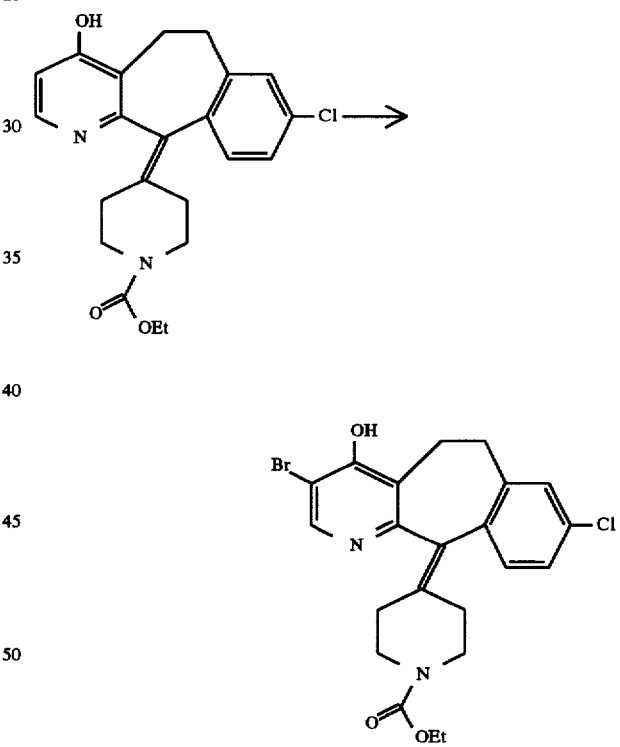

To a solution of the title compound from Preparative Example 43 (1.3 grams) and glacial HOAc (5 mL) was added a 0.7M bromine-HOAc solution (4 mL) at 25° C. under $N_2$. The solution was poured into 200 mL of water and the resulting solid was filtered, then washed with water. The solid was dried under vacuum overnight to provide the title compound (Yield: 1.2 grams, 81%, $MH^+$ 477).

PREPARATIVE EXAMPLE 45

ETHYL 4-[3-BROMO-4,8-DICHLORO-5,6-DIHYDRO-11H-BENZO[5,6]CYCLOHEPTA[1,2-b]PYRIDIN-11-YLIDENE]-1-PIPERIDINE CARBOXYLATE

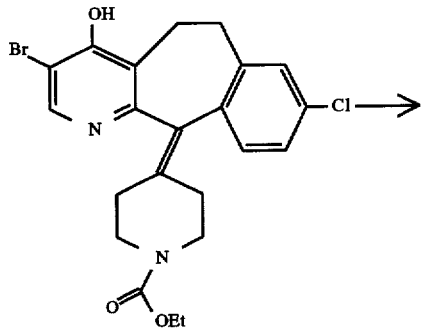

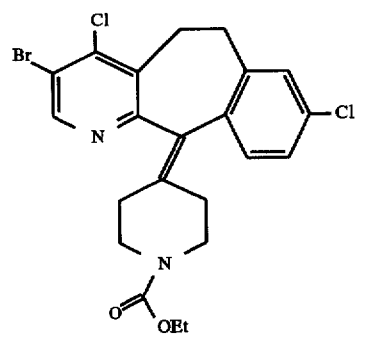

A mixture of the title compound from Preparative Example 44 (5.1 grams), phosphorous oxychloride (20 mL) and CHCl₃ (40 mL) was stirred at reflux over night. The reaction mixture was made basic by the snow addition of 1N aqueous NaOH, and the resultant mixture was diluted with CH₂Cl₂. The mixture was shaken well and after separation of the phases, the organic phase was washed with 1N aqueous NaOH. The organic phase was dried over anhydrous MgSO₄, filtered and concentrated in vacuo to provide a solid which was mixed with MeOH and filtered. Concentration of the filtrate provided the title compound as a solid (Yield: 5.7 grams, MH⁺ 497).

PREPARATIVE EXAMPLE 46

3-BROMO-4,8-DICHLORO-11-(4-PIPERIDYLIDENE)-6,11-5H-BENZO[5,6]CYCLOHEPTA[1,2-b]PYRIDINE

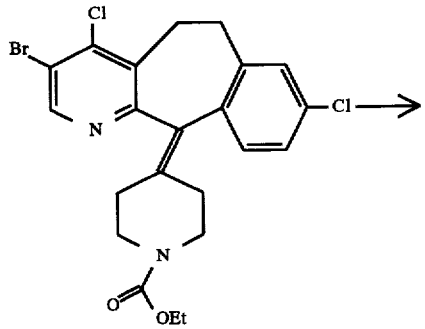

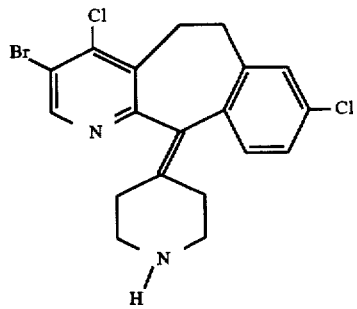

A solution of the title compound from Preparative Example 45 (5.7 grams) dissolved in absolute EtOH (100 mL) and concentrated HCl (200 mL) was stirred at reflux for 24 hours. The reaction mixture was cooled in an ice-water bath and was made basic by the addition of solid KOH. Extraction with CH₂Cl₂ and concentration of the organic phase in vacuo afforded the title compound as a solid (1.7 grams, 35% yield, MH⁺ 425).

PREPARATIVE EXAMPLE 47

A. 4-(8-CHLORO-3-NITRO-5,6-DIHYDRO-11H-BENZO[5,6]CYCLOHEPTA[1,2-b]PYRIDIN-11-YLIDENE)-1-PIPERIDINE-1-CARBOXYLIC ACID ETHYL ESTER

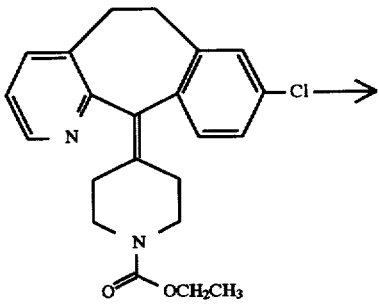

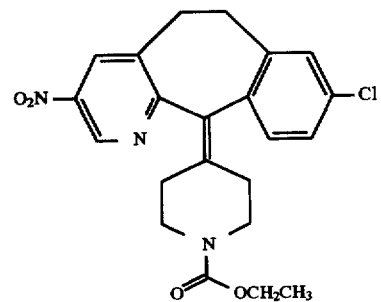

Tetrabutyl ammonium nitrate (4.98 g, 16.3 mmol) was dissolved in CH₂Cl₂(20 mL) and TFAA (3.12 g, 14.9 mmol, 2.1 mL) was then added. The solution was cooled to 0° C. and then added (by cannulation) to a solution of 4-(8-chloro-5,6-dihydro-11 H-benzo[5,6]-cyclohepta[1,2-b]pyridin-11-ylidene)-1-piperidine-1-carboxylic aid ethyl ester (5.69 g, 14.9 mmol) in CH₂Cl₂ (35 mL) also cooled to 0° C. The reaction mixture was stirred at 0° C. for 3 h and then allowed to go to room temperature (25° C.) overnight. The reaction mixture was then extracted with saturated NaHCO₃ (60 mL) dried over MgSO₄ and concentrated to give a semi-solid material that was chromatographed on silica gel eluting first with 10% and then 20% EtOAc-hexane. Removal of the organic solvents gave the title compound in 44% yield as a light yellow solid. MP=90.4°–91.0° C., MH+ 428.

B. 4-(8-CHLORO-3-AMINO-5,6-DIHYDRO-11H-BENZO[5,6]CYCLOHEPTA[1,2-b]PYRIDIN-11-YLIDENE)-1-PIPERIDINE-1-CARBOXYLIC ACID ETHYL ESTER

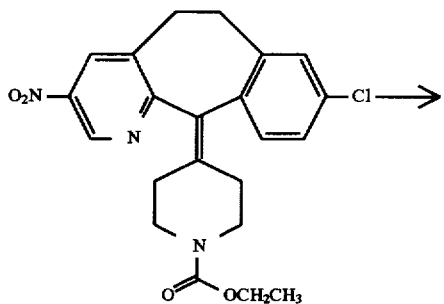

The title compound from Preparative Example 47A (5.99 g, 14 mmol) was dissolved in 85% aqueous EtOH. To this solution was added iron filings (7.01 g, 125.57 mmol) and CaCl₂ (0.69 g, 6.29 mmol) and the reaction mixture was refluxed for 16 h. The reaction mixture was filtered through a bed of celite while hot and the celite was washed with hot EtOH (700 mL). The EtOH solution was then decolorized with activated charcoal (2.4 g) and then filtered through celite. EtOH was then rotary evaporated to give the title compound in 100% yield as an off-white solid. MP=102.4°–103.1° C., MH⁺398.

C. 4-(8-CHLORO-3-BROMO-5,6-DIHYDRO-11H-BENZO[5,6]CYCLOHEPTA[1,2-b]PYRIDIN-11-YLIDENE)-1-PIPERIDINE-1-CARBOXYLIC ACID ETHYL ESTER

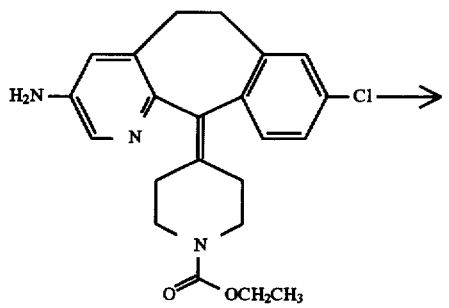

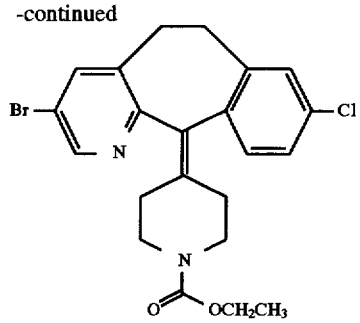

The title compound from Preparative Example 47B (3.00 g, 7.60 mmol) was dissolved in HBr (48%, 30 mL). The reaction mixture was cooled to –5° C. (ice-ethylene glycol bath) and bromine (2 mL) was added dropwise. The reaction mixture was stirred at –5° C. for 15 minutes. Sodium nitrite (1.57 g, 22.8 mmol) dissolved in water (15 mL) was slowly added to the reaction mixture. The reaction mixture was then stirred for 45 minutes and then quenched with 40% NaOH to pH~10. The aqueous phase was then extracted with EtOAc (3×100 mL). Combined EtOAc fractions were dried over Na₂SO₄ and then concentrated to give the title compound in 83% yield as a light brown solid. Mp=146°–148° C., MH+ 463.

PREPARATIVE EXAMPLE 48

Step A:

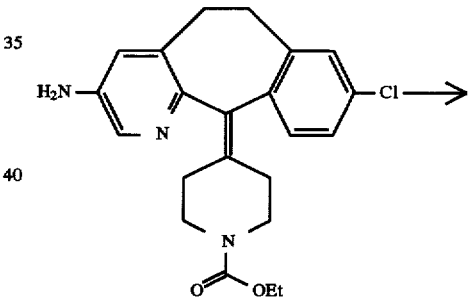

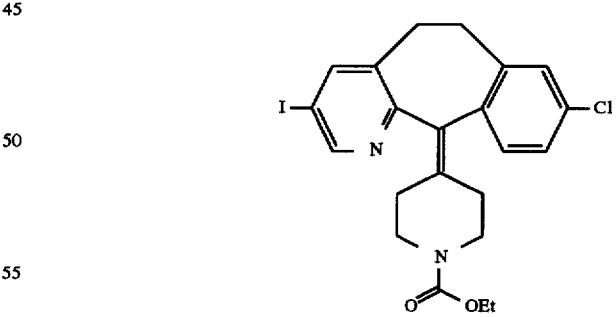

Combine 6 g (15.11 mmol) of the title compound of Preparative Example 47B and benzene, and add 2.3 g (9.06 mmol) of iodine. Heat the mixture at reflux for 3 hours, cool, then dilute with 50 mL of CH₂Cl₂. Wash the organic phase with 5% NaHSO₃(aqeuous) (3×80 mL), then with 1M NaOH (aqueous) (2×80 mL), and dry over MgSO₄. Concentrate to a residue chromatograph (silica gel, 30% EtOAc/hexanes), to give 3.2 g (42% yield) of the product iodo compound. Mass Spec., MH+=509

Step B:

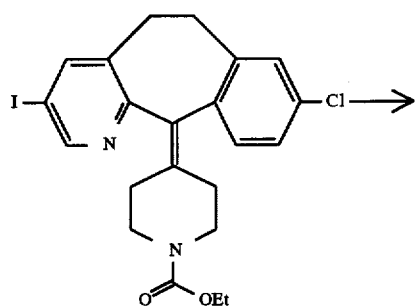

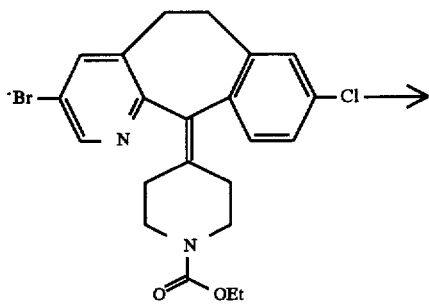

The product of Step A is hydrolyzed via substantially the same procedure as described in Example 358, Step A, to give the iodoamine product in 89% yield.

PREPARATIVE EXAMPLE 49

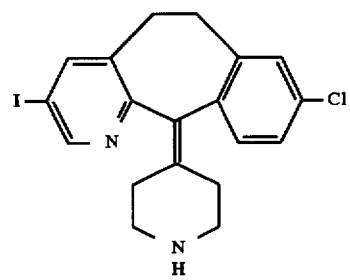

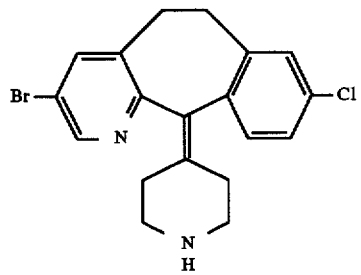

The product of Preparative Example 47, Step C, (2.42 g) is hydrolyzed via substantially the same procedure as described in Example 358, Step A, to give 1.39 g (69% yield) of the bromoamine product.

Using the starting compound indicated and following essentially the same procedure as for Preparative Example 49, the following compounds were prepared:

| Starting Compound | Compound | Analytical Data |
|---|---|---|
| Preparative Example 51, Step C | 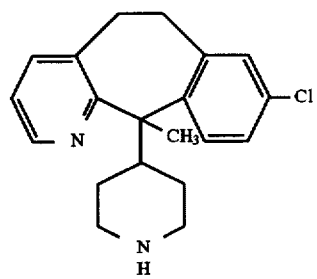 Preparative Example 49A | Mass Spec.: MH+ = 407 |

PREPARATIVE EXAMPLE 50

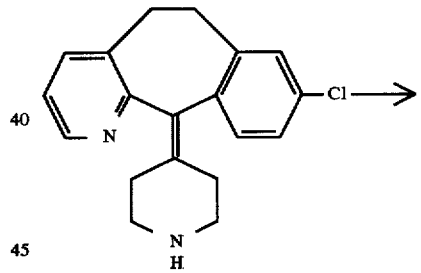

Step A:

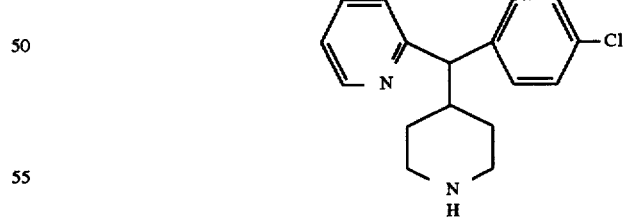

Combine 82.0 g (0.26 mole) of the product of Preparative Example 1, Step G, and 1 L of toluene, then add 20.06 g (0.53 mole) of LiAlH$_4$ and heat the reaction mixture at reflux overnight. Cool the mixture to room temperature and add ~1 L of Et$_2$O, followed by dropwise addition of saturated Na$_2$SO$_4$ (aqueous) until a precipitate forms. Filter and stir the filtrate over MgSO$_4$ for 30 minutes, then concentrate in vacuo to give the product compound in 83% yield. Mass Spec.: MH+=313

Step B:

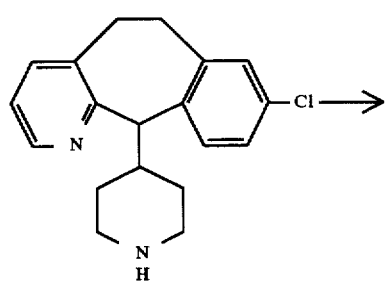

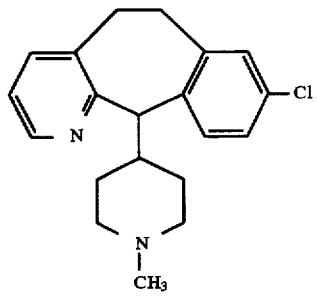

Combine 74 g (0.24 mol) of the Product from Step A and 95 g (6.84 equiv.) of HCO$_2$H, then add 129 g of 7% formadehyde and heat the mixture to ~80° C. for 2 hours. Cool the mixture to room temperature and basify with 25% NaOH (aqueous). Extract with EtOAc (3×1.3 L), dry the extracts over Na$_2$SO$_4$ and concentrate to a residue. Recystallize the residue from iPr$_2$O and Et$_2$O to give the product compound. Mass Spec.: MH$^+$=326.

Step C:

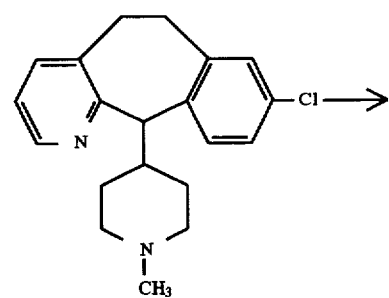

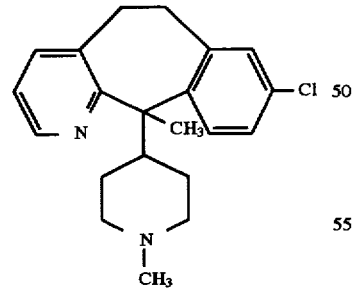

Combine 28 g of the Product of Step B and 800 mL of THF and cool to −65° C. Add a solution of 41.2 mL (1.2 equiv.) of 2.5M n-BuLi in hexanes, stir for 1 hour at −65° C., then warm to −30° C. and stirred at that temperature for 1 hour. Cool to −65° C. and add 10.5 mL of CH$_3$I, then warm to −10° C. and quench with 1.5 mL of Et$_2$O followed by 10 mL of NH$_4$OH (aqueous). Dry the organic phase over K$_2$CO$_3$ and concentrate in vacuo to a residue. Dissolve the residue in CH$_2$Cl$_2$, wash with H$_2$O, dry over Na$_2$SO$_4$ and concentrate in vacuo to give a residue. Chromatograph (silica gel, 5% MeOH/EtOAc+NH$_4$OH) to give 26 g of the product compound.

Step D:

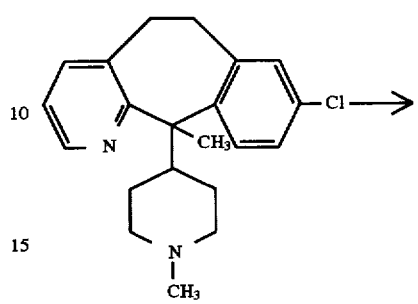

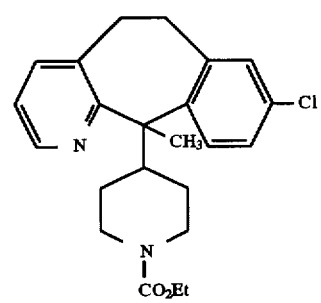

Combine 26 g of the Product of Step C, toluene, and 33 mL (3 equiv.) of Et$_3$N, then heat to 70° C. Slowly add 45 mL (6 equiv.) of ClCO$_2$Et over a period of 45 min. Stir for 15 min. then pour the mixture into ice and add 100 mL of 1N NaOH (aqueous). Extract with EtOAc, dry the extract and concentrate in vacuo to give 37 g of the product compound.

Step E:

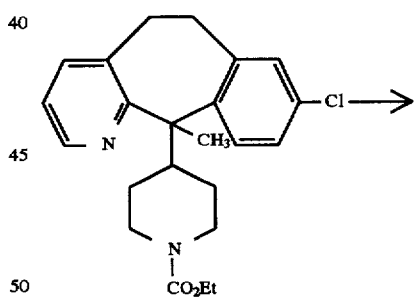

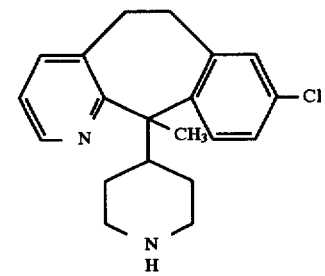

Hydrolyze 3.5 g (8.8 mmol) of the Product of Step D, by substantially the same procedure as described for Example 358, Step A, to give 2.26 g (79% yield) of the product compound. Mass Spec.: MH$^+$=327

PREPARATIVE EXAMPLE 51

Step A:

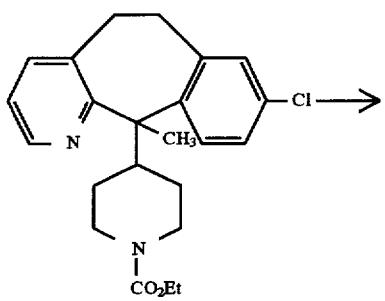

Dissolve 8.66 g (28.6 mmol) of tetra-n-butylammonium nitrate in 50 mL of $CH_2Cl_2$ and add 5.99 g (28.57 mmol, 2.1 mL) of TFAA. Cool to 0° C. and add the mixture (via cannula) to a solution of 10.36 g (14.9 mmol) of the product of Preparative Example 50, Step D in 150 mL of $CH_2Cl_2$ at 0° C., then stir at 0° C. for 3 hours. Allow the mixture to warm to 25° C. while stirring overnight, then extract with 150 mL of saturated $NaHCO_3$ (aqueous) and dry over $MgSO_4$. Concentrate in vacuo to a residue and chromatograph the residue (silica gel, 10% EtOc/hexane, then 20% EtOAc/hexane) to give a 57% yield of the product compound. Mass Spec.: $MH^+$=442.

Step B:

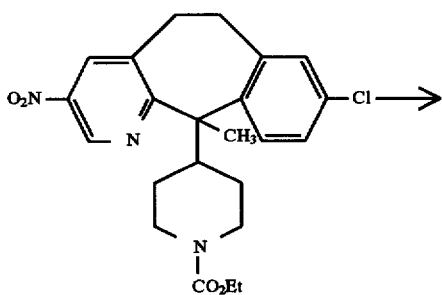

Combine 5.9 g (13.29 mmol) of the Product of Step A and 400 mL of 85% EtOH (aqueous), add 6.6 g (119 mmol) of Fe filings and 0.66 g (5.98 mmol) of $CaCl_2$, and heat at reflux for 16 hours. Filter the hot mixture through a bed of celite®, wash the celite® with 700 mL of hot EtOH. Concentrate the filtrate in vacuo to give a 100% yield of the product compound. Mass Spec.: $MH^+$=414.

Step C:

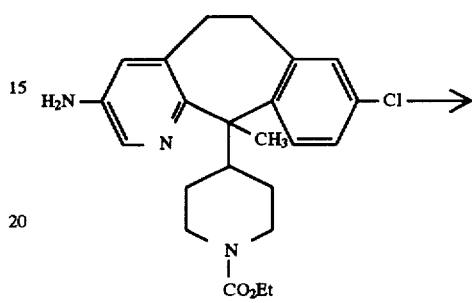

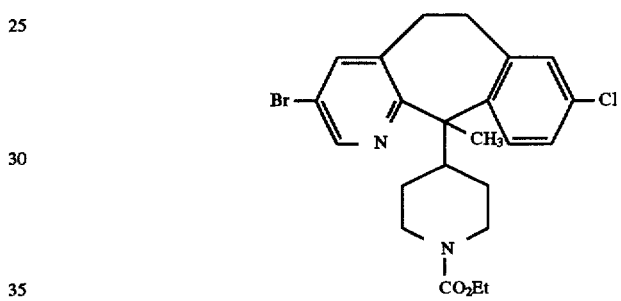

Combine 6.5 g (15.7 mmol) of the Product of Step B and 63 mL of 48% HBr, cool the mixture to –5° C. and slowly (dropwise) add 4.4 mL of $Br_2$ bromine (4.4 mL). Stir the mixture at –5° C. for 15 minutes and slowly add a solution of 3.25 g (47.1 mmol) of $NaNO_2$ in 30 mL of water. Stir for 45 minutes, then quench with 50% NaOH (aqueous) to pH~10. Extract with EtOAc (3×200 mL), dry the combined extracts over $Na_2SO_4$ and concentrate in vacuo to give 6.32 g (81% yield) of the product compound. Mass Spec.: $MH^+$= 479

PREPARATIVE EXAMPLE 51A

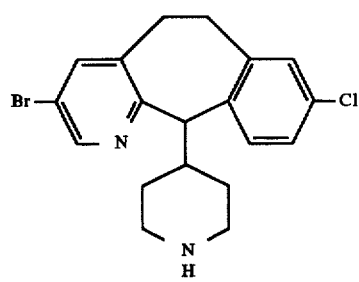

Step A:

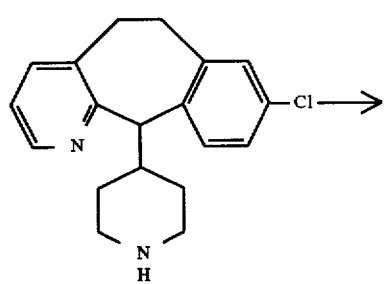

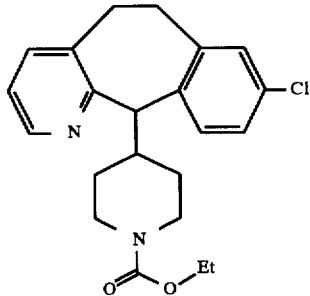

Combine 24.32 g (74.9 mmol) of the Product from Preparative Example 50, Step A, 500 mL of toulene, 83 mL of Et$_3$N and 65.9 mL of ethyl chloroformate and heat the mixture at reflux overnight. Cool to 25° C., pour into 200 mL of water and extract with EtOAc. Dry the extract over MgSO$_4$, concentrate in vacuo to a residue and chromatograph (silica gel, 50% EtOAc/hexane) to give 15 g of the product compound. Mass Spec.: MH$^+$=385.

Step B:

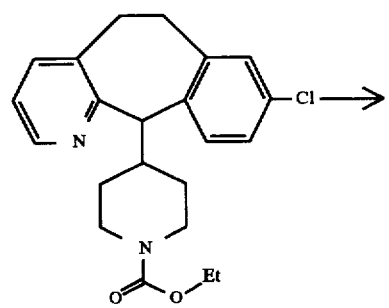

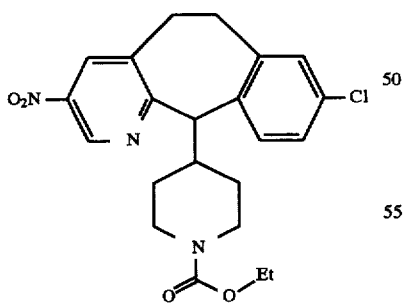

Dissolve 3.2 g (10.51 mmol) of tetra-n-butylammonium nitrate in 25 mL of CH$_2$Cl$_2$ and add 2.2 g (10.51 mmol, 1.5 mL) of TFAA. Cool to 0° C. and add the mixture (via cannula) to a solution of 3.68 g (9.56 mmol) of the product of Step A in 50 mL of CH$_2$Cl$_2$ at 0° C., then stir at 0° C. for 3 hours. Allow the mixture to warm to 25° C. while stirring overnight, then extract with saturated NaHCO$_3$ (aqueous) and dry over MgSO$_4$. Concentrate in vacuo to a residue and chromatograph (silica gel, 30% EtOc/hexane) to give a 1.2 g of the product compound. Mass Spec.: MH$^+$=430.

Step C:

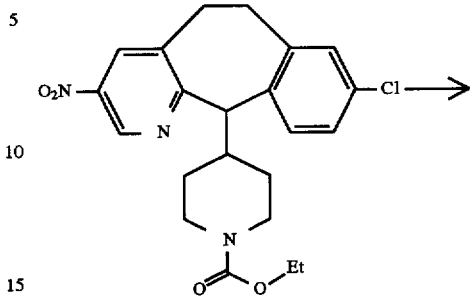

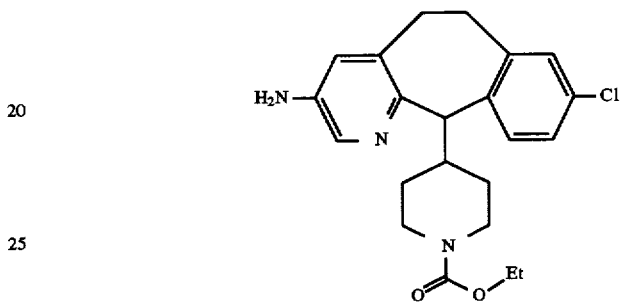

Combine 2.0 g (4.7 mmol) of the Product of Step B and 150 mL of 85% EtOH (aqueous), add 2.4 g (42 mmol) of Fe filings and 0.24 g (2.1 retool) of CaCl$_2$, and heat at reflux for 16 hours. Filter the hot mixture through a bed of celite®, wash the celite® with hot EtOH. Concentrate the filtrate in vacuo to give a 100% yield of the product compound. Mass Spec.: MH$^+$=400.

Step D:

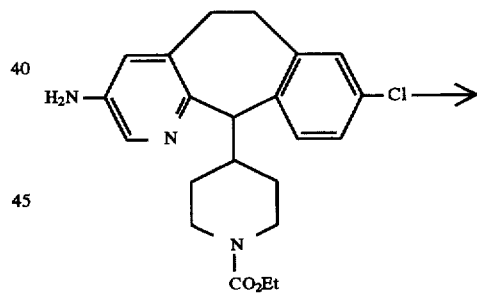

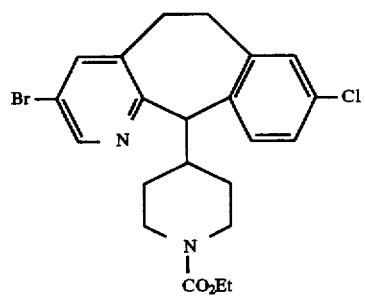

Combine 2.0 g (5.2 mmol) of the Product of Step C and 20 mL of 48% HBr, cool the mixture to −5° C. Stir the mixture at −5° C. for 15 minutes and slowly add a solution of 1.07 g (15.5 mmol) of NaNO$_2$ in 10 mL of water. Stir for 45 minutes, then quench with 50% NaOH (aqueous) to pH~10. Extract with EtOAc, dry the combined extracts over MgSO₄ and concentrate in vacuo to give the product compound. Mass Spec.: MH⁺=465

Step E:

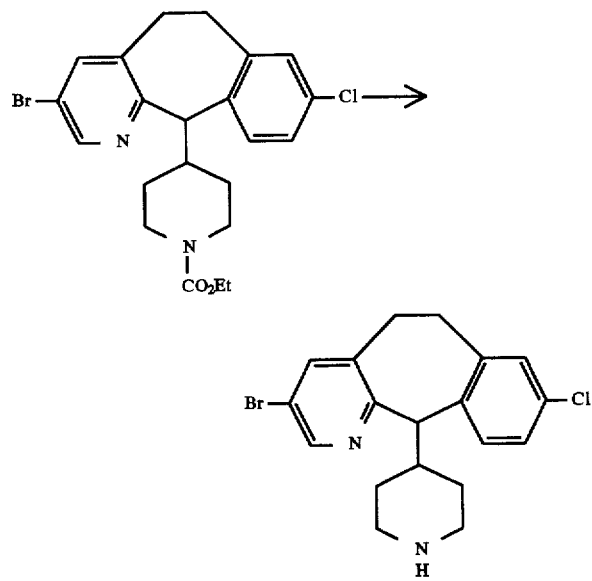

Hydroyze 4.0 g of the Product of Step D via substantially the same process as described for Example 358, Step A, to give 1.39 g of the product compound. Mass Spec.: MH⁺= 392

PREPARATIVE EXAMPLE 52

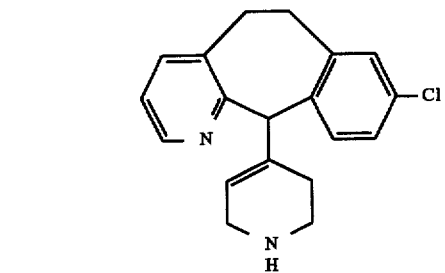

Step A:

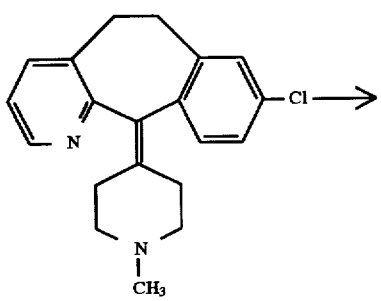

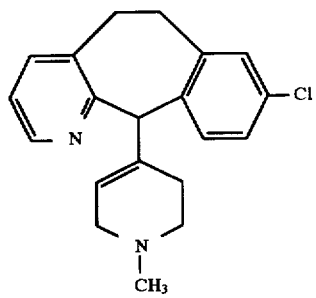

Dissolve 9.8 g (30.2 mmol) of the Product of Preparative Example 1, Step E, in THF under nitrogen, cool the mixture to −15° C., then add 17.76 mL (30.3 mmol) of 2.5M n-butyllithium in hexanes and stir for 1.5 hours. Cool the reaction mixture to −70° C. and add 2.45 mL (60 mmol) of MeOH and warm to room temperature overnight. Add 300 mL of (Et₂O) and extract with water (3×100 mL). Dry the extracts, concentrate in vacuo to a residue and chromatograph the residue (silica gel, 5% Et₃N/EtOAc) to give 6.59 g (68% yeild) of the product compound.

Via substantially the same procedure as described in Preparative Example 52, Step A, except that methyl iodide is used in place of MeOH, the following product compound is prepared:

| Starting Compound | Compound | Analytical Data |
|---|---|---|
| Preparative Example 1, Step E | (structure) | Mass Spec.: MH⁺ = 339 |

Preparative Example 52A

Step B:

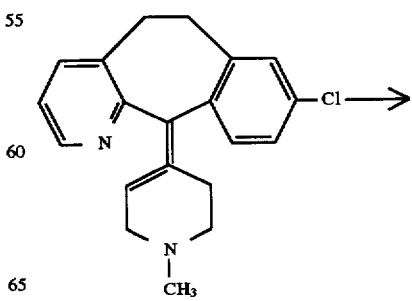

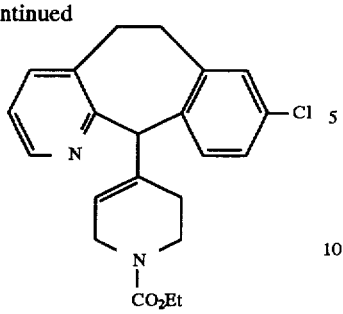

Treat 3 g (9.23 mmol) of the Product of Step A with 10 mL of ClCO$_2$Et and 10 mL of Et$_3$N via substantially the same procedure as described in Preparative Example 50, Step D, to give 2.2 g (64% yield) of the product compound. Mass Spec.: MH$^+$=383

Using the starting compound indicated and substantially the same procedure as described in Preparative Example 52, Step B, the following product compound is prepared:

| Starting Compound | Compound | Analytical Data |
|---|---|---|
| Preparative Example 52A, Step E | 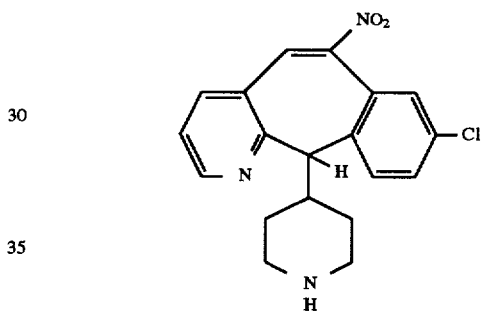 Preparative Example 52A | Mass Spec.: MH$^+$ = 397 |

Step C:

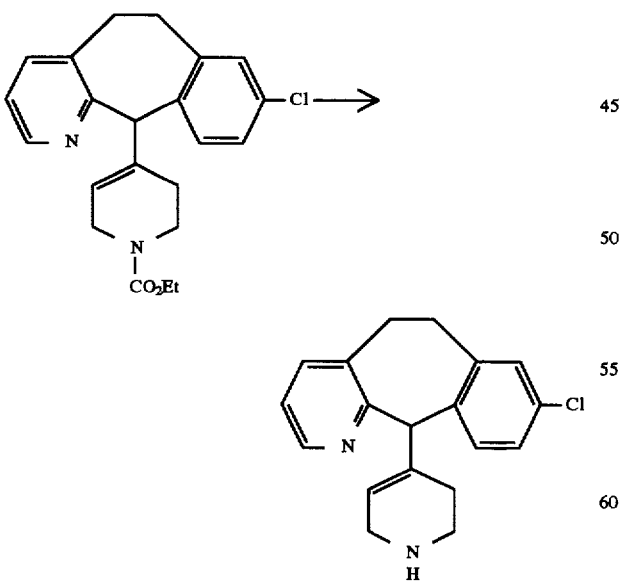

Treat the Product of Step B via substantially the same procedure as described in Preparative Example 1, Step F, to give the product compound. Mass Spec.: MH$^+$=310

Using the starting compound indicated and substantially the same procedure as described in Preparative Example 52, Step C, the following product compound is prepared:

| Starting Compound | Compound | Analytical Data |
|---|---|---|
| Preparative Example 52A, Step B | Preparative Example 52A | Mass Spec.: MH$^+$ = 325 |

PREPARATIVE EXAMPLE 53

Step A:

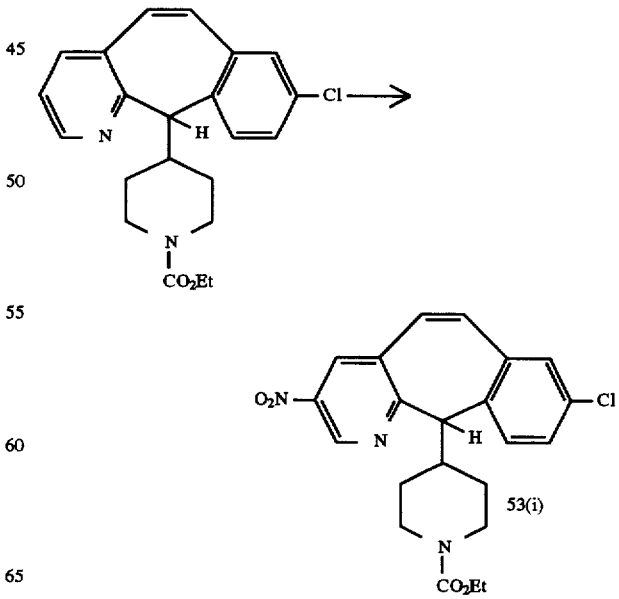

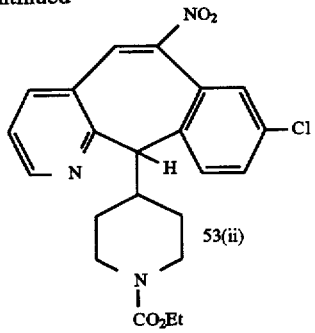

Combine 14.95 g (39 mmol) of the Product of Preparative Example 34A and 150 mL of $CH_2Cl_2$, then add 13.07 g (42.9 mmol) of $(nBu)_4NNO_3$ and cool the mixture to 0° C. Slowly add (dropwise) a solution of 6.09 mL (42.9 mmol) of TFAA in 20 mL of $CH_2Cl_2$ over 1.5 hours. Keep the mixture at 0° C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 53(i) and 53(ii), respectively.

Mass Spec. for compound 53(i): $MH^+$=428.2;

Mass Spec. for compound 53(ii): $MH^+$=428.3

Step B:

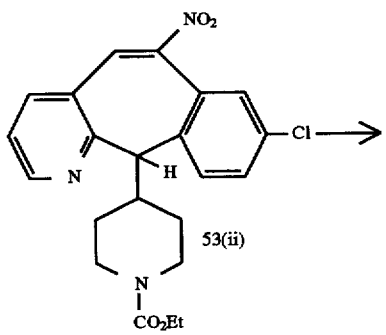

The compound 53(ii) from Step A (0.20 g) is hydrolyzed via substantially the same procedure as described for Example 356, Step A, to give 0.16 g of the product compound.

Using the starting compound indicated and substantially the same procedure as described in Preparative Example 53, Step B, the following product compound is prepared:

| Starting Compound | Compound | Analytical Data |
|---|---|---|
| Preparative Example 53, Step A, compound 53(i) | Preparative Example 53A 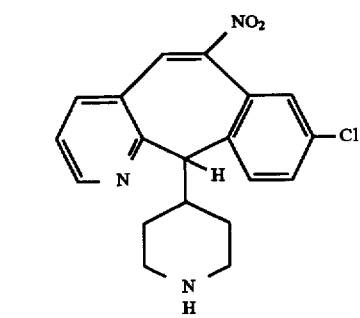 | — |
| Preparative Example 54, Step B, compound 54(ii) | Preparative Example 53B | Mass Spec.: $MH^+$ = 466.9 |
| Preparative Example 54, Step B, compound 54(i) | Preparative Example 53C | Mass Spec.: $MH^+$ = 466.9 |

PREPARATIVE EXAMPLE 54

Step A:

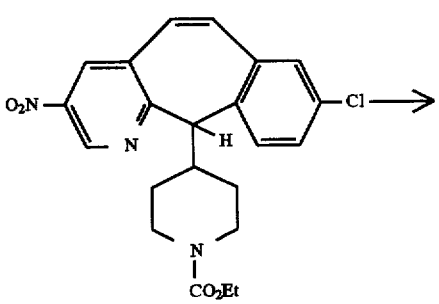

-continued

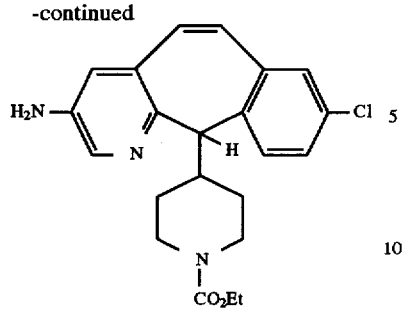

Combine 22.0 g (51.4 mmol) of the product 53(i) from Preparation 53, Step A, 150 mL of 85% EtOH (aqueous), 25.85 g (0.463 mole) of Fe powder and 2.42 g (21.8 mmol) of $CaCl_2$, and heat at reflux overnight. Add 12.4 g (0.222 mole) of Fe powder and 1.2 g (10.8 mmol) of $CaCl_2$ and heat at reflux for 2 hours. Add another 12.4 g (0.222 mole) of Fe powder and 1.2 g (10.8 mmol) of $CaCl_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, $MeOH/CH_2Cl_2$ gradient) to give 16.47 g of the product compound.

Step B:

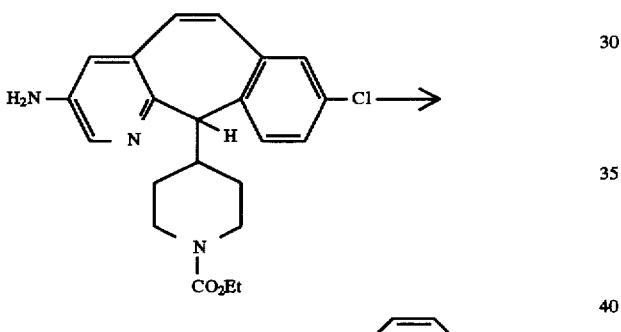

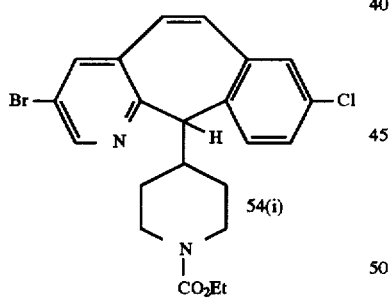

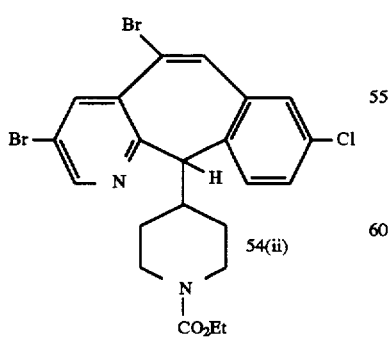

Combine 16.47 g (41.4 mmol) of the product compound from Preparative Example 54, Step A, and 150 mL of 48% HBr (aqueous) and cool to −3° C. Slowly add (dropwise) 18 mL of bromine, then slowly add (dropwise) a solution of 8.55 g (0.124 mole) of $NaNO_3$ in 85 mL of water. Stir for 45 minutes at −3° to 0° C., then adjust to pH=10 by adding 50% NaOH (aqueous). Extract with EtOAc, wash the extracts with brine and dry the extracts over $Na_2SO_4$. Concentrate to a residue and chromatograph (silica gel, EtOAc/hexane gradient) to give 10.6 g and 3.28 g of the two product compounds 54(i) and 54(ii), respectively.

Mass Spec. for compound 54(i): $MH^+=461.2$;

Mass Spec. for compound 54(ii): $MH^+=539$

PREPARATIVE EXAMPLE 55

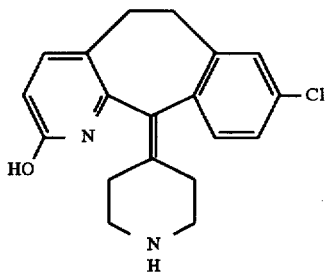

The title compound is known and is prepared by the procedure described in *Bioorg. & Med. Chem. Lett.*, 3, (No. 6) 1073–1078 (1993).

PREPARATIVE EXAMPLE 56

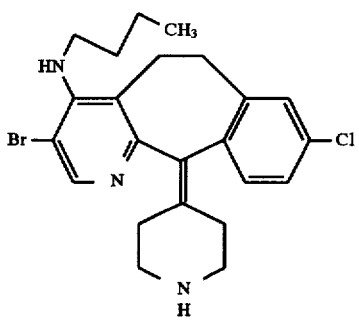

Step A:

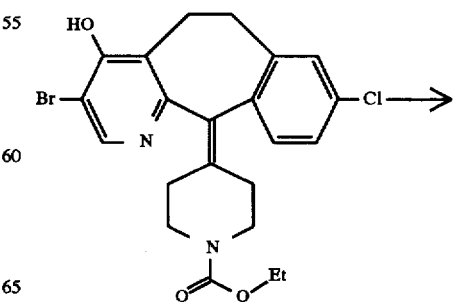

137

-continued

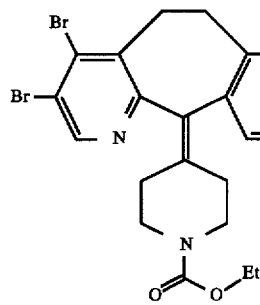

Combine 2.04 g of the product of Preparative Example 44, 1.3 mL of PBr₃, 1.0 mL of Et₃N and 20 mL of CH₂Br₂, and heat the mixture at reflux overnight. Cool the mixture, dilute with CH₂Cl₂ and wash with 1N NaOH (aqueous). Dry over MgSO₄ and concentrate in vacuo to give 1.22 g (53% yield) of the product compound. Mass Spec.: MH⁺=541

Step B:

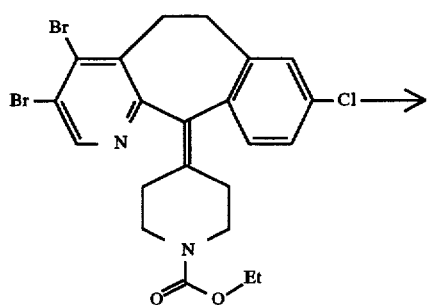

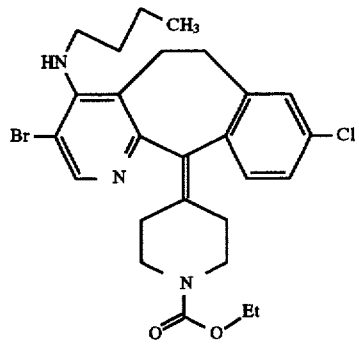

Combine 0.3 g of the product compound from Preparative Example 56, Step A, and 8 mL of n-butylamine and stir at 120° C. in a sealed tube for 48 hours. Concentrate in vacuo to a residue and purify by preparative plate chromatography (silica gel, 1.5–2.5% MeOH/CH₂Cl₂) to give 80 mg (27%) yield of the product compound. Mass Spec.: MH⁺=534

138

Step C:

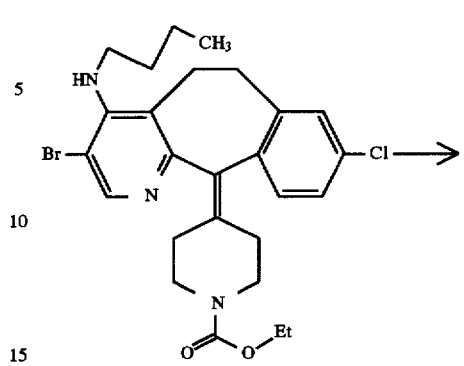

Combine 66 mg of the product compound from Preparative Example 56, Step B, 4 mL of anhydrous EtOH, and 15 mL of concentrated HCl stir at reflux for 60 hours. Cool the reaction mixture to about 0° C. and basify by the adding KOH. Extract with CH₂Cl₂, dry the extract over MgSO₄, and concentrate in vacuo to give 46 mg (81% yield) of the product compound. Mass Spec.: MH⁺=462

PREPARATIVE EXAMPLE 57

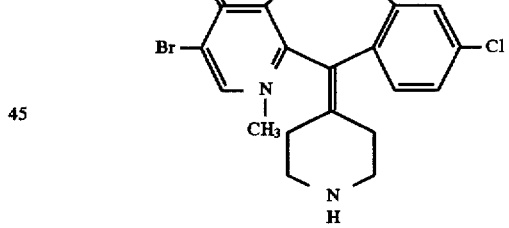

Step A:

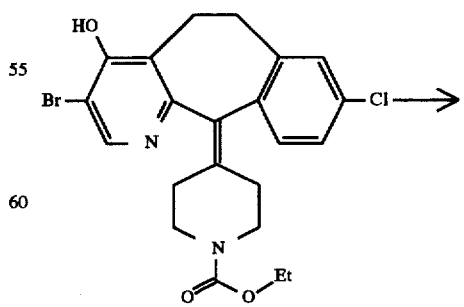

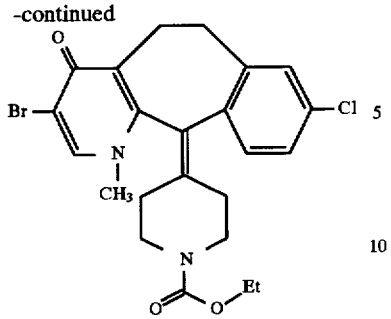

Combine 1.19 g of the product of Preparative Example 44, 10 mL of anhydrous DMF, 0.2 g of NaH (60% in mineral oil) and 0.19 mL of methyl iodide, and stirr at room temperature overnight. Concentrate in vacuo to a residue, dilute the residue with $CH_2Cl_2$, wash with saturated $NaHCO_3$ (aqueous), and dry over $MgSO_4$. Concentrate in vacuo to give 1.13 g (92% yield) of the product compound. Mass Spec.: $MH^+=493$.

Step B:

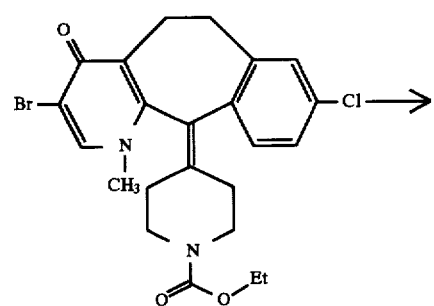

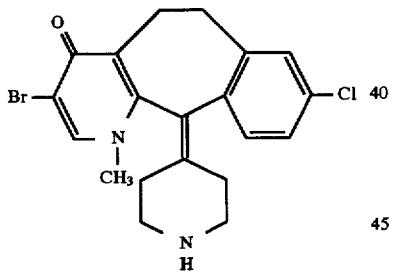

Hydrolyze 1.13 g of the product of Step A via substantially the same procedure as describe for Preparative Example 56, Step C, to give 0.61 g (63% yield) of the product compound.

PREPARATIVE EXAMPLE 58

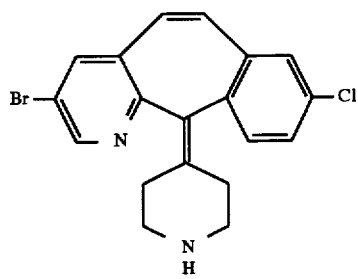

Step A:

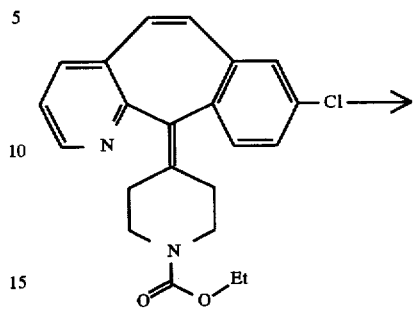

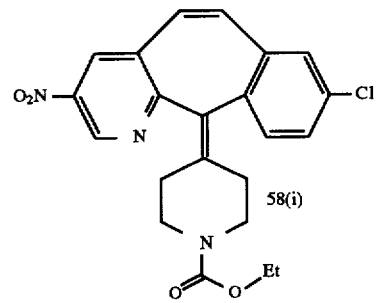

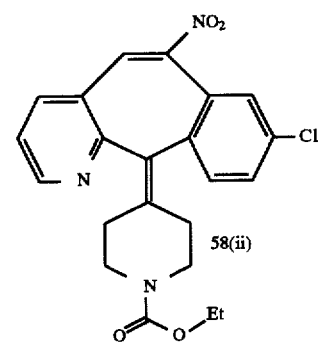

Combine 1.07 g (3.52 mmol) of tetrabutylammonium nitrate, 4 mL of anhydrous $CH_2Cl_2$ and 0.743 g (3.52 mmol) of TFAA, and add the resulting mixture to a solution of 1.22 g (3.20 mmol) of the title compound of Preparative Example 37 in 8 mL of anhydrous $CH_2Cl_2$ at room temperature. Stir at room temperature overnight, then wash with 20 mL of saturated $NaHCO_3$ (aqueous) and 20 mL of brine, and dry over $MgSO_4$. Concentrate in vacuo and chromatograph the resulting residue (silica gel, EtOAc/hexane) to give 0.216 g of the product compound 58(i) and 0.27 g of the product compound 58(ii).

Analytical data for Compound 58(i): Mass Spec. $MH^+=$ 426.

Analytical data for Compound 58(i): m.p. 97.5°–99.2° C.

Step B:

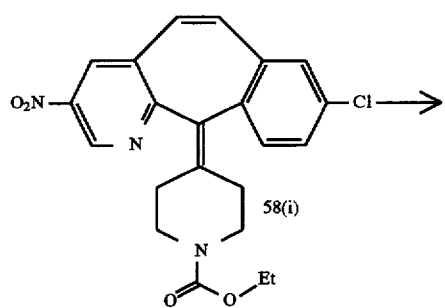

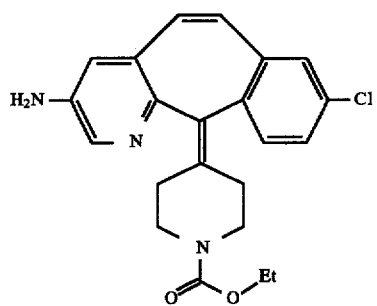

Reduce the product 58(i) from Step A via essentially the same procedure as described in Preparative Example 47, Step B, to give the product compound. Mass Spec.: MH$^+$= 396

Step C:

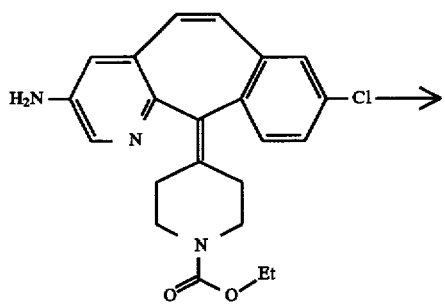

React the product from Step B with HBr and bromine via essentially the same procedure as described in Preparative Example 47, Step C, to give the product compound. Mass Spec.: MH$^+$=459

Step D:

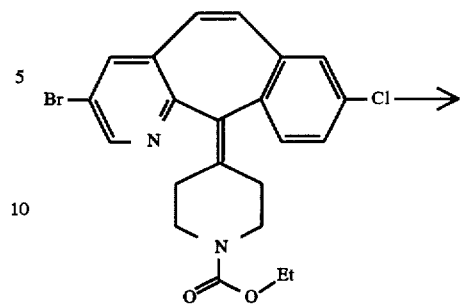

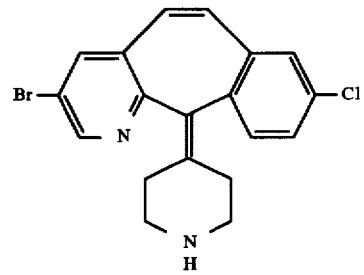

Hydrolyze 0.83 g of the product from Step C via essentially the same procedure as described in Preparative Example 56, Step C, to give 0.56 g of the product compound. Mass Spec.: MH$^+$=387

PREPARATIVE EXAMPLE 59

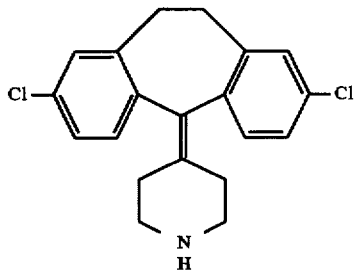

Step A:

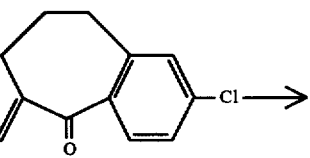

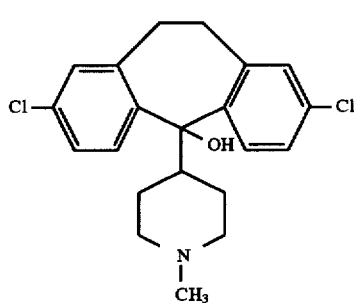

Combine 7.3 g (26.4 mmol) of the starting ketone (see *J. Med. Chem.*, 4238 (1992)) and 230 mL of THF and cool to 0° C. Add a solution of 32.2 mmol) of N-methyl-piperidine- 4-magnesium bromide in 26 mL of THF and stir at 0°–5° C. for 4 hours. Add 400 mL of EtOAc, wash with saturated NH₄Cl (aqueous), and dry over MgSO₄. Concentrate in vacuo to a residue, add ~200 mL of CH₂Cl₂ and stir for 0.5 hours. Filter to collect the resulting solid and concentrate the filtrate to a volume of ~100 mL and let sit at 5° C. for 18 hours. Filter and combine the solids to obtain a total of 7 g (19.4 mmol) of the product compound. m.p.=153.7°–158° C.; Mass Spec.: (CI) MH⁺=376

Step B:

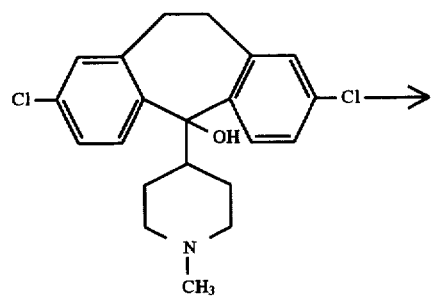

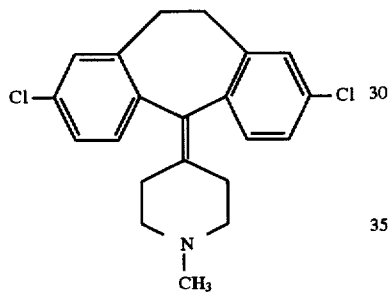

Combine 5 g of the product from Step A and 30 mL of TFA at ambient temperature and stir for 1 hour. Concentrate in vacuo to a residue, dissolve the residue in CH₂Cl₂ and wash with a saturated NaHCO₃ (aqueous). Concentrate in vacuo to give 4.64 g of the product compound. m.p.= 136.7°–138° C.; Mass Spec.: (FAB) MH⁺=358.1

Step C:

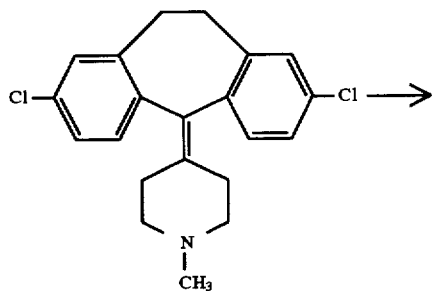

-continued

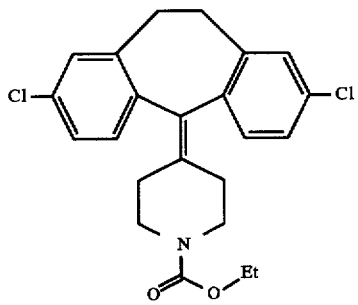

Combine 0.6 g (1.75 mmol) of the product of Step B and 25 mL of toluene, add 0.73 mL (5.27 mmol) of Et₃N and 1.34 mL (14 mmol) of ClCO₂Et, and heat to 80° C. for 2 hours. Add 0.7 mL more of ClCO₂Et, heat for 1 more hour, then cool to 25° C. and concentrate in vacuo to a residue. Dissolve the residue in EtOAc and wash with 1N NaOH (aqueous) followed by brine. Dry over MgSO₄, concentrate in vacuo to a residue and chromatograph (silica gel, 10% EtOAc/hexanes) to give 0.55 g of the product compound. Mass Spec.: (FAB) MH⁺=416.2

Step D:

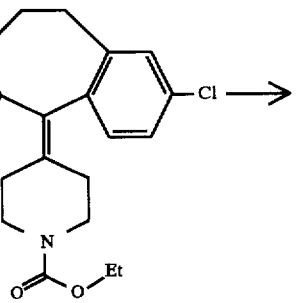

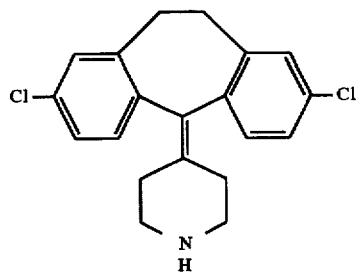

Dissolve 5 g (12.5 mmol) of the product of Step C in 30% HBr in HOAc and heat at 40° C. for 24 hours, then cautiously add the mixture to cold 25 % NaOH (aqueous). Extract with CH₂Cl₂ (3×100 mL), concentrate the extracts to a residue and chromatograph (silica gel, 5% to 30% MeOH/CH₂Cl₂) to give 2.18 g of the product compound. m.p.= 159.5°–160.8° C.; Mass Spec.: (FAB) MH⁺=344.1

PREPARATIVE EXAMPLE 60

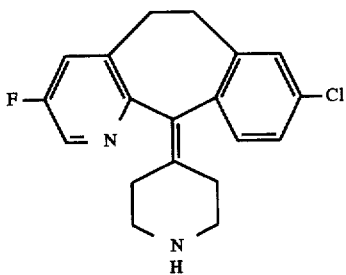

Step B:

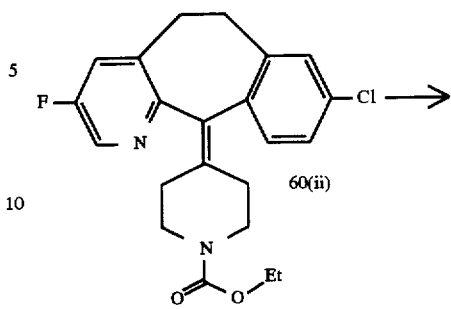

Step A:

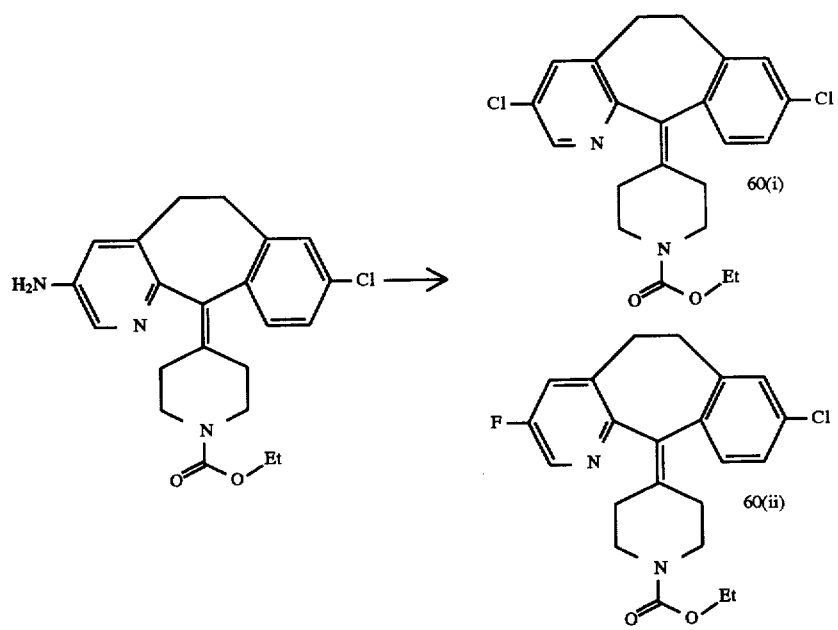

Combine 16.25 g (40.83 mmol) of the product of Preparative Example 47, Step B, and a slurry of 7.14 g (61.11 mmol) of $NOBF_4$ in 100 mL of $CH_2Cl_2$ and stir the mixture for 3 hours. Add 100 mL of o-dichlorobenzene and heat for 5 hours, distilling the $CH_2Cl_2$ from the mixture. Concentrate in vacuo to a residue, add 200 mL of $CH_2Cl_2$ and wash with water (2×200 mL). Dry over $MgSO_4$, concentrate in vacuo to a residue, and chromatograph (silica gel, 20% EtOAc/hexane) to give 4.1 g of product compound 60(i) and 4.01 g of Product compound 60(ii).

Analytical data for compound 60(i): Mass Spec.: $MH^+$=418

Analytical data for compound 60(ii): Mass Spec.: $MH^+$=401

Hydrolyze 3.4 g of the product 60(ii) from Step A via essentially the same process as described for Example 358, Step A, to give 3.01 g of product compound. Mass Spec.: $MH^+$=329

Using the starting compound indicated and substantially the same procedure as described in Preparative Example 60, Step B, the following product compound is prepared:

| Starting Compound | Compound | Analytical Data |
|---|---|---|
| Preparative Example 60, Step A, compound 60(i) | 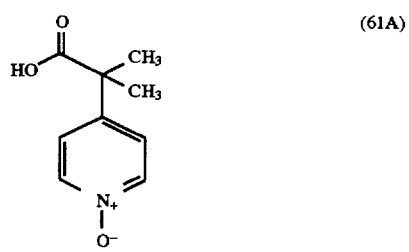<br>Preparative Example 60A | Mass Spec.: MH⁺ = 346 |

PREPARATIVE EXAMPLE 61

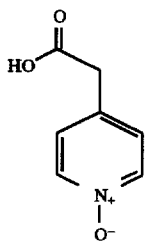

Step A:

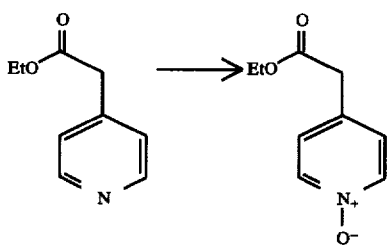

Combine 10 g (60.5 mmol) of ethyl 4-pyridylacetate and 120 mL of dry CH$_2$Cl$_2$ at −20° C., add 10.45 g (60.5 mmol) of MCPBA and stir at −20° C. for 1 hour and then at 25° C. for 67 hours. Add an additional 3.48 g (20.2 mmoles) of MCPBA and stir at 25° C. for 24 hours. Dilute with CH$_2$Cl$_2$ and wash with saturated NaHCO$_3$ (aqueous) and then water. Dry over MgSO$_4$, concentrate in vacuo to a residue, and chromatograph (silica gel, 2%–5.5% (10% NH$_4$OH in MeOH)/CH$_2$Cl$_2$) to give 8.12 g of the product compound. Mass Spec.: MH⁺=182.15

Step B:

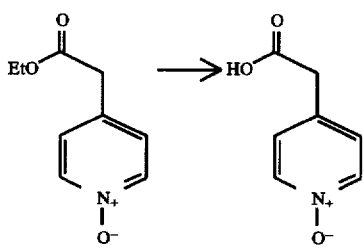

Combine 3.5 g (19.3 mmol) of the product of Step A, 17.5 mL of EtOH and 96.6 mL of 10% NaOH (aqueous) and heat the mixture at 67° C. for 2 hours. Add 2N HCl (aqueous) to adjust to pH=2.37 and concentrate in vacuo to a residue. Add 200 mL of dry EtOH, filter through celite® and wash the filter cake with dry EtOH (2×50 ml). Concentrate the combined filtrates in vacuo to give 2.43 g of the title compound.

Using the product of Preparative Example 26 and substantially the same procedure as described for Preparative Example 61, Steps A and B, the following compound was prepared:

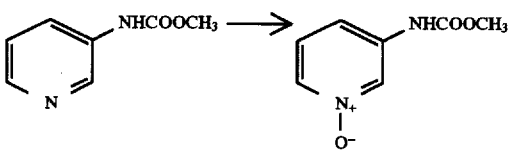

(61A)

PREPARATIVE EXAMPLE 62

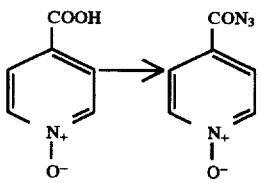

Combine 10 g (65.7 mmol) of 3-methoxycarbonylaminopyridine and 150 mL of CH$_2$Cl$_2$, cool to 0° C. and slowly add (dropwise) a solution of 13.61 g (78.84 mmol) of MCPBA in 120 mL of CH$_2$Cl$_2$ at 0° C. over a period of 1 hour. Stir the mixture at 25° C. for 5 days, then wash with saturated NaHCO$_3$ (aqueous), then water and dry over MgSO$_4$. Concentrate in vacuo to a residue and chromatograph (silica gel, 2%–5% (10% NH$_4$OH in MeOH) /CH$_2$Cl$_2$) to give the product compound. Mass Spec.: MH⁺= 169

PREPARATIVE EXAMPLE 63

Combine 5 g (36.0 mmol) of isonicotinic acid 1-N-oxide and 150 mL of anhydrous DMF, add 5.5 mL (39.6 mmol) of Et$_3$N and stir at 0° C. for 0.5 hours. Slowly add (dropwise) 8.5 mL (39.6 mmol) of diphenylphosphoryl azide at 0° C. over 10 minutes, stir at 0° C. for 1 hour and then at 25° C. for 24 hours (as generally described in Pavia, et al., *Journal of Medicinal Chemistry*, 33, 854–861 (1990). Concentrate in vacuo to a residue and chromatograph (silica gel, 0.5%–1% MeOH/CH$_2$Cl$_2$) to give 5.9 g of the product compound.

Using nicotinic acid 1-N-oxide and substantially the same procedure as described for Preparative Example 63 the following compound was prepared:

149

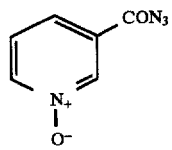 (63A)

PREPARATIVE EXAMPLE 64

Step A:

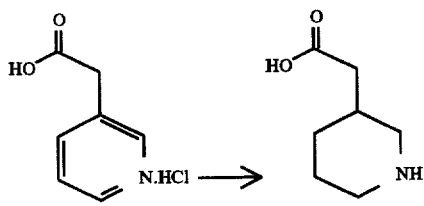

Hydrogenate 25 g (144 mmol) of 3-pyridylacetic acid hydrochloride for 144 hours using the procedure described in Preparative Example 15 to give 20 g of the product compound. Mass Spec.: $MH^+=144$.

Step B:

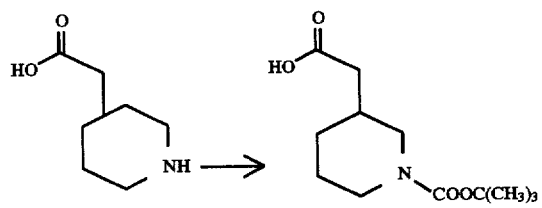

React 12 g (83.8 mmol) of the product of Step B for 148 hours using the procedure described in Preparative Example 13, Step B, to give 17.5 g of the product compound. Mass Spec.: $MH^+=244.25$

PREPARATIVE EXAMPLE 65

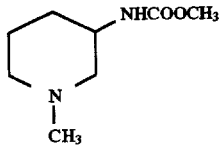

Combine 25 g (164.4 mmol) of methyl 3-pyridylcarbamate and 163.3 mL of 1N HCl (aqueous), stir until all of the solid dissolves, then hydrogenate over 10% Pd/C at 25° C. at 55 psi for 220 hours. Filter, wash the solids with water and treat the combined filtrates with 150 mL of BioRad AG1X8 ion exchange resin (OH⁻). Filter, wash the resin with water and concentrate the filtrate to a volume of 100 mL. Add 16.43 mL (197.3 mmol) of 37% formalin and hydrogenate over 10% Pd/C at 25° C. at 55 psi for 89 hours. Filter, wash the solids with water and concentrate in vacuo to give 24.3 g of the title compound. Mass Spec.: $MH^+=173.2$

150

PREPARATIVE EXAMPLE 66

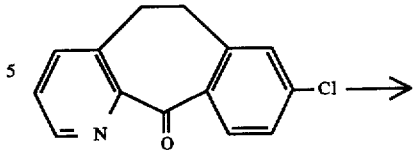

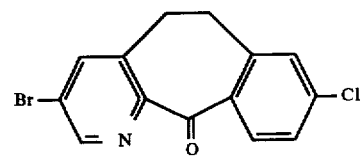

Cool 50.0 g (20.5 mmol) of 8-chloro-5,6-dihydro-11H-benzo[5,6]cyclohepta[1,2-b]pyridin-11-one to 0° C., slowly add 75 mL (93.69 mmol) of sulfur monochloride over 20 minutes, then slowly add 25 mL (48.59 mmol) of $Br_2$ over 15. Heat at 95° C. for 20 hour, add 12.5 mL (24.3 mmol) of $Br_2$ and heat for a another 24 hours. Cool the mixture, and slowly add to a mixture of $CH_2Cl_2$ and 1N NaOH (aqueous) at 0° C. Wash the organic phase with water, dry over $MgSO_4$ and concentrate in vacuo to a residue. Chromatograph the residue (silica gel, 500 mL $CH_2Cl_2$ then 0.2%–5% (10% $NH_4OH$ in MeOH)/$CH_2Cl_2$), then chromatograph again (silica gel, 3%–8.5% EtOAc/hexane) to give 8.66 g of the product compound. Mass Spec.: $MH^+=322$

PREPARATIVE EXAMPLE 67

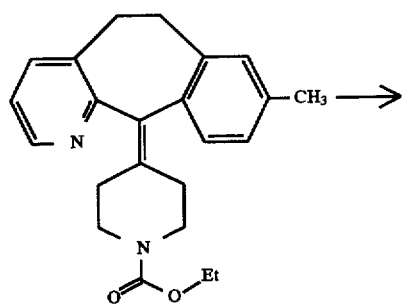

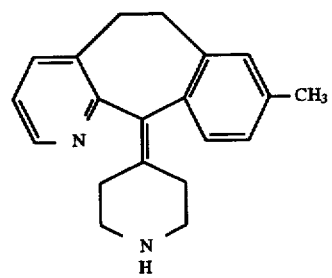

Dissolve 0.16 g (0.46 mmol) of 4-(8-methyl-5,6-dihydro-11H-benzo[5,6]cyclohepta[1,2-b]pyridin-11-ylidine)-1-ethoxycarbonylpiperidine, in 2 mL EtOH and add 4 mL of 12N HCl. Heat the solution for 3 hours at 85° C., then cool to 25° C. Adjust to pH=10 with 50% NaOH (aqueous) and extract several times with 50 mL of EtOAc. Combine the organic layers, dry them over $MgSO_4$, and concentrate in vacuo to give the product compound.

PREPARATIVE EXAMPLE 68

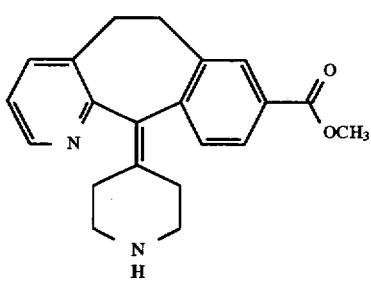

Step A:

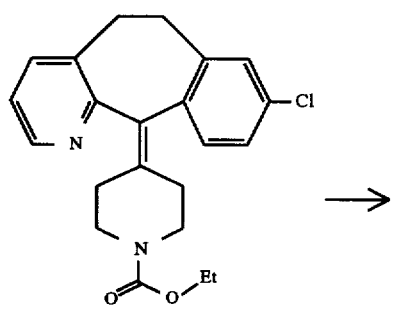

Dissolve 2 g (5.22 mmol) of the title compound of Preparative Example 1F in 2.6 mL of dry N-methyl-2-pyridone. Add 0.87 g (9.4 mmol) of CuCN and 0.139 g (0.93 mmol) of sodium iodide. Heat the mixture at 200° C. under nitrogen for 20 hours, cool to 25° C. and repeatedly grind and mix with five 50 mL portions of CH$_2$Cl$_2$ and 7M NH$_4$OH (aqueous). Wash the organic layer with 7M NH$_4$OH until the organic layer is no longer blue or green. Dry the combined organic layers over MgSO$_4$ and concentrate in vacuo to a residue. Chromatograph (silica gel 70% EtOAc/hexane), then recrystallize from EtOAc/hexane to give the product compound. m.p.=152.4°–153.5° C.; Mass Spec.: MH$^+$=374

Step B:

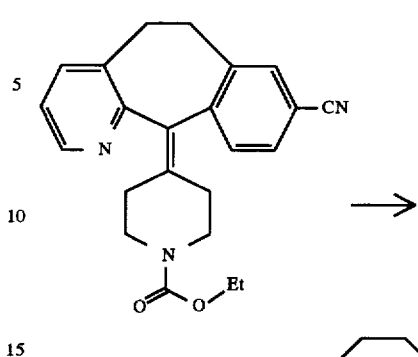

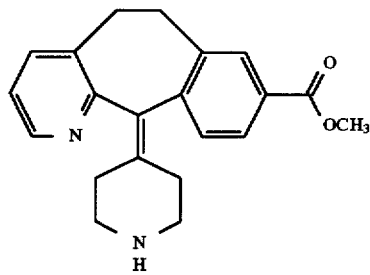

Dissolve 4.08 g (10.93 mmol) of the product of Step A in 12M HCl and heat at 85° C. for 18 hours. Concentrate in vacuo to a residue. Dissolve the residue in 175 mL of MeOH, saturate with HCl gas, and heat at reflux for 18 hours. Concentrate in vacuo to give the product compound as its HCl salt. Mass Spec.: MH$^+$=335

PREPARATIVE EXAMPLE 68

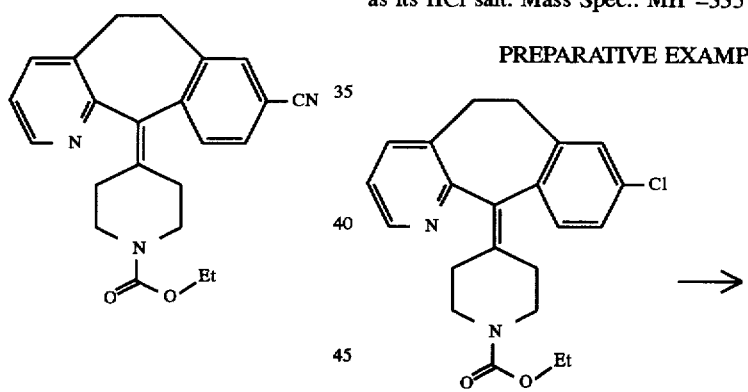

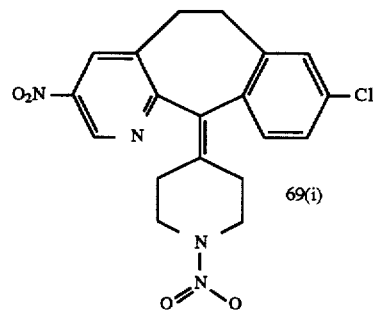

69(i)

153
-continued

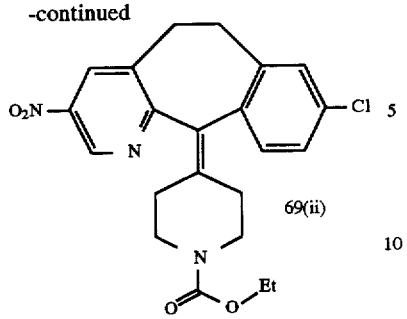
69(ii)

Combine 75 g (0.196 mole) of the Product of Example 1, Step F, and 300 mL of $CH_2Cl_2$ at 0° C., and slowly add (dropwise) a solution of 72 g (0.236 mole) of tetrabutylammonium nitrate and 35 mL (0.247 mole) of TFAA in 500 mL of $CH_2Cl_2$. Stir at 25° C. overnight, slowly add (dropwise) 1 L of saturated $NaHCO_3$ (aqueous). Separate the layers, wash the organic phase with brine and dry over $MgSO_4$. Concentrate in vacuo to a residue, chromatograph twice (1 kg silica gel, gradient of $EtOAc/CH_2Cl_2$) to give 8.63 g of product compound 69(i), and 34 g of product compound (ii). Recrystallize compound 69(i) from $CH_2Cl_2$/hexane to give the purified product compound 69(i). m.p.=186°–187° C.; Mass Spec.: (FAB) $MH^+$=401

PREPARATIVE EXAMPLE 69

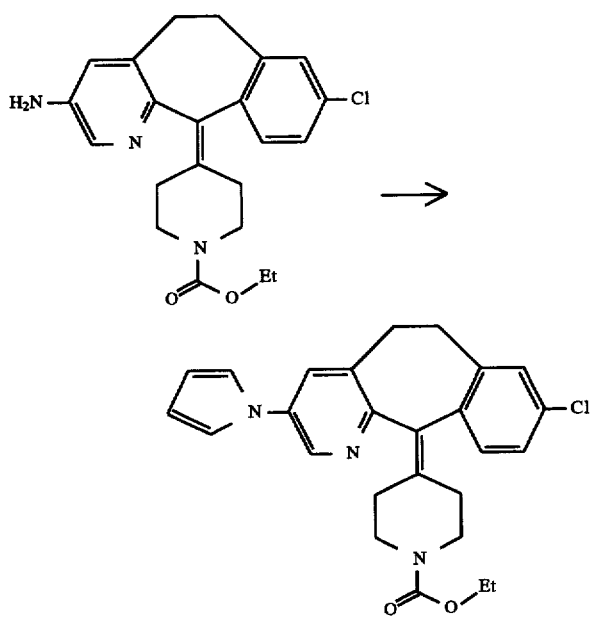

Combine 0.4 g (1 mmol) of the Product of Example 47, Step B, and 0.2 mL (1.2 mmoles) of 2,5-diethoxytetrahydrofuran in 3 mL of glacial HOAc, and heat at reflux for 1.5 hours. Cool the mixture, wash with saturated $NaHCO_3$ (aqueous), then with brine, dry over $MgSO_4$, and concentrate in vacuo to a residue. Chromatograph (silica gel, 5%–15% $EtOAc/CH_2Cl_2$) to give 0.34 g of the product compound. Mass Spec.: (FAB) $MH^+$=448

154
PREPARATIVE EXAMPLE 70

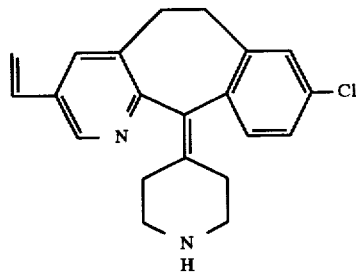

Step A:

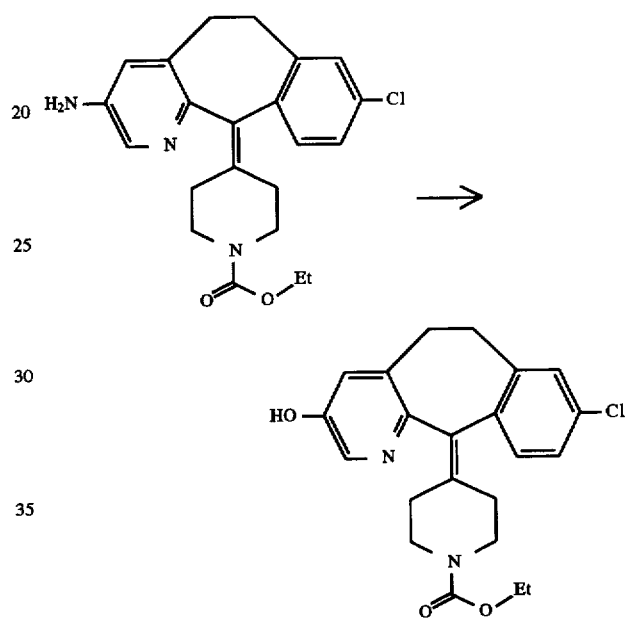

Combine 13.8 g (34.7 mmol) of the Product of Example 47, Step B, and 90 mL of water at 0° C., add a solution of 6.9 mL of concentrated $H_2SO_4$ in 45 mL of water and stir the mixture. Slowly add (dropwise) a solution of 2.55 g (40 mmol) of $NaNO_2$ in 75 mL of water and stir at 0°–5° C. for 0.5 hours. Add a boiling solution of 35.1 g $CuSO_4$ in 135 mL of water and heat at 100° C. for 15 min. Cool the mixture, extract with $CH_2Cl_2$ (2×200 mL), wash the extracts with brine, dry over $MgSO_4$, and concentrate in vacuo to a residue. Chromatograph (silica gel, 1.5%–10% MeOH/$CH_2Cl_2$) to give 11.36 g of the product compound.

Step B:

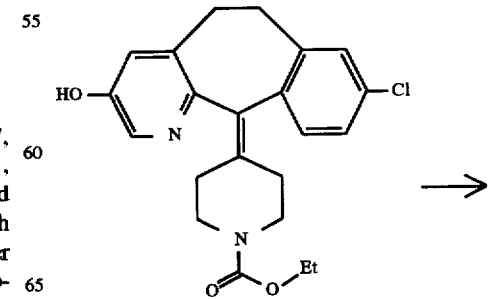

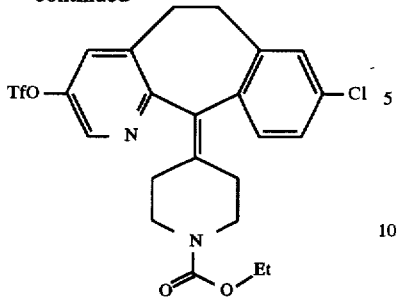

Combine 11.36 g (28.5 mmol) of the Product of Step A and 12.4 g (34.7 mmol) of N-phenyltriflimide in 120 mL of dry $CH_2Cl_2$ at 0° C., add 4.6 mL (33 mmol) of $Et_3N$ and stir at 25° C. overnight. Concentrate in vacuo to a residue and chromatograph (silica gel, 2%–5% $EtOAc/CH_2Cl_2$) to give 10.95 g of the product compound. Recrystallize from hot MeOH. m.p.=154.5°–156° C.; Mass Spec.: (FAB) $MH^+$=531

Step C:

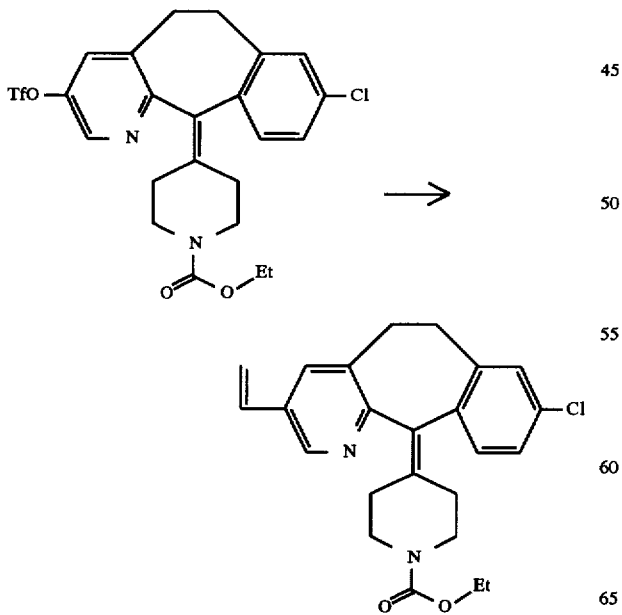

Combine 12.2 g (23 mmol) of the Product of Step B and 85 mL of 1-methyl-2-pyrrolidinone at 25° C., then add 2.84 g LiCl, 0.212 g of trisfurylphosphine and 0.585 g of dipalladiumtribenzylideneacetone and stir for 15 min. Slowly add (dropwise) 7.5 mL (25.77 mmol) of tributylvinyltin and stir at 25° C. for 2.5 hours. Dilute with 500 mL of water at 0° C. and extract with 6700 mL of EtOAc. Filter the organic phase through celite®, wash the celite with EtOAc, then wash the filtrate twice with 30% NaF (aqueous). Filter the organic solution wash with brine and dry over $MgSO_4$. Concentrate in vacuo to a residue and chromatograph (silica gel, 15%–40% EtOAc/hexane) to give 8.58 g of the product compound. Mass Spec.: (FAB) $MH^+$=409

Using the stannane indicated, the following compounds were prepared via substantially the same procedure as described for Preparative Example 70, Step C:

| Starting Compound | Product Compound | Analytical Data |
|---|---|---|
| 2-(tributylstannyl)-thiophene and Preparative Example 70 Step B | Preparative Example 70-A | m.p. = 155°–157° C. Mass Spec.: $MH^+$ = 465 |

Step D:

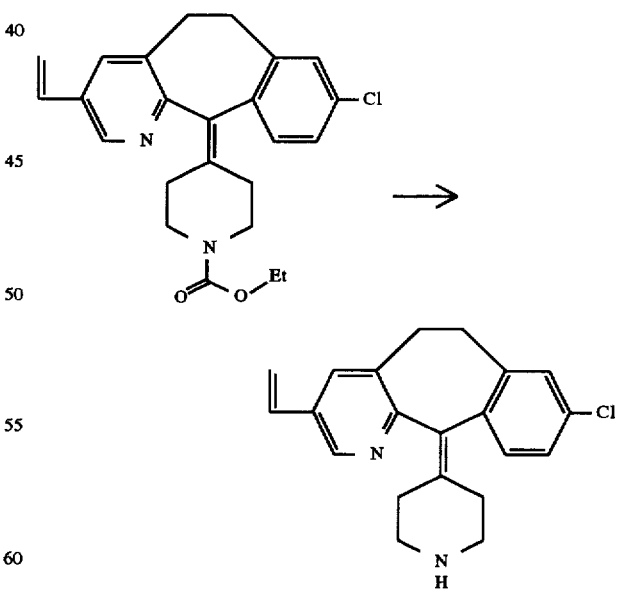

Hydrolyze 1.18 g (2.89 mmol) of the product of Step C via substantially the same procedure as described in Example 358, Step A, to give 0.95 g of the product compound. Mass Spec.: (FAB) $MH^+$=337

PREPARATIVE EXAMPLE 71

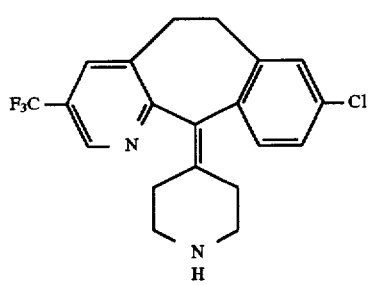

Step A:

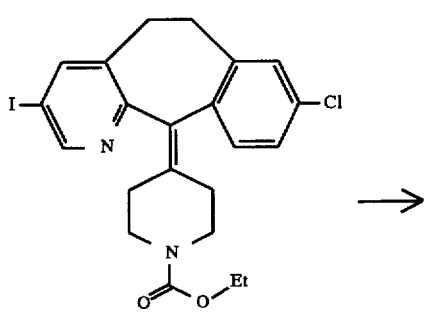

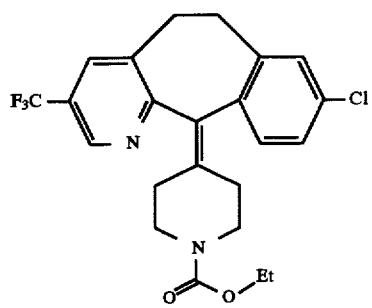

Combine 1.01 g (19.9 mmol) of the Product of Example 48, Step A, 30 mL of DMF, 1.33 g (6.96 mmol) of methyl 2,2-difluoro-2-(fluorosulfonyl)acetate and 0.75 g (3.97 g) of CuI. Heat the mixture at 60°–80° C. for 3 hours, then concentrate to a residue. Dilute the residue with water, extract with $CH_2Cl_2$, and concentrate in vacuo to a residue. Chromatograph (silica gel, 30% EtOAc/hexane, then 10% MeOH/$CH_2Cl_2$+$NH_4OH$) to give 0.15 g of the product compound. Mass Spec.: $MH^+$=451.1

Step B:

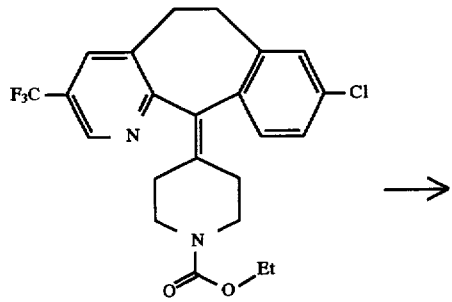

-continued

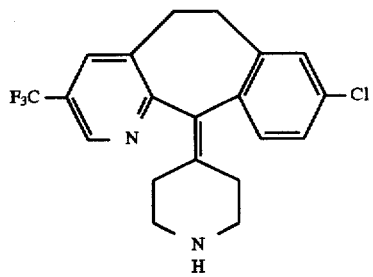

Hydrolyze the product of Step A using essentially the same procedure as described in Preparative Example 1, Step G, to give the product compound. Mass Spec.: $MH^+$=379

PREPARATIVE EXAMPLE 72

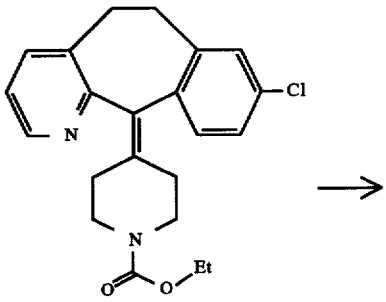

Step A:

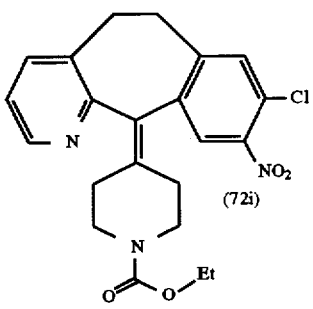

(72i)

+

-continued

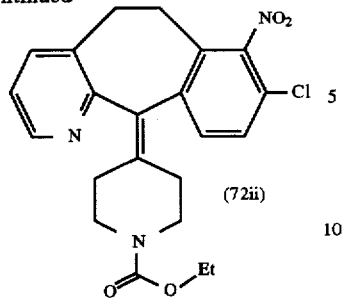

(72ii)

Dissolve 20 g (50 mmol) of the Product of Example 1, Step F, in 400 mL of concentrated H₂SO₄, cool to –5° C. and add 5.1 g (50 mmol) of KNO₃ in small portions. Stir for 3 hours, cool the mixture and slowly basify with 50% NaOH (aqueous). Extract with CH₂Cl₂ (3×500 mL), dry the combined extracts over MgSO₄, and concentrate in vacuo to a residue. Chromatograph (silica gel, 50% EtOAc/hexane) to give 16.33 g of the product compound (72i) and 2.6 g of the product compound (72ii).

For product compound (72i), Mass Spec.: MH⁺=428.
For product compound (72ii), Mass Spec.: MH⁺=428.

Step B:

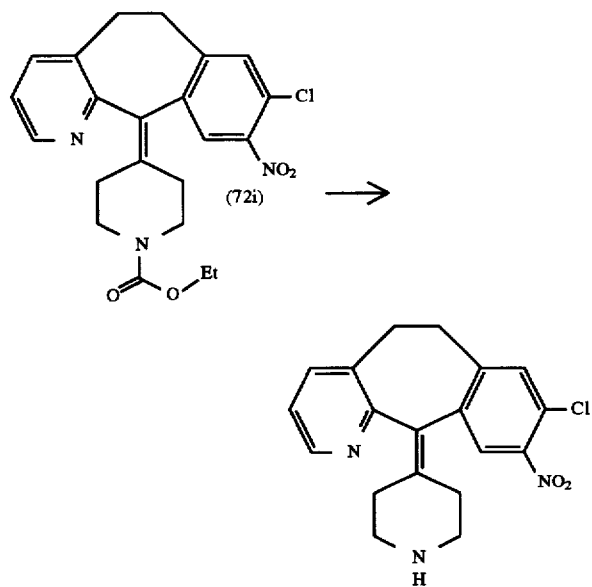

Hydrolyze 5.46 g (12.76 mmol) of the Product of (72i) from Step A, via substantially the same procedure as described for Example 358, Step A, to give 4.34 g of the product compound. Mass Spec.: MH⁺=356

PREPARATIVE EXAMPLE 73

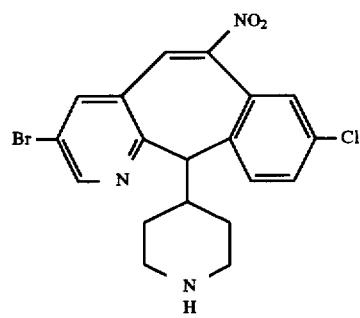

Step A:

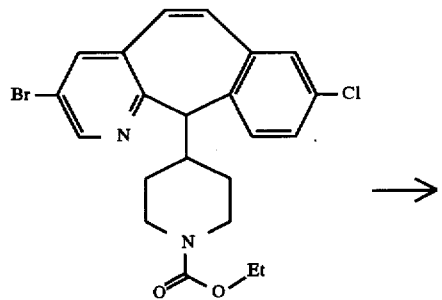

Combine 1.6 g of the Product (54i) of Preparative Example 54, Step B, 12 mL of CH₂Cl₂, and 1.16 g of tetrabutylammonium nitrate, cool to 0° C. and slowly add (dropwise) a solution of 0.8 g of TFAA in 2 mL of CH₂Cl₂. Stir for 6 hours at 0° C., let the mixture stand at 0° C. overnight, then wash successively with saturated NaHCO₃ (aqueous), water and brine, and dry over Na₂SO₄. Concentrate in vacuo to a residue, then chromatograph (silica gel, 30% EtOAc/hexane) to give 0.38 g of the product compound.

Step B:

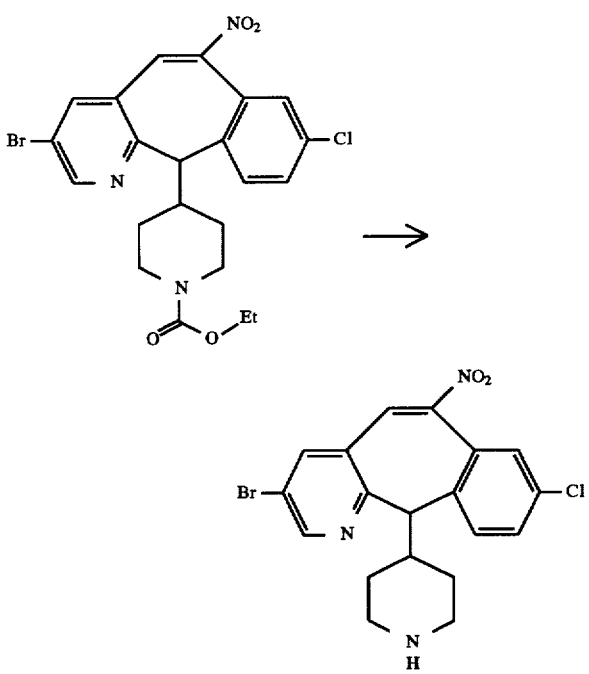

Hydrolyze 0.38 g of the Product of Step A via substantially the same procedure as described for Example 358, Step A, to give 0.235 g of the product compound.

EXAMPLE 1

1-(4-PYRIDYLACETYL)-4-(8-CHLORO-5,6-DIHYDRO-11H-BENZO[5,6]CYCLOHEPTA[1,2-b]PYRIDIN-11-YLIDENE)PIPERIDINE

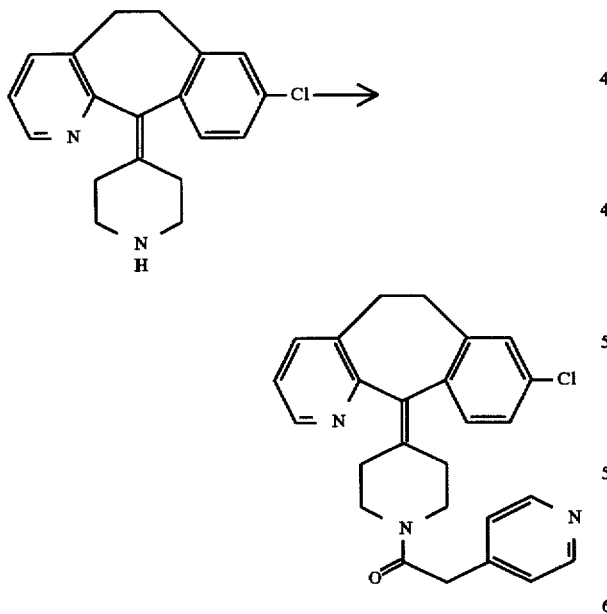

To a mixture of 528 mg (1.7 mmol) of 4-(8-chloro-5,6-dihydro-11H-benzo[5,6]cyclohepta [1,2-b]pyridin-11-ylidene)piperidine (product from Preparative Example 1, Step G), 274 mg (1.7 mmol) of 4-pyridylacetic acid hydrochloride, and 242 mg (1.8 mmol) of HOBT in 5 mL of dry $CH_2Cl_2$ at $-15°$ C. and under a nitrogen atmosphere was added dropwise 0.17 mL (1.5 mmol) of $Et_3N$ followed by a solution of 363 mg (1.9 mmol) of DEC in 5 mL of dry $CH_2Cl_2$. The reaction mixture was slowly allowed to warm to room temperature. After 4 hours the mixture was poured into water and extracted several times with $CH_2Cl_2$. The combined organic portions were dried over $MgSO_4$, filtered, and concentrated in vacuo to give a product which was purified via flash chromatography (3% MeOH saturated with ammonia in $CH_2Cl_2$) 155 mg of 1-(4-pyridylacetyl)-4-(8-chloro-5,6-dihydro-11H-benzo[5,6]cyclohepta[1,2-b]pyridin-11-ylidene)piperidine as a solid: mp 152°–155° C.

By essentially the same procedure as set forth in Example 1, but using the carboxylic acids set forth in column 1, of Table 2 below, in place of 4-pyridylacetic acid, one can obtain the compounds listed in column 2 of Table 2. The compounds listed in Table 2 refer to compounds of Formula 500.00:

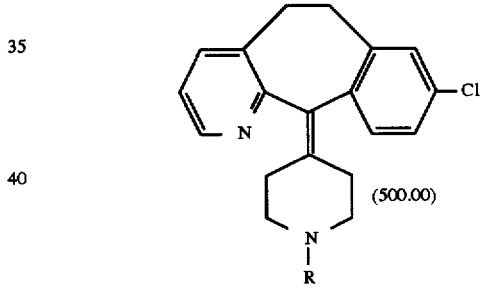

(500.00)

wherein R is the substituent in Column 2.

TABLE 2

| EXAMPLE | COLUMN 1 | COLUMN 2 | COMPOUND |
|---|---|---|---|
| 2 | 2-(pyridin-3-yl)acetic acid | 1-(pyridin-3-yl)propan-2-one | glass |
| 3 | 2-(1,3-dioxoisoindolin-2-yl)acetic acid | 2-(2-oxopropyl)isoindoline-1,3-dione | white powder |
| 4 | (2S,3S)-2-(4-fluorophenyl)-1-methyl-6-oxopiperidine-3-carboxylic acid | (2S,3S)-3-acetyl-2-(4-fluorophenyl)-1-methylpiperidin-6-one | white solid |
| 5 | 4-oxocyclohexane-1-carboxylic acid | 4-acetylcyclohexan-1-one | white crystals mp 200° C. |
| 6 | 2-(pyridin-2-yl)acetic acid | 1-(pyridin-2-yl)propan-2-one | mp 122–125° C. |
| 7 | 4-hydroxybenzoic acid | 1-(4-hydroxyphenyl)ethan-1-one | — |
| 8 | 3,4-dihydroxybenzoic acid | 1-(3,4-dihydroxyphenyl)ethan-1-one | off white powder |
| 9 | propiolic acid | but-3-yn-2-one | glass |
| 10 | 4-nitrobenzoic acid | 1-(4-nitrophenyl)ethan-1-one | white solid |
| 11 | 4-phenylbutanoic acid | 5-phenylpentan-2-one | white solid |

TABLE 2-continued

| EXAMPLE | COLUMN 1 | COLUMN 2 | COMPOUND |
|---|---|---|---|
| 12 | HOOC-CH₂-S-(pyrimidin-2-yl) | CH₃-CO-CH₂-S-(pyrimidin-2-yl) | glass |
| 13 | 4-(methoxycarbonyl)benzoic acid | methyl 4-acetylbenzoate | white solid |
| 14 | pyridazine-4-carboxylic acid | 4-acetylpyridazine | glass |
| 15 | isonicotinic acid (pyridine-4-carboxylic acid) | 4-acetylpyridine | mp 176–178° C. |
| 16 | 1H-pyrrole-3-carboxylic acid | 3-acetyl-1H-pyrrole | glass |
| 17 | 4-(dimethylamino)benzoic acid | 4'-(dimethylamino)acetophenone | mp 200–204° C. |
| 18 | 1H-pyrazole-4-carboxylic acid | 4-acetyl-1H-pyrazole | glass |
| 19 | tetrahydrofuran-2-carboxylic acid | 2-acetyltetrahydrofuran | glass |
| 20 | 4-hydroxy-7-methyl-1,8-naphthyridine-3-carboxylic acid | 3-acetyl-4-hydroxy-7-methyl-1,8-naphthyridine | yellow solid |
| 21 | 4-aminobenzoic acid | 4'-aminoacetophenone | off white solid |

TABLE 2-continued
| EXAMPLE | COLUMN 1 | COLUMN 2 | COMPOUND |
|---|---|---|---|
| 22 | 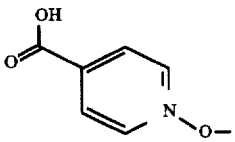 | 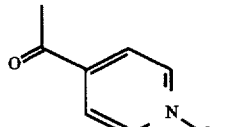 | white solid<br>mp 228° C. (dec) |
| 23 | 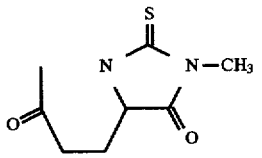 | 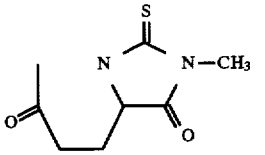 | white solid<br>mp 205–207° C. |
| 24 | 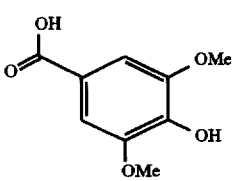 | 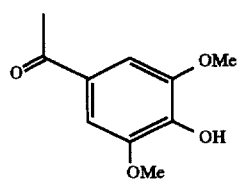 | white powder |
| 25 | 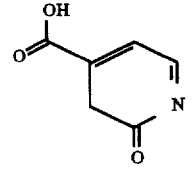 | 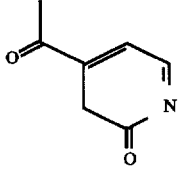 | white powder |
| 26 | 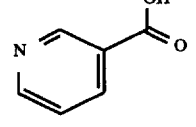 | 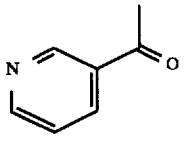 | glass |
| 27 | 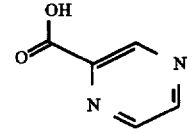 | 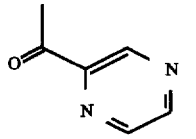 | glass |
| 28 | 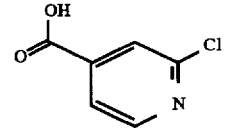 | 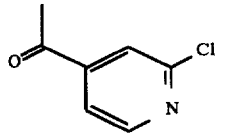 | glass |
| 29 | 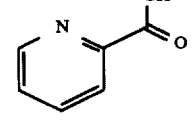 | 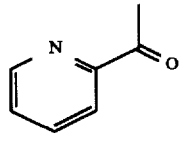 | glass |
| 30 | 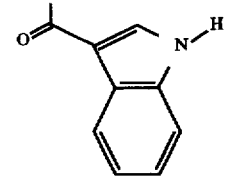 | 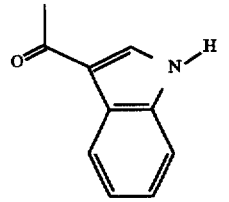 | mp<br>211–215° C. |

TABLE 2-continued

| EXAMPLE | COLUMN 1 | COLUMN 2 | COMPOUND |
|---|---|---|---|
| 31 | 4-hydroxy-3,5-dinitrobenzoic acid | 1-(4-hydroxy-3,5-dinitrophenyl)ethanone | yellow solid |
| 32 | isoquinoline-4-carboxylic acid | 1-(isoquinolin-4-yl)ethanone | white solid |
| 33 | 2,6-dihydroxypyrimidine-5-carboxylic acid | 1-(2,6-dihydroxypyrimidin-5-yl)ethanone | white solid |
| 34 | 2-(2-(N-oxido)pyridinyl)acrylic acid | 1-(2-(2-(N-oxido)pyridinyl)allyl)ethanone | glass |
| 35 | 6-oxo-1,4,5,6-tetrahydropyridazine-3-carboxylic acid | 1-(6-oxo-1,4,5,6-tetrahydropyridazin-3-yl)ethanone | solid mp 190–193° C. |
| 36 | 1-methyl-6-oxo-1,6-dihydropyridine-3-carboxylic acid | 1-(1-methyl-6-oxo-1,6-dihydropyridin-3-yl)ethanone | solid |
| 37 | 2-chloro-6-methyl-1-oxidopyridine-4-carboxylic acid | 1-(2-chloro-6-methyl-1-oxidopyridin-4-yl)ethanone | glass |
| 38 | quinoline-4-carboxylic acid | 1-(quinolin-4-yl)ethanone | white solid |
| 39 | 2-(5-oxotetrahydrofuran-2-yl)acetic acid | 1-(5-oxotetrahydrofuran-2-yl)ethanone | glass |

TABLE 2-continued

| EXAMPLE | COLUMN 1 | COLUMN 2 | COMPOUND |
|---|---|---|---|
| 40 | indole-2-carboxylic acid | 2-acetylindole | mp 218–220° C. |
| 41 | 2-phenyl-3-hydroxypropanoic acid | 1-phenyl-3-hydroxy-propan-2-one (with CH on phenyl carbon) | light brown solid mp = 92.7–93° C. MS M+ = 459 |
| 42 | 2,2-diphenylacetic acid | 1,1-diphenylpropan-2-one | white solid mp = 114.2–115.8° C. MS M+ = 506 |
| 43 | 4-bromophenylacetic acid | 1-(4-bromophenyl)propan-2-one | white solid mp = 93.3–94.6° C. MS M+ = 506 |
| 44 | phenylacetic acid | 1-phenylpropan-2-one | white solid mp = 112–114.6° C. MS M+ = 428 |
| 45 | 3-nitrophenylacetic acid | 1-(3-nitrophenyl)propan-2-one | white solid mp = 94.3–95.5° C. MS M+ = 474 |
| 46 | N-CBZ-tyrosine | N-CBZ-tyrosine methyl ketone | white solid mp = 126.5–127.5° C. MS M+ = 607 |
| 47 | 4-methylphenylacetic acid | 1-(4-methylphenyl)propan-2-one | white solid mp = 83.6–85.0° C. |
| 48 | 2-phenylbutanoic acid | 3-phenylbutan-2-one | white solid mp = 82.7–83.8° C. MS M+ = 456 |
| 49 | 4-methoxyphenylacetic acid | 1-(4-methoxyphenyl)propan-2-one | white solid MS M+ = 534 |
| 49a | glycolic acid | hydroxyacetone | white solid mp = 73.5–73.8° C. |

TABLE 2-continued

| EXAMPLE | COLUMN 1 | COLUMN 2 | COMPOUND |
|---|---|---|---|
| 288 | 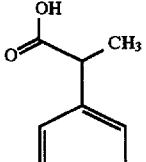<br>Preparative Ex. 25 | 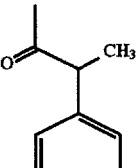 | white solid<br>MH+ 452 |
| 299 | 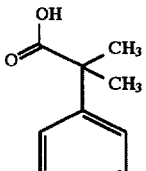<br>Preparative Ex. 26 | 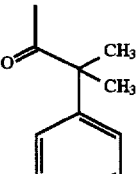 | off white solid<br>MH+ 459 |
| 300 | 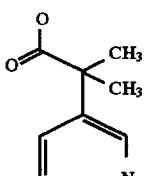<br>Preparation Ex. 10 | 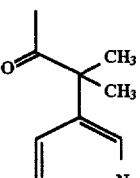 | white solid<br>MH+ 459 |

EXAMPLE 50

1-(2-THIOPHENEACETYL)-4-(8-CHLORO-5,6-DIHYDRO-11H-BENZO[5,6]CYCLOHEPTA[1,2-b]PYRIDIN-11-YLIDENE)PIPERIDINE

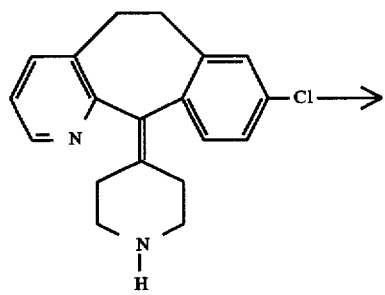

To a solution of 1.0 gm (3.22 mmole) of 4-(8-chloro-5,6-dihydro-11H-benzo[5,6]cyclohepta[1,2-b] pyridin-11-ylidene)piperidine and 0.29 mL of pyridine in 20 mL of dry CH$_2$Cl$_2$ at 0° C. and under an argon atmosphere was added dropwise 0.438 mL (3.55 mmol) of 2-thiopheneacetyl chloride. After 30 minutes the mixture was washed with 1.0N aqueous NaOH and then brine. The organic portion was dried over Na$_2$SO$_4$, filtered and converted in vacuo to provide a residue which was purified via flash chromatography (3% MeOH in CH$_2$Cl$_2$) and treated with activated carbon to provide the title compound as a glass.

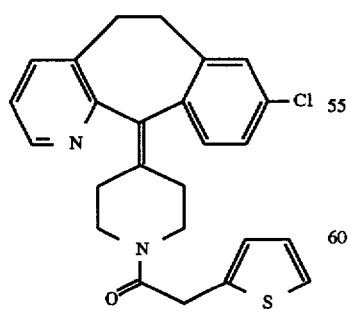

EXAMPLE 51

By essentially the same procedure as set forth in Example 50, but using the acid chlorides set forth in Column 1, in Table 3 below, in place of 2-thiopheneacetyl chloride, one can obtain the compounds listed in Column 2 of Table 3. The compounds listed in Table 3 refer to compounds of Formula 500.00:

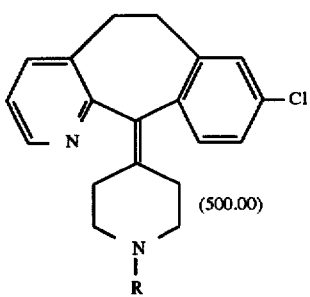

(500.00)

wherein R is the substituent in Column 2

TABLE 3

| EXAMPLE | COLUMN 1 | COLUMN 2 | COMPOUND |
|---------|----------|----------|----------|
| 52 |  |  | solid |
| 53 | 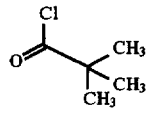 | 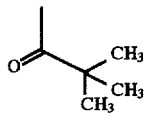 | solid<br>mp<br>158–160° C. |
| 54 | 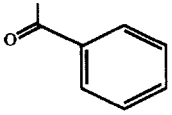 | 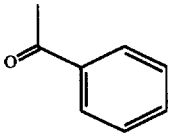 | glass |
| 55 | 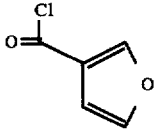 | 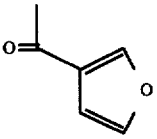 | white powder |
| 56 | 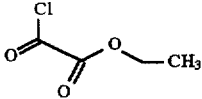 | 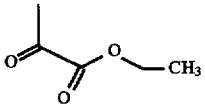 | solid<br>mp<br>126–128° C. |
| 57 | 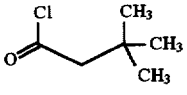 | 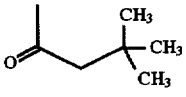 | solid<br>mp<br>137–139° C. |
| 58 | 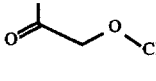 | 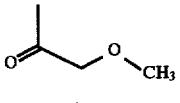 | solid<br>mp<br>104–106° C. |
| 59 |  |  | white solid<br>mp<br>155–157° C. |

EXAMPLE 65

By essentially the same procedures as set forth in Example 50 above, or Example 4 of U.S. Pat. No. 5,089,496, but using

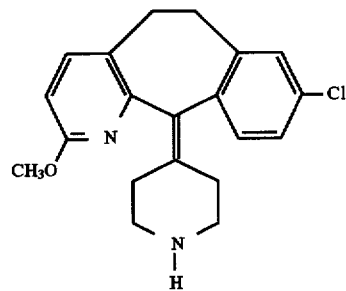

in place of 4-(8-chloro-5,6-dihydro-11 H-benzo[5,6]cyclohepta[1,2-b]pyridin-11ylidene)piperidine, one can obtain the compound

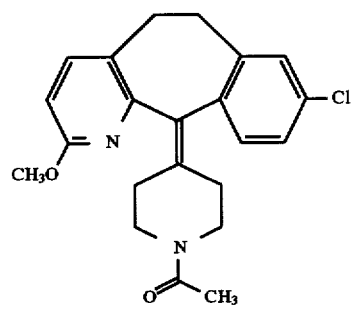

as a white solid.

EXAMPLE 75

1-(8-CHLORO-5,6-DIHYDRO-11H-BENZO[5,6]CYCLO-HEPTA[1,2-b]PYRIDIN-11-YL-4-(4-PYRIDYLACETYL)-PIPERAZINE

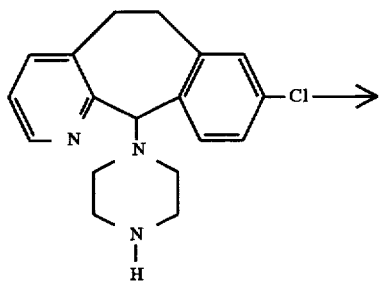

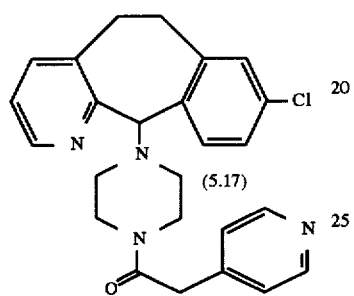
(5.17)

To a mixture of 8.5 g (27.2 m mole) of 8-chloro-11-(1-piperazinyl)-6,11-dihydro-5H-benzo[5,6]cyclohepta[1,2-b]pyridine (Preparative Example 7) in 256 mL of anhydrous DMF at room temperature and under an argon atmosphere was added 2.98 g (27.2 m mole of 4-methylmorpholine, 7.81 g (27.2 m mole) of DEC, 3.68 g (27.2 m mole) of HOBT, and 3.72 g (27.2 m mole) of 4-pyridylacetic acid. The mixture was stirred at room temperature for 22 hours. The mixture was poured into 3300 mL of $CH_2Cl_2$ and washed with 500 mL of water. The aqueous layer was extracted with 500 mL of $CH_2Cl_2$. The combined organic portions were dried over $MgSO_4$, filtered, and concentrated in vacuo. The residue was purified by silica gel column chromatography using a solution of 1.5% (10% $NH_4OH$ in MeOH) in $CH_2Cl_2$. The product was obtained as a white amorphous solid, M.S. (Mass Spec) M+=433.

By essentially the same procedures as set forth in Example 75 above but using the compounds set forth in Column 1, Table 4 below, in place of 4-pyridylacetic acid, one can obtain compounds of the formula

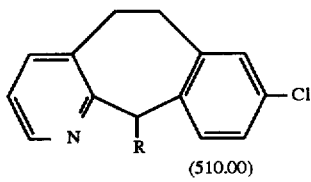
(510.00)

wherein R is as listed in Column 2 of Table 4.

TABLE 4

| EX. | COLUMN 1 | COLUMN 2 | CMPD |
|---|---|---|---|
| 76 | ![structure with OH, carbonyl, phthalimide] | ![piperazine with N-methyl and phthalimide acetyl] | white amorphous solid Mass Spec M+ = 501 |
| 77 | ![4-bromophenylacetic acid] | ![piperazine with N-methyl and 4-bromophenylacetyl] | white amorphous solid Mass Spec M+ = 512 |
| 78 | ![3-pyridylacetic acid] | ![piperazine with N-methyl and 3-pyridylacetyl] | white amorphous solid Mass Spec M+ = 433 |

TABLE 4-continued

| EX. | COLUMN 1 | COLUMN 2 | CMPD |
|---|---|---|---|
| 79 | (diphenylacetic acid structure) | (N-methylpiperazine with diphenylacetyl group) | white amorphous solid Mass Spec M+ = 508 |
| 80 | (phenylacetic acid structure) | (N-methylpiperazine with phenylacetyl group) | white amorphous solid Mass Spec M+ = 432 |
| 81 | (structure with OH, NH, SH, CH₃) | (N-methylpiperazine derivative with SH, CH₃) | white amorphous solid Mass Spec M+ = 459 |

EXAMPLE 82

8-CHLORO-11-[1-(2-(4-PYRIDYL)ACETYL)-4-PIPERIDYL]-6,11-DIHYDRO-5H-BENZO[5,6]CYCLOHEPTA[1,2-b]PYRIDINE

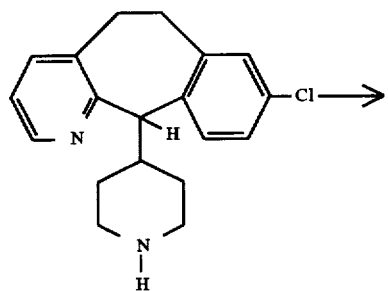

Dissolve 0.1 g (0.32 m mole) of 8-chloro-11-4-piperidyl] -6,11-dihydro-5H-benzo[5,6]cyclohepta[1,2-b]-pyridine (from Example 233), 0.06 g (0.32 m mole) of 4-pyridylacetic acid, 0.092 g (0.48 m mole) of DEC, 0.065 g (0.48 m mole) of HOBT and 0.048 g (0.50 m mole) of N-methyl morpholine in 5 mL of DMF and stir at room temperature for 18 hours under nitrogen. Concentrate under vacuo and partition between 100 mL each of EtOAc and water. Dry the organic layer over sodium sulfate and concentrate under vacuo. The resulting residue is chromatographed on silica gel using 98% dichloro methane and 2% MeOH, saturated with ammonia as the solvent, giving the product as a white waxy solid, mass spec M+=431.

EXAMPLE 82A

8-CHLORO-11-[1-(2-(PYRIDYL)ACETYL)-4-PIPERIDYL]-6,11-DIHYDRO-5H-BENZO[5,6]CYCLOHEPTA[1,2-b]PYRIDINE

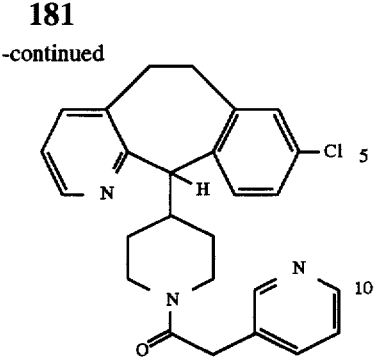

By essentially the same procedure as set forth in Example 82, but using 3-pyridylacetic acid instead of 4-pyridylacetic acid, the title compound is obtained as a white solid (M+= 431, mp=81.7°–82° C.).

EXAMPLE 83

8-CHLORO-11-[1-(2-METHYLSULFONYLOXY-1-PHENYLETHYLCARBONYL)-4-PIPERIDYLIDENE]-6,11-DIHYDRO-5H-BENZO[5,6]CYCLOHEPTA[1,2-b]-PYRIDINE

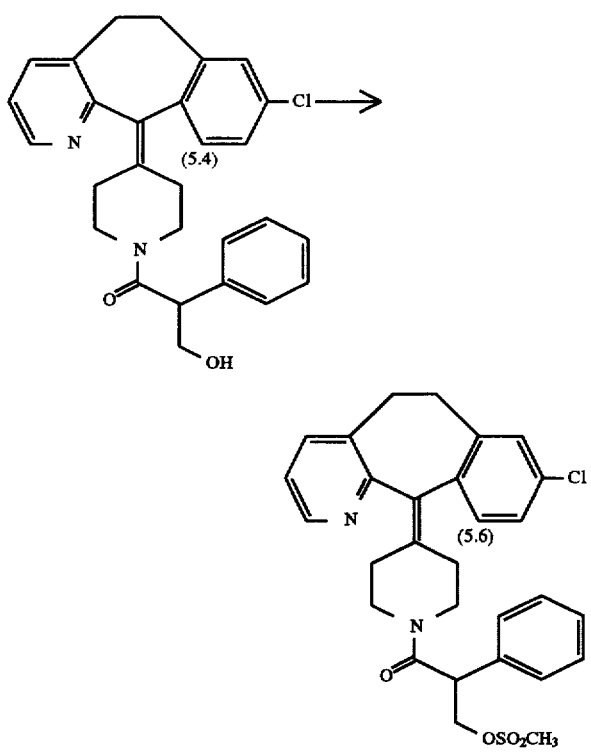

Dissolve 0.40 g (0.9 m mole) of 8-chloro-11-[1-(2-hydroxy-1-phenylethylcarbonyl)-4-piperidylidene]-6,11-dihydro-5H-benzo[5,6]cyclohepta-[1,2-b]pyridine (Example 41 of Table 2) in 10 mL of pyridine and stir under nitrogen. Add 0.15 g (1.3 m mole) of methanesulfonyl chloride and stir for 20 hours. Concentrate under vacuo and triturate the residue with ether. Purify the resulting solid by silica gel chromatography using 2% MeOH saturated with ammonia, and 98% CH$_2$Cl$_2$ as the solvent. The product is obtained as a white solid, mp=110.7°–111.6° C.

EXAMPLE 84

8-CHLORO-11-[1-(2-ACETYLMERCAPTO-1-PHENYLETHYLCARBONYL)-4-PIPERIDYLIDENE]-6,11-DIHYDRO-5H-BENZO[5,6]CYCLOHEPTA[1,2-b]-PYRIDINE

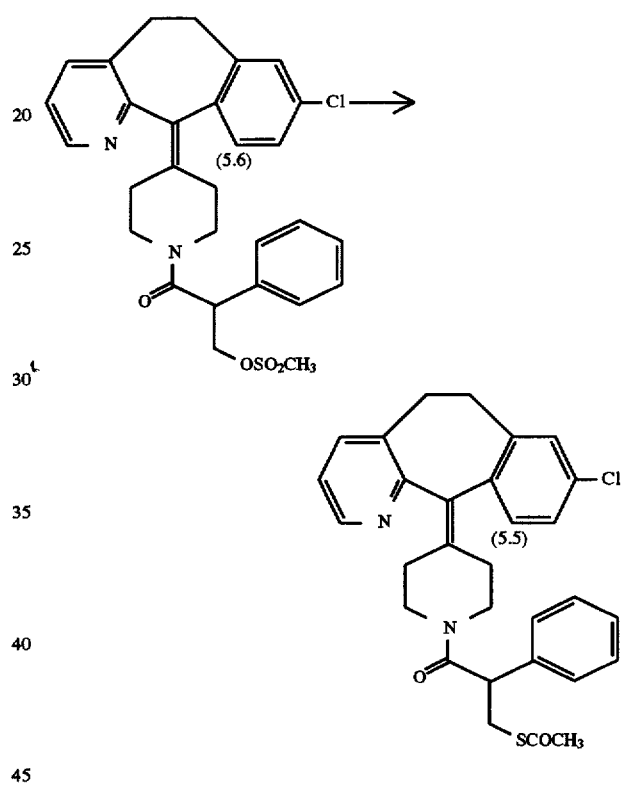

Dissolve 0.3 g (0.56 m mole) of 8-chloro-11-[1-(2-methanesulfonyloxy-1-phenylethylcarbonyl)-4-piperidylidene]-6,11-dihydro-5H-benzo[5,6]cyclohepta-[1,2-b]pyridine (Formula 5.6 of Example 83) in 5 mL of DMF and add 0.2 g (0.6 m mole) of cesium thioacetate (preparation described in Synthetic Communications, 13, 553, 1983). Stir the reaction at 80° C. for twenty hours then concentrate under vacuo. Purify the residue by silica gel chromatography using 70% EtOAc and 30% hexane as the solvent. The product is obtained as a light brown solid, mp=92.7°–93° C.

EXAMPLE 85

8-CHLORO-11-[1-(1-(2,3-DIHYDRO-3-OXO-1,2-BENZOISOTHIAZOL-S,S-DIOXIDE-2-YL)METHYLCARBONYL)-4-PIPERIDYLIDENE]-6,11-DIHYDRO-5H-BENZO[5,6]CYCLOHEPTA[1,2-b]-PYRIDINE

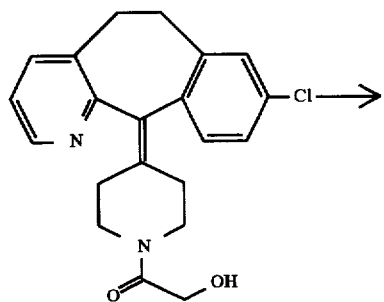

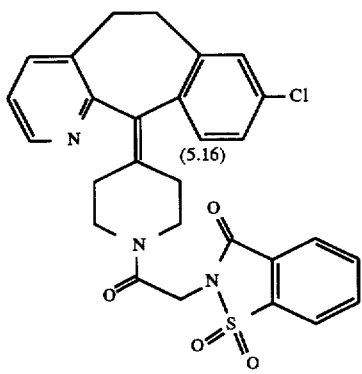
(5.16)

Dissolve 0.46 g (1.7 m mole) of 8-chloro-11-[1-(2-hydroxyethylcarbonyl)-4-piperidylidene]-6,11-dihydro-5H-benzo[5,6]cyclohepta[1,2,b]pyridine (Example 49a of Table 2) in 30 mL of DMF and stir at 0° C. under nitrogen. Add 0.55 g (2.1 m mole) of triphenyl phosphine and 0.36 g (2.1 m mole) of diethyl azodicarboxylate. Stir reaction mixture at 70° C. for 3 days, then concentrate under vacuo. The residue was dissolved in mL of 1N HCl and washed with 100 mL of EtOAc. The water layer was neutralized with 1N NaOH and the mixture was extracted with EtOAc. The organic layer was dried over MgSO₄ and concentrated under vacuo. The residue was purified by silica gel chromatography using 90% EtOAc and 10% hexane as the solvent, giving the product as a white solid, mass spec. M+=534.

EXAMPLE 86

8-CHLORO-11-[1-(1-(3-PYRIDYL)METHYLTHIOCARBONYL)-4-PIPERIDYLIDENE]-6,11-DIHYDRO-5H-BENZO[5,6]CYCLOHEPTA[1,2-b]PYRIDINE

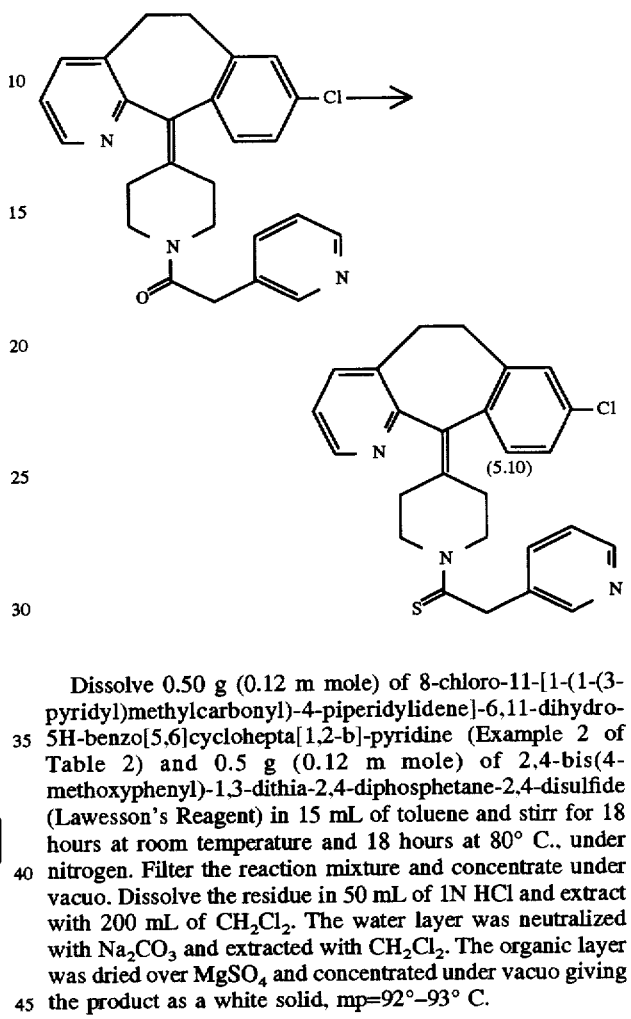

Dissolve 0.50 g (0.12 m mole) of 8-chloro-11-[1-(1-(3-pyridyl)methylcarbonyl)-4-piperidylidene]-6,11-dihydro-5H-benzo[5,6]cyclohepta[1,2-b]-pyridine (Example 2 of Table 2) and 0.5 g (0.12 m mole) of 2,4-bis(4-methoxyphenyl)-1,3-dithia-2,4-diphosphetane-2,4-disulfide (Lawesson's Reagent) in 15 mL of toluene and stirr for 18 hours at room temperature and 18 hours at 80° C., under nitrogen. Filter the reaction mixture and concentrate under vacuo. Dissolve the residue in 50 mL of 1N HCl and extract with 200 mL of CH₂Cl₂. The water layer was neutralized with Na₂CO₃ and extracted with CH₂Cl₂. The organic layer was dried over MgSO₄ and concentrated under vacuo giving the product as a white solid, mp=92°–93° C.

EXAMPLE 87

10,11-DIHYDRO-5-[1-(1-(4-PYRIDYL)METHYLCARBONYL)-4-PIPERIDYLIDENE]-5H-DIBENZO[a,d]CYCLOHEPTENE

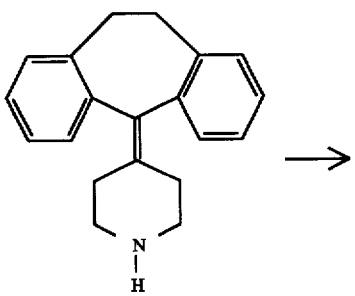

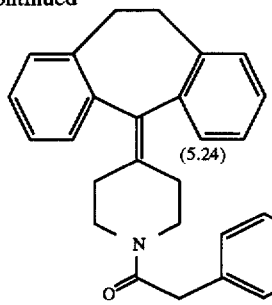

(5.24)

Dissolve 0.15 g (0.6 m mole) of 10,11-dihydro-5-(4-piperidylidene)-5H-dibenzo[a,d]cycloheptene, 0.096 g (0.55 m mole) of 4-pyridylacetic acid hydrochloride, 0.16 g (0.83 m mole) of DEC and 0.075 g (0.55 m mole) of HOBT in 5 mL of DMF and stir at room temperature for 18 hours under nitrogen. Concentrate under vacuo and partition between 100 mL each of EtOAc and 10% aqueous sodium hydrogenphosphate. Dry the organic layer over MgSO₄ and concentrate under vacuo. The resulting residue is chromatographed on silica gel using 98% dichloro methane and 2% MeOH, saturated with ammonia as the solvent, giving the product as a white waxy solid, mp=162.8°–163.4° C.

EXAMPLE 180

1-1-(4-PYRIDINYLACETYL)-4-[3,8-DICHLORO-5,6-DIHYDRO-11H-BENZO[5,6]CYCLOHEPTA[1,2-b]PYRIDIN-11-YLIDENE]PIPERIDINE

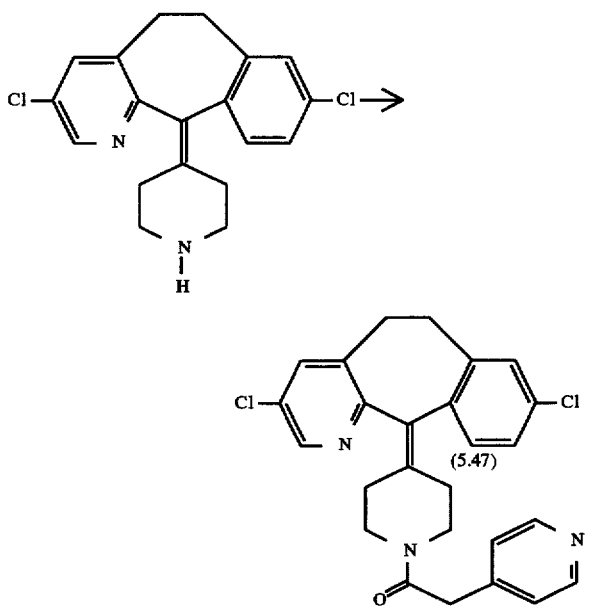

(5.47)

Dissolve 0.18 g (0.51 mmole) of 3,8-dichloro 11-(1-acetyl-4-piperidylidene)-6,11-dihydro-5H-benzo[5,6]cycohepta[1,2-b]pyridine, 0.088 g (0.51 mmole ) 4-pyridylacetic acid, 0.117 g (0.61 mmole) of DEC, 0.082 g (0.61 mmole) HOBT and 0.071 g (0.71 mmole) N-methyl morpholine in 5 mL of DMF and stir for 18 hours under nitrogen. Concentrate under vacuo and partion between EtOAc and water. Dry organic layer over sodium sulfate and concentrate in vacuo. The resulting residue is chromatogaphed on silica gel using 95% CH₂Cl₂ and 5% MeOH, saturated with ammonia as the solvent. The product is obtained as white solid, mp=113°–114° C.

EXAMPLE 181

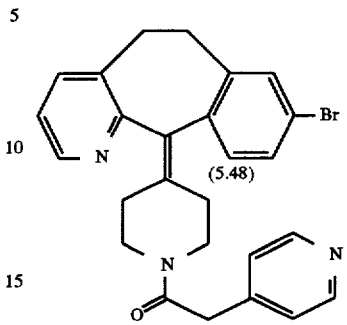

(5.48)

By essentially the same procedure as set forth in Example 180, but using 8-bromo-11-(1-acetyl-4-piperidylidene)-6,11-dihydro-5H-benzo[5,6]cyclohepta[1,2-b]pyridine instead of 3,8-dichloro-11-(1-acetyl-4-piperidylidene)-6,11-dihydro-5H-benzo[5,6]-cyclohepta[1,2-b]pyridine, compound 5.48 was obtained as an off-white solid, mp=94.3°–94.7° C.

EXAMPLE 182

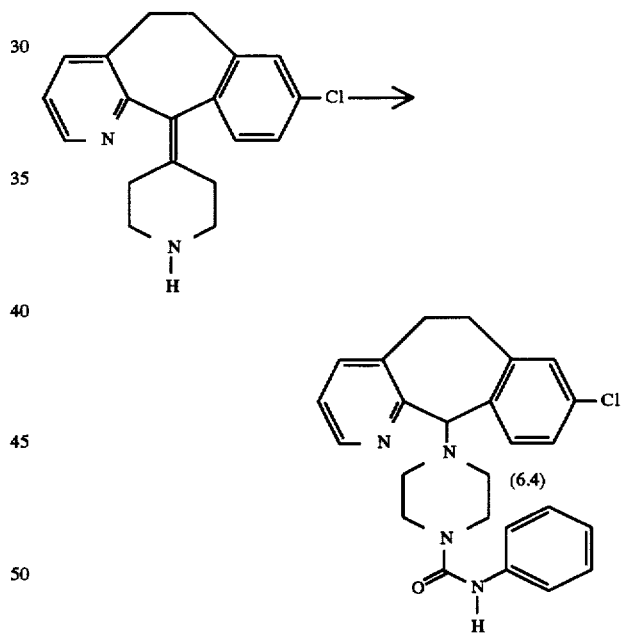

(6.4)

To a stirred solution of phenyl isocyanate (1.27 mmole) in 15 ml of anhydrous CH₂Cl₂ at room temperature and under an argon atmosphere was added dropwise over 20 minutes, a solution of 8-chloro-11-(1-piperazinyl)-6,11-dihydro-5H-benzo[5,6]cyclohepta[1,2-b]pyridine (1.27 mmole) in 5 ml of anhydrous CH₂Cl₂. The mixture was stirred at room temperature for 20 hours. The mixture was poured into 700 ml of CH₂Cl₂ and washed with 100 ml of saturated NaHCO₃. The organic portion was dried over MgSO₄, filtered, and concentrated in vacuo. The residue was purified by silica gel chromatography using a solution of 1.0% (10% NH₄OH in MeOH) in CH₂Cl₂. The product was obtained as a white amorphous solid, M.S. (Mass Spec) M+=433.

EXAMPLE 183

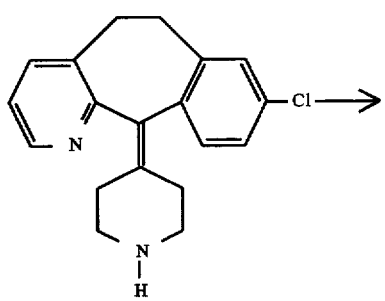

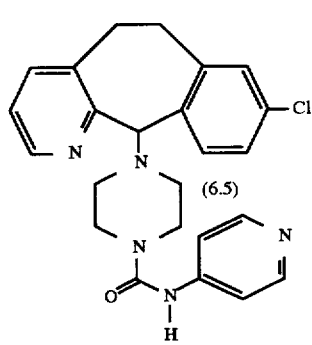

To a 5.0 ml reaction vial was added 8-chloro-11-(1-piperazinyl)-6,11-dihydro-5H-benzo[5,6]cyclohepta[1,2-b]pyridine (1.0 mmole) and N-ethoxycarbonyl-4-aminopyridine (0.99 mmole). The vial was capped and placed in an oil bath at 170° C. and stirred for 5 hours. The residue was purified by silica gel chromatography using a solution of 3.0% (10% NH$_4$OH in MeOH) in CH$_2$Cl$_2$. The product was obtained as a white amorphous solid, M.S. (Mass Spec) M+=434.

EXAMPLE 184

1-(8-CHLORO-6,11-DIHYDRO-5H-BENZO[5,6]CYCLOHEPTA[1,2-b]PYRIDIN-11-YL)-4-(3-PYRIDINYLACETYL)piperazine 1-N-OXIDE

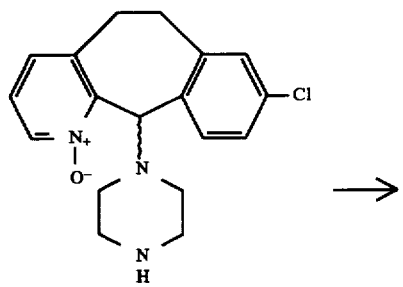

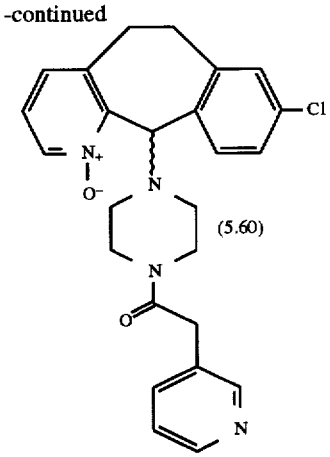

The title compound from Preparative Example 11D (0.5 grams) (1.5 mmoles) was reacted with 3-pyridylacetic acid (0.208 grams) (1.5 mmoles) under the conditions described in Example 75 to give the title compound (Yield: 0.439 grams, 95%, MH$^+$ 449).

EXAMPLE 185

1-(8-CHLORO-6,11-DIHYDRO-5H-BENZO[5,6]CYCLOHEPTA[1,2-b]PYRIDIN-11-YL)-4-(3-PYRIDINYLACETYL 1-N-OXIDE)PIPERAZINE 1-N-OXIDE

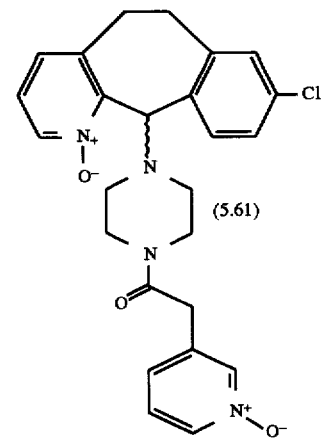

The title compound from Preparative Example 11D (0.5 grams) (1.5 mmoles) was reacted with the title compound from Preparative Example 8 (0.232 grams) (1.5 mmoles) under the conditions described in Example 75 to give the title compound (Yield: 0.6454 grams, 92%, MH$^+$ 465.2).

EXAMPLE 186

N-BENZYL 4-(8-CHLORO-6,11-DIHYDRO-5H-BENZO[5,6]CYCLOHEPTA[1,2-b]PYRIDIN-11-YL)-1-PIPERAZINECARBOXAMIDE

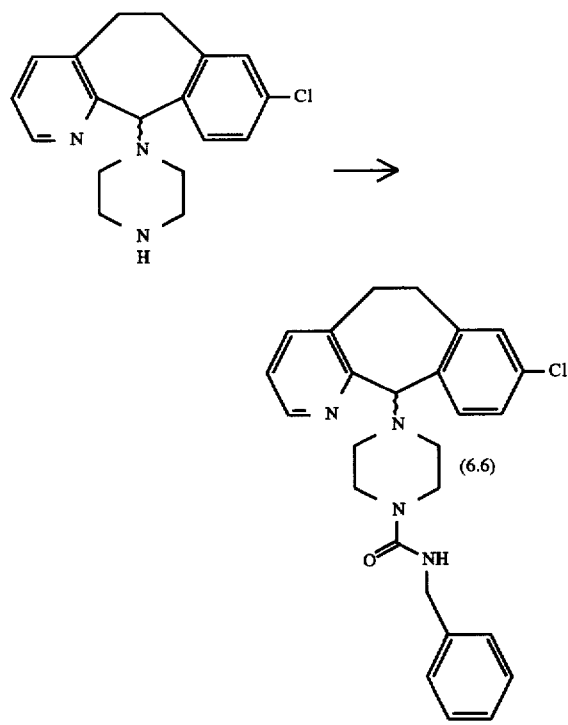

The title compound from Example 75 was reacted with benzyl isocyanate under the conditions described in Example 182 above to give the title compound (Yield: 79%, $MH^+$ 447).

EXAMPLE 187

By essentially the same procedure as Example 183, with the exception that 3-ethoxycarbonylaminopyridine or 2-ethoxycarbonylaminopyridine (Preparative Example 12) is used instead of using 4-ethoxycarbonylaminopyridine, the compound

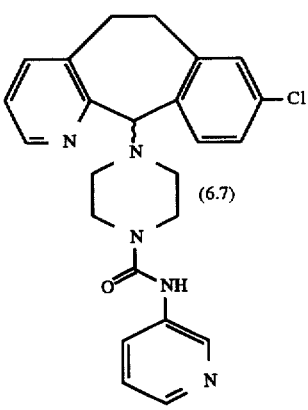

White amorphous solid, $MH^+$ 434.3 or

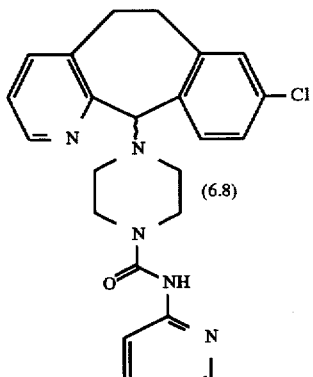

White amorphous solid, $MH^+$ 434.3 was obtained, respectively.

EXAMPLE 188

4-(8-CHLORO-6,11-DIHYDRO-5H-BENZO[5,6]CYCLOHEPTA[1,2-b]PYRIDIN-11-YL)-N-METHYL-N-(3-PYRIDINYL)-1-PIPERAZINECARBOXAMIDE

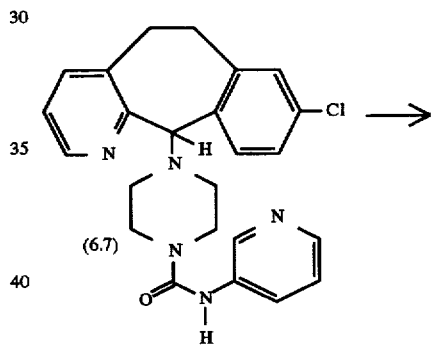

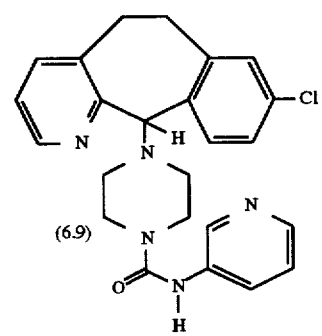

Compound 6.7 from Example 187 (10 grams) (23.1 mmoles) in DMSO (37.6 ml.) was added to a solution of powdered KOH (2.62 grams) (23.1 mmoles) in DMSO (25 ml.) and the mixture was stirred at 25° C. for 3 minutes. Iodomethane (1.4518 ml.) (23.1 mmoles) was added and the mixture was stirred at 25° C. for 15 minutes. The mixture was poured into water and extracted with $CH_2Cl_2$. The latter was dried (magnesium sulphate), filtered and evaporated to dryness. The product was purified by chromatography on silica gel using 3–5% (10% concentrated ammonium hydroxide in MeOH)—CH$_2$Cl$_2$ as the eluant to give the title compound (Yield: 6.28 grams, 61%, MH$^+$ 448).

EXAMPLES 189–218

By essentially the same procedures as set forth in Example 75 above but using the compounds set forth in Column 1, Table 5 below, in place of 4-pyridylacetic acid, one can obtain compounds of the formula

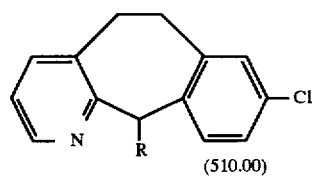

(510.00)

wherein R is as listed in Column 2 of Table 5.

TABLE 5

| EX. | COLUMN 1 | COLUMN 2 | CMPD |
|---|---|---|---|
| 189 | (structure: 4-(dimethylamino)phenylacetic acid) | (structure 5.62) | white amorphous solid MH$^+$ 475 |
| 190 | (structure: 2-methyl-2-phenylpropanoic acid) | (structure 5.63) | white amorphous solid MH$^+$ 460 |
| 191 | (structure: 2-(pyridin-3-yl)propanoic acid) | (structure 5.64) | white amorphous solid MH$^+$ 447 |
| 192 | (structure: 1-acetylpiperidine-4-carboxylic acid) | (structure 5.65) | white amorphous solid MH$^+$ 467 |

TABLE 5-continued

| EX. | COLUMN 1 | COLUMN 2 | CMPD |
|-----|----------|----------|------|
| 193 | [structure] | (5.66) | white amorphous solid MH+ 539 |
| 194 | [structure] | (5.67) | white amorphous solid MH+ 467 |
| 195 | [structure] | (5.68) | white amorphous solid MH+ 439 |
| 196 | [structure] | (5.69) | white amorphous solid MH+ 433 |

TABLE 5-continued

| EX. | COLUMN 1 | COLUMN 2 | CMPD |
|---|---|---|---|
| 197 | (structure: pyridine N-oxide with CH₂COOH) | (5.70) (structure: N-methylpiperazine coupled via amide to CH₂-pyridine N-oxide) | white amorphous solid MH⁺ 449 |
| 198 | (structure: pyridine with C(CH₃)₂COOH) | (5.71) (structure: N-methylpiperazine coupled via amide to C(CH₃)₂-pyridine) | white amorphous solid MH⁺ 461 |
| 199 | (structure: N-acetylpiperidine-2-carboxylic acid) | (5.72) (structure: N-methylpiperazine coupled via amide to N-acetylpiperidine-2-yl)<br>5.72A = Isomer A<br>5.72B = Isomer B | white amorphous solid MH⁺ 467 |
| 200 | (structure: 1-acetylpiperidine-4-yl-CH₂COOH) | (5.73) (structure: N-methylpiperazine coupled via amide to CH₂-(1-acetylpiperidin-4-yl)) | white amorphous solid MH⁺ 467 |
| 201 | (structure: 1-methylpiperidine-4-yl-CH₂COOH) | (5.74) (structure: N-methylpiperazine coupled via amide to CH₂-(1-methylpiperidin-4-yl)) | white amorphous solid MH⁺ 453 |

TABLE 5-continued

| EX. | COLUMN 1 | COLUMN 2 | CMPD |
|---|---|---|---|
| 202 | [piperidine-4-carboxylic acid, N-Boc] | (5.75) [4-methylpiperazine coupled to N-Boc-piperidine-4-carbonyl] | white amorphous solid MH+ 525 |
| 203 | Trifluroacetic Acid deprotection of Compound 5.75 of Example 202 | (5.76) [4-methylpiperazine coupled to piperidine-4-carbonyl, NH] | white amorphous solid MH+ 525 |
| 204 | [piperidine-4-carboxylic acid, N-CO-OEt] | (5.77) [4-methylpiperazine coupled to N-ethoxycarbonyl-piperidine-4-carbonyl] | white amorphous solid MH+ 497 |
| 205 | [1-acetyl-3-(carboxymethyl)piperidine] | (5.78) [4-methylpiperazine coupled to 1-acetyl-3-piperidinyl acetyl] | white amorphous solid MH+ 481 |
| 206 | [3-(carboxymethyl)-1-methylpiperidine] type structure with N-CH3] | (5.79) [4-methylpiperazine coupled to 1-methyl-3-piperidinyl acetyl] | white amorphous solid MH+ 453 |
| 207 | [N-Cbz-glycine] (Ph = phenyl) | (5.80) [4-methylpiperazine coupled to N-Cbz-glycyl] | white amorphous solid MH+ 505 |

TABLE 5-continued
| EX. | COLUMN 1 | COLUMN 2 | CMPD |
|---|---|---|---|
| 208 | 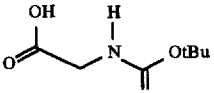 (tBu = t-butyl) | 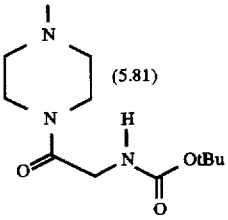 (5.81) | white amorphous solid MH+ 471 |
| 209 | 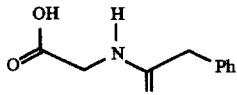 | 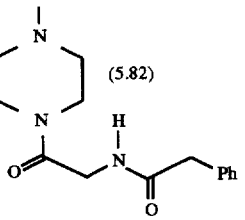 (5.82) | white amorphous solid MH+ 489 |
| 210 | 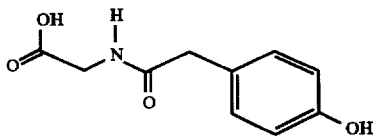 | 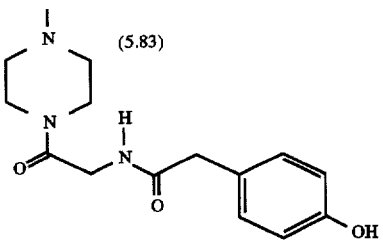 (5.83) | white amorphous solid MH+ 505 |
| 211 | 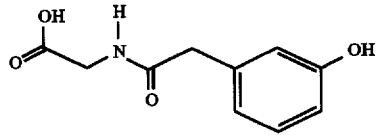 | 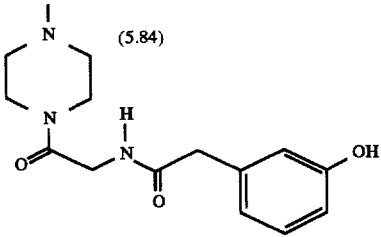 (5.84) | white amorphous solid MH+ 505 |
| 212 | 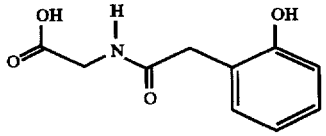 | 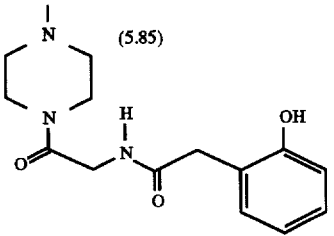 (5.85) | white amorphous solid MH+ 505 |
| 213 | 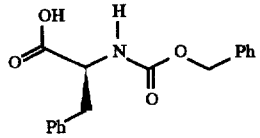 | 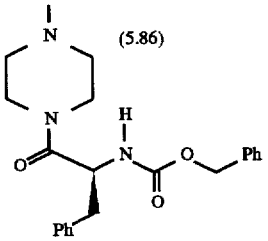 (5.86) | white amorphous solid MH+ 595 |

TABLE 5-continued

| EX. | COLUMN 1 | COLUMN 2 | CMPD |
|---|---|---|---|
| 214 | (structure: N-Boc-phenylalanine) | (5.87) (structure: 4-methylpiperazine amide of N-Boc-phenylalanine) | white amorphous solid MH+ 561 |
| 215 | (structure: phenylalanine) | (5.88) (structure: 4-methylpiperazine amide of phenylalanine) | white amorphous solid MH+ 461 |
| 216 | (structure: N-phthaloyl-phenylalanine) | (5.89) (structure: 4-methylpiperazine amide of N-phthaloyl-phenylalanine) | white amorphous solid MH+ 591 |
| 217 | (structure: N-(3-phenylpropanoyl)glycine) | (5.90) (structure: 4-methylpiperazine amide of N-(3-phenylpropanoyl)glycine) | white amorphous solid MH+ 503 |
| 218 | (structure: N-(3-(4-hydroxyphenyl)propanoyl)glycine) | (5.91) (structure: 4-methylpiperazine amide of N-(3-(4-hydroxyphenyl)propanoyl)glycine) | white amorphous solid MH+ 519 |

EXAMPLES 219–222

By essentially the same procedure as set forth in Example 1, but using the acids set forth in Column 1 of Table 6 below in place of 4-pyridylacetic acid, the compounds listed in Column 2 of Table 6 are obtained. The compounds listed in Table 6 refer to compounds of Formula 500.00:

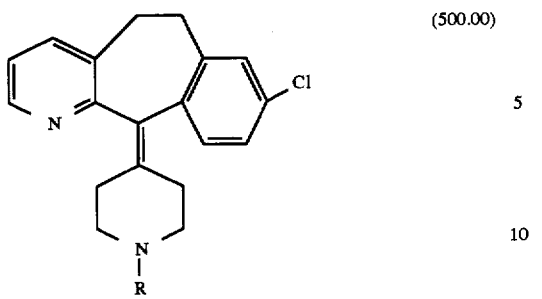
wherein R is the substituent in Column 2.
TABLE 6
| EX. | COLUMN 1 | COLUMN 2 | CMPD |
|---|---|---|---|
| 219 | (structure: indole-CH=C(COOH)–) | (5.92) | white amorphous solid MH+ 482 m.p. = 192–193° C. |
| 220 | (structure: 2-nitrophenyl-CH2–CO–COOH) | (5.93) | white amorphous solid MH+ 502 m.p. = 282–285° C. |
| 221 | (structure: benzothiophene-CH=CH–COOH) | (5.94) | white amorphous solid MH+ 485 |
| 222 | (structure: 4-pyridyl-S-CH2-COOH) | (5.95) | white amorphous solid MH+ 514 |

EXAMPLE 223

A. (+)-1-(8-CHLORO-5,6-DIHYDRO-11H-BENZO[5,6]CYCLOHEPTA[1,2-b]PYRIDIN-11(R)-YL)-4-(3-PYRIDINYLACETYL)PIPERAZINE

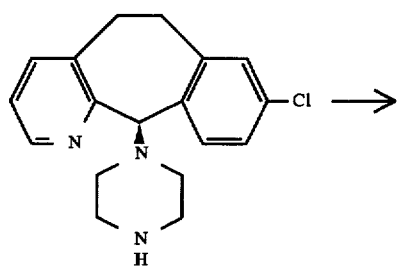

→

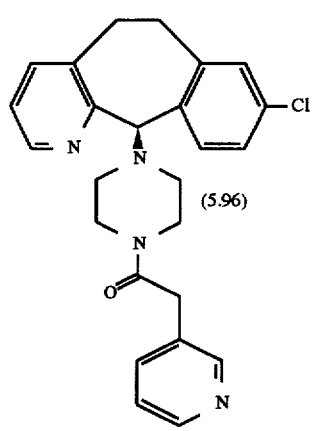

(5.96)

The title R(+) diastereoisomer from Preparative Example 19 was reacted with 3-pyridylacetic acid under the same conditions as described in Example 75 to give the title compound (Yield: 88%, MH⁺ 433).

B. (−)-1-(8-CHLORO-5,6-DIHYDRO-11H-BENZO[5,6]CYCLOHEPTA[2-b]PYRIDIN-11(S)-YL)-4-(3-PYRIDINYLACETYL)PIPERAZINE

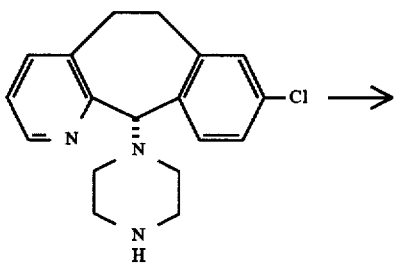

→

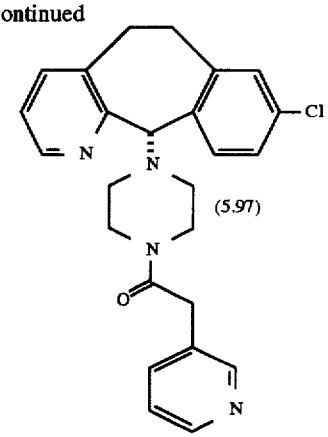

(5.97)

The title S(−) diastereoisomer from Preparative Example 19 above was reacted with 3-pyridylacetic acid under the same conditions as described in Example 75 to give the title compound (Yield: 96%, MH⁺ 433).

EXAMPLE 224

A. (+)-4-(8-CHLORO-6,11-DIHYDRO-5H-BENZO[5,6]CYCLOHEPTA[1,2-b]PYRIDIN-11(R)-YL)-N-(3-PYRIDINYL)-1-PIPERAZINECARBOXYLATE

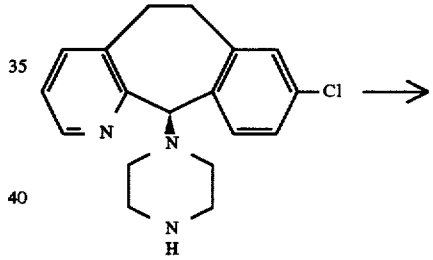

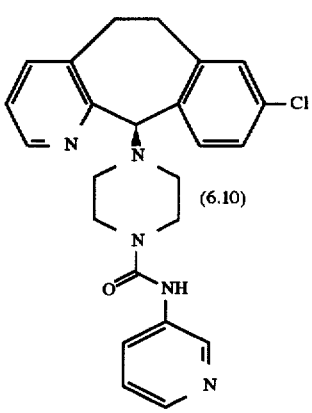

(6.10)

The title R(+) diastereoisomer from Preparative Example 19 was reacted with 3-ethoxycarbonylaminopyridine under the same conditions as described in Example 75 to give the title compound (Yield: 81%, MH⁺ 434).

207

B. (−)-4-(8-CHLORO-6,11-DIHYDRO-5H-BENZO[5,6]CYCLOHEPTA[1,2-b]PYRIDIN-11(S)-YL)-N-(3-PYRIDINYL)-1-PIPERAZINECARBOXAMIDE

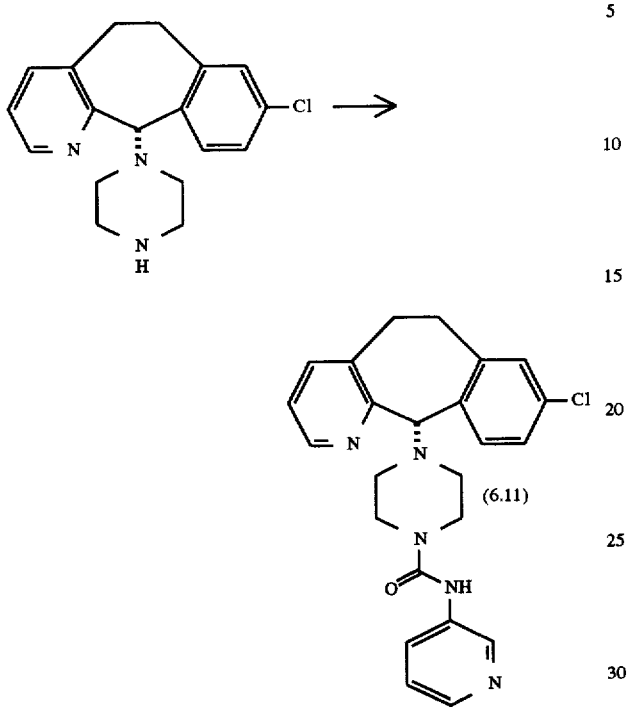

The title S(−) diastereoisomer from Preparative Example 19 was reacted with 3-ethoxycarbonylaminopyridine under the same conditions as described in Example 75 to give the title compound (Yield: 80%, MH$^+$ 434).

EXAMPLE 225

A. (+)-1-(8-CHLORO-5,6-DIHYDRO-11H-BENZO[5,6]CYCLOHEPTA[1,2-b]PYRIDIN-11(R)-YL)-4-[(1-ACETYL-4-PIPERIDINYL)ACETYL]PIPERAZINE

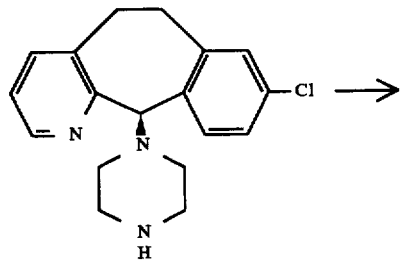

208

-continued

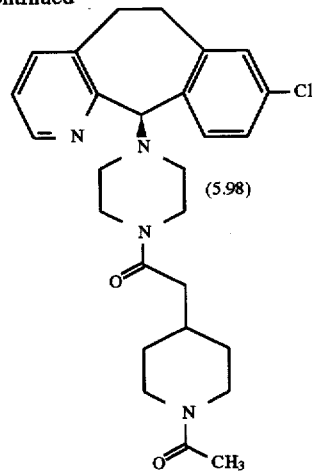

The title R(+) diastereoisomer from Preparative Example 19 above was reacted with 1-N-acetylpiperidinyl-3-acetic acid under the same conditions as described in Example 75 to give the title compound (Yield: 52% MH$^+$ 481).

B. (+1-(8-CHLORO-5,6-DIHYDRO-11H-BENZO[5,6]CYCLOHEPTA[1,2-b]PYRIDIN-11(S)-YL)-4-[(1-ACETYL-4-PIPERIDINYL)ACETYL]PIPERAZINE

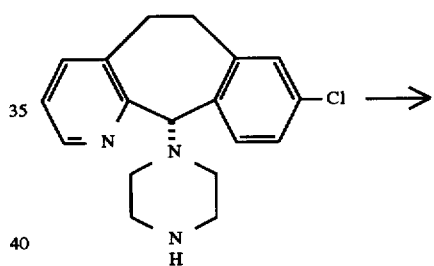

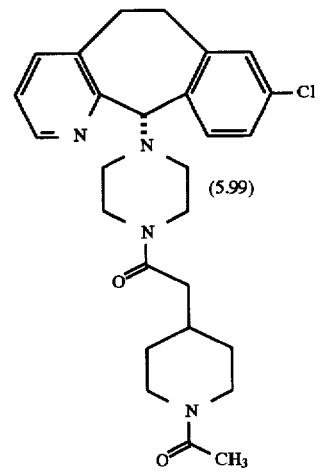

The title S(−) diastereoisomer from Preparative Example 19 above was reacted with 1-N-acetylpiperidinyl-3-acetic acid under the same conditions as described in Example 75 to give the title compound (Yield: 53% MH$^+$ 481).

EXAMPLE 226

A. (+)-1-(8-CHLORO-6,11-DIHYDRO-5H-BENZO[5,6]CYCLOHEPTA[1,2-b]PYRIDIN-11(R)-YL)-4-[(1-ACETYL-4-PIPERIDINYL)CARBONYL]PIPERAZINE

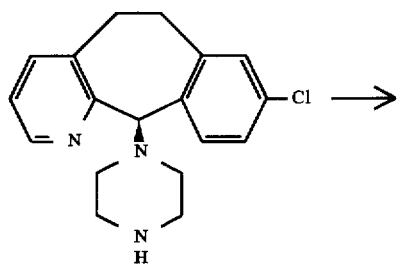 →

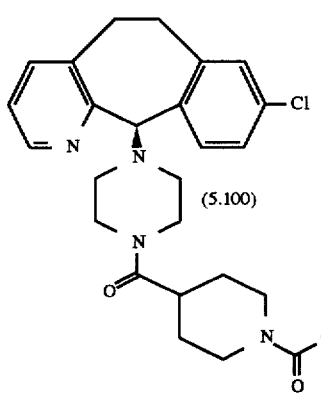
(5.100)

The title R(+) diastereoisomer from Preparative Example 19 was reacted with 1-N-acetylisonipecotic acid under the same conditions as described in Example 75 to give the title compound (Yield: 90%, MH⁺ 467).

B. (−)-1-(8-CHLORO-6,11-DIHYDRO-5H-BENZO[5,6]CYCLOHEPTA[1,2-b]PYRIDIN-11(S)-YL)-4-[(1-ACETYL-4-PIPERIDINYL)CARBONYL]PIPERAZINE

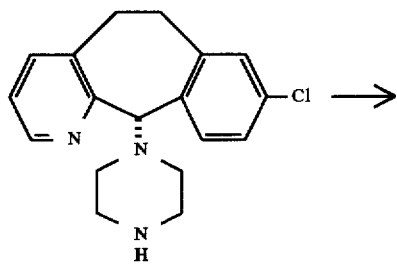 →

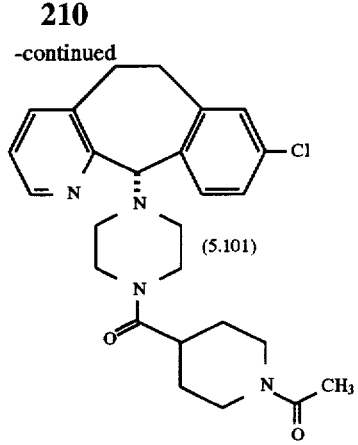
(5.101)

The title S(−) diastereoisomer from Preparative Example 19 was reacted with 1-N-acetylisonipecotic acid under the same conditions as described in Example 75 to give the title compound (Yield: 93%, MH⁺ 467).

EXAMPLE 227

4-(8-CHLORO-5,6-DIHYDRO-11H-BENZO-[5,6]CYCLOHEPTA[1,2-b]PYRIDIN-11-YLIDENE)-1-[(4-PYRIDINYL)ACETYL]-PIPERIDINE N1OXIDE

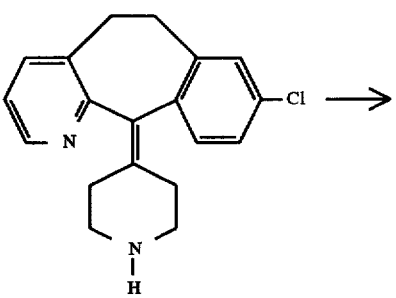 →

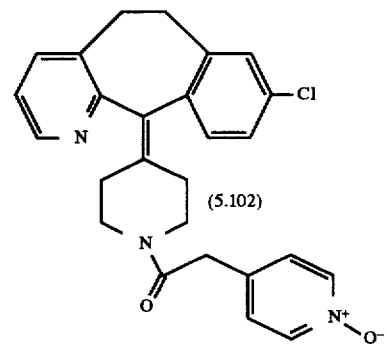
(5.102)

To a mixture of 0.933g (3 mmol) of 4-(8-chloro-5,6-dihydro-11H-benzo-[5,6]cyclohepta(1,2-b]pyridin-11-ylidene)-piperidine (product from Preparative Example 1, step G), 0.46g (3 mmol) of 4-pyridyl acetic acid N-oxide (prepared as described in Preparative Example 8) 1-hydroxybenzotriazole (0.40 g, 3 mmol) in 20 mL of DMF at −4° C. and under nitrogen atmosphere was added N-methyl morpholine (1.65 mL, 15 mmol) followed by DEC an reaction stirred overnight at room temperature. The volatiles were stripped off and the resulting semi-solid was partitioned between water and EtOAc. The aqueous phase was washed twice with EtOAc. Combined EtOAc fractions were dried over Na₂SO₄ and concentrated. The crude product was purified via flash chromatography on silica gel (first eluting with 3% and then 5% MeOH saturated with ammonia in CH₂Cl₂) to give the title compound as a light brown solid (0.2 g mp=128°–130° C. MH⁺ 446).

EXAMPLE 228

4-(8-CHLORO-5,6-DIHYDRO-11H-BENZO-[5,6] CYCLOHEPTA[1,2-b]PYRIDIN-11-YLIDENE)-1-[(3-PYRIDINYL)ACETYL]-PIPERIDINE N1OXIDE

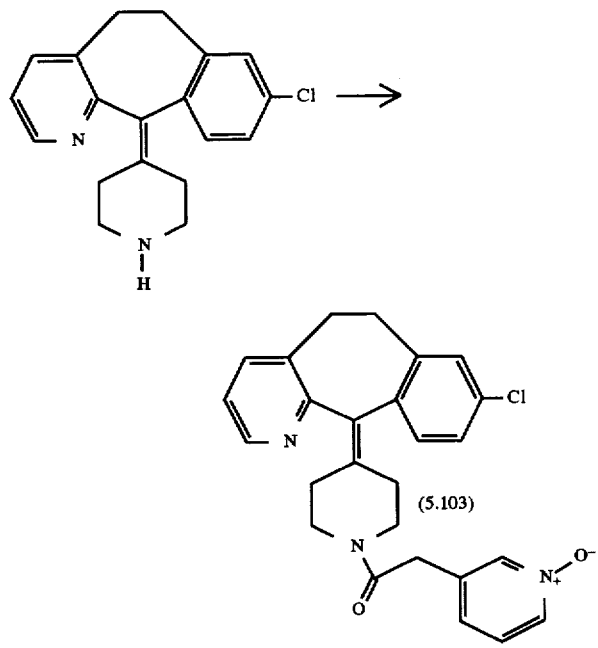

By essentially the same procedure as set forth in Example 227, but using 3-pyridyl acetic acid N-oxide (Preparative Example 9) instead of 4-pyridyl acetic acid N-oxide the title compound was obtained as a white solid (mp=120°–121° C., MH⁺=466).

EXAMPLE 229

4-(8-CHLORO-5,6-DIHYDRO-11H-BENZO-[-5,6] CYCLOHEPTA[1,2-b]PYRIDIN-11-YLIDENE)-1-[(-3-PYRIDINYL)ACETYL]-PIPERIDINE N4 OXIDE

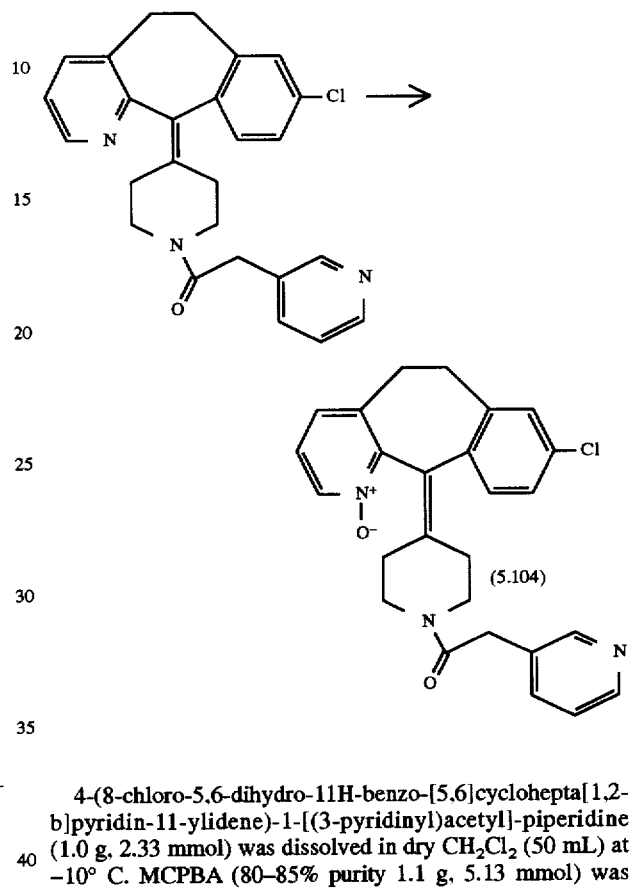

4-(8-chloro-5,6-dihydro-11H-benzo-[5,6]cyclohepta[1,2-b]pyridin-11-ylidene)-1-[(3-pyridinyl)acetyl]-piperidine (1.0 g, 2.33 mmol) was dissolved in dry CH₂Cl₂ (50 mL) at −10° C. MCPBA (80–85% purity 1.1 g, 5.13 mmol) was added and the reaction stirred at that temperature for 95 minutes. The reaction mixture was washed with sodium bisulfite and then with 10% NaOH. The organic phase was dried over MgSO₄ and then concentrated. Purification on silica gel eluting, first with 4%, 6% and then 10% MeOH in CH₂Cl₂ gave rise to the title compound as a white solid (0.2 g, 0.77 mmol MH⁺=446).

EXAMPLE 230

4-(8-CHLORO-5,6-DIHYDRO-11H-BENZO-[5,6] CYCLOHEPTA[1,2-b]PYRIDIN-11-YLIDENE)-1-[(4-PYRIDINYL)ACETYL]-PIPERIDINE N4 OXIDE

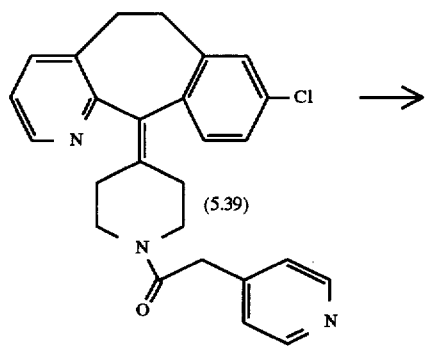

(5.39)

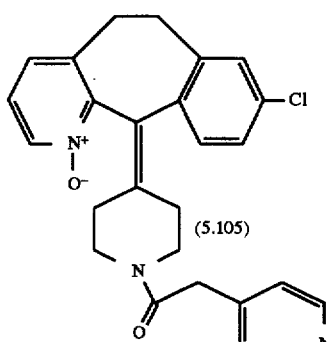

(5.105)

By essentially the same procedures as set forth in Example 229 above, but using 4-(8-chloro-5,6-dihydro-11H-benzo-[5,6]cyclohepta[1,2-b]pyridin-11-ylidene)-1-[(4-pyridinyl)acetyl]-piperidine instead of 4-(8-chloro-5,6-dihydro-11H-benzo-[5,6]cyclohepta[1,2-b]pyridin-11-ylidene)-1-[(3-pyridinyl)acetyl]-piperidine the title compound was obtained as an off-white solid (MH$^+$=446).

EXAMPLE 231

A. 8-CHLORO-11-(1-ETHOXYCARBONYL-4-PIPERIDYLIDENE)-6,11-DIHYDRO-5H-BENZO[5,6]CYCLOHEPTA[1,2-b]PYRIDINE N-OXIDE

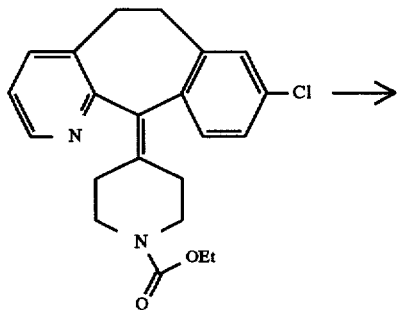

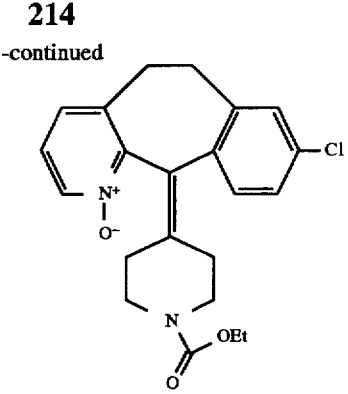

8-chloro-11-(1-ethoxycarbonyl-4-piperidylidene)-6,11-dihydro-5H-benzo[5,6]cyclohepta[1,2-b]pyridine (5 g, 13.06 mmol) was dissolved in CH$_2$Cl$_2$ at −10° C. 3-Chlorobenzoic acid (4.9 g, 15.67 mmol) was then added and the reaction mixture stirred for 95 minutes. The reaction mixture was taken up in CH$_2$Cl$_2$ and extracted with sodium bisulfite, 10% NaOH. The crude reaction product was purified on silica gel eluting first with 1% and then with 2% MeOH in CH$_2$Cl$_2$ to give the title compound (2.7 g, MH$^+$ 399).

B. 8-CHLORO-11-(4-PIPERIDYLIDENE)-6,11-DIHYDRO-5H-BENZO[5,6]CYCLOHEPTA[1,2-b]PYRIRIDINE N-OXIDE

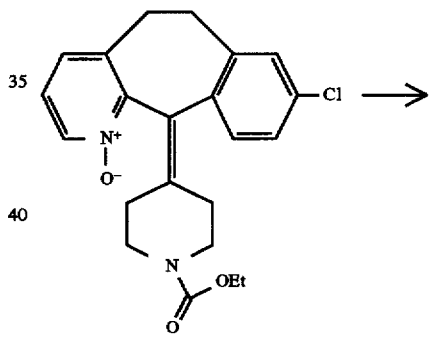

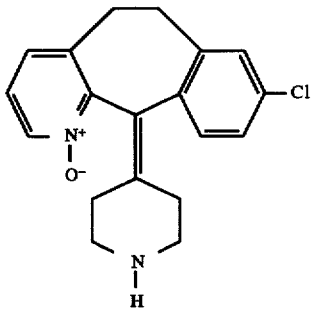

By essentially the same procedures as set forth in Preparative Example 1 step G, but using 8-chloro-11-(1-ethoxycarbonyl-4-piperidylidene)-6,11-dihydro-5H-benzo[5,6]cyclohepta[1,2-b]pyridine N-oxide instead of 8-chloro-11-(1-ethoxycarbonyl-4-piperidylidene)-6,11-dihydro-5H-benzo[5,6]cyclohepta[1,2-b]pyridine, the title compound was obtained and used for the next reaction without further purification (MH+ 327).

215

C. 4-(8-CHLORO-5,6-DIHYDRO-11H-BENZO[5,6]CYCLOHEPTA(1,2-b]PYRIDIN-11-YLIDENE)-1-[(3-PYRIDINYL)ACETYL]PIPERIDINE N1,N4 DIOXIDE

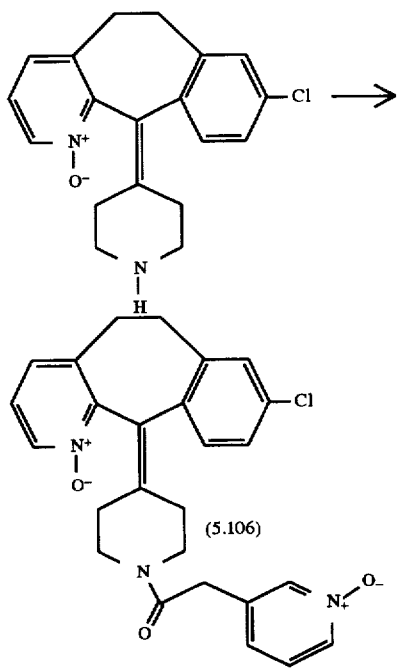

(5.106)

By essentially the same procedure as set forth in Example 227, but using 3-pyridyl acetic acid N-oxide (Preparative Example 9) instead of 4-pyridyl acetic acid N-oxide and 8-chloro-11-(4-piperidylidene)-6,11-dihydro-5H-benzo[5,6]cyclohepta[1,2-b]pyridine N-oxide instead of 8-chloro-11-(4-piperidylidene)-6,11-dihydro-5H-benzo[5,6]cyclohepta[1,2-b]pyridine, the title compound was obtained as a white solid (mp=105°–107° C., MH⁺=462).

EXAMPLE 232

4-(8-CHLORO-5,6-DIHYDRO-11H-BENZO-[5,6]CYCLOHEPTA[1,2-b]PYRIDIN-11-YLIDENE)-1-[(4-PYRIDINYL)ACETYL]-PIPERIDINE N1,N4 DIOXIDE

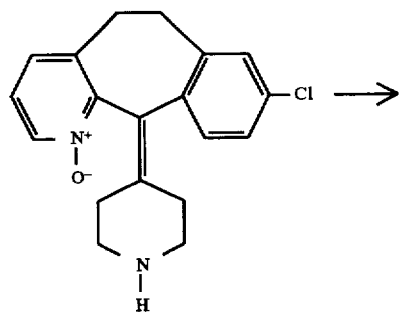

216

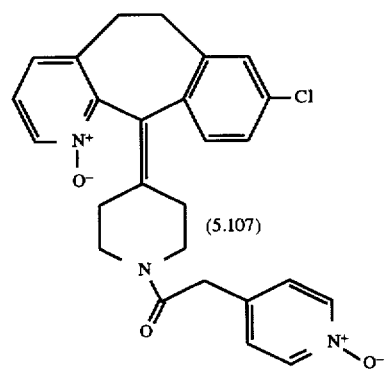

(5.107)

By essentially the same procedure as set forth in Example 227, but using 8-chloro-11-(4-piperidylidene)-6,11-dihydro-5H-benzo[5,6]cyclohepta[1,2-b]pyridine N-oxide instead of 8-chloro-11-(4-piperidylidene)-6,11-dihydro-5H-benzo[5,6]cyclohepta[1,2-b]pyridine, the title compound was obtained as a light brown solid (MH⁺=462).

EXAMPLE 233

A. 8-CHLORO-6,11-DIHYDRO-11-(4-PIPERIDINYL)-5H-BENZO[5,6]CYCLOHEPTA[1,2]PYRIDINE (Product A) and 6,11-DIHYDRO-11-(4-PIPERIDINYL)-5H-BENZO[5,6]-CYCLOHEPTA[1,2-b]PYRIDINE (Product B)

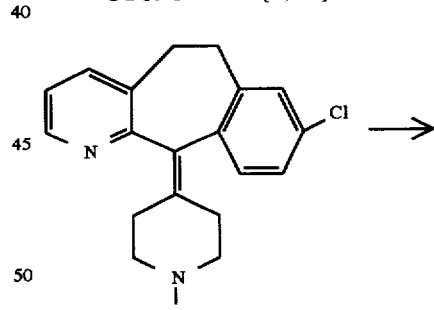

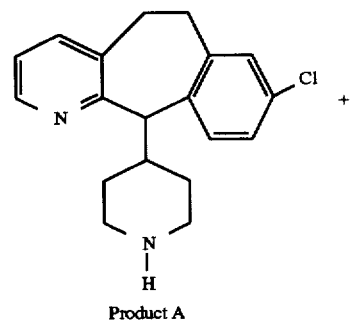

Product A

217
-continued

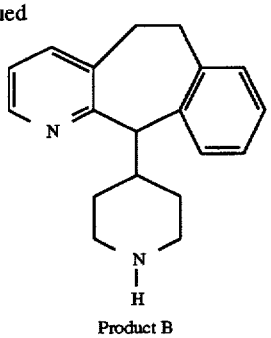

Product B

To a solution 66.27 g (0.21 mole) of 4-(8-chloro-5,6-dihydro-11H-benzo[5,6]cyclohepta(1,2-b]pyridin-11-ylidene)-piperidine (product from Preparative Example 1 Example, step G), in THF (1 L) was added lithium aluminum hydride (24.32 g, 0.64 mole) and the reaction mixture was heated to reflux overnight. The reaction mixture was then cooled to room temperature and ~3 L of diethyl ether is added followed by dropwise addition of saturated sodium sulfate until a white gray precipitate forms. $MgSO_4$ was then added to the separated organic layer and stirred for 30 minutes. All the volatiles were then removed and the resulting crude mixture was chromatographed on a silica gel column eluting with 10% MeOH saturated with ammonia in $CH_2Cl_2$. The material obtained contained both the desired compound and the des-chloro compound. Separation on HPLC using reverse phase column and eluting with 40% MeOH-water afforded the desired compounds as white solids (Product A's mp=95.2°–96.1° C., Product B's mp=145.1°–145.7° C.).

B. 4-(8-CHLORO-6,11-DIHYDRO-5H-BENZO[5,6]CYCLOHEPTA[1,2-b]PYRIDIN-11-YL)-1-[(3-PYRIDINYL)ACETYL]-PIPERIDINE N1 OXIDE

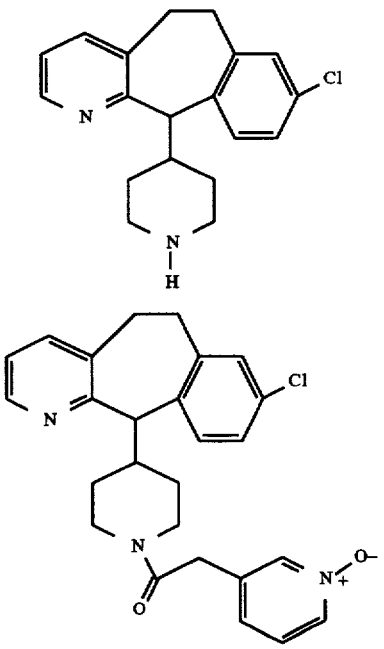

(5.108)

By essentially the same procedure as set forth in Example 227, but using 3-pyridyl acetic acid N-oxide (Preparative Example 9) instead of 4-pyridyl acetic acid N-oxide and

218

8-chloro-6,11-dihydro-11-(4-piperidinyl)-5H-benzo[5,6]cyclohepta[1,2-b]pyridine (product from Example 233A ) instead of 4-(8-chloro-5,6-dihydro-11H-benzo-[5,6]cyclohepta(1,2-b]pyridin-11-ylidene)-piperidine, the title compound was obtained as a white solid (mp=117°–118° C., $MH^+$=414).

EXAMPLE 234

4-(8-CHLORO-6,11-DIHYDRO-5H-BENZO[5,6]CYCLOHEPTA(1,2-b]PYRIDIN-11-YL)-1-[(4-PYRIDINYL)ACETYL]-PIPERIDINE N1 OXIDE

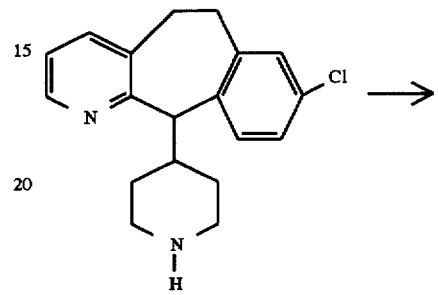

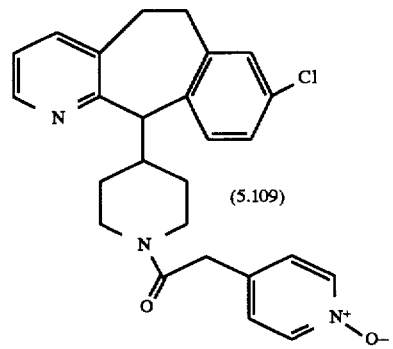

(5.109)

By essentially the same procedure as set forth in Example 227, but using 8-chloro-6,11-dihydro-11-(4-piperidinyl)-5H-benzo[5,6]cyclohepta[1,2-b]pyridine (product from Example 233A) instead of 4-(8-chloro-5,6-dihydro-11H-benzo-[5,6]cyclohepta(1,2-b]pyridin-11-ylidene)-piperidine (product from Preparative Example 1, step G), the title compound was obtained as a white solid (mp=125°–126° C., $MH^+$=414).

EXAMPLE 235

A. ETHYL 4-(8-CHLORO-6,11-DIHYDRO-5H-BENZO[5,6]CYCLOHEPTA(1,2-b]PYRIDIN-11-YL)-1-PIPERIDINECARBOXYLATE

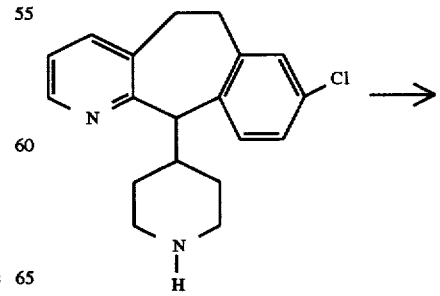

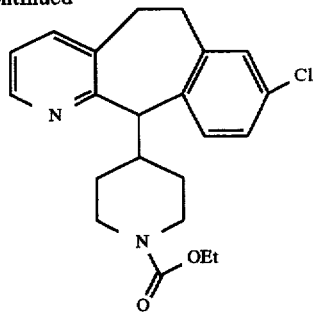

8-Chloro-6,11-dihydro-11-(4-piperidinyl)-5H-benzo[5,6]cyclohepta[1,2-b]pyridine (product from Example 233A) (4.18 g, 13 mmol) was dissolved in toluene (175 mL). Ethyl chloroformate (11.6 g, 110 mmol, 10.2 mL) was then added and the reaction mixture was heated to ~120° C. overnight. All volatiles were stripped off and the crude product was purified on silica gel column eluting with 50% EtOAc-hexanes to give the title compound as a white solid (MH+ 385).

B. ETHYL 4-(8-CHLORO-6,11-DIHYDRO-5H-BENZO[5,6]CYCLOHEPTA(1,2-b]PYRIDIN-11-YL)-1-PIPERIDINECARBOXYLATE N OXIDE

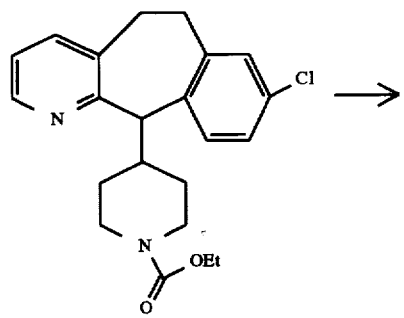

By essentially the same procedure as set forth in Example 231, but using ethyl 4-(8-chloro-6,11-dihydro-5H-benzo-[5,6]cyclohepta(1,2-b]pyridin-11-yl)-1-piperidinecarboxylate (product from Example 235A) instead of 8-chloro-11-(1-ethoxycarbonyl-4-piperidylidene)-6,11-dihydro-5H-benzo[5,6]cyclohepta[1,2-b]pyridine, the title compound was obtained as a white solid (mp=81.7°–82.5° C., MH+=400).

C. 4-(8-CHLORO-6,11-DIHYDRO-5H-BENZO[5,6]CYCLOHEPTA(1,2-b]PYRIDIN-11-YL)-1-PIPERIDINE N OXIDE

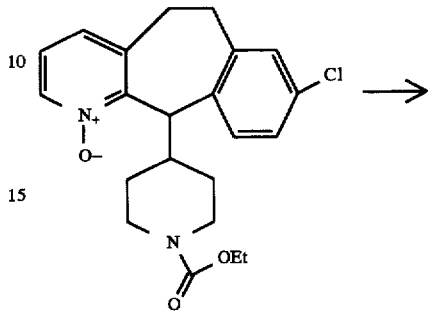

By essentially the same procedure as set forth in Preparative Example 1 step G, but using ethyl 4-(8-chloro-6,11-dihydro-5H-benzo-[5,6]cyclohepta[1,2-b]pyridin-11-yl)-1-piperidinecarboxylate N1 oxide (product from Example 235B) instead of 8-chloro-11-(1-ethoxycarbonyl-4-piperidylidene)-6,11-dihydro-5H-benzo[5,6]cyclohepta[1,2-b]pyridine, the title compound was obtained as a solid (MH+=329).

D. 4-(8-CHLORO-6,11-DIHYDRO-5H-BENZO[5,6]CYCLOHEPTA(1,2-b]PYRIDIN-11-YL)-1-[(3-PYRIDINYL)ACETYL]-PIPIERIDINE N4 OXIDE

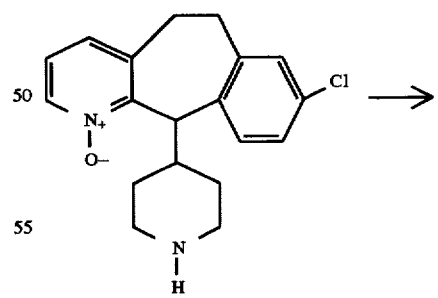

-continued

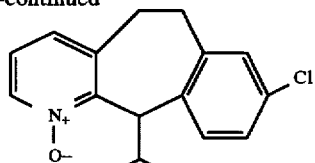

(5.110)

By essentially the same procedure as set forth in Example 227, but using 3-pyridyl acetic acid instead of 4-pyridyl acetic acid N-oxide and 4-(8-chloro-6,11-dihydro-5H-benzo-[5,6]cyclohepta[1,2-b]pyridin-11-yl)-1-piperidine N oxide (product from Example 235C) instead of 4-(8-chloro-5,6-dihydro-11H-benzo-[5,6]cyclohepta[1,2-b]pyridin-11-ylidene)piperidine, the title compound was obtained as a white solid (mp=61.8°–62.3° C., MH$^+$=448).

EXAMPLE 236

4-(8-CHLORO-6,11-DIHYDRO-5H-BENZO-[5,6]CYCLOHEPTA(1,2-b]PYRIDIN-11-YL)-1-[(4-PYRIDINYL)ACETYL]-PIPERIDINE N4 OXIDE

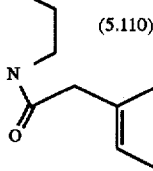 →

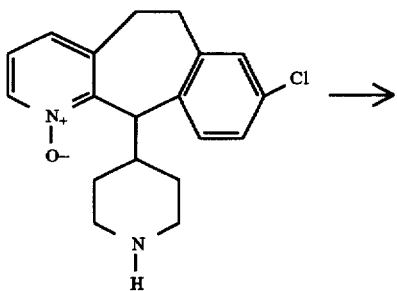

(5.111)

By essentially the same procedure as set forth in Example 227, but using 4-pyridyl acetic acid instead of 4-pyridyl acetic acid N-oxide and 4-(8-chloro-6,11-dihydro-5H-benzo-[5,6]cyclohepta(1,2-b]pyridin-11-yl)-1-piperidine N oxide (product from Example 235C) instead of 4-(8-chloro-5,6-dihydro-11H-benzo-[5,6]cyclohepta[1,2-b]pyridin-11-ylidene)piperidine, the title compound was obtained as a white solid (mp=116.7°–117.6° C., MH$^+$=448).

EXAMPLE 237

4-(8-CHLORO-6,11-DIHYDRO-5H-BENZO-[5,6]CYCLOHEPTA(1,2-b]PYRIDIN-11-YL)-1-[(3-PYRIDINYL)ACETYL]-PIPERIDINE N1, N4 OXIDE

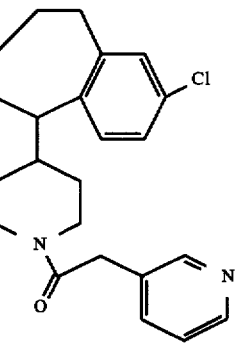 →

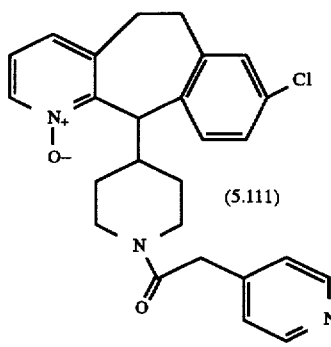

(5.112)

4-(8-Chloro-6,11-dihydro-5H-benzo-[5,6]cyclohepta(1,2-b]pyridin-11-yl)-1-[(3-pyridinyl)acetyl]-piperidine, from Example 82A, (0.5 g, 1.2 mmol) was dissolved in CH$_2$Cl$_2$ at about −18° C. MCPBA (0.62 g, 3.6 mmol) was added and the reaction stirred for 1.5 hours. The reaction mixture was extracted with 10% sodium bisulfite, 10% NaOH and then dried with MgSO$_4$, filtered and concentrated. The crude product was purified on silica gel eluting with 7% MeOH saturated with ammonia in CH$_2$Cl$_2$ to give the title compound as a white solid (0.51 g, 91% yield MH$^+$ 464).

EXAMPLE 238

4-(8-CHLORO-6,11-DIHYDRO-5H-BENZO-[5,6]CYCLOHEPTA(1,2-b]PYRIDIN-11-YL)-1-[(4-PYRIDINYL)ACETYL]-PIPERIDINE N1, N4 OXIDE

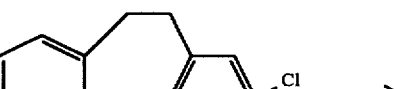 →

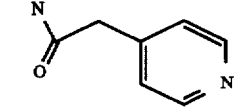

(5.25)

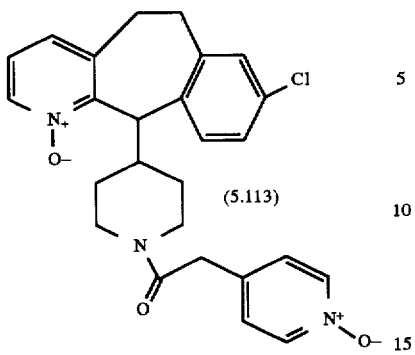

(5.113)

By essentially the same procedure as set forth in Example 237, but using 4-(8-chloro-6,11-dihydro-5H-benzo-[5,6]cyclohepta[1,2-b]pyridin-11-yl)-1-[(4-pyridinyl)acetyl]-piperidine (product from Example 82) instead of 4-(8-chloro-6,11-dihydro-5H-benzo-[5,6]cyclohepta[1,2-b]pyridin-11-yl)-1-[(3-pyridinyl)acetyl]-piperidine, the title compound was obtained as a white solid (mp=85°–85.6° C., MH$^+$=464).

EXAMPLE 239

4-(8-CHLORO-3-METHOXY-5,6-DIHYDRO-11H-BENZO[5,6]CYCLOHEPTA[1,2-b]PYRIDIN-11-YLIDENE)-1-[(3-PYRIDINYL)ACETYL]-PIPERIDINE

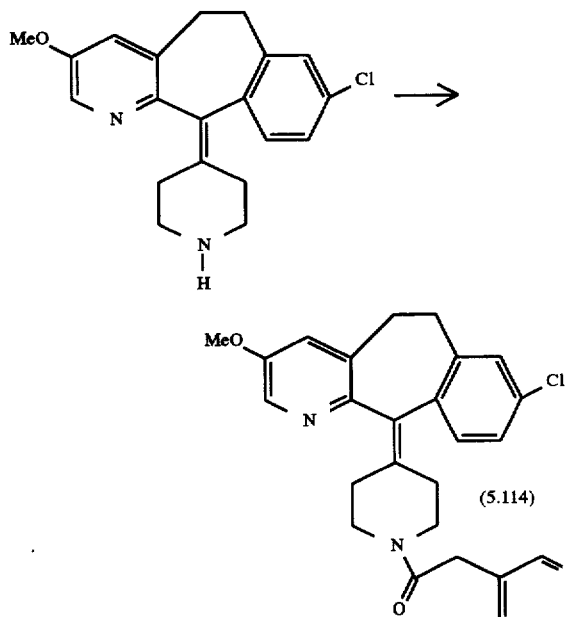

(5.114)

By essentially the same procedure as set forth in Example 180, but using 8-chloro-3-methoxy-11-(4-piperidylidene)-6,11-dihydro-5H-benzo[5,6]-cyclohepta[1,2-b]pyridine (Preparative Example 20) instead of 3,8-dichloro-11-(1-acetyl-4-piperidylidene)-6,11-dihydro-5H-benzo[5,6]cyclohepta[1,2-b]pyridine the title compound was obtained as a white solid (MH$^+$ 460).

EXAMPLE 240

4-(8-CHLORO-3-HYDROXY-5,6-DIHYDRO-11H-BENZO[5,6]CYCLOHEPTA[1,2-b]PYRIDIN-11-YLIDENE)-1-[(3-PYRIDINYL)-ACETYL]-PIPERIDINE

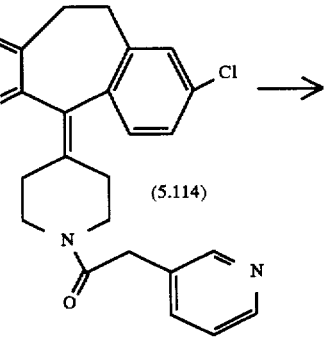

(5.114)

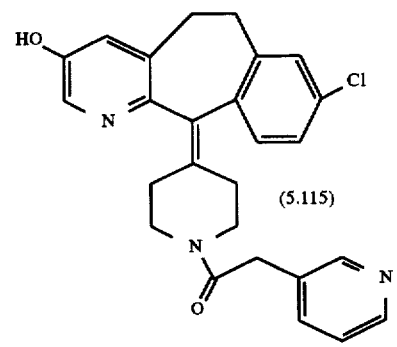

(5.115)

4-(8-Chloro-3-methoxy-5,6-dihydro-11H-benzo[5,6]cyclohepta[1,2-b]pyridin-11-ylidene)-1-[(3-pyridinyl)acetyl]-piperidine (0.24 g, 0.54 mmol) (Example 239) was dissolved in CH$_2$Cl$_2$ at 0° C. under nitrogen atmosphere. Bromine tribromide (0.9 g, 3.6 mmol, 3.6 mL) was added and the reaction was run at room temperature for two days. The reaction mixture was concentrated and chromatographed on a silica gel column eluting with 3% MeOH saturated with ammonia in CH$_2$Cl$_2$ to give an off white borate salt solid (0.14 g, 61% yield, MH$^+$ 446).

EXAMPLE 246

1-1(4-PYRIDINYLACETYL)-4-[3-BROMO8-CHLORO5-6-DIHYDRO-11H-BENZO[5,6]CYCLOHEPTA[1,2-b]PYRIDIN-11YLIDENE]-PIPERIDINE

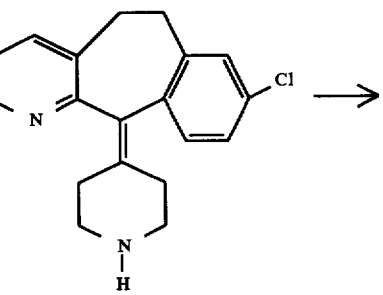

225

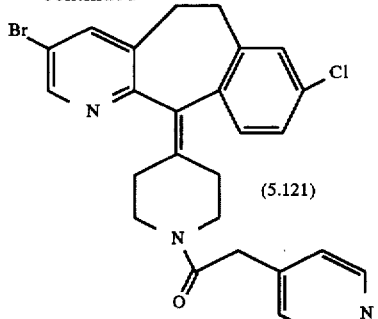

(5.121)

-continued

226

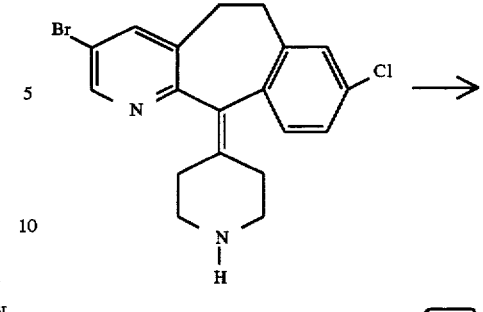

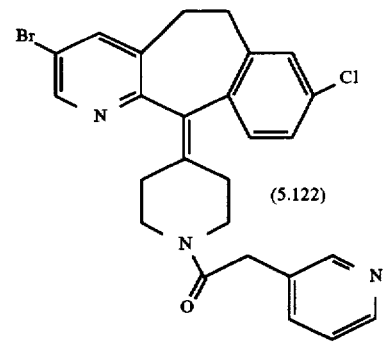

(5.122)

By essentialy the same procedure as set forth in Example 180 but using 4-(3-bromo-8-chloro-5,6-dihydro-11H-benzo[5,6]cyclohepta(1,2-b]pyridin-11-ylidene)-piperidine instead of 4-(3,8-dichloro-5,6-dihydro-11H-benzo-[5,6]cyclohepta(1,2-b]pyridin-11-ylidene)-piperidine, the title compound was obtained as a glassy solid ($MH^+$ 508).

EXAMPLE 247

1-1(3-PYRIDINYLACETYL)-4-[3-BROMO8-CHLORO5-6-DIHYDRO-11H-BENZO[5,6]CYCLOHEPTA[1,2-b]PYRIDIN-11YLIDENE]-PIPERIDINE

By essentialy the same procedure as set forth in Example 180, but using 4-(3-bromo-8-chloro-5,6-dihydro-11H-benzo[5,6]cyclohepta(1,2-b]pyridin-11-ylidene)-piperidine instead of 4-(3,8-dichloro-5,6-dihydro-11H-benzo[5,6]cyclohepta[1,2-b]pyridin-11-ylidene)-piperidine and 3-pyridyl acetic acid instead of 4-pyridyl acetic acid, the title compound was obtained as a white solid (mp=92°–93° C. $MH^+$ 508).

EXAMPLE 248

4-[4,8-DICHLORO-5,6-DIHYDRO-11H-BENZO[5,6]CYCLOHEPTA[1,2-b]PYRIDIN-11-YLIDENE]-1-(4-PYRIDINYLACETYL)-PIPERIDINE and 4-[2,8-DICHLORO-5,6-DIHYDRO-11H-BENZO[5,6]CYCLOHEPTA[[1,2-b]PYRIDIN-11-YLIDENE]-1-(4-PYRIDINYLACETYL)-PIPERIDINE

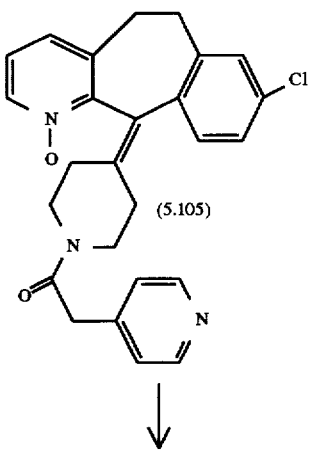

(5.105)

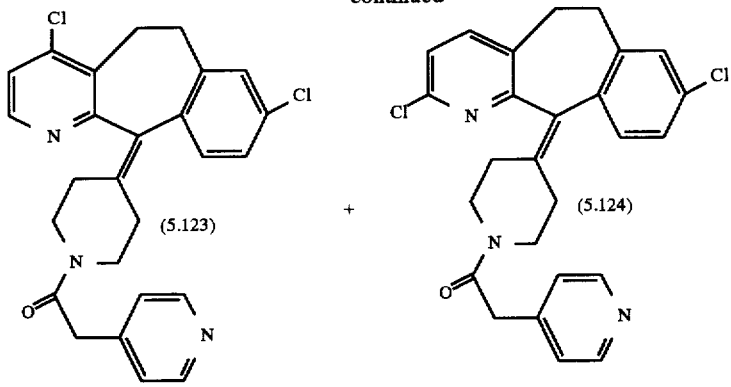

A solution of the title compound from Example 230 (1.7 grams) and phosphorous oxychloride (21 mL) dissolved in chloroform (12 mL) was stirred at reflux for 1 hour. Concentration in vacuo provided a residue which was diluted with $CH_2Cl_2$ and washed with saturated aqueous sodium bicarbonate and brine. The organic phase was dried over anhydrous $MgSO_4$, concentrated in vacuo, and purified by flash column chromatography (silica gel) using 2% MeOH-$CH_2Cl_2$ to afford the title 4,8-dichloro compound (0.34 grams, 20% yield, mp 84°–91° C., $MH^+$ 464) and the title 2,8-dichloro compound (0.18 grams, 11% yield, mp 163.8°–164.6° C., $MH^+$ 464).

EXAMPLE 249

4-[4-[(1H-BENZOTRIAZOL-1-YL)OXY]-8-CHLORO-5,6-DIHYDRO-11H-BENZO[5,6]CYCLOHEPTA[1,2-b]PYRIDIN-11-YLIDENE]-1-(4-PYRIDINYLACETYL)-PIPERIDINE

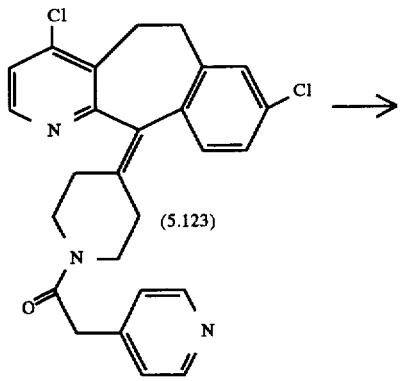

A mixture of the 4,8-dichloro compound from Example 248 (0.5 grams), HOBT hydrate (0.4 grams) and anhydrous DMF (20 mL) was stirred at 25° C. under $N_2$ for 5 days. The mixture was concentrated in vacuo, diluted with $CH_2Cl_2$, and washed with 1N aqueous NaOH. The organic phase was dried over anhydrous $MgSO_4$, concentrated in vacuo and purified by flash column chromatography (silica gel) using 3–5% MeOH-$CH_2Cl_2$ to give the title compound (0.58 grams, 96%, mp 98.6°–101.6° C., $MH^+$ 563).

EXAMPLE 250

4-[4,8-DICHLORO-5,6-DIHYDRO-11H-BENZO[5,6]CYCLOHEPTA[1,2-b]PYRIDIN-11-YLIDENE]-1-(3-PYRIDINYLACETYL)-PIPERIDINE

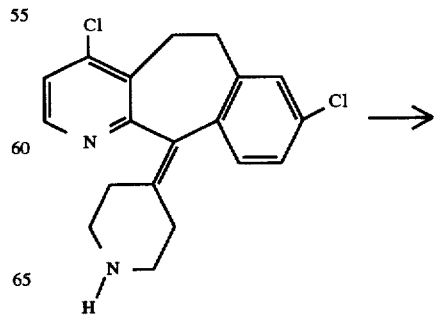

229

-continued

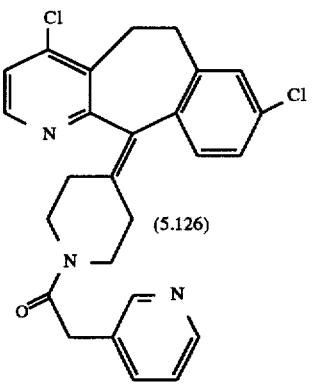

(5.126)

A mixture of the 4,8-dichloro product from Preparative Example 28 (1.91 grams), 3-pyridylacetic acid hydrochloride (2.1 grams), DEC (1.6 grams), 4-methylmorpholine (1.4 mL) and anhydrous DMF (100 mL) was stirred at 25° C. overnight. Concentration in vacuo provided a residue which was diluted with $CH_2Cl_2$ and water. The organic phase was dried over anhydrous $MgSO_4$ and concentrated in vacuo to provide the title compound (2.2 grams, 87%, mp 59.8°–63.5° C., $MH^+$ 464).

EXAMPLE 251

4-[4-[(1H-BENZOTRIAZOL-1-YL)OXY]-8-CHLORO-5,6-DIHYDRO-11H-BENZO[5,6]CYCLOHEPTA[1,2-b]PYRIDIN-11-YLIDENE]-1-(3-PYRIDINYLACETYL)-PIPERIDINE

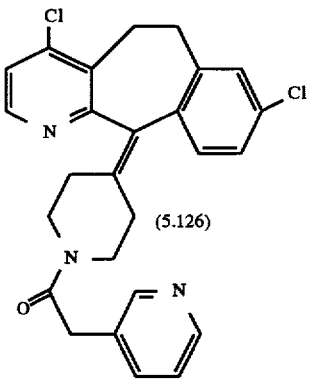

(5.126)

230

-continued

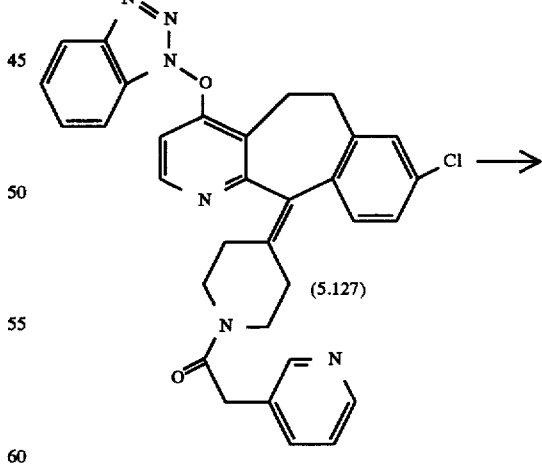

(5.127)

The 4,8-dichloro compound from Example 250 (0.8 grams) was added to a solution of HOBT (1.2 grams) and sodium hydride (0.14 grams, 60% in mineral oil) in anhydrous dimethyl-formamide (60 mL). The resulting solution was irradiated with a 200 W lamp while stirring at 25° C. for 60 hours. The solution was poured into 1N aqueous NaOH while stirring and an additional 400 mL of water was added to the resulting mixture. Filtration provided a solid which was washed with water several times. The solid was dissolved in $CH_2Cl_2$-acetone, dried over anhydrous $MgSO_4$, and concentrated in vacuo to proved the title compound (0.87 grams, 90%, mp=120°–122° C., $MH^+$ 563).

EXAMPLE 252

4-[4-HYDROXY-8-CHLORO-5,6-DIHYDRO-11H-BENZO[5,6]CYCLOHEPTA[1,2-b]PYRIDIN-11-YLIDENE]-1-(3-PYRIDINEYLACETYL)-PIPERIDINE (5.127)

-continued

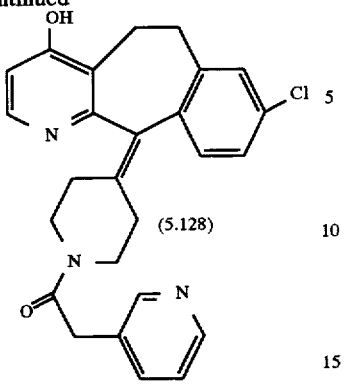
(5.128)

To a solution of the title compound form Example 251 (0.8 grams) and glacial acetic acid (30 mL) was added zinc dust (0.4 grams). After stirring at 25° C. for 18 hour, the mixture was filtered through celite and the filtrate concentrated in vacuo. The residue was diluted with EtOAc, washed with saturated aqueous sodium bicarbonate and brine. The organic layer was separated, dried over MgSO₄ and concentrated in vacuo to give the title compound (Yield 0.346 grams, 58%, MH+ 446).

EXAMPLE 253

4-[3-BROMO-4-HYDROXY-8-CHLORO-5,6-DIHYDRO-11H-BENZO[5,6]CYCLOHEPTA[1,2-b]PYRIDIN-11-YLIDENE]-1-(3-PYRIDINYLACETYL)-PIPERIDINE

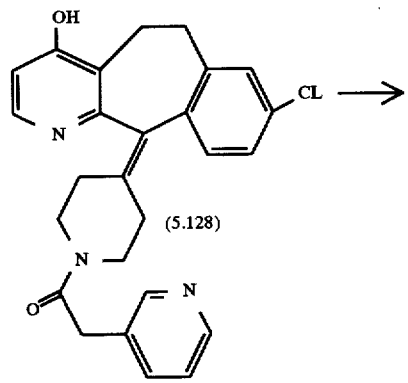
(5.128)

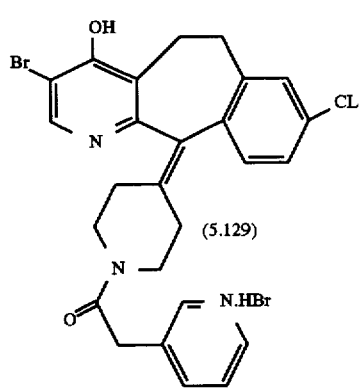
(5.129)

To a solution of the title compound from Example 252 (0.19 grams) and glacial acetic acid (4 mL) was added a 0.7M bromine-acetic acid solution (0.7 mL) at 25° C. under N₂. After 10 minutes, water was added and the resulting solid was filtered and washed with water several times and dried to give the title compound (0.18 grams, 71%, MH⁺ 526).

EXAMPLE 255

4-[8-CHLORO-4-(METHYLTHIO)-5,6-DIHYDRO-11H-BENZO[5,6]CYCLOHEPTA[1,2-b]PYRIDIN-11-YLIDENE]-1-(3-PYRIDINYLACETYL)-PIPERIDINE

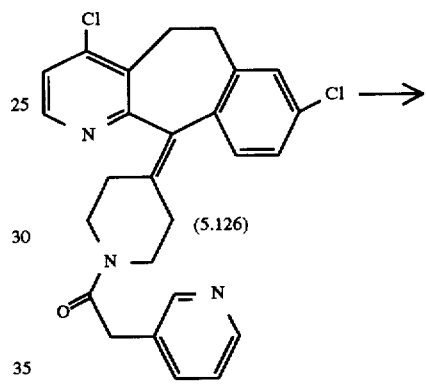
(5.126)

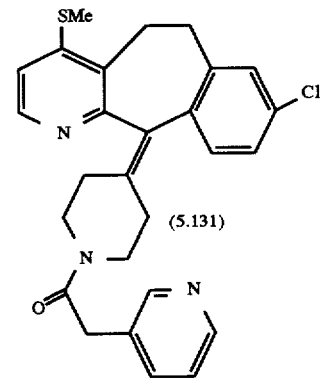
(5.131)

A mixture of the title compound from Example 250 (0.26 grams), sodium methylthiolate (0.06 grams) and anhydrous DMF (10 mL) was stirred while being irradiated with a 200 W lamp for 1 hour. After stirring an additional 12 hours at room temperature without irradiation, the mixture was concentrated in vacuo, diluted with CH₂Cl₂, and washed with 1N aqueous NaOH and brine. The organic phase was dried over anhydrous MgSO₄ and concentrated in vacuo to afford the title compound as a white foam (0.3 grams, 100%, MH⁺ 476).

EXAMPLE 256

4-[8-CHLORO-4-(METHYLSULFINYL)-5,6-DIHYDRO-11H-BENZO[5,6]CYCLOHEPTA[1,2-b]PYRIDIN-11-YLIDENE]-1-(3-PYRIDINYLACETYL)-PIPERIDINE

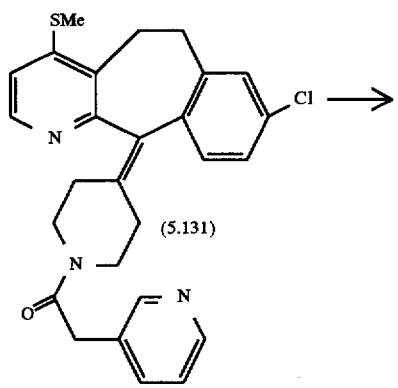

(5.131)

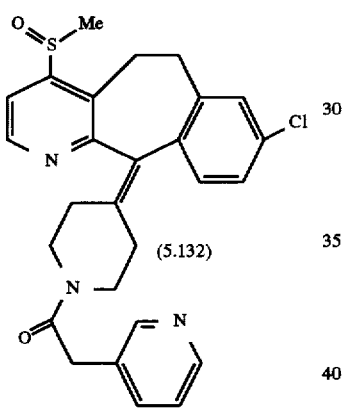

(5.132)

To the title compound from Example 255 (0.18 grams) dissolved in anhydrous THF (10 mL) was added 30% aqueous hydrogen peroxide (3 mL) and the resulting solution was stirred for 12 hours at 73° C. The solution was concentrated in vacuo, diluted with $CH_2Cl_2$, and washed with water. The organic phase was dried over anhydrous $MgSO_4$ and concentrated in vacuo to afford the title compound after preparative plate chromatography (silica gel) using 3% MeOH-$CH_2Cl_2$ (0.04 grams, 26%, $MH^+$ 492).

EXAMPLE 257

METHYL[[8-CHLORO-6,11-DIHYDRO-11-[1-[1-OXO-2-(3-PYRIDINYL)ETHYL]-4-PIPERIDINYLIDENE]-5H-BENZO[5,6]CYCLOHEPTA[1,2-b]PYRIDIN-4-YL]THIO]ACETATE

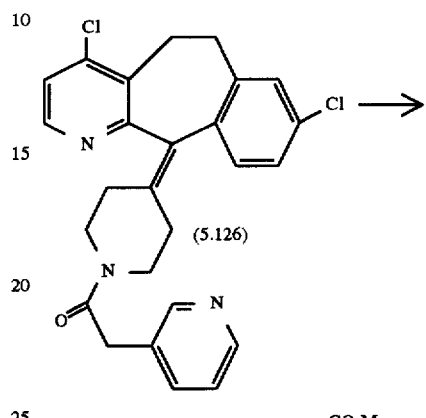

(5.126)

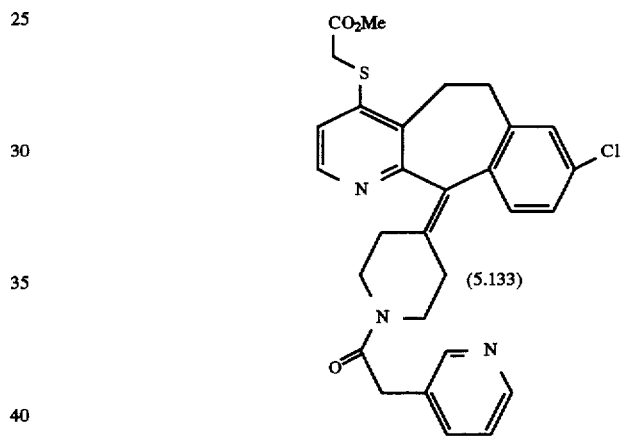

(5.133)

A mixture of the title compound from Example 250 (0.26 grams), sodium hydride (0.08 grams, 60% in mineral oil), methyl thioglycolate (0.19 mL) and anhydrous DMF (15 mL) was stirred while being irradiated with a 200 W lamp for 16 hours. The mixture was diluted with MeOH, concentrated in vacuo, diluted with $CH_2Cl_2$ and water, and washed with 1N aqueous NaOH and brine. The organic phase was dried over anhydrous $MgSO_4$ and concentrated in vacuo and the residue purified by preparative plate chromatography (silica gel) using 3% MeOH-$CH_2Cl_2$ to afford the title compound (0.05 grams, 15%, $MH^+$ 534).

EXAMPLE 258

4-[8-CHLORO-5,6-DIHYDRO-4-(PHENYLMETHYLTHIO)-11H-BENZO[5,6]CYCLOHEPTA[1,2-b]PYRIDIN-11-YLIDENE]-1-(3-PYRIDINYLACETYL)-PIPERIDINE

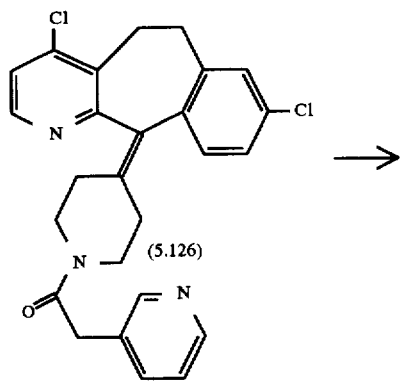

(5.126)

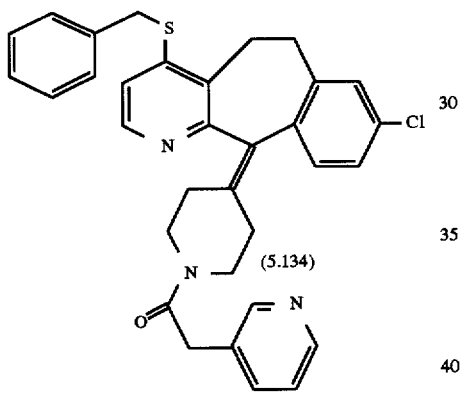

(5.134)

A mixture of the title compound from Example 250 (0.25 grams), sodium hydride (0.11 grams, 60% in mineral oil), benzyl mercaptan (0.13 mL) and anhydrous DMF (15 mL) was stirred while being irradiated with 200 W lamp for 10 days. Isolation and purification as in Example 257 provided the title compound (0.02 grams, 8%, MH⁺ 552).

EXAMPLE 259

4-[8-CHLORO-5,6-DIHYDRO-4-[(2-METHYL-2H-TETRAZOL-5-YL)THIO]-11H-BENZO[5,6]CYCLOHEPTA[1,2-b]PYRIDIN-11-YLIDENE]-1-(3-PYRIDINYLACETYL)-PIPERIDINE

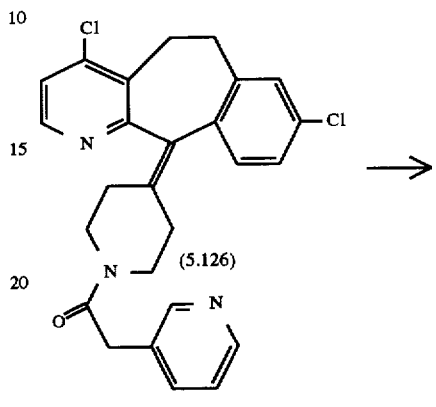

(5.126)

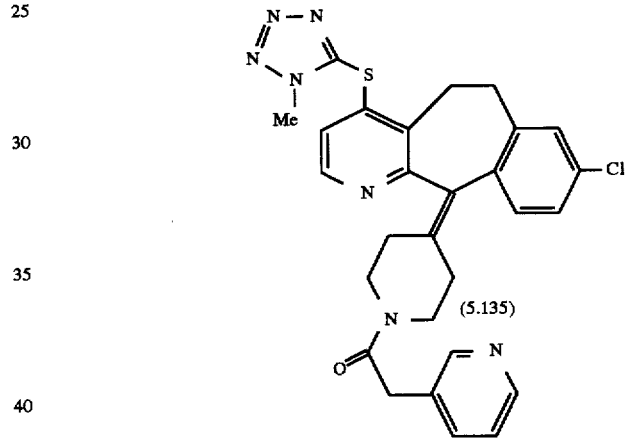

(5.135)

A mixture of the title compound from Example 250 (0.24 grams), 5-mercapto-1-methyltetrazole sodium salt (0.6 grams) and anhydrous DMF (10 mL) was stirred while being irradiated with a 200 W lamp for 10 days. Isolation and purification as in Example 257 provided the title compound (0.2 grams, 68%, MH⁺ 544).

EXAMPLE 260

1,1-DIMETHYLETHYL[2-[[8-CHLORO-6,11-DIHYDRO-11-[1-[1-OXO-2-(3-PYRIDINYL)ETHYL]-4-PIPERIDINYLIDENE]-5H-BENZO[5,6]CYCLOHEPTA[1,2-b]PYRIDIN-4-YL]THIO]ETHYL]CARBAMATE

EXAMPLE 261

4-(4,8-DICHLORO-5,6-DIHYDRO-11H-BENZO[5,6]CYCLOHEPTA[1,2-b]PYRIRIDIN-11-YLIDENE)-N-(3-PYRIDYL)-1-PIPERIDINECARBOXAMIDE

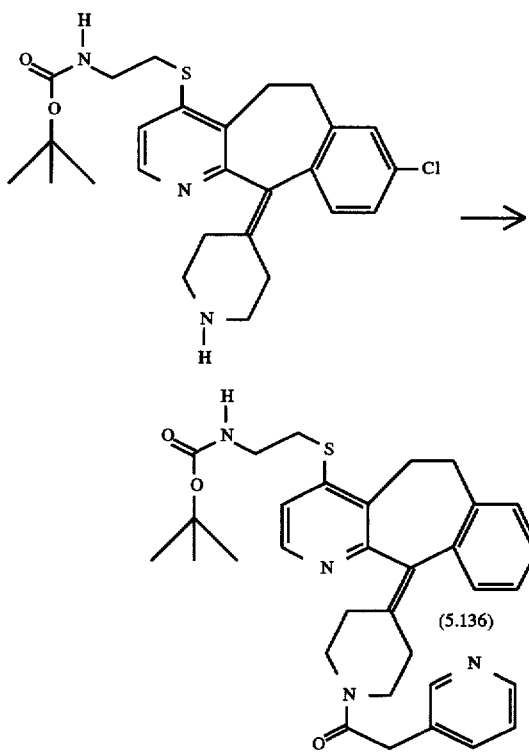

(5.136)

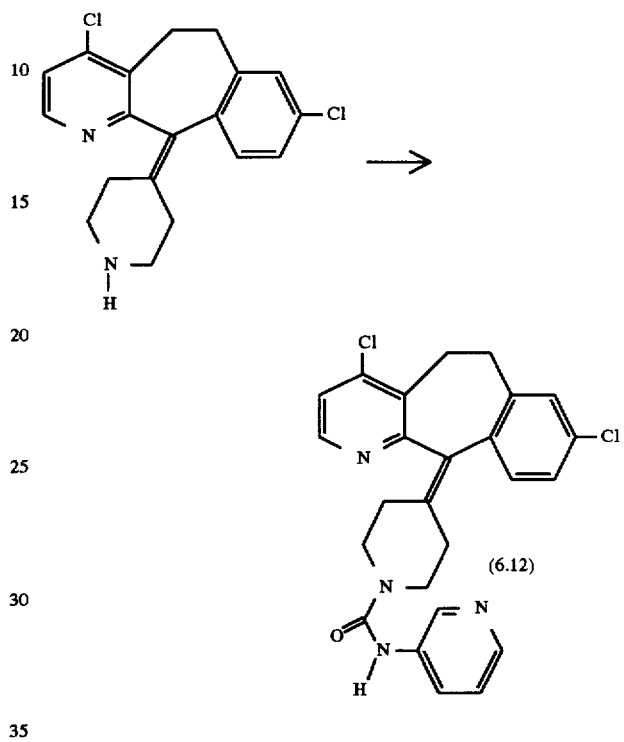

(6.12)

A mixture of the title compound from Preparative Example 32 (0.032 grams), 3-pyridylacetic acid hydrochloride (0.05 grams), DEC (0.03 grams), Et$_3$N (0.08 mL) and anhydrous DMF (4 mL) was stirred at 25° C. for 48 hours. Concentration in vacuo provided a residue which was diluted with CH$_2$Cl$_2$ and washed with 1N aqueous NaOH. The organic phase was dried over anhydrous MgSO$_4$ and concentrated in vacuo to provide the title compound (0.02 grams, 50%, mp 59.8°–63.5° C., MH$^+$ 605).

A portion of the stock solution of 3-pyridylisocyanate (32 mL) prepared as described in Preparative Example 33 was added to the 4,6-dichloro product from Preparative Example 28 (1.37 grams) and the mixture was stirred at 25° C. for 4 days. The mixture was evaporated to dryness and the residue was taken up in CH$_2$Cl$_2$ and washed with saturated aqueous sodium bicarbonate and then water. The organic solution was dried over MgSO$_4$, filtered and evaporated to dryness. The residue was purified by flash column chromatography silica gel) using 2% MeOH-CH$_2$Cl$_2$ as eluent to give the title compound (Yield 1.25 grams, 70%, MH+ 465).

EXAMPLE 262

4-[4-[(1H-BENZOTRIAZOL-1-YL)OXY]-8-CHLORO-5,6-DIHYDRO-11H-BENZO[5,6]CYCLOHEPTA[1,2-b]PYRIDIN-11-YLIDENE]-N-(3-PYRIDYL)-1-PIPERIDINECARBOXAMIDE

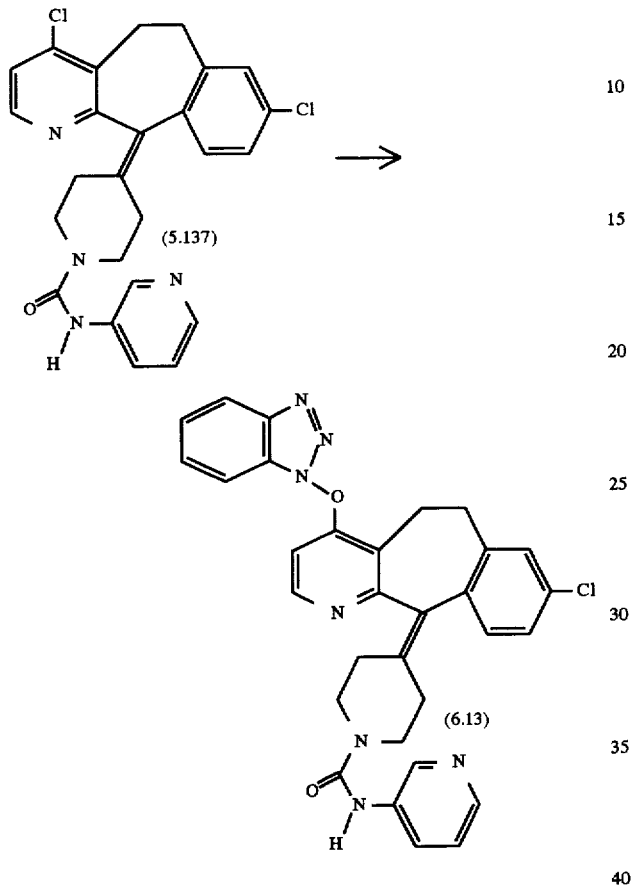

To a solution of the title compound from Example 261 (1.0 grams) in dry DMF (60 mL) was added HOBT (1.4 grams), sodium hydride (0.2 grams, 60% in mineral oil) and distilled water (0.5 mL). The solution was stirred at 25° C. under nitrogen while being irradiated with a 200 Watt lamp for 20 hours. The reaction mixture was concentrated in vacuo, diluted with CH$_2$Cl$_2$ and saturated aqueous sodium bicarbonate and after two hours, the organic phase was separated, dried over MgSO$_4$ and concentrated. Purification by flash column chromatography (silica gel) using 3–5% MeOH-CH$_2$Cl$_2$ afforded the title compound (Yield 1.1 grams, 87%, MH+ 564).

EXAMPLE 263

4-[4-HYDROXY-8-CHLORO-5,6-DIHYDRO-11H-BENZO[5,6]CYCLOHEPTA[1,2-b]PYRIDIN-11-YLIDENE]-N-(3-PYRIDYL)-1-PIPERDINECARBOXAMIDE

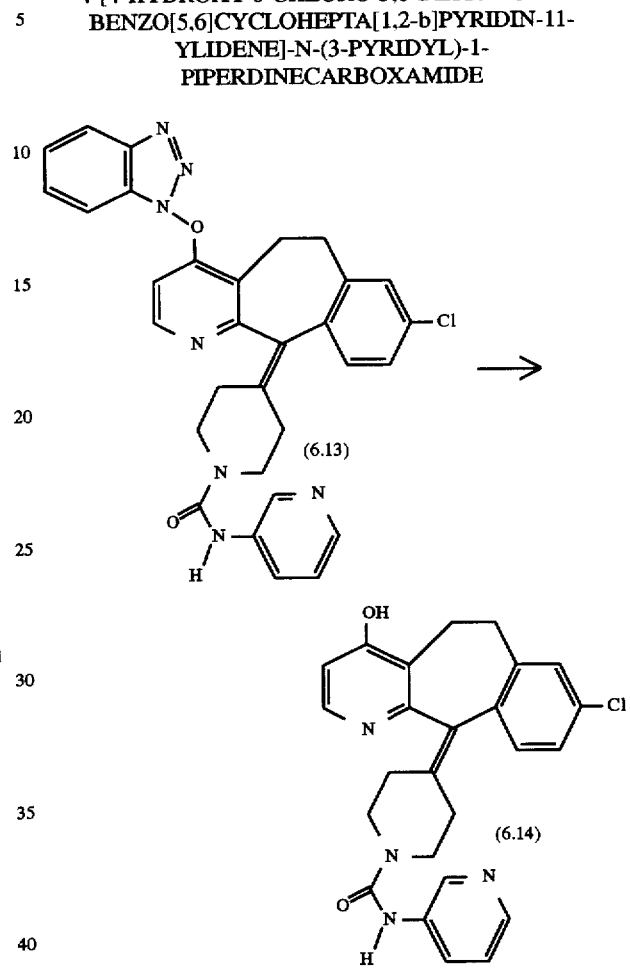

To a solution of the title compound form Example 262 (0.86 grams) and glacial acetic acid (20 mL) was added zinc dust (0.5 grams). After stirring at 25° C. for 1.5 hours, the mixture was filtered through celite and the filtrate concentrated in vacuo. The residue was purified by flash column chromatography (silica gel) using 5–10% MeOH-CH$_2$Cl$_2$ saturated with ammonium hydroxide to give the title compound (Yield 0.47 grams, MH+448).

EXAMPLE 264

4-[3-BROMO-4-HYDROXY-8-CHLORO-5,6-DIHYDRO-11H-BENZO[5,6]CYCLOHEPTA[1,2-b]PYRIDIN-11-YLIDENE]-N-(3-PYRIDYL)-1-PIPERIDINECARBOXAMIDE

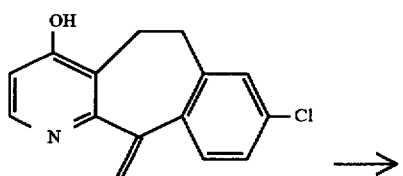
(6.14)

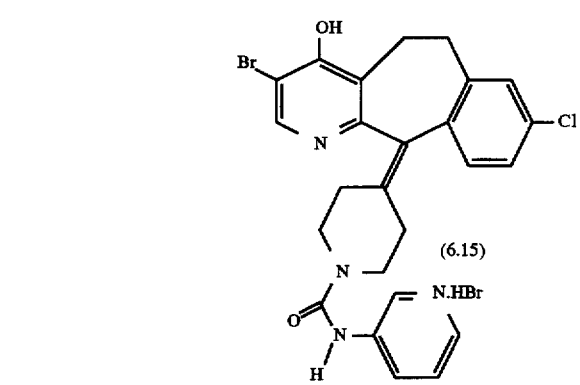
(6.15)

To a solution of the title compound from Example 263 (0.34 grams) and glacial acetic acid (10 mL) was added a 0.7M bromine-acetic acid solution (4 mL) at 25° C. under N₂. After 10 minutes, water was added and the resulting solid was filtered and washed with water several times and dried to give the title compound (Yield 0.31 grams, 67%, MH⁺ 527).

EXAMPLE 266

4-(8-CHLORO-5H-BENZO[5,6]CYCLOHEPTA[1,2-b]PYRIDIN-11-YL)-1-(3-PYRIDINYLACETYL)-PIPERIDINE

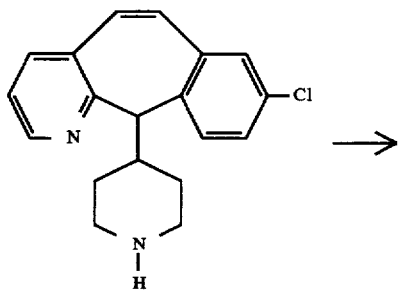

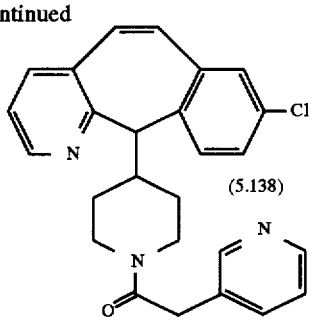
(5.138)

The title compound from Preparative Example 34C (2.0 g, 6.4 mmole) was dissolved in anhydrous DMF (70 mL) and the solution was cooled with an ice bath for 30 minutes. 4-Methylmorpholine (3.3 g, 32 mmole), DEC (1.8 g, 9.7 mmole) and HOBT (0.87 g 6.4 mmole) were added to the cold solution. 3-Pyridylacetic acid (0.88 g, 6.4 mmole) was added and the cooling bath removed. Stir the mixture at room temperature for 18 hours. The reaction mixture was evaporated to dryness and the residue was diluted with water (50 mL). The aqueous mixture was extracted with EtOAc and the combined extracts dried (MgSO₄), filtered and evaporated. The resulting residue was purifed by silica gel chromatography using a gradient of 97% CH₂Cl₂/3% MeOH saturated with ammonia to 93% dichlormethane/7% MeOH saturated with ammonia as eluent to give the title compound (0.87 g MH⁺ 430).

EXAMPLE 267

E. 4-(8-CHLORO-11H-BENZO[5,6]CYCLOHEPTA[1,2-b]PYRIDIN-11-YL)-N-(3-PYRIDINYL)-1-PIPERIDINECARBOXAMIDE

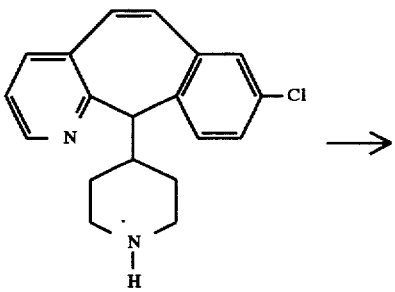

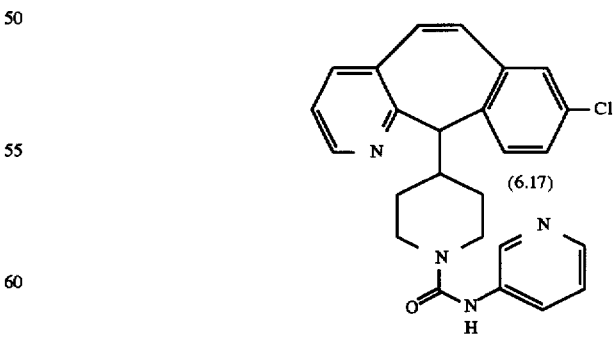
(6.17)

The title compound from Preparative Example 34C was treated with 3-pyridylisocyanate, similar to the procedure in Example 261, to afford the title compound (MH⁺ 431).

EXAMPLE 268

4-(8-CHLORO-5H-BENZO[5,6]CYCLOHEPTA[1,2-b]PYRIDIN-11-YL)-1-[2-METHYL-2-(3-PYRIDINYL)-1-OXOPROPYL]-PIPERIDINE

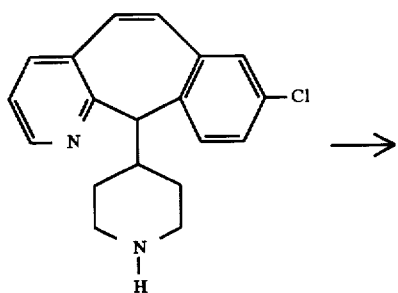

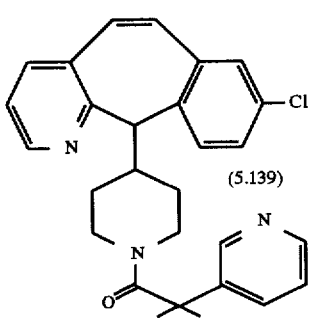

(5.139)

The title compound from Preparative Example 34C was treated as described in Example 266, using α,α-dimethyl-3-pyridylacetic acid (described in Preparative Example 10B) in place of 3-pyridylacetic acid, to afford the title compound (M+ 458).

EXAMPLE 269

4-(8-CHLORO-5 H-BENZO[5,6]CYCLOHEPTA[1,2-b]PYRIDIN-11-YL)-1-(4-PYRIDINYLACETYL)-PIPERIDINE

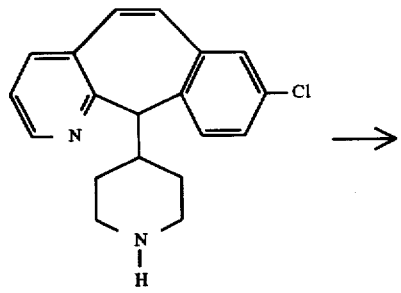

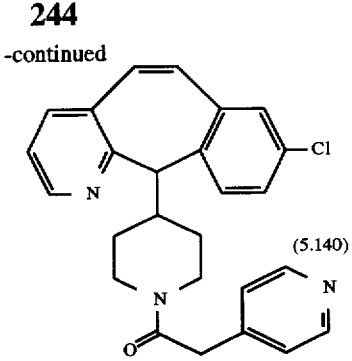

(5.140)

The title compound from Preparative Example 34C above was treated as descibed in Example 266, using 4-pyridylacetic acid in place of 3-pyridylacetic acid, to give the title compound (M+ 430).

EXAMPLE 270

4-(8-CHLORO-9-ETHYL-5H-BENZO[5,6]CYCLOHEPTA-[1,2-b]PYRIDIN-11-YL)-1-(3-PYRIDINYLACETYL)-PIPERIDINE

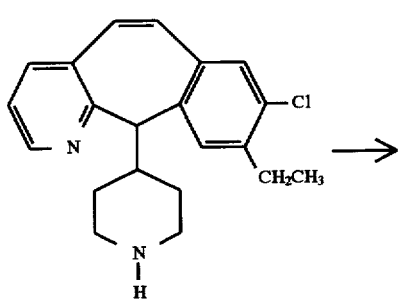

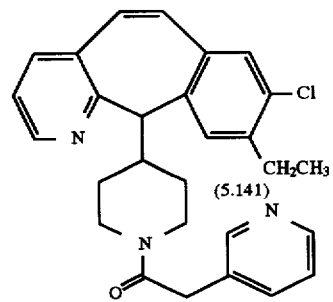

(5.141)

The title compound from Preparative Example 2A was treated as descibed in Example 266 to give the title compound (M+=458, mp=67.2°–69.8° C.).

EXAMPLE 273

4-(4,8-DiCHLORO-5H-BENZO[5,6]CYCLOHEPTA[1,2-B]PYRDIN-11-YL)-1-(3-PYRIDINYLACETYL)-PIPERIDINE

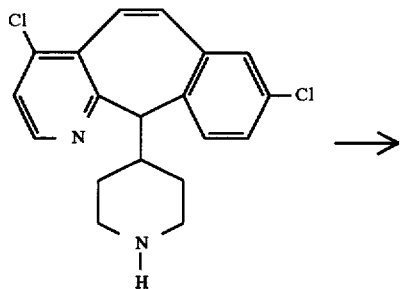

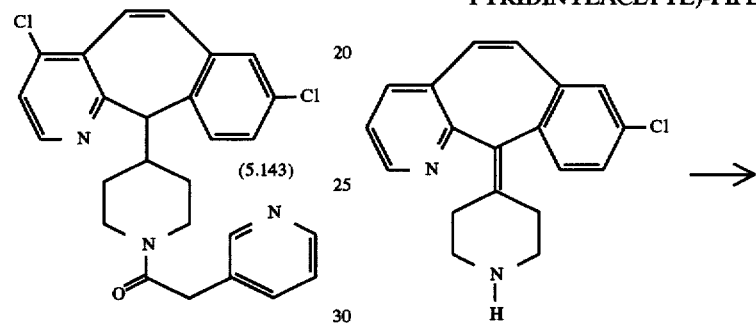

(5.143)

The title compound from Preparative Example 36C was treated as descibed in Example 266 to give the title compound (mp 100.1°–103.4° C.).

EXAMPLE 274

4-(4,8-DICHLORO-11H-BENZO[5,6]CYCLOHEPTA[1,2-b]PYRIDIN-11-YL)-N-(3-PYRIDINYL)-1-PIPERIDINECARBOXAMIDE

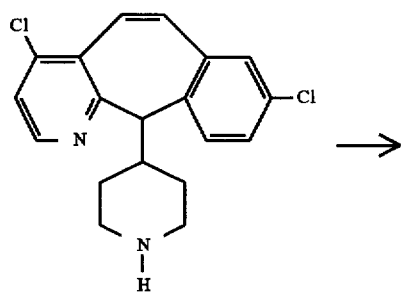

(6.19)

The title compound from Preparative Example 36C (0.75 g, 2.17 mmol) was treated with a pyridine solution of 3-pyridylisocyanate (from Preparative Example 33). The reaction mixture was evaporated to dryness and the residue dissolved in $CH_2Cl_2$. This solution was washed with saturated sodium bicarbonate solution and brine, dried ($MgSO_4$), filtered and evaporated to give a dark syrup. The syrup was purified by silica gel chromatography using a gradient of 97% $CH_2Cl_2$/3% MeOH saturated with ammonia to 93% $CH_2Cl_2$/7% MeOH saturated with ammonia. The title compound was obtained as a yellow solid (0.13 g, M+ 465)

EXAMPLE 276

4-(8-CHLORO-11H-BENZO[5,6]CYCLOHEPTA[1,2-b]PYRIDIN-11YLIDENE)-1-(3-PYRIDINYLACETYL)-PIPERIDINE

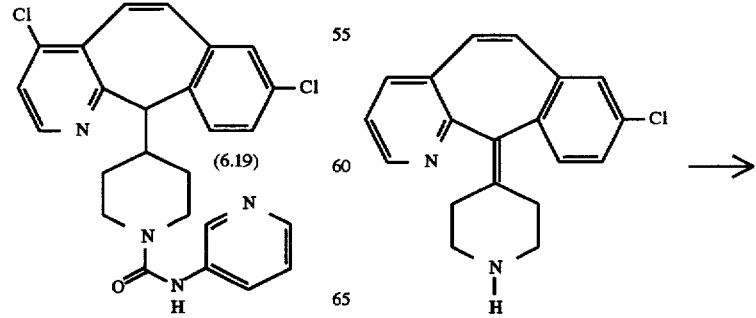

(5.145)

The title compound from Preparative Example 37B was treated as descibed in Example 266 to give the title compound ($MH^+$ 428).

EXAMPLE 277

4-(8CHLORO-11H-BENZO[5,6]CYCLOHEPTA[1,2-b]PYRIDIN-11YLIDENE)-N-(3-PYRIDINYL)-1-PIPERIDINECARBOXAMIDE

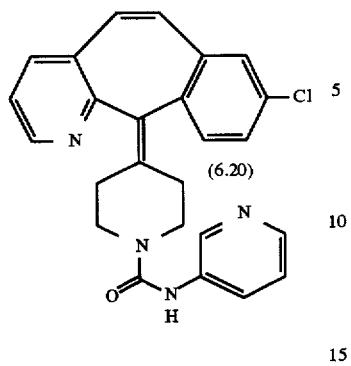

(6.20)

The title compound from Preparative Example 37B above was treated as descibed in Example 261 above to give the title compound (mp 95.9°–97.6° C.).

EXAMPLE 278

4-(8-CHLORO-11H-BENZO[5,6]CYCLOHEPTA[1,2-b]PYRIDIN-11YLIDENE)-1-[2-METHYL-2-(3-PYRIDINYL)-1-OXO-PROPYL]-PIPERDINE

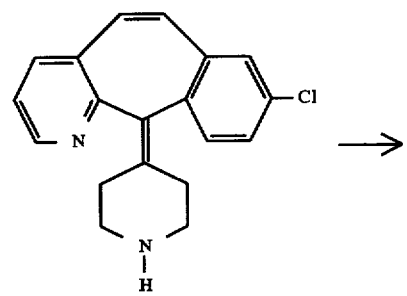

→

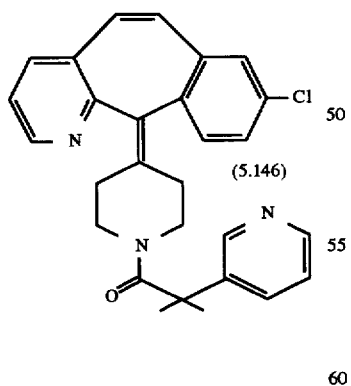

(5.146)

The title compound from Preparative Example 37B was treated as descibed in Example 266 using α,α-dimethyl-3-pyridylacetic acid (described in Preparative Example 10B) in place of 3-pyridylacetic acid, to give the title compound (M+ 456).

EXAMPLE 279

4-(8-CHLORO-5,6-DIHYDROXY-5-OXO-11H-BENZO[5,6]-CYCLOHEPTA[1,2-b]PYRIDIN-11YLIDENE)-1-(3-PYRIDINYLACETYL)-PIPERIDINE

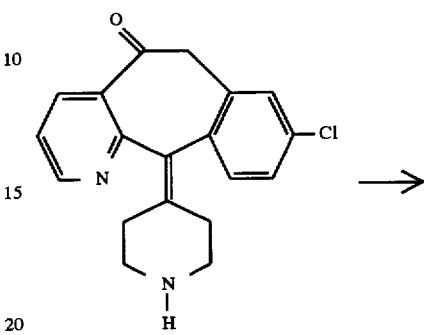

→

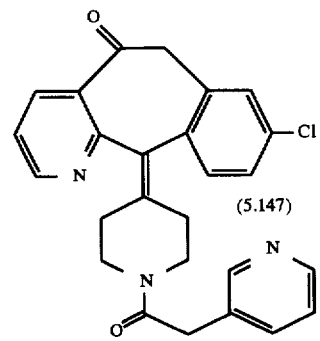

(5.147)

The preparation of the starting material for this reaction was described in The Journal of Organic Chemistry, 1990, 55, pp. 3341–3350 by Piwinski, J. J.; Wong, J. K.; Chan, T.-M.; Green, M. J.; and Ganguly, A. K. The procedure described in Example 266 was followed using 8-chloro-6,11-dihydro-11-(4-piperidinylidene)-5H-benzo[5,6]cyclohepta[1,2-b]pyridin-5-one to give the title compound (M+ 443).

EXAMPLE 280

4-(8-CHLORO-5,6-DIHYDRO-5-HYDROXY-11H-BENZO[5,6]CYCLOHEPTA[1,2-b]PYRIDIN-11YLIDENE)-1-(3-PYRIDINYLACETYL)-PIPERIDINE

→

-continued

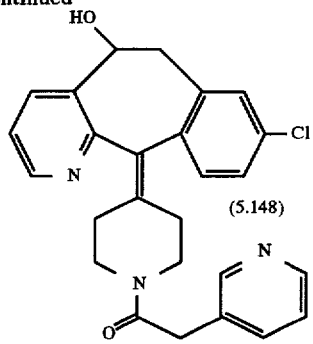

(5.148)

The preparation of the starting material for this reaction was described in *The Journal of Organic Chemistry*, 1990, 55, pp. 3341–3350 by Piwinski, J. J.; Wong, J. K.; Chan, T.-M.; Green, M. J.; and Ganguly, A. K. The procedure described in Example 266 was followed using 8-chloro-6,11-dihydro-5-hydroxy-11-(4-piperidinylidene)-5H-benzo[5,6]cyclohepta[1,2-b]pyridine to give the title compound (MH$^+$ 446).

EXAMPLE 281

4-(8-CHLORO-5,6-DIHYDRO-5-OXO-11H-BENZO[5,6]CYCLOHEPTA[1,2-b]PYRIDIN-11YLIDENE)-1-(4-PYRIDINYLACETYL)-PIPERIDINE

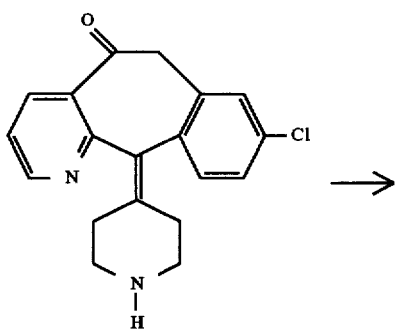

(5.149)

The procedure of Example 279 was followed with the exception that 4-pyridylacetic acid was used in place of 3-pyridylacetic acid to give the title compound (MH$^+$ 444).

EXAMPLE 282

4-(8-CHLORO-5,6-DIHYDRO-5-HYDROXY-11H-BENZO[5,6]CYCLOHEPTA[1,2-b]PYRIDIN-11YLIDENE)-1-(4-PYRIDINYLACETYL)-PIPERIDINE

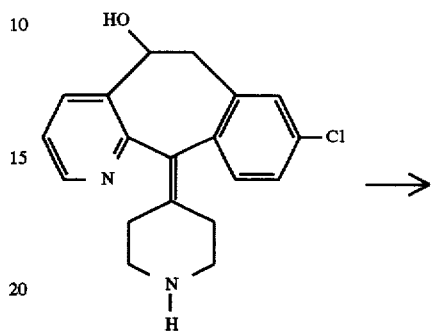

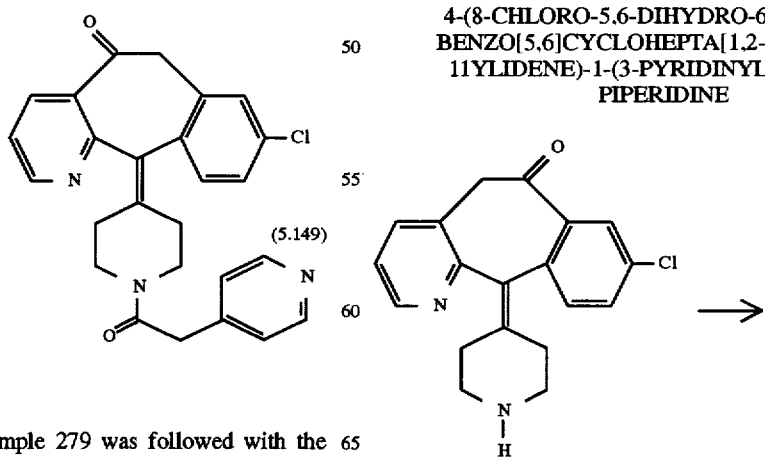

(5.150)

The procedure of Example 280 was followed with the exception that 4-pyridylacetic acid was used in place of 3-pyridylacetic acid to give the title compound (MH$^+$ 446).

EXAMPLE 283

4-(8-CHLORO-5,6-DIHYDRO-6-OXO-11H-BENZO[5,6]CYCLOHEPTA[1,2-b]PYRIDIN-11YLIDENE)-1-(3-PYRIDINYLACETYL)-PIPERIDINE

-continued

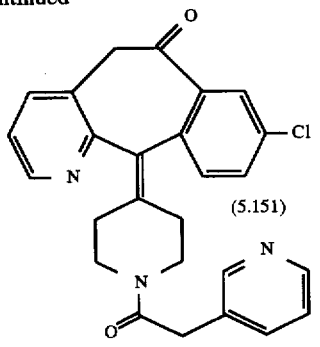

(5.151)

The preparation of the starting material for this reaction was described in *The Journal of Organic Chemistry*, 1990, 55, pp. 3341–3350 by Piwinski, J. J.; Wong, J. K.; Chan, T.-M.; Green, M. J.; and Ganguly, A. K. The procedure described in Example 266 was followed using 8-chloro-6,11-dihydro-11-(4-piperidinylidene)-5H-benzo[5,6]cyclohepta[1,2-b]pyridin-6-one to give the title compound ($M^+$ 444).

EXAMPLE 284

4-(8-CHLORO-5,6-DIHYDRO-6-HYDROXY-11H-BENZO[5,6]CYCLOHEPTA[1,2-b]PYRIDIN-11YLIDENE)-1-(3-PYRIDINYLACETYL)-PIPERIDINE

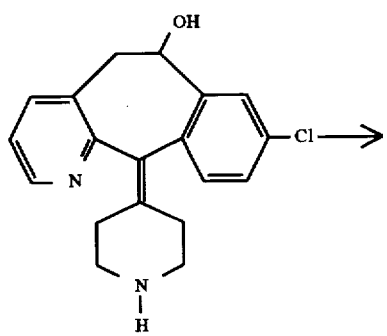

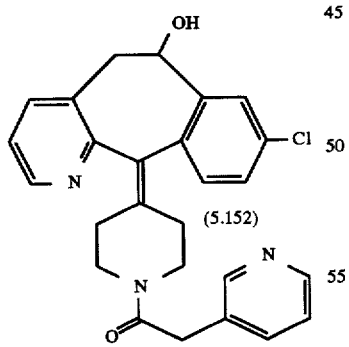

(5.152)

The preparation of the starting material for this reaction was described in *The Journal of Organic Chemistry*, 1990, 55, pp. 2241–3350 by Piwinski, J. J.; Wong, J. K.; Chan, T.-M.; Green, M. J.; and Ganguly, A. K. The procedure described in Example 266 above was followed using 8-chloro-6,11-dihydro-6-hydroxy-11-(4-piperidinylidene)-5H-benzo[5,6]cyclohepta[1,2-b]pyridine to give the title compound ($MH^+$ 446).

EXAMPLE 285

4-(8-CHLORO-5,6-DIHYDRO-6-OXO-11H-BENZO[5,6]CYCLOHEPTA[1,2-b]PYRIDIN-11YLIDENE)-1-(4-PYRIDINYLACETYL)-PIPERIDINE

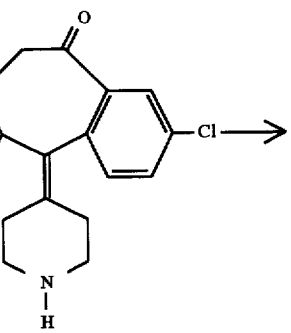

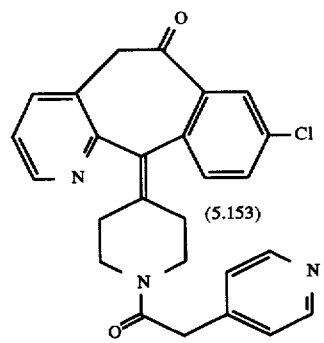

(5.153)

The procedure of Example 283 was followed with the exception 4-pyridylacetic acid was used in place of 3-pyridylacetic acid to give the title compound ($M^+$ 444).

EXAMPLE 286

4-(8-CHLORO-5,6-DIHYDRO-6-HYDROXY-11H-BENZO[5,6]CYCLOHEPTA[1,2-b]PYRIDIN-11YLIDENE)-1-(4-PYRIDINYLACETYL)-PIPERIDINE

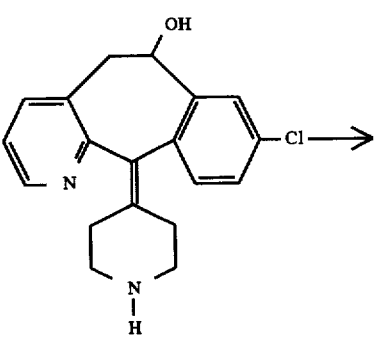

253
-continued

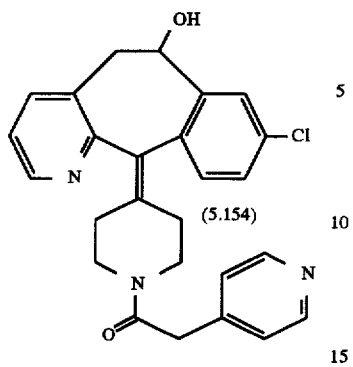

(5.154)

The procedure of Example 284 was followed with the exception that 4-pyridylacetic acid was used in place of 3-pyridylacetic acid to give the title compound (MH+ 446).

EXAMPLES 287, 289 AND 290

By essentially the same procedure as in Example 1, but using either (R)-(+)-α-methoxy-α-(trifluromethyl)-phenylacetic acid (Example 290), (S)-(−)-α-methoxy-α-(trifluromethyl)-phenylacetic acid (Example 287), or α,α-dimethylphenylacetic acid (Example 289), the compounds of Example 290, 287 and 289 were obtained. The structures for these compounds are in Table 7. Data for these compounds are: compound of Example 290, white solid MH+ 527; compound of Example 287, white solid MH+ 527; and compound of Example 289, white solid M+ 457.

EXAMPLES 291, 292, 294, 313 AND 314

By essentially the same procedure as in Example 183, and using either 4-, 3-, or 2-ethoxycarbonylaminopyridine and either 4-(8-chloro-5,6-dihydro-11H-benzo[5,6]cyclohepta[1,2-b]pyridin-11-ylidene)piperidine or 8-chloro-6,11-dihydro-11-(4-piperidinyl)-5H-benzo[5,6]cyclohepta[1,2-b]pyridine (product of Example 233A), the compounds of Examples 291, 292, 294, 313 and 314 were obtained. The structures for the compounds of Examples 291, 292, and 294 are given in Table 7. The structures for the compounds of Examples 313 and 314 are given in Table 10. Data are: the compound of Example 291 was a yellow solid (MH+ 431), the compound of Example 292 was an off white solid (MH+ 431), the compound of Example 294 was an off white solid (MH+ 431), the compound of Example 313 was a white solid (MH+ 433), and the compound of Example 314 was a white solid (MH+ 433).

254
EXAMPLE 301

1-1-(4-PYRIDINYLACETYL)-4-[3-METHYL-8-CHLORO-5,6-DIHYDRO-11H-BENZO[5,6]CYCLOHEPTA[1,2-b]PYRIDIN-11-YLIDENE]-PIPERIDINE

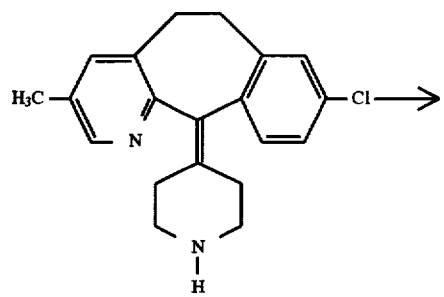

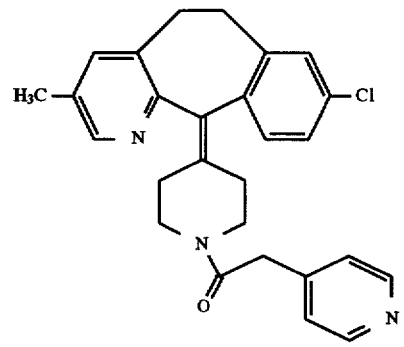

By essentially the same procedure as set forth in Example 180, but using 4-(8-chloro-3-methyl-5,6-dihydro-11-(4-piperidylidene)-11H-benzo[5,6]cyclohepta[1,2-b]pyridine (from Preparative Example 3E) instead of 4-(3,8-dichloro-5,6-dihydro-11-(4-piperidylidene)-11H-benzo[5,6]cyclohepta[1,2-b]pyridine, the title compound was obtained as an off-white solid MH+ 444

EXAMPLE 303

1-1-(3-PYRIDINYLACETYL)-4-[3-METHYL-8-CHLORO-5,6-DIHYDRO-11H-BENZO[5,6]CYCLOHEPTA[1,2-b]PYRIDIN-11-YLIDENE]-PIPERIDINE

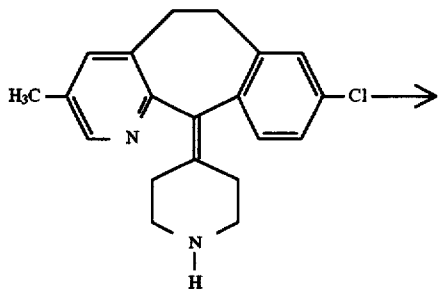

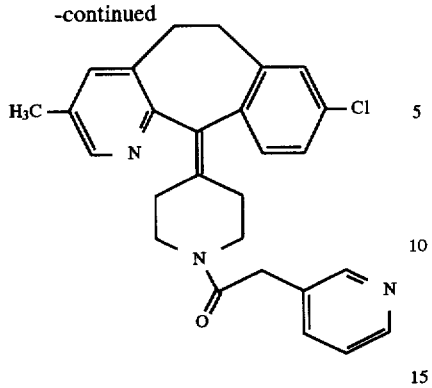

By essentially the same procedure as set forth in Example 180, but using 4-(8-chloro-3-methyl-5,6-dihydro-11-(4-piperidylidene)-11H-benzo[5,6]cyclohepta[1,2-b]pyridine (from Preparative Example 3E) instead of 4-(3,8-dichloro-5,6-dihydro-11-(4-piperidylidene)-11H-benzo[5,6]cyclohepta[1,2-b]pyridine, and 3-pyridylacetic acid instead of 4-pyridylacetic acid, the title compound was obtained as white solid MH+ 444.

EXAMPLE 307

By essentially the same procedure as in Example 1, using the title compound from Preparative Example 37B, and 4-pyridylacetic acid the compound of Example 307, identified in Table 8, was obtained, MH$^+$ 428.

EXAMPLE 309

1-1-(4-PYRIDINYLACETYL)-4-[2-METHYL-8-CHLORO-5,6-DIHYDRO-11H-BENZO[5,6]CYCLOHEPTA[1,2-b]PYRIDIN-11-YLIDENE]-PIPERIDINE

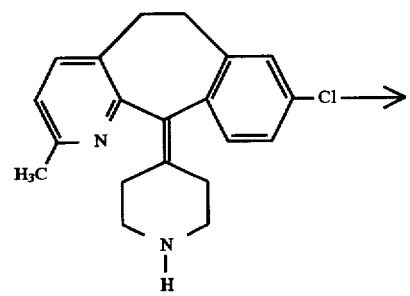

By essentially the same procedure as set forth in Example 180, but using 4-(8-chloro-2-methyl-5,6-dihydro-11-(4-piperidylidene)-11H-benzo[5,6]cyclohepta[1,2-b]pyridine (from Preparative Example 3E) instead of 4-(3,8-dichloro-5,6-dihydro-11-(4-piperidylidene)-11H-benzo[5,6]cyclohepta[1,2-b]pyridine, and 3-pyridylacetic acid instead of 4-pyridylacetic acid, the title compound was obtained as white solid MH+ 444.

EXAMPLE 311

1-1-(4-PYRIDINYLACETYL)-4-[8,9 DICHLORO-5,6-DIHYDRO-11H-BENZO[5,6]CYCLOHEPTA[1,2-b]PYRIDIN-11-YLIDENE]-PIPERIDINE

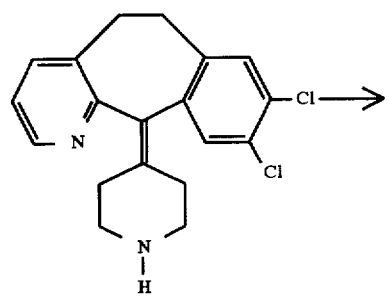

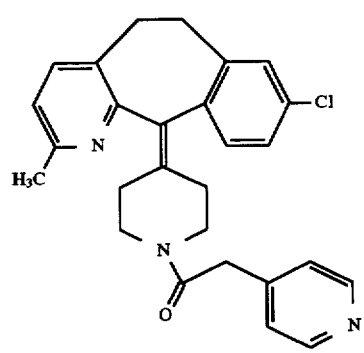

By essentially the same procedure as set forth in Example 180, but using 4-(8,9-dichloro-5,6-dihydro-11-(4-piperidylidene)-11H-benzo[5,6]cyclohepta[1,2-b]pyridine (from Preparative Example 1H) instead of 4-(3,8-dichloro-5,6-dihydro-11-(4-piperidylidene)-11H-benzo[5,6]cyclohepta[1,2-b]pyridine, and 3-pyridylacetic acid instead of 4-pyridylacetic acid, the title compound was obtained as white solid MH+ 464.

EXAMPLE 312

By essentially the same procedure as in Example 182, with the exception that 8-chloro-6,11-dihydro-11-(4-piperidinyl)-5H-benzo[5,6]cyclohepta[1,2-b]pyridine is used instead of 8-chloro-11-(1-piperazinyl)-6,11-dihydro-5H-benzo[5,6]cyclohepta[1,2-b]pyridine, the compound of Example 312 was obtained as a white solid (MH$^+$ 432). The structure for this compound is given in Table 10.

EXAMPLE 350

8-CHLORO-11H-BENZO[5,5]CYCLOHEPTA[1,2-b]PYRIDIN-11-YLIDENE)-4-(3-PYRIDINYLACETYL)PIPERAZINE

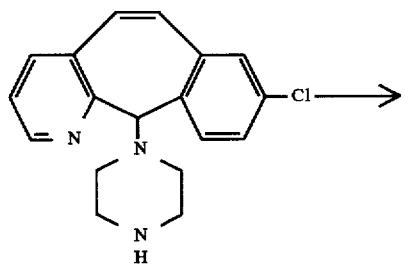

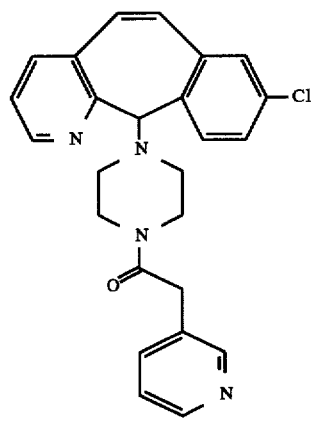

By substituting in Example 75, 0.4 g (1.28 mmoles) of 8-chloro-11-(1-piperazinyl)-11H-benzo[5,6]cyclohepta[1,2-b]pyridine (Preparative Example 38) for 8-chloro-11-(1-piperazinyl)-6,11-dihydro-5H-benzo[5,6]cyclohepta[1,2-b]pyridine and 0.1765 g (1.28 mmoles) of 3-pyridylacetic acid for 4-pyridylacetic acid and using the same method as described in Example 75, one obtains the title compound (0.513 g, 93%, MH+ 431).

EXAMPLE 351

1-(3-BROMO-8-CHLORO-6,11-DIHYDRO-5H-BENZO[5,6]CYCLOHEPTA[1,2-b]PYRIDIN-11-YL)-4-(3-PYRIDINYLACETYL)PIPERAZINE

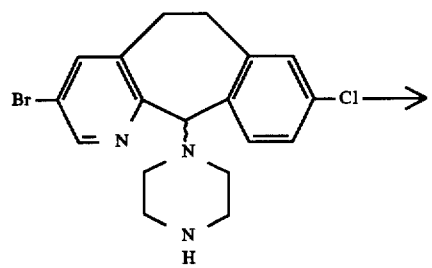

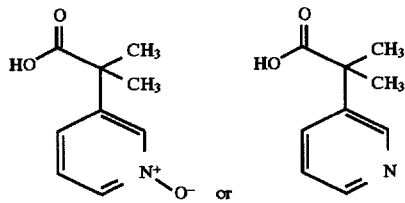

By substituting in Example 75, 3-bromo-8-chloro-11-(1-piperazinyl)-6,11-dihydro-5H-benzo[5,6]cyclohepta[1,2-b]pyridine (0.32 g, 0.81 mmoles) (Preparative Example 40) for 8-chloro-11-(1-piperazinyl)-6,11-dihydro-5H-benzo[5,6]cyclohepta[1,2-b]pyridine and 3-pyridylacetic acid (0.117 g, 0.86 mmoles) for 4-pyridylacetic acid and using the method described in Example 75, one obtains the title compound (0.3942 g, 95%, MH+ 511).

EXAMPLES 352–353

By essentially the same procedures as set forth in Example 351, but using

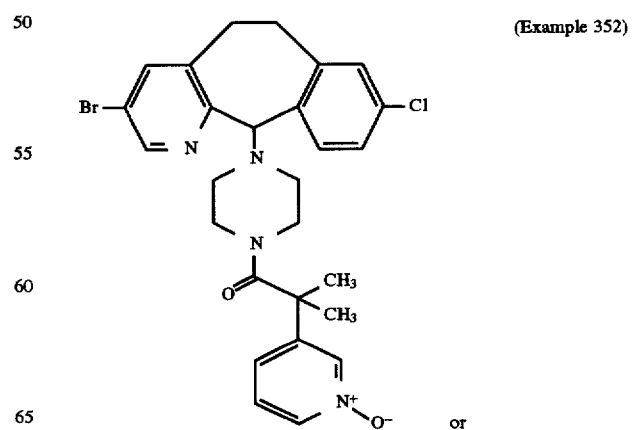

in place of 3-pyridylacetic acid, one obtains compounds of the formulas (Example 352)

-continued (Example 353)

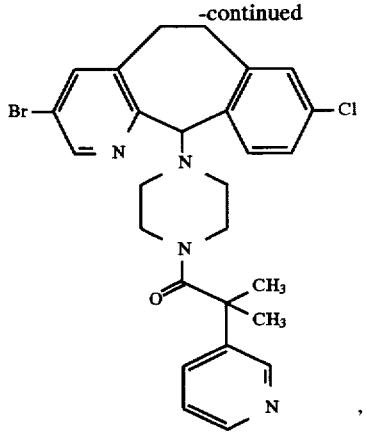

respectively. The compound of Example 352 is a white amorphous solid, yield 65%, Mass Spec MH⁺ 555. The compound of Example 353 is a white amorphous solid, yield 59%, Mass Spec MH⁺ 539.

EXAMPLE 354

4-(3-BROMO 8-CHLORO-6,11-DIHYDRO-5H-BENZO[5,6]CYCLOHEPTA[1,2-b]PYRIDIN-11-YL)-N-(3-PYRIDINYL)-1-PIPERAZINECARBOXAMIDE

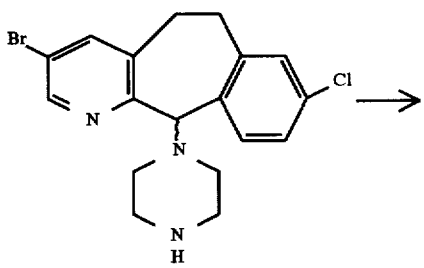

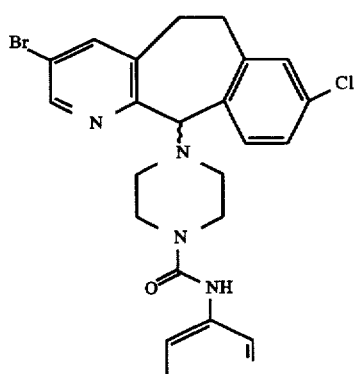

The title compound from Preparative Example 40 (0.37 g, 0.94 mmoles) was reacted with 3-ethoxycarbonylaminopyridine (Preparative Example 12) (0.123 g, 0.94 mmoles) under essentially the same conditions as described in Example 183, to give the title compound (0.3164 g, 66%, MH⁺ 512).

EXAMPLE 355

1-(4,8-DICHLORO-6,11-DIHYDRO-5H-BENZO[5,6]CYCLOHEPTA[1,2-b]-PYRIDIN-11-YL)-4-(3-PYRIDYLACETYL)PIPERAZINE

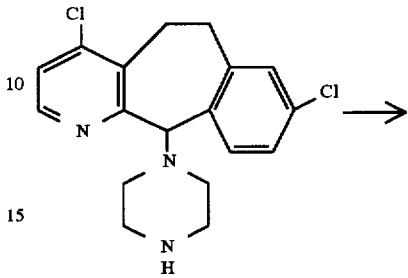

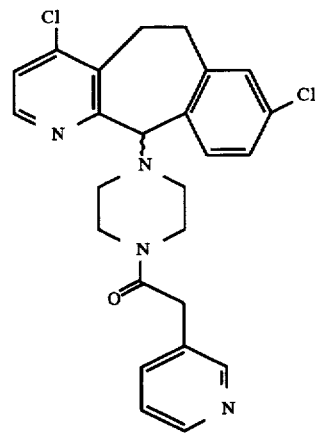

By substituting in Example 75, 4,8-chloro-11-(1-piperazinyl)-6,11-dihydro-5H-benzo[5,6]cyclohepta[1,2-b]pyridine (0.3 g, 0.86 mmoles) (Preparative Example 41) for 8-chloro-11-(1-piperazinyl)-6,11-dihydro-5H-benzo[5,6]cyclohepta[1,2-b]pyridine and 3-pyridylacetic acid (0.1181 g, 0.86 mmoles) for 4-pyridylacetic acid and using the method described in Example 75 ,one obtains the title compound (0.357 g, 88%, MH⁺ 467).

EXAMPLE 356

4-[3-BROMO-4,8-DICHLORO-5,6-DIHYDRO-11H-BENZO[5,6]CYCLOHEPTA[1,2-b]PYRIDIN-11-YLIDENE]-1-(4-PYRIDINYLACETYL)-PIPERIDINE

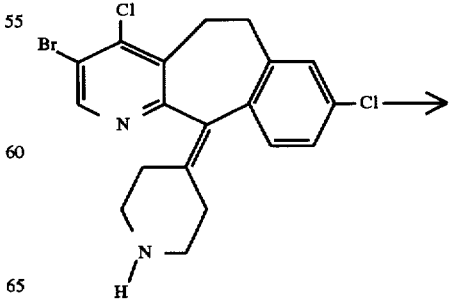

-continued

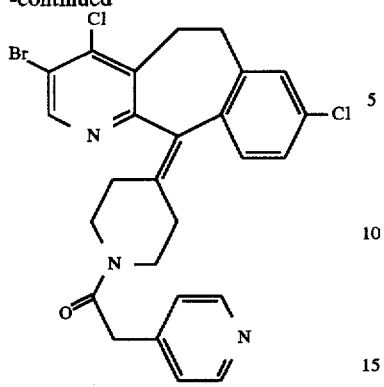

A mixture of the title compound from Preparative Example 46 (0.68 grams), 4-pyridylacetic acid hydrochloride (0.60 grams), DEC (0.65 grams), 4-methyl-morpholine (0.6 mL) and anhydrous DMF (20 mL) was stirred at 25° C. for 48 hours. Concentration in vacuo provided a residue which was diluted with $CH_2Cl_2$ and washed with 1N aqueous NaOH and brine. The organic phase was dried over anhydrous $MgSO_4$ and concentrated in vacuo to provide a residue which was purified by flash column chromatography (silica gel) using 2–5% $MeOH$-$CH_2Cl_2$ saturated with ammonium hydroxide to afford the title compound (0.06 grams, 7%, $MH^+$ 544).

EXAMPLE 358

A. 4-(8-CHLORO-3-NITRO-5,6-DIHYDRO-11-(4-PIPERIDYLIDENE)-11H-BENZO[5,6]CYCLOHEPTA[1,2-b]PYRIDINE,

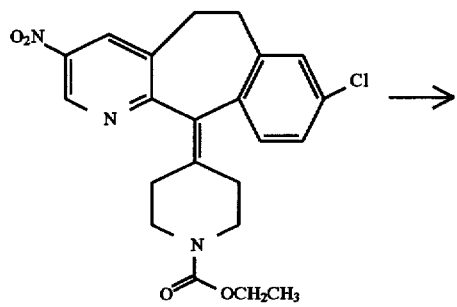

Hydrolyze the title compound of Preparative Example 47A (10.0 g, mmol) by dissolving in conc. HCl (250 mL) and heating to 100° C. for 16 h. The cooled acidic mixture was neutralized with 1M NaOH (950 mL). The mixture was extracted with $CH_2Cl_2$. The latter was dried over $MgSO_4$. Filtration and concentration afforded the title compound in 99% yield as a solid. MH+ 358.

B. 1-1-(4-PYRIDINYLACETYL)-4-[3-BROMO-8-CHLORO-5,6-DIHYDRO-11H-BENZO[5,6]CYCLOHEPTA[1,2-b]PYRIDIN-11-YLIDENE]-PIPERIDINE

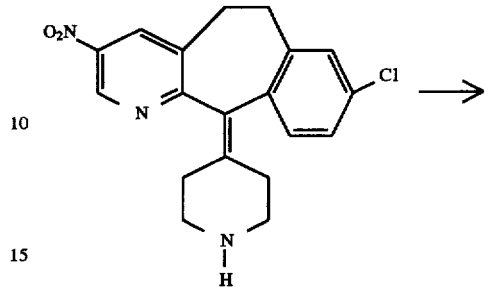

By essentially the same procedure as set forth in Example 180, but using 4-(8-chloro-3-nitro-5,6-dihydro-11-(4-piperidylidene)-11H-benzo[5,6]cyclohepta[1,2-b]pyridine instead of 4-(3,8-dichloro-5,6-dihydro-11-(4-piperidylidene)-11H-benzo[5,6]cyclohepta[1,2-b]pyridine, the title compound was obtained as an off-white solid. Mp=111.3°–112.2° C., MH+ 475.

EXAMPLE 400

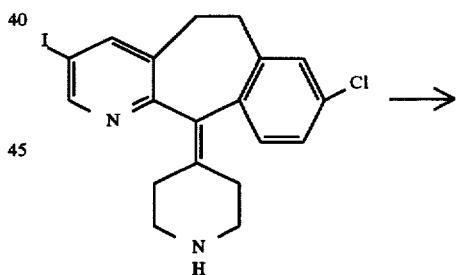

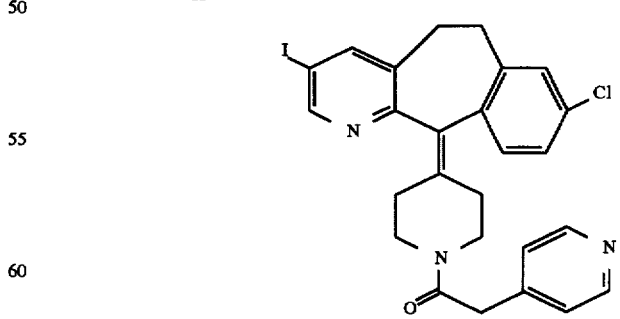

The product of Preparative Example 48, Step B, is reacted with 4-pyridyl acetic acid via essentially the same procedure as described in Example 180 to give the product compound (5.210). Mass Spec.: $MH^+$=556

Using the appropriate carboxylic acid and the starting compound indicated, the following compounds were prepared via substantially the same procedure as described for Example 400:

| Starting Compound | Product Compound | Analytical Data |
|---|---|---|
| Preparative Example 49 | 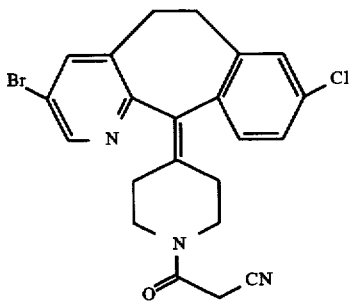<br>Example 400-A | Mass Spec.:<br>$MH^+ = 458$ |
| Preparative Example 53C | 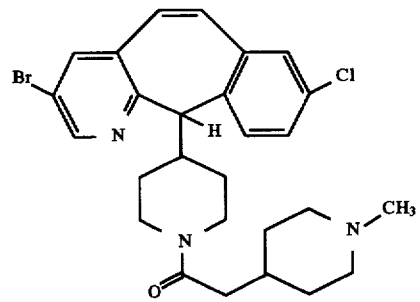<br>Example 400-B (5.203) | Mass Spec.:<br>$MH^+ = 528.2$ |
| Preparative Example 53C | 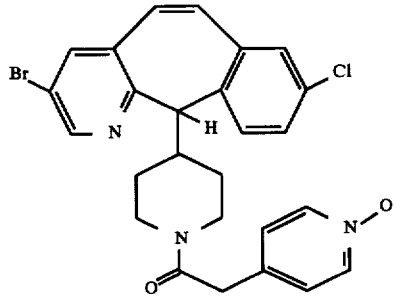<br>Example 400-C (5.200) | Mass Spec.:<br>$MH^+ = 524.2$ |
| Preparative Example 53C | 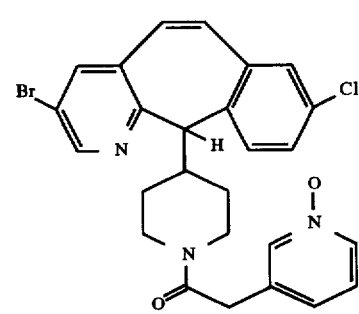<br>Example 400-D (5.217) | Mass Spec.:<br>$MH^+ = 524.1$ |

-continued
| Starting Compound | Product Compound | Analytical Data |
|---|---|---|
| Preparative Example 51A | 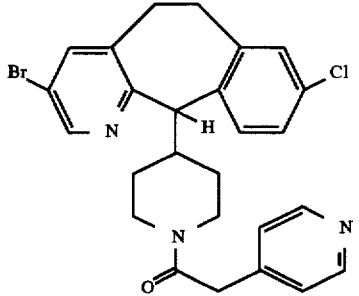<br>Example 400-E (5.208) | Mass Spec.: MH$^+$ = 512.1 |
| Preparative Example 51A | 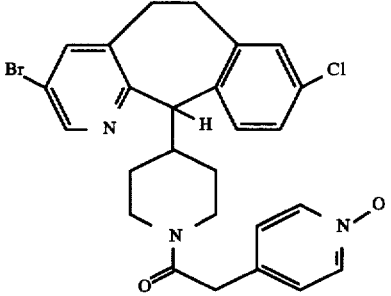<br>Example 400-F (5.201) | Mass Spec.: MH$^+$ = 528 |
| Preparative Example 53C | 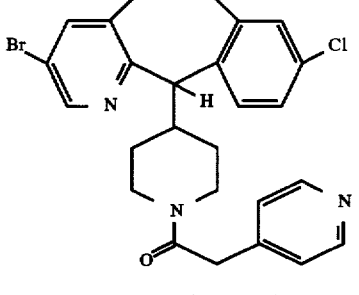<br>Example 400-G (5.204) | Mass Spec.: MH$^+$ = 508.0 |
| Preparative Example 49 | 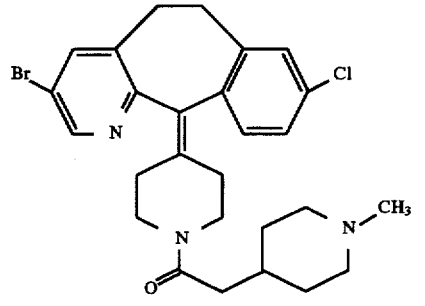<br>Example 400-H (5.220) | Mass Spec.: MH$^+$ = 530.2 |

-continued
| Starting Compound | Product Compound | Analytical Data |
|---|---|---|
| Preparative Example 51A | 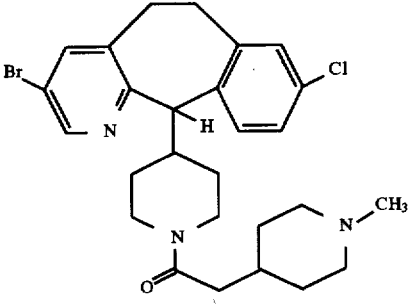<br>Example 400-J (5.212) | Mass Spec.: MH$^+$ = 532.3 |
| Preparative Example 49 | 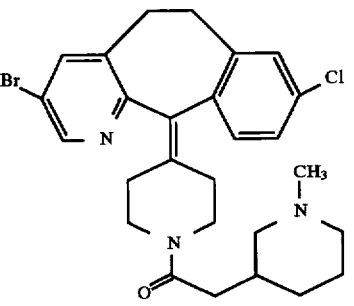<br>Example 400-K (5.218) | Mass Spec.: MH$^+$ = 530.2 |
| Preparative Example 49 | 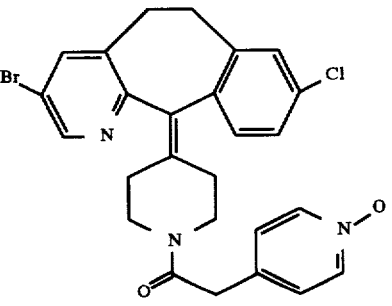<br>Example 400-L (5.206) | Mass Spec.: MH$^+$ = 526 |
| Preparative Example 56 Step C | 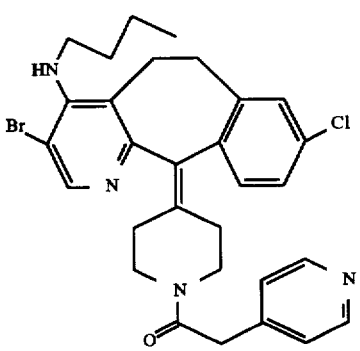<br>Example 400-M | Mass Spec.: MH$^+$ = 581 |

-continued
| Starting Compound | Product Compound | Analytical Data |
|---|---|---|
| Preparative Example 49 | 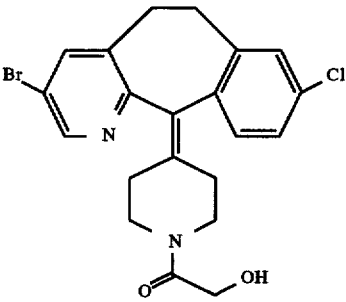<br>Example 400-N | Mass Spec.:<br>MH+ = 449.2 |
| Preparative Example 51A | 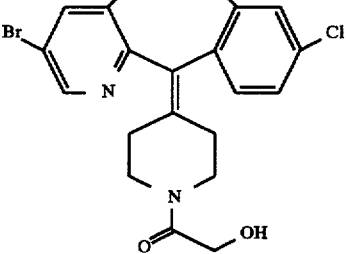<br>Example 400-P | m.p. = 62.8°–63.5° C.<br>Mass Spec.:<br>MH+ = 451 |
| Preparative Example 53B | 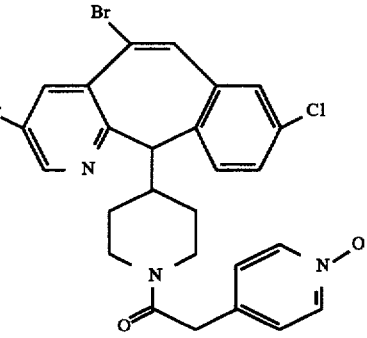<br>Example 400-Q | Mass Spec.:<br>MH+ = 602 |
EXAMPLE 401
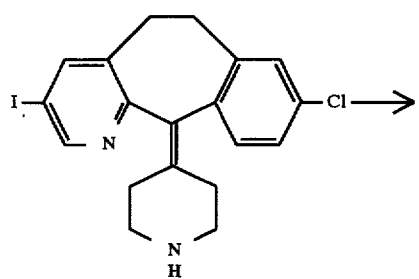
-continued
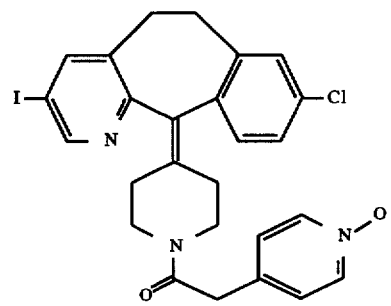

The product of Preparative Example 48, Step B, is reacted with 4-pyridyl acetic acid N-oxide via essentially the same procedure as described in Example 227 to give the product compound (5.209). Mass Spec.: MH⁺=572

Using the appropriate carboxylic acid and the starting compound indicated, the following compounds were prepared via substantially the same procedure as described for Example 401:

| Starting Compound | Product Compound | Analytical Data |
|---|---|---|
| Preparative Example 50 | 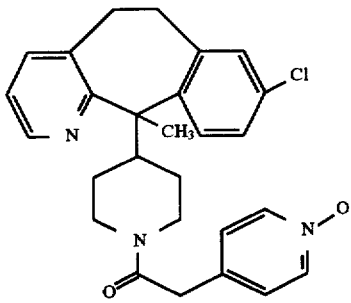 Example 401-A | Mass Spec.: MH⁺ = 462 |

EXAMPLE 402

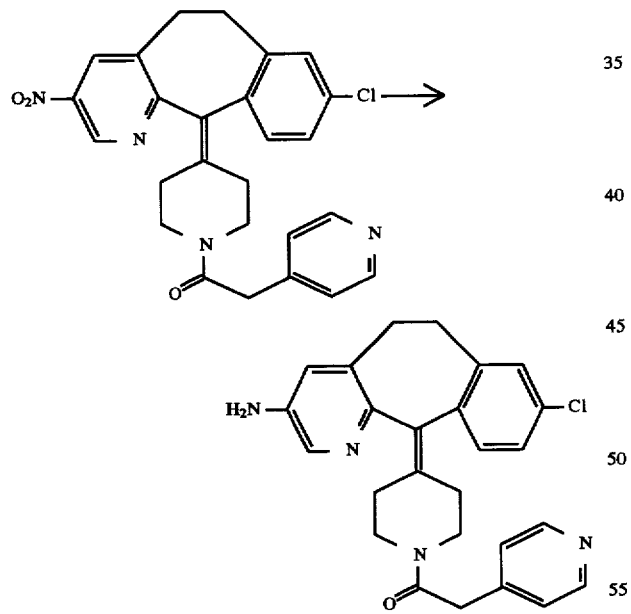

The product of Example 358, Step B, is reduced via essentially the same procedure as described in Step B of Preparative Example 47 to give the product compound. mp=133.2°–133.4° C. MH⁺ 445

Using the starting compound indicated, the following compounds were prepared via substantially the same procedure as described for Example 402:

| Starting Compound | Product Compound | Analytical Data |
|---|---|---|
| Example 411-B | 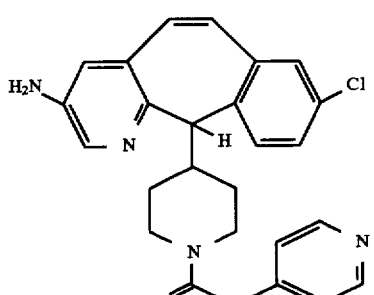 Example 402-A | Mass Spec.: MH⁺ = 445.2 |

EXAMPLE 403

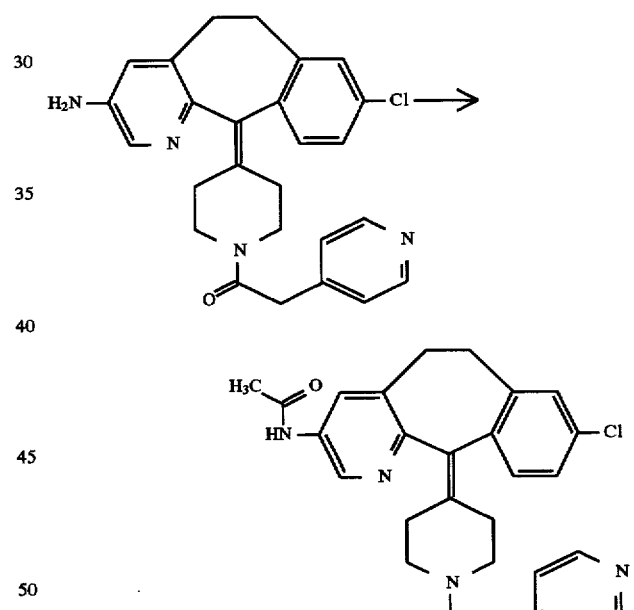

Combine 0.3 g (0.67 mmol) of the product of Example 402, 5 mL of pyridine and 0.1 g (1.01 mmol) of acetic anhydride and stir the mixture at room temperature for 2 days. Add another 100 μL of acetic anhydride, warm to 60° C. and stir for 6 h. Neutralize the reaction mixture then basify with 1N NaOH (aqueous) to pH=10. Extract with CH₂Cl₂, dry the extract over MgSO₄ and concentrate to a residue. Purify the residue by HPLC eluting 8% MeOH/ CH₂Cl₂+concentrated NH₄OH (aqueous) to give 0.22 g of the product compound. Mass Spec.: MH⁺=487

EXAMPLE 404

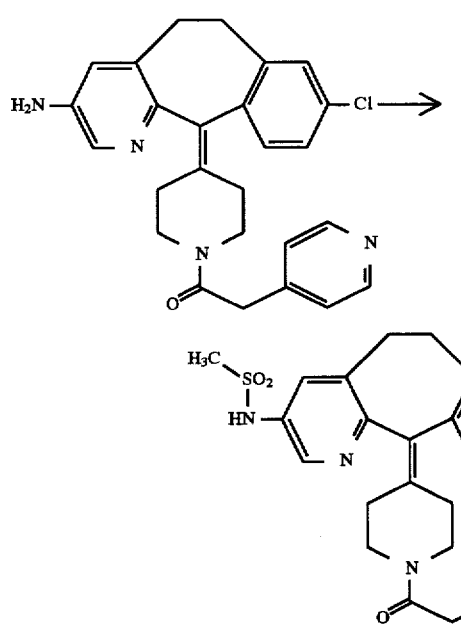

The product of Example 402 is reacted with methanesulfonyl chloride via substantially the same procedure as described for Example 403 to give the 0.32 g of the product compound. Mass Spec.: MH+=523

EXAMPLE 405

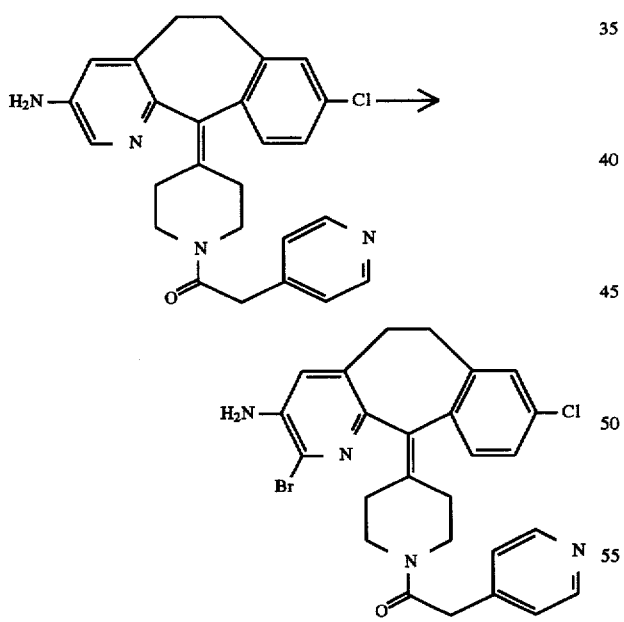

Combine 1.5 g (3.37 mmol) of the product of Example 402 and 10 mL of AcOH, then add 3.37 mL of a solution of bromine in AcOH and stir the mixture at room temperature overnight. Basify the mixture with 1N NaOH (aqueous) to basic pH, then extract with EtOAc. Concentrate the extract to a residue and chromatograph (silica gel, 90% EtOAc/hexane, then 5% Et₃N/EtOAc) to give the product compound. Mass Spec.: MH+=525.

EXAMPLE 406

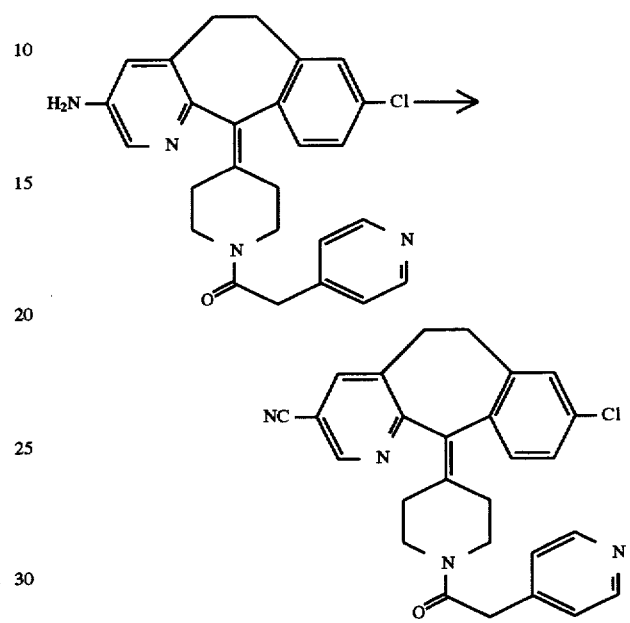

Combine 0.5 g (1.12 mmol) of the product of Example 402 and 10 mL of acetone, add 230 µL of conc. HCl (aqueous) and 4 mL of water, and cool to −10° C. Add a solution of 0.085 g NaNO₂ in 4 mL of water, stir for 15 min., then add the reaction mixture to a solution of CuCN [freshly prepared by adding 0.336 g (1.34 mmol) of CuSO₄ in 2 mL of water to H₂O a solution of 0.365 g (5.6 mmol) of KCN in 2 mL of H₂O]. Heat the mixture to 60°–70° C., then at 70°–80° C. to remove acetone. Cool the mixture and dilute with H₂O, then exhaustively extracted with CH₂Cl₂. Concentrate the extracts to a residue then purify by HPLC using 3% methanolic ammonia in CH₂Cl₂ to give 0.25 g (50% yield) of the product compound. Mass Spec.: MH+=455.

EXAMPLE 407

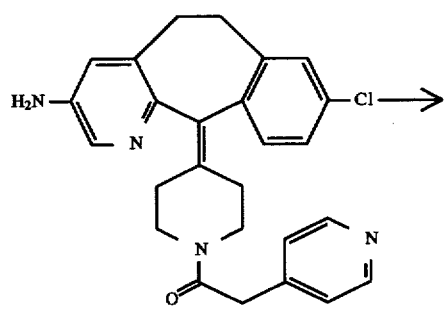

275
-continued

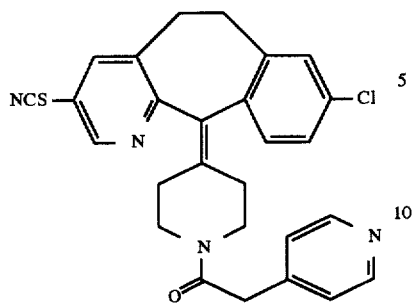

Combine 0.55 g (1.25 mmol) of the product of Example 402 and 50 mL of dilute $H_2SO_4$ at room temperature. Cool the mixture to $-10°$ C., add a solution of 0.092 g of $NaNO_2$ in 5 mL of water was added and stir for 15 min. Slowly add a solution of 0.46 g (4.7 mmol) of KSCN and 0.3 g (2.49 mmol) of CuSCN in 15 mL of water over a period of 0.5 hours. Stir for 0.5 hour then heat at reflux for 15 min. Cool the mixture and adjust the pH to ~7, then extract with $CH_2Cl_2$. Concentrate the extracts to a residue and chromatograph (silica gel, 3% $MeOH/CH_2Cl_2+NH_4OH$) to give the product compound. Mass Spec.: $MH^+=487$

276
EXAMPLE 410

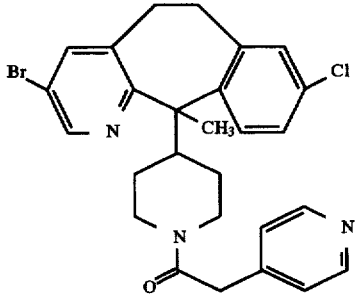

The product of Preparative Example 50 was reacted with 4-pyridylacetic acid via substantially the same procedure as described for Example 180 to give the product compound. Mass Spec.: $MH^+=446$ Using the appropriate carboxylic acid and the starting compound indicated, the following compounds were prepared via substantially the same procedure as described for Example 410:

| Starting Compound | Product Compound | Analytical Data |
|---|---|---|
| Preparative Example 49A | 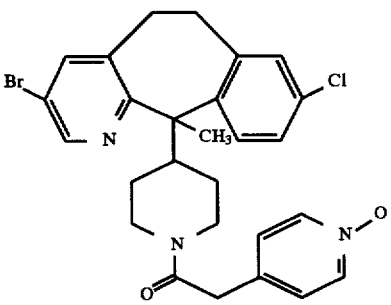  Example 410-A | Mass Spec.: $MH^+ = 526$ |
| Preparative Example 49A | Example 410-B | Mass Spec.: $MH^+ = 542$ |

-continued

| Starting Compound | Product Compound | Analytical Data |
|---|---|---|
| Preparative Example 49A | Example 410-C | Mass Spec.: MH⁺ = 542 |
| Preparative Example 52 | Example 410-D | m.p. = 67°–69° C. Mass Spec.: MH⁺ = 430 |
| Preparative Example 52A | Example 410-E | m.p. = 77°–78° C. Mass Spec.: MH⁺ = 444 |
| Preparative Example 52A | Example 410-F | m.p. = 78°–79° C. Mass Spec.: MH⁺ = 444 |

-continued
| Starting Compound | Product Compound | Analytical Data |
|---|---|---|
| Preparative Example 49 | 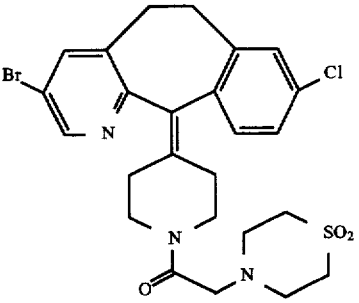<br>Example 410-G | m.p. = 137°–138° C.<br>Mass Spec.:<br>MH+ = 565 |
| Preparative Example 1 | 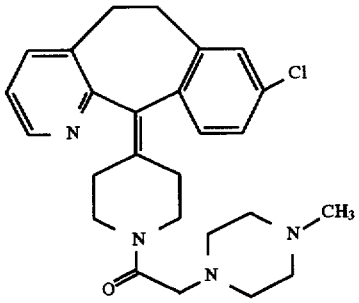<br>Example 410-H | Mass Spec.:<br>MH+ = 451.2 |
| Preparative Example 49 | 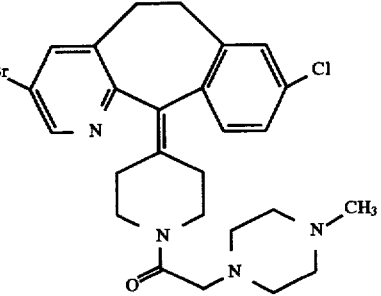<br>Example 410-J | Mass Spec.:<br>MH+ = 531.2 |
| Preparative Example 49A | 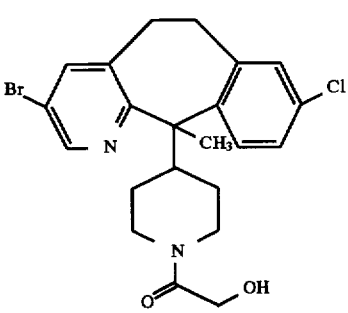<br>Example 410-K | m.p. = 108.8°–109.7° C.<br>Mass Spec.:<br>MH+ = 465.4 |

-continued

| Starting Compound | Product Compound | Analytical Data |
|---|---|---|
| Preparative Example 53 | Example 410-L | Mass Spec.: MH$^+$ = 475.2 |
| Preparative Example 57 | Example 410-M | m.p. = 151°–153° C. Mass Spec.: MH$^+$ = 560 |
| Preparative Example 49A | Example 410-N | m.p. = 164.8°–165.2° C. Mass Spec.: MH$^+$ = 546 |
| Preparative Example 49A | Example 410-P | m.p. = 124.2°–125° C. Mass Spec.: MH$^+$ = 546 |

-continued
| Starting Compound | Product Compound | Analytical Data |
|---|---|---|
| Preparative Example 49 | 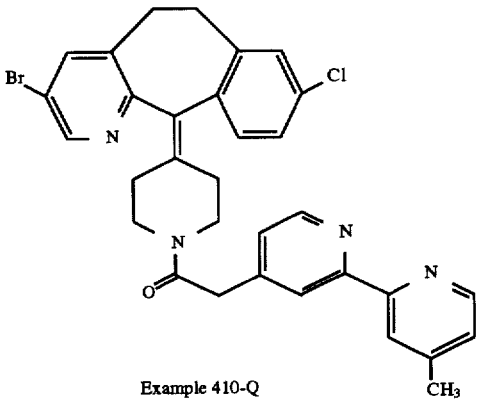<br>Example 410-Q | m.p. = 102.6°–103° C.<br>Mass Spec.:<br>MH+ = 601.2 |
| Preparative Example 73 | 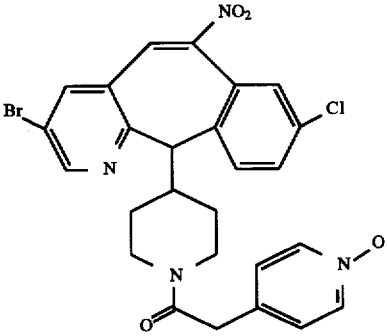<br>Example 410-R | Mass Spec.:<br>MH+ = 569 |
| Preparative Example 49 | 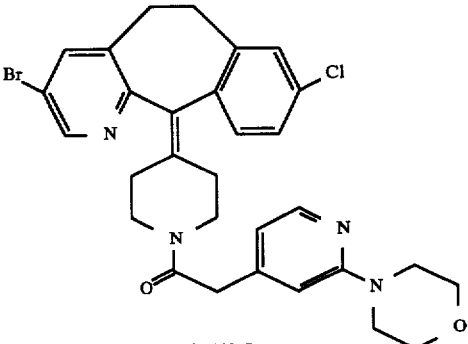<br>Example 410-S | m.p. = 97° C. (dec.)<br>Mass Spec.:<br>MH+ = 595 |
| Preparative Example 49 | 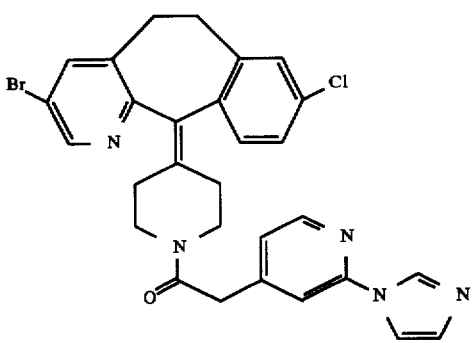<br>Example 410-T | m.p. = 132.6° C. (dec.)<br>Mass Spec.:<br>MH+ = 576 |

-continued
| Starting Compound | Product Compound | Analytical Data |
|---|---|---|
| Preparative Example 49 | 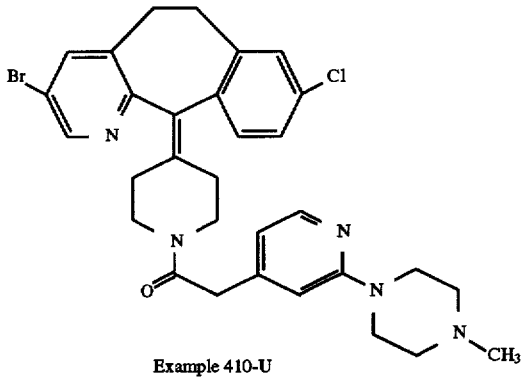<br>Example 410-U | m.p. = 111.2° C. (dec.)<br>Mass Spec.:<br>MH+ = 608 |
| Preparative Example 49 | 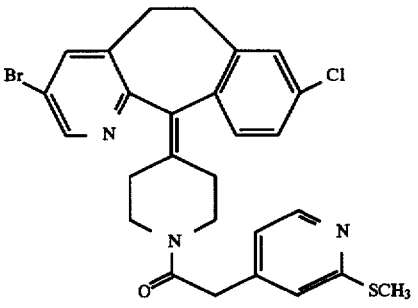<br>Example 410-V | m.p. = 85.1° C. (dec.)<br>Mass Spec.:<br>MH+ = 556 |
| Preparative Example 49 | 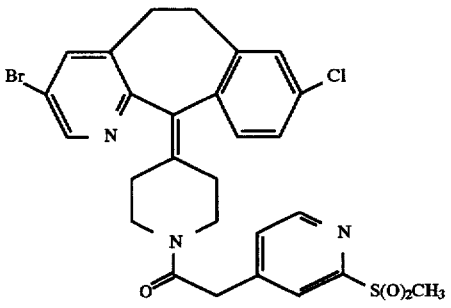<br>Example 410-W | m.p. = 114° C. (dec.)<br>Mass Spec.:<br>MH+ = 588 |
| Preparative Example 49 | 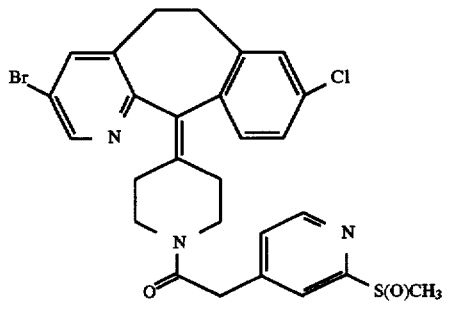<br>Example 410-X | m.p. = 122.5°–126.0° C. (dec.)<br>Mass Spec.:<br>MH+ = 572 |

EXAMPLE 411

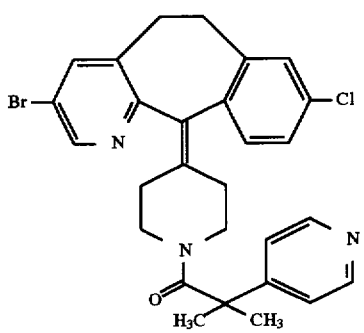

The product of Preparative Example 49 was reacted with 2-methyl-2-(4-pyridyl)propanoic acid via substantially the same procedure as described for Example 180 to give the product compound. Mass Spec.: MH$^+$=538

Using the appropriate carboxylic acid (or carboxylate salt, e.g. lithium carboxylate) and the starting compound indicated, the following compounds were prepared via substantially the same procedure as described for Example 410:

| Starting Compound | Product Compound | Analytical Data |
|---|---|---|
| Preparative Example 49 | Example 411-A | Mass Spec.: MH$^+$ = 554 |
| Preparative Example 53A | Example 411-B | Mass Spec.: MH$^+$ = 475.2 |
| Preparative Example 55 | Example 411-C | m.p. = 155.2°–158.9° C. Mass Spec.: MH$^+$ = 446 |

| Starting Compound | Product Compound | Analytical Data |
|---|---|---|
| Preparative Example 49 | 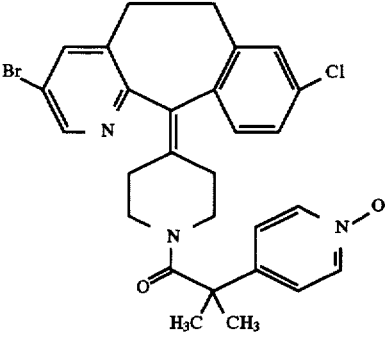<br>Example 411-D | Mass Spec.:<br>MH+ = 554 |
| Preparative Example 1 | 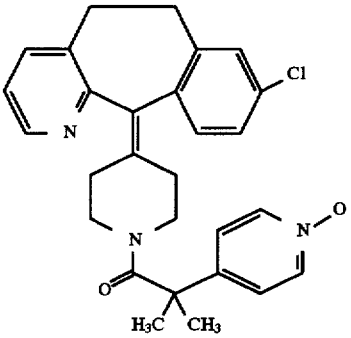<br>Example 411-E | Mass Spec.:<br>MH+ = 474 |
| Preparative Example 72 | 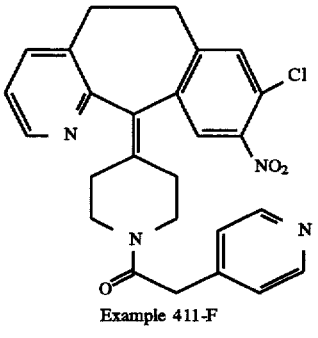<br>Example 411-F | Mass Spec.:<br>MH+ = 475 |
| Preparative Example 49 | 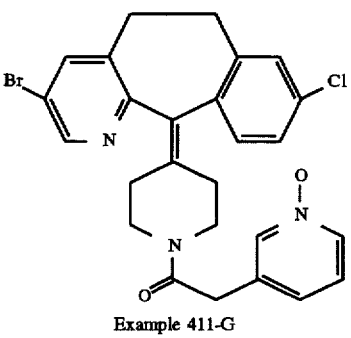<br>Example 411-G | Mass Spec.:<br>MH+ = 526.1 |

-continued
| Starting Compound | Product Compound | Analytical Data |
|---|---|---|
| Preparative Example 71 | 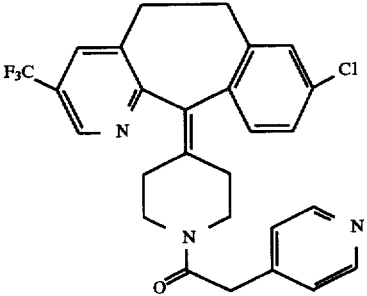<br>Example 411-H | Mass Spec.: MH+ = 498 |
| Preparative Example 53B | 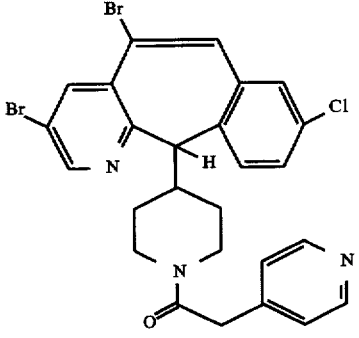<br>Example 411-J | Mass Spec.: MH+ = 589 |
| Preparative Example 53B | 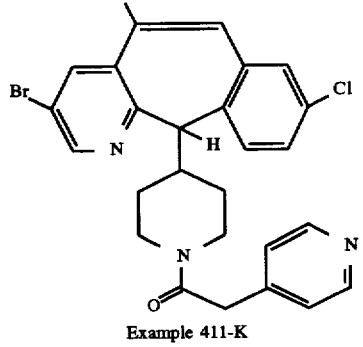<br>Example 411-K | Mass Spec.: MH+ = 581 |
| Preparative Example 59 | 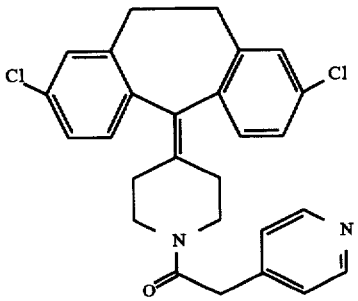<br>Example 411-L | m.p. = 97°–98° C.<br>Mass Spec.: (FAB) MH+ = 463.1 |

-continued
| Starting Compound | Product Compound | Analytical Data |
|---|---|---|
| Preparative Example 60 | 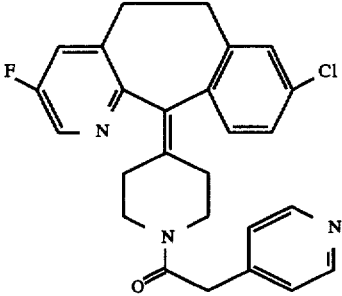Example 411-M | Mass Spec.: MH⁺ = 448 |
| Preparative Example 60 | 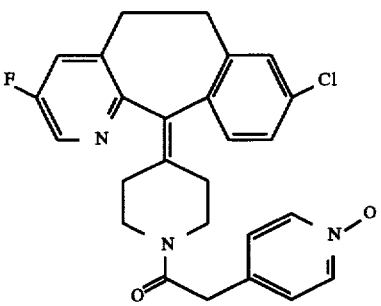Example 411-N | Mass Spec.: MH⁺ = 464 |
| Preparative Example 60 | 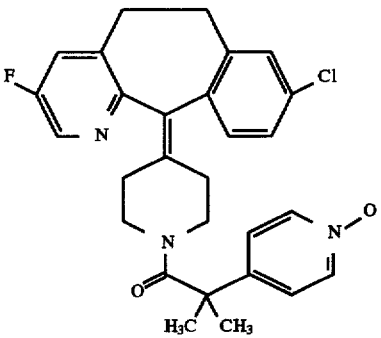Example 411-O | Mass Spec.: MH⁺ = 492 |
| Preparative Example 60 | 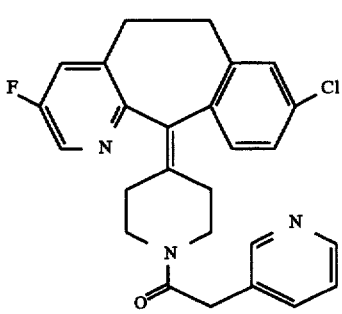Example 411-P | Mass Spec.: MH⁺ = 448 |

| Starting Compound | Product Compound | Analytical Data |
|---|---|---|
| Preparative Example 60 | 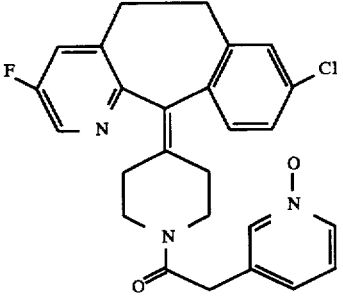<br>Example 411-Q | Mass Spec.:<br>$MH^+ = 464$ |
| Preparative Example 60 | 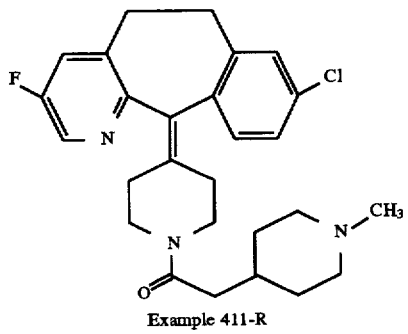<br>Example 411-R | Mass Spec.:<br>$MH^+ = 469$ |
| Preparative Example 60 | 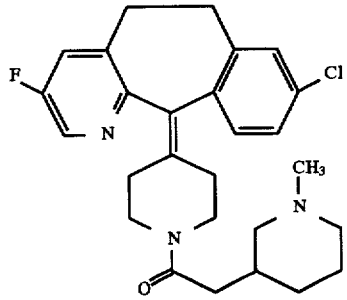<br>Example 411-S | Mass Spec.:<br>$MH^+ = 469$ |
| Preparative Example 60A | 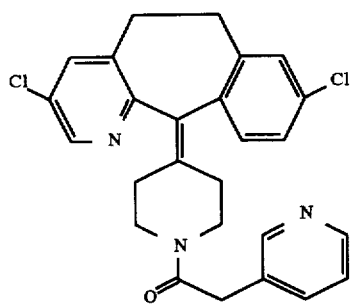<br>Example 411-T | Mass Spec.:<br>$MH^+ = 465$ |

| Starting Compound | Product Compound | Analytical Data |
|---|---|---|
| Preparative Example 60A | 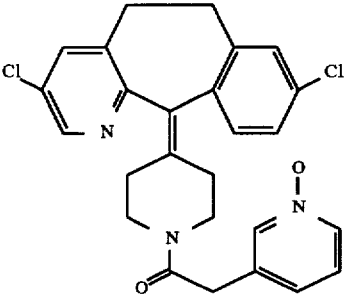
Example 411-U | Mass Spec.: MH+ = 481 |
| Preparative Example 60A | 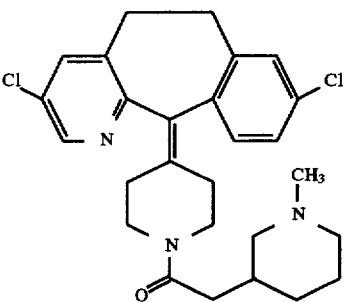
Example 411-V | Mass Spec.: MH+ = 485 |
| Preparative Example 60A | 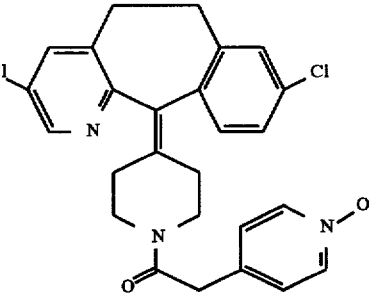
Example 411-W | Mass Spec.: MH+ = 481 |
| Preparative Example 60A | 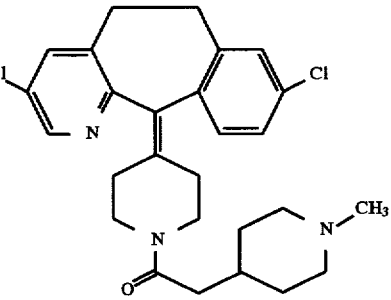
Example 411-X | Mass Spec.: MH+ = 485 |

| Starting Compound | Product Compound | Analytical Data |
|---|---|---|
| Preparative Example 1 Step G | 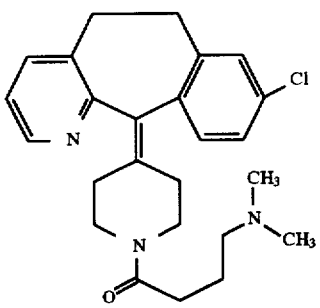  Example 411-Z | — |
| Preparative Example 51A | 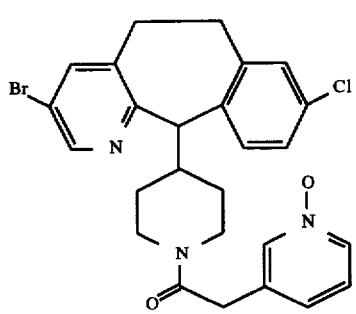  Example 411-AA | m.p. = 125°–125.4° C. Mass Spec.: MH+ = 528 |
| Preparative Example 3 Step E | 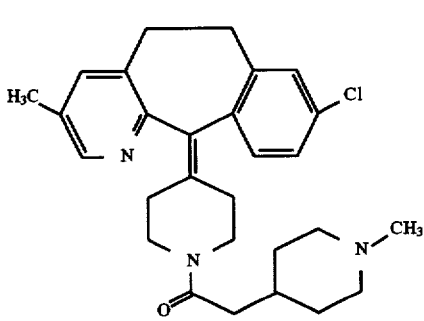  Example 411-BB | m.p. = 186.6°–187° C. Mass Spec.: MH+ = 464 |
| Preparative Example 3 Step E | 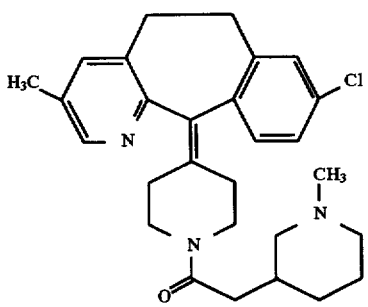  Example 411-CC | Mass Spec.: MH+ = 464 |

-continued
| Starting Compound | Product Compound | Analytical Data |
|---|---|---|
| Preparative Example 51A | 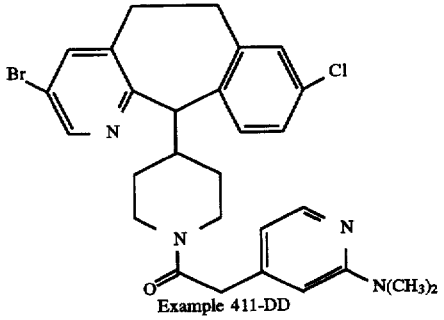<br>Example 411-DD | — |
| Preparative Example 49 | 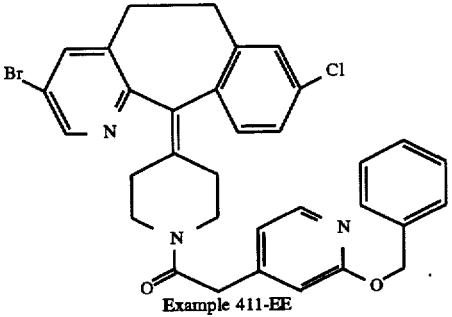<br>Example 411-EE | m.p. = 83°–86° C.<br>Mass Spec.: MH+ = 616 |
| Preparative Example 49 | 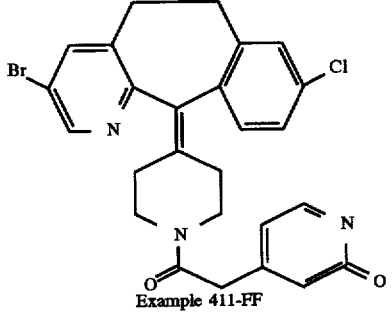<br>Example 411-FF | m.p. = 167°–171° C.<br>Mass Spec.: MH+ = 526 |
| Preparative Example 49 | 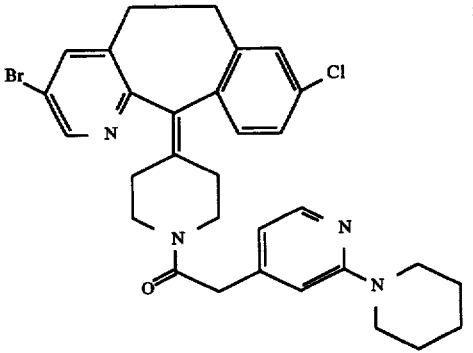<br>Example 411-GG | m.p. = 134°–140° C.<br>Mass Spec.: MH+ = 593 |

EXAMPLE 412

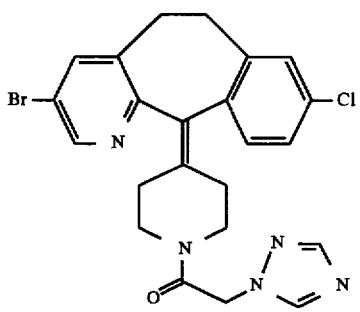

→

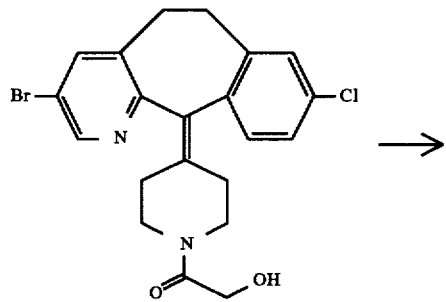

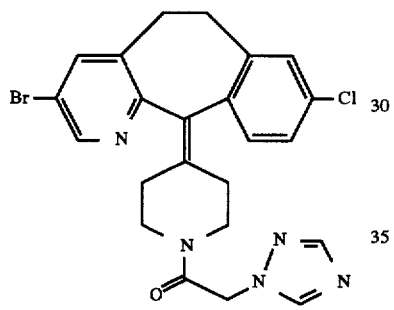

Combine 50 mg (0.11 mmol) of the compound of Example 400-N, and 1.5 mL of $SOCl_2$ and stir a room temperature overnight. Concentrate in vacuo to a residue, add 2.0 mL of DMF to the residue, then add 20 mg (0.2 mmol) of 1,2,4-triazole sodium salt and heat to 100° C. overnight. Cool the mixture, concentrate in vacuo to remove most of the solvent, wash with water (3 times), then dry the residue over $Na_2SO_4$. Concentrate in vacuo to a residue and chromatograph (silica gel, 75% (10% $NH_4OH$ in MeOH) in $CH_2Cl_2$) to give 26 mg of the product compound. Mass Spec.: $MH^+=498$ Using the appropriate starting compound and substantially the same procedure as described for Example 412, but substituting the amine nucleophile indicated in place of the 1,2,4-triazole sodium salt, the following compounds were prepared:

| Amine Nucleophile | Product Compound | Analytical Data |
|---|---|---|
| piperidine (solvent is $CH_2Cl_2$ instead of DMF) | Example 412-A | Mass Spec.: $MH^+ = 514.2$ |

-continued

| Amine Nucleophile | Product Compound | Analytical Data |
|---|---|---|
| thiomorpholine (solvent is CH$_2$Cl$_2$ instead of DMF) | 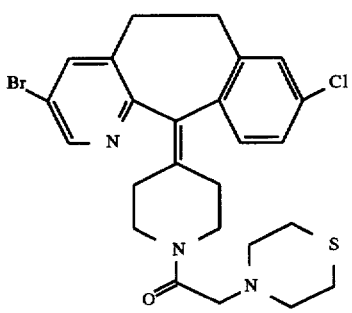<br>Example 412-B | Mass Spec.: MH$^+$ = 532.1 |
| piperazine (solvent is CH$_2$Cl$_2$ instead of DMF) | 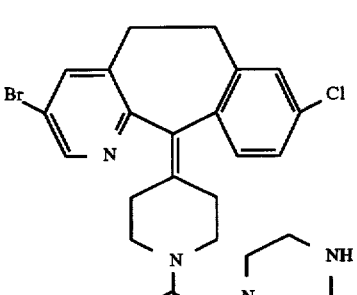<br>Example 412-C | Mass Spec.: MH$^+$ = 515 |
| morpholine (solvent is CH$_2$Cl$_2$ instead of DMF) | 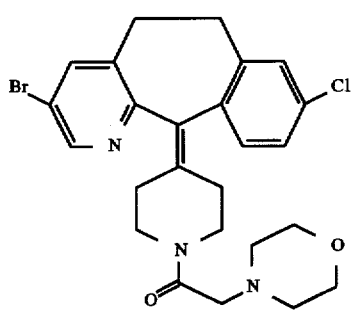<br>Example 412-D | Mass Spec.: MH$^+$ = 516.1 |
| imidazole (solvent is CH$_2$Cl$_2$ instead of DMF) | 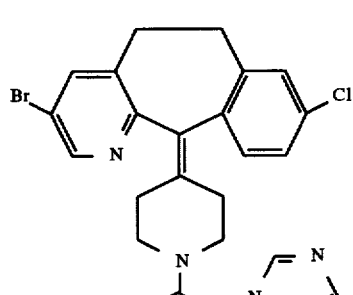<br>Example 412-E | Mass Spec.: MH$^+$ = 497.2 |

-continued
| Amine Nucleophile | Product Compound | Analytical Data |
|---|---|---|
| N-(2-methyl-phenyl)-piperazine (solvent is CH$_2$Cl$_2$ instead of DMF) | 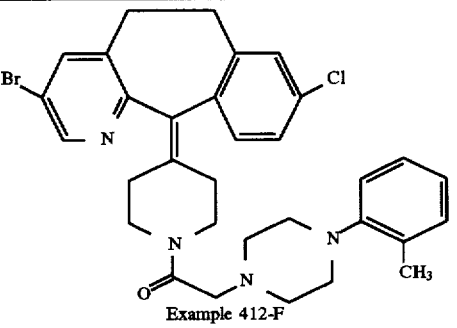Example 412-F | Mass Spec.: MH$^+$ = 605.1 |
| 4(3H)-pyrimidone | 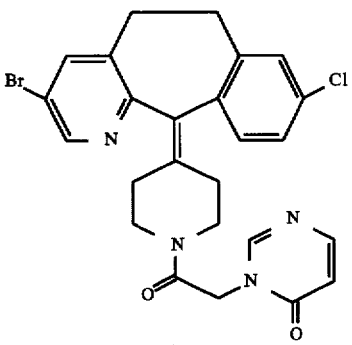Example 412-G | Mass Spec.: MH$^+$ = 525.1 |
| thiomorpholine | 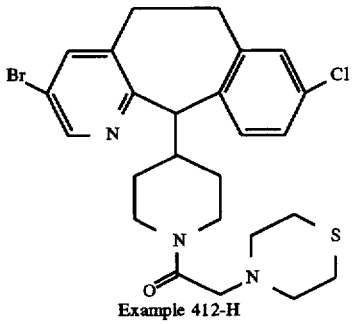Example 412-H | m.p. = 105°–105.6° C. Mass Spec.: MH$^+$ = 536 |
| thiomorpholine | 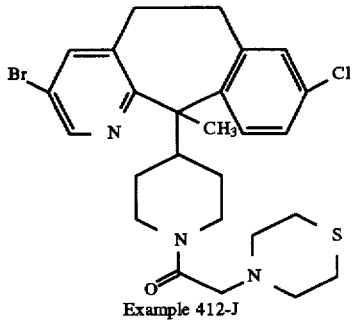Example 412-J | m.p. = 102.5°–102.9° C. Mass Spec.: MH$^+$ = 550 |

EXAMPLE 413

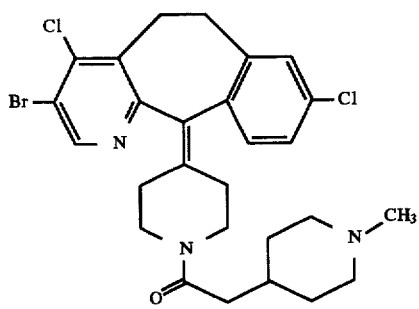

Combine 0.32 g of the product from Preparative Example 46 and 2 mL of anhydrous CH$_2$Cl$_2$ and add 6 mL of a mixture of 4.17 g of N-methyl-4-piperidylacetic acid, 1.03 mL of methanesulfonyl chloride, 6.83 mL of Et$_3$N and 50 mL of CH$_2$Cl$_2$. Stir at 25° C. overnight, then add 1N NaOH (aqueous) and shake well. Separate the layers, dry the organic phase over MgSO$_4$, and concentrate to a residue. Chromatograph the residue (silica gel, 3% MeOH/CH$_2$Cl$_2$+ NH$_4$OH) to give 0.19 g (45% yield) of the product compound. m.p.=105° C. (dec); Mass Spec.: MH$^+$=564.

EXAMPLE 414

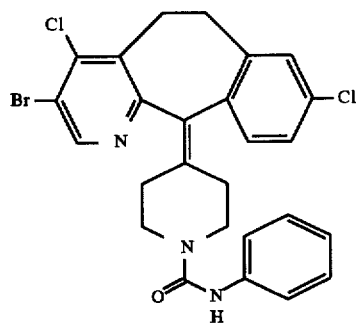

Combine 84 mg of the product from Preparative Example 46, 5 mL of pyridine and 0.04 mL of phenylisocyanate and stir at 25° C. for 48 hours. Concentrate in vacuo to a residue, dilute with CH$_2$Cl$_2$ and wash with saturated NaHCO$_3$ (aqueous). Dry over MgSO$_4$, concentrate to s residue and chromatograph (silica gel, 50–70% hexane/EtOAc) to give 14 mg (13% yield) of the product compound. m.p.=125.6° C. (dec); Mass Spec.: MH$^+$=544

Using the starting compound indicated, the following compounds were prepared via substantially the same procedure as described for Example 414:

| Starting Compound | Product Compound | Analytical Data |
|---|---|---|
| Preparative Example 28 | 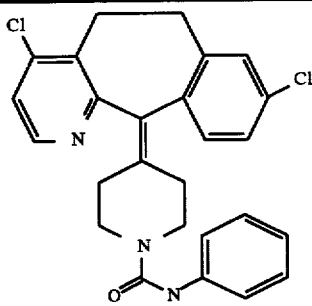<br>Example 414-A | m.p. = 131.8° C. (dec.)<br>Mass Spec.:<br>MH$^+$ = 464 |
| Preparative Example 53A | 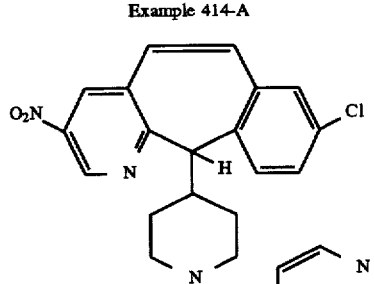<br>Example 414-B | Mass Spec.:<br>MH$^+$ = 475.2 |

EXAMPLE 415

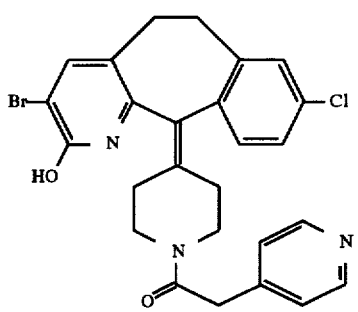

Combine 0.64 g of the product from Example 411-C and 16 mL of glacial HOAc, and add 15 mL of a 0.54M solution of bromine in HOAc at 25° C. under $N_2$. After 10 minutes, pour the mixture into water, filter to collect the resulting solid, and wash with water. Dry the solid under vacuum, then chromatograph (silica gel, 6–15% MeOH/$CH_2Cl_2$) to give 0.26 grams (35% yield) of the product compound. m.p.=150.0° C. (dec), Mass Spec.: $MH^+$=526

EXAMPLE 416

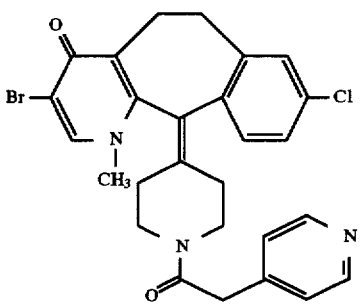

Combine 0.33 g of the product from Preparative Example 57, 2 mL of anhydrous $CH_2Cl_2$, and 10 mL of a mixture of 7.20 g of 4-pyridylacetic acid hydrochloride, 1.61 mL of methanesulfonylchloride, 27 mL of $Et_3N$ and 60 mL of $CH_2Cl_2$, and stir at 25° C. for 48 hours. Dilute the mixture with $CH_2Cl_2$, wash with saturated $NaHCO_3$ (aqueous), then with brine. Dry over $MgSO_4$, concentrate to a residue and chromatograph (silica gel, 5% MeOH/$CH_2Cl_2$+$NH_4OH$) to give 0.23 g (55% yield) of the product compound. m.p.= 142° C. (dec); Mass Spec.: $MH^+$=540

EXAMPLE 417

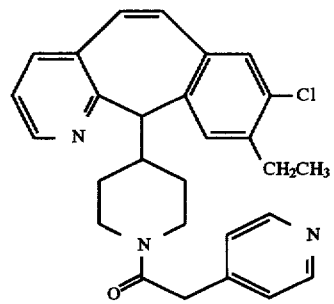

React the product from Preparative Example 35 with 4-pyridylacetic acid via substantially the same procedure as described for Example 266 to give the product compound. Mass Spec.: $MH^+$=458

Using the appropriate carboxylic acid and the starting compound indicated, the following compounds were prepared via substantially the same procedure as described for Example 417:

| Starting Compound | Product Compound | Analytical Data |
|---|---|---|
| Preparative Example 37B | 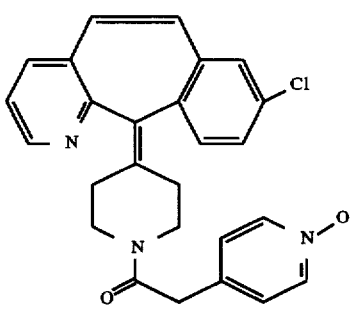<br>Example 417-A | Mass Spec.:<br>$MH^+$ = 444 |

| Starting Compound | Product Compound | Analytical Data |
|---|---|---|
| Preparative Example 58 | 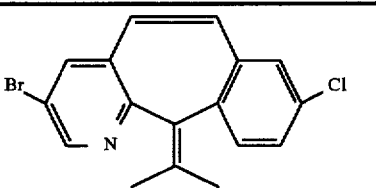 Example 417-B | Mass Spec.: MH⁺ = 522 |

EXAMPLE 418

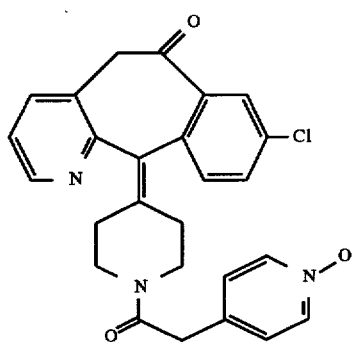

Follow the procedure of Example 283 except using 4-pyridylacetic acid N-oxide to give the product compound. Mass Spec.: MH⁺=460

EXAMPLE 419

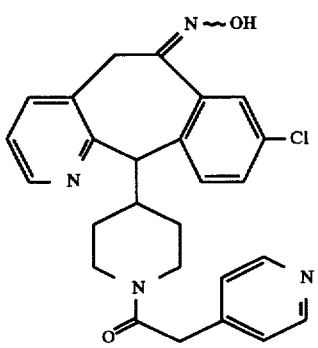

Dissolve 4.01 g (8.42 mmol) of the compound of Example 410-L in EtOAc and add 14.25 g (63.1 mmol) of finely powdered SnCl₂ dihydrate and stir the mixture for 5 hours. Add 150 mL of saturated NaF (aqueous) and stir for 15 min, then separate the layers and dry the organic phase over MgSO₄. Filtration and concentrate in vacuo to a residue, then chromatograph (silica gel, 95% CH₂Cl₂/MeOH+ NH₄OH) to give 2.95 g of the product compound. Mass Spec.: MH⁺=461

EXAMPLE 420

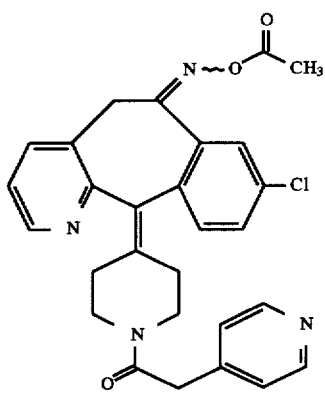

Combine 0.50 g (1.08 mmol) of the compound of Example 419 and 10 mL of anhydrous CH₂Cl₂, and add 0.11 mL (1.62 mmol) of CH₃COCl. Add 0.34 mL (4.32 mmol) of pyridine and stir at room temperature for 2.5 hours. Dilute the mixture with saturated NaHCO₃ (aqueous), extract with CH₂Cl₂, wash the extracts with brine and dry over MgSO₄. Concentrate in vacuo to a residue and chromatograph (silica gel, 10% MeOH/CH₂Cl₂+NH₄OH) to give 0.271 g of the product compound. Mass Spec.: MH⁺=503

EXAMPLE 421

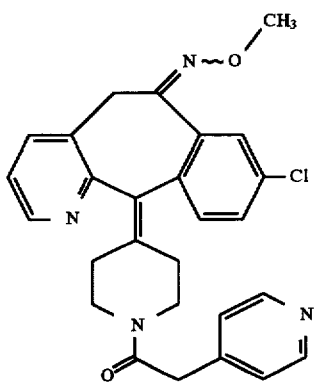

Combine 0.65 g (1.41 mmol) of the product compound of Example 419, 20 mL of CH₂Cl₂, 0.22 mL (3.52 mmol) of methyl iodide, 4.4 mL of 10% NaOH (aqueous) and 68 mg (0.21 mmol) of tetra-n-butyl-ammonium bromide. Stir the mixture for 5 hours, then separate the layers and dry the organic phase over MgSO$_4$. Concentrate in vacuo to a residue and chromatograph (silica gel, 5% MeOH/CH$_2$Cl$_2$+ NH$_4$OH) to give 169 mg of the product compound. Mass Spec.: MH$^+$=475

EXAMPLE 422

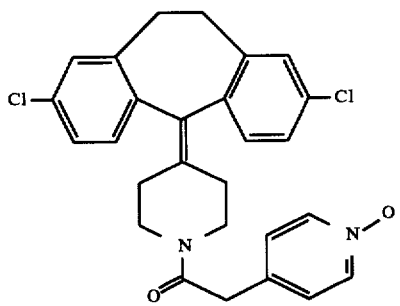

Combine 0.1 g (0.21 mmol) of the product compound of Example 411-L and 10 mL of CH$_2$Cl$_2$, add 0.11 g (0.66 mmol) of MCPBA and stir at ambient temperature for 1 hour. Wash with saturated NaHCO$_3$ (aqueous), dry over MgSO$_4$, and concentrate in vacuo to give 0.14 gm of the product compound. m.p.=100°–104° C.

Using the starting compound indicated, the following compounds were prepared via substantially the same procedure as described for Example 422:

EXAMPLE 423

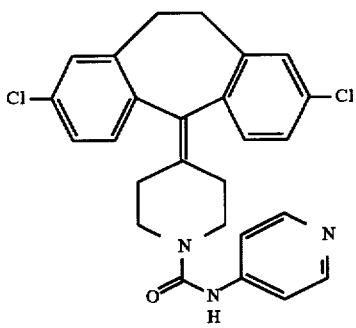

Combine 0.4 g (1.22 mmol) of the product compound of Preparative Example 59 and 0.2 g (1.2 mmol) of 4-aminopyridylethylcarbamate and heat to 180° C. under a dry N$_2$ atmosphere for 2 hours. Cool the mixture and crystallize the product by adding EtOAc to give 0.49 g of the product compound. m.p.=206.4°–207° C.; Mass Spec.: (FAB) MH$^+$=464.0

Using the appropriate ethylcarbamate and the starting compound indicated, the following compounds were prepared via substantially the same procedure as described for Example 423:

| Starting Compound | Product Compound | Analytical Data |
|---|---|---|
| Preparative Example 423 | Example 422-A | Mass Spec.: (FAB) MH$^+$ = 480.2 |

| Starting Compound | Product Compound | Analytical Data |
|---|---|---|
| Preparative Example 1, Step G | Example 423-A | — |
| Preparative Example 1, Step G | Example 423-B | — |

EXAMPLE 424

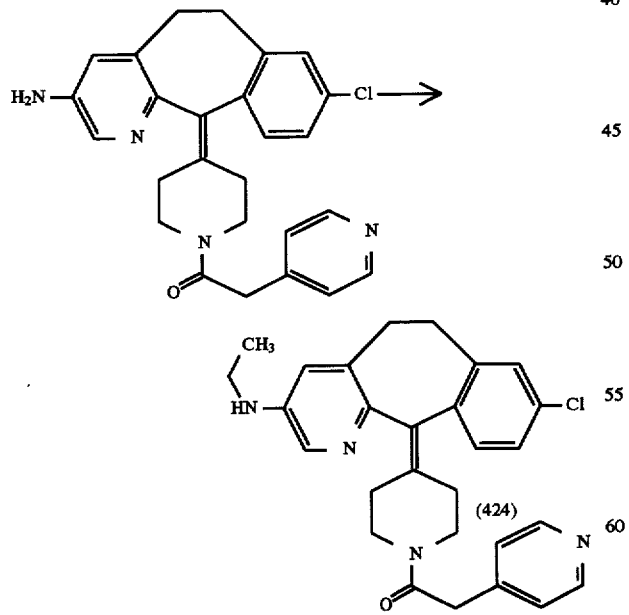

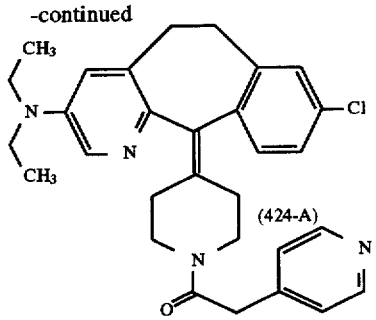

Combine 1 g of the product of Example 402 and 20 mL of MeOH, cool to ~0° C., and adjust to pH=3 by adding 1N HCl (aqueous). Add 1.25 mL of CH$_3$CHO and 1.41 g of NaCNBH$_3$, and stir the mixture for 1 hour. Concentrate in vacuo to a residue, extract with 100 mL of CH$_2$Cl$_2$ and wash the extract with 100 mL of 10% NaHCO$_3$, then with 100 mL of water. Dry over MgSO, concentrate in vacuo to a residue and chromatograph (silica gel, 1.5% (10% NH$_4$OH in MeOH)/CH$_2$Cl$_2$) to give 0.158 g of the product compound of Example 424 and 0.198 g of the product compound Example 424-A.

Analytical data for Example 424: Mass Spec.: MH$^+$=474

Analytical data for Example 424-A: Mass Spec.: MH$^+$=502

EXAMPLE 425

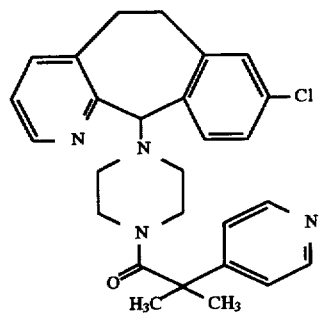

React the products of Preparative Example 7, Step C and Preparative Example 26, via substantially the same procedure as described for Example 75 to give the title compound. Mass Spec.: MH$^+$=461.35

Using the appropriate carboxylic acid and the starting compound indicated, the following compounds were prepared via substantially the same procedure as described for Example 425:

| Starting Compound | Product Compound | Analytical Data |
|---|---|---|
| Preparative Example 7 | 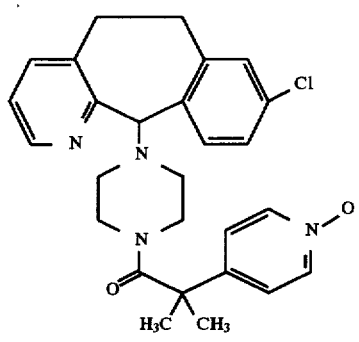<br>Example 425-A | Mass Spec.:<br>MH+ = 477.2 |
| Preparative Example 7 | 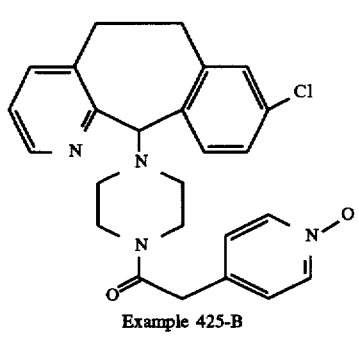<br>Example 425-B | Mass Spec.:<br>MH+ = 449.3 |
| Preparative Example 7 | 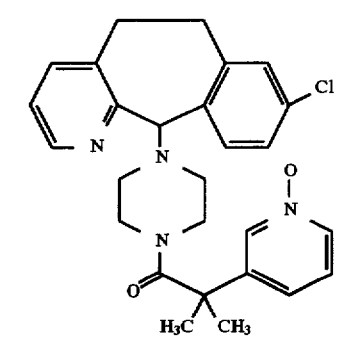<br>Example 425-C | Mass Spec.:<br>MH+ = 477.2 |
| Preparative Example 19<br>R(+)-isomer | 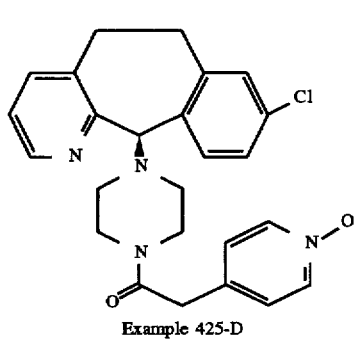<br>Example 425-D | Mass Spec.:<br>MH+ = 449.2 |

-continued
| Starting Compound | Product Compound | Analytical Data |
|---|---|---|
| Preparative Example 19 S(−)-isomer | 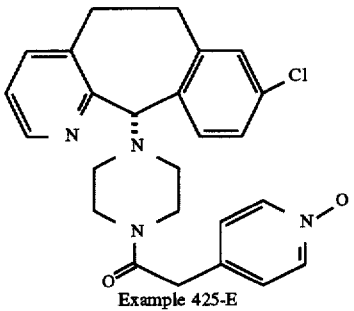<br>Example 425-E | Mass Spec.: MH+ = 449.2 |
| Preparative Example 19 R(+)-isomer | 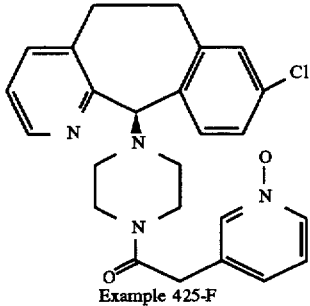<br>Example 425-F | Mass Spec.: MH+ = 449.3 |
| Preparative Example 19 S(−)-isomer | 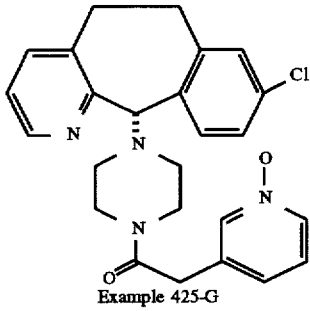<br>Example 425-G | Mass Spec.: MH+ = 449.3 |
| Preparative Example 40 | 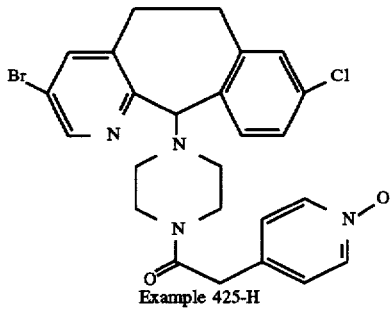<br>Example 425-H | Mass Spec.: MH+ = 527.0 |
| Preparative Example 40 | 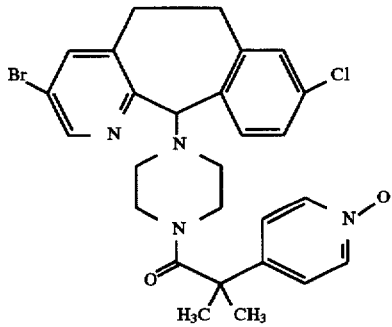 | Mass Spec.: MH+ = 555.3 |

-continued

| Starting Compound | Product Compound | Analytical Data |
|---|---|---|
| Preparative Example 40 | Example 425-K | Mass Spec.: MH+ = 527.1 |
| Preparative Example 38 | Example 425-L | Mass Spec.: MH+ = 447.2 |
| Preparative Example 19 R(+)-isomer | Example 425-M | Mass Spec.: MH+ = 453 |
| Preparative Example 19 S(−)-isomer | Example 425-N | Mass Spec.: MH+ = 453 |
| Preparative Example 40 | | Mass Spec.: MH+ = 531.25 |

-continued
| Starting Compound | Product Compound | Analytical Data |
|---|---|---|
| Preparative Example 41 | Example 425-O 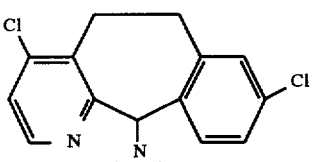 | Mass Spec.: MH⁺ = 487.35 |
| Preparative Example 38 | Example 425-P 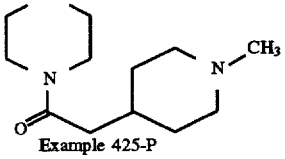 | Mass Spec.: MH⁺ = 451.35 |
| Preparative Example 19 R(+)-isomer | Example 425-Q 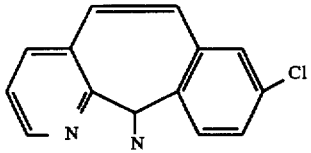 | Mass Spec.: MH⁺ = 453.35 |
| Preparative Example 19 S(−)-isomer | Example 425-R 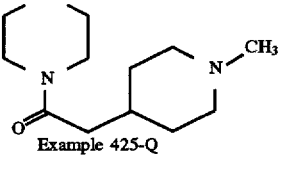 | Mass Spec.: MH⁺ = 453.35 |
| Preparative Example 7 Step C | Example 425-S 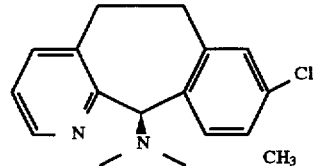 | Mass Spec.: MH⁺ = 539.45 |

-continued

| Starting Compound | Product Compound | Analytical Data |
|---|---|---|
| Preparative Example 40 | Example 425-T 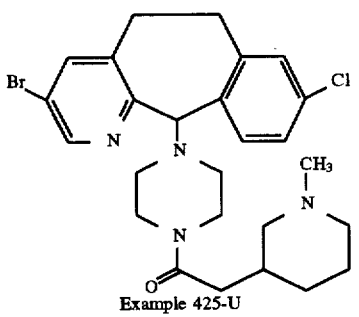 | Mass Spec.: MH⁺ = 531.35 |
| Preparative Example 38 | Example 425-U 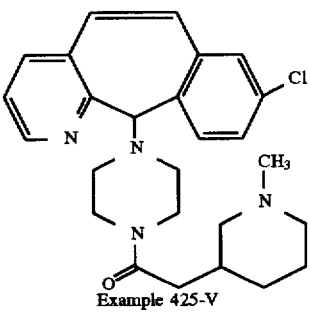 | Mass Spec.: MH⁺ = 451.4 |

Example 425-V

EXAMPLE 426

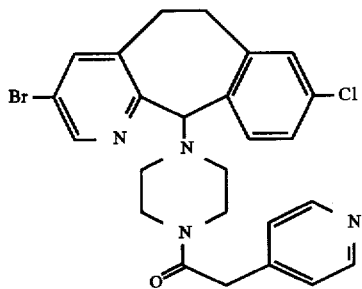

React the product of Preparative Example 40 and 3-pyridylacetic acid via substantially the same procedure as described for Example 351 to give the title compound. Mass Spec.: MH⁺=511

Using the appropriate carboxylic acid and the starting compound indicated, the following compounds were prepared via substantially the same procedure as described for Example 426:

| Starting Compound | Product Compound | Analytical Data |
|---|---|---|
| Preparative Example 41 | Example 426-A | Mass Spec.: MH⁺ = 483.2 |

EXAMPLE 427

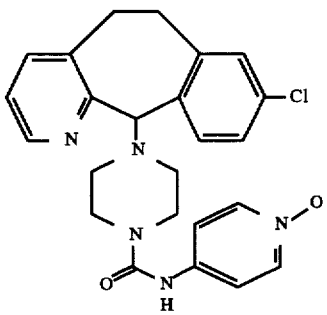

Combine 0.288 g (1.76 mmol) of the product of Preparative Example 63 and 25 mL of anhydrous toluene, heated at (110° C.) for 0.5 hours, then cool to 25° C. Add a solution of 0.1 g (0.293 mmol) of the product Preparative Example 7, Step C, in 1.5 mL of anhydrous toluene, and stir at 25° C. under an argon atmosphere for 112 hours. Concentrate in vacuo to a residue and chromatograph (silica gel, 3%–4% (10% $NH_4OH$ in MeOH)/$CH_2Cl_2$) to give 0.065 g of the title compound. Mass Spec.: MH⁺=450.3

Using the appropriate azide and the starting compound indicated, the following compounds were prepared via substantially the same procedure as described for Example 427:

| Starting Compound | Product Compound | Analytical Data |
|---|---|---|
| Preparative Example 7, Step C | Example 427-A | Mass Spec.: MH⁺ = 450.1 |

| Starting Compound | Product Compound | Analytical Data |
|---|---|---|
| Preparative Example 40 | 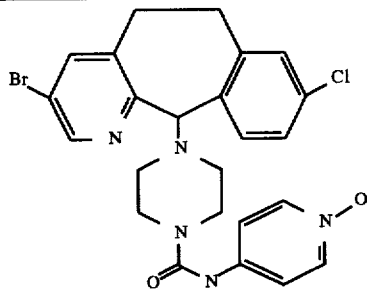<br>Example 427-B | Mass Spec.: MH+ = 528.1 |
| Preparative Example 40 | 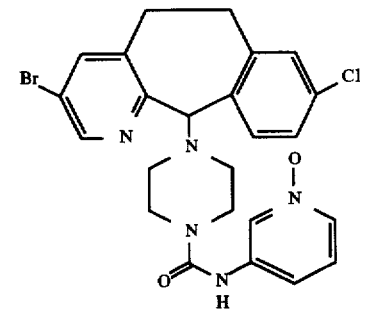<br>Example 427-C | Mass Spec.: MH+ = 528.1 |

EXAMPLE 428

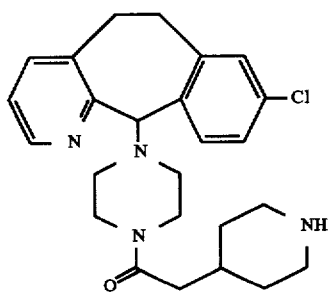

Combine 14.73 g (27.3 mmol) of the compound from Example 193 and 125 mL of anhydrous MeOH, and add (in portions) 300 mL of a 10% solution of concentrated $H_2SO_4$ in dioxane. Stir the mixture at 25° C. for 2 hours, then pour into water and adjust to pH=13 with 50% NaOH (aqueous). Extract with $CH_2Cl_2$, wash the extract with water and dry over $MgSO_4$. Concentrate in vacuo to a residue and chromatograph (silica gel, 10% (10% $NH_4OH$ in MeOH)/$CH_2Cl_2$) to give 8.9 g of the title compound. Mass Spec.: MH+=539

Using the starting compound indicated, the following compounds were prepared via substantially the same procedure as described for Example 428:

| Starting Compound | Product Compound | Analytical Data |
|---|---|---|
| Example 425-T | 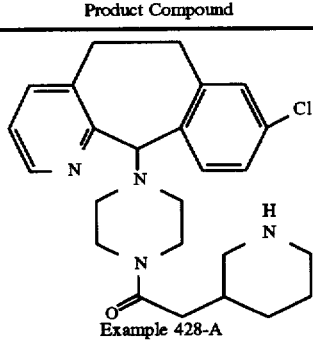<br>Example 428-A | Mass Spec.: MH+ = 439.45 |

EXAMPLE 429

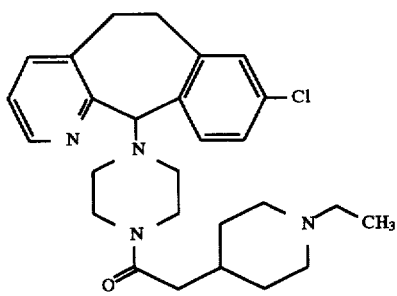

Combine 0.5 g (1.14 mmol) of the compound of Example 428 and 10 mL of 0.6N HCl in $CH_2Cl_2$, stir for 10 minutes and concentrate n vacuo to a residue. Add 20 mL of anhydrous MeOH, then add 0.2006 g (4.56 mmol) of $CH_3CHO$, 0.0859 g (1.36 mmol) $NaCNBH_3$ and 0.5 g of 3A molecular sieves, and heat at 40° C. for 115 hours. Filter the mixture, wash the sieves with MeOH and concentrate the combined filtrates in vacuo to a residue. Dissolve the residue in $CH_2Cl_2$ and wash with saturated $NaHCO_3$ (aqueous), then water and dry over $MgSO_4$. Concentrate in vacuo to a residue and chromatograph (silica gel, 8% (10% $NH_4OH$ in MeOH)/$CH_2Cl_2$) to give the title compound. Mass Spec.: $MH^+=467.3$

EXAMPLE 430

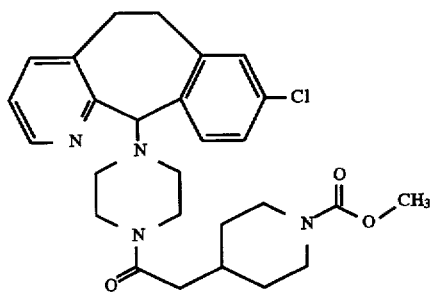

Combine 0.5 g (1.14 mmol) of the compound of Example 428 and 5 mL of anhydrous THF, add 0.1076 g (1.14 mmol) $ClCO_2CH_3$, and stir at 25° C. for 1 hour. Concentrate in vacuo to a residue, add $CH_2Cl_2$ and wash with saturated $NaHCO_3$ (aqueous), then water. Dry the organic phase over $MgSO_4$, concentrate in vacuo to a residue and chromatograph (silica gel, 1.5% (10% $NH_4OH$ in MeOH)/$CH_2Cl_2$) to give 0.4213 g of the title compound. Mass Spec.: $MH^+=497.35$ Using the starting compound indicated, the following compounds were prepared via substantially the same procedure as described for Example 430:

EXAMPLE 431

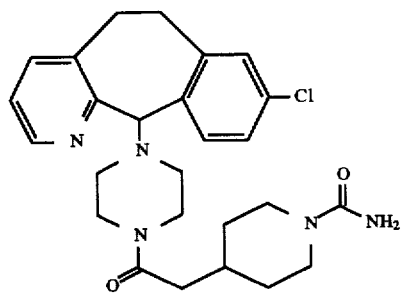

Combine 0.5 g (1.14 mmol) of the compound of Example 428 and 5 mL of anhydrous $CH_2Cl_2$, add 0.2624 g (2.28 mmol) of trimethylsilylisocyanate and stir under argon at 25° C. for 22 hours. Add 0.1312 g (1.14 mmol) of trimethylsilylisocyanate and stir for 8 hours, then dilute with $CH_2Cl_2$ and wash with saturated $NaHCO_3$ (aqueous), then water. Dry over $MgSO_4$, concentrate in vacuo to a residue and chromatograph (silica gel, 5% (10% $NH_4OH$ in MeOH)/$CH_2Cl_2$) to give 0.3878 g of the title compound. Mass Spec.: $MH^+=482.2$ Using the isocyanate (or isothiocyanate) and starting compound indicated, the following compounds were prepared via substantially the same procedure as described for Example 431:

| Starting Compound | Product Compound | Analytical Data |
|---|---|---|
| Example 428-A | Example 430-A | Mass Spec.: $MH^+=497.35$ |

| Starting Compound | Product Compound | Analytical Data |
|---|---|---|
| CH₃NCO Example 428 | Example 431-A | Mass Spec.: MH⁺ = 496.45 |
| CH₃CH₂NCO Example 428 | Example 431-B | Mass Spec.: MH⁺ = 510.35 |
| CH₃(CH₂)₂NCO Example 428 | Example 431-C | Mass Spec.: MH⁺ = 524.35 |
| (CH₃)₃C—NCO Example 428 | Example 431-D | Mass Spec.: MH⁺ = 538.35 |
| CH₃NCS and Example 428 | Example 431-E | Mass Spec.: MH⁺ = 512.25 |

| Starting Compound | Product Compound | Analytical Data |
|---|---|---|
| (CH₃)₃Si—NCO<br>Example 428-A | 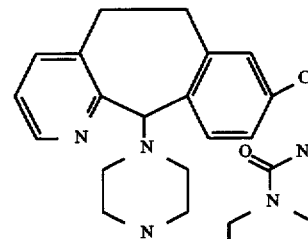<br>Example 431-F | Mass Spec.:<br>MH⁺ = 482.3 |
| CH₃NCO<br>Example 428-A | 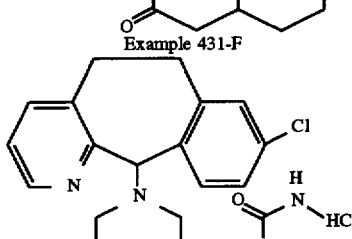<br>Example 431-G | Mass Spec.:<br>MH⁺ = 496.35 |

EXAMPLE 432

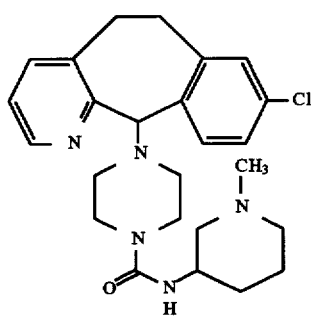

Combine 0.5 g (1.6 mmol) of the compound of Preparative Example 7 and 1.098 g (6.4 mmol) of the compound from Preparative Example 65 and heat in a sealed vessel at 160° C. for 17 hours. Cool the mixture, add CH₂Cl₂, wash with water and dry the organic phase over MgSO₄. Concentrate in vacuo to a residue and chromatograph (silica gel, 1.5% (10% NH₄OH in MeOH)/CH₂Cl₂) to give 0.0364 g of the title compound. Mass Spec.: MH⁺=454.25

EXAMPLE 433

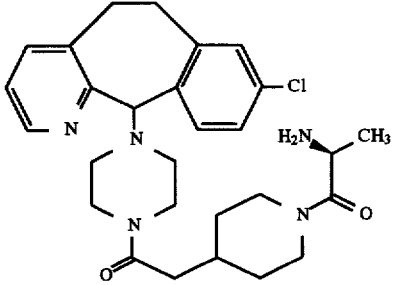

Step A:

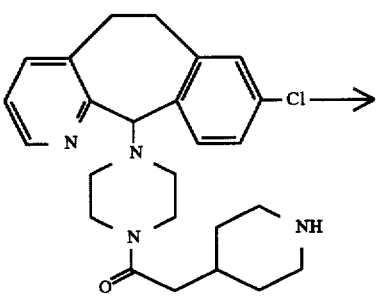

339
-continued

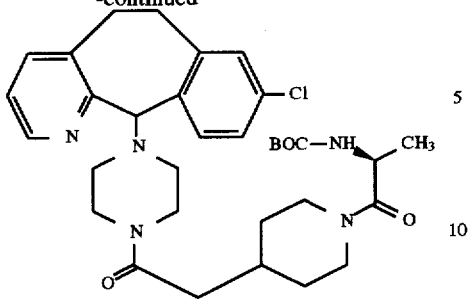

React 0.5 g (1.59 mmol) of the compound of Example 428 and 0.3232 g (2.39 mmol) of N-(tert-butoxycarbonyl)-L-alanine (0.3232 grams) (2.39 mmoles) via essentially the same conditions as described in Example 425 to give the product compound.

Step B:

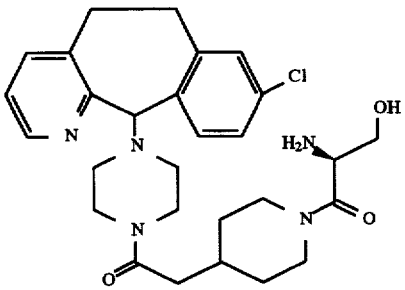

340
-continued

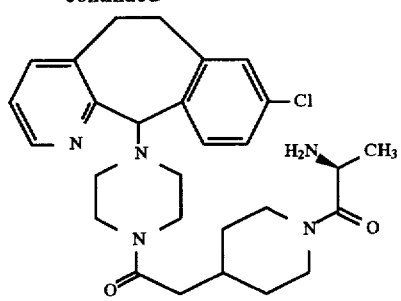

Combine the product of Step A, 5 mL of MeOH and 10 mL of 10% concentrated $H_2SO_4$ in dioxane and stir at 25° C. for 2 hours. Neutralize with Biorad AG1X8 ($OH^-$) ion exchange resin, filter, wash the resin with 1:1 MeOH/water and concentrate the filtrate to a residue. Chromatograph the residue (silica gel, 8% (10% $NH_4OH$ in MeOH)/$CH_2Cl_2$) to give the title compound. Mass Spec.: $MH^+$=510.35

Using the appropriate BOC-amino acid and the starting compound indicated, the following compounds were prepared via substantially the same procedure as described for Example 433:

| Starting Compound | Product Compound | Analytical Data |
|---|---|---|
| BOC-L-serine and Example 428 | 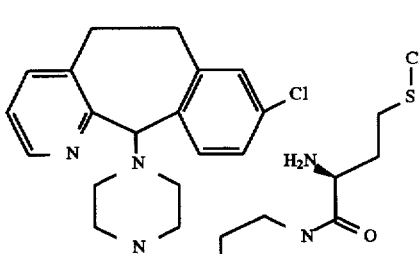<br>Example 433-A | Mass Spec.: $MH^+$ = 526.2 |
| BOC-L-methionine and Example 428 | Example 433-B | Mass Spec.: $MH^+$ = 570.3 |

-continued

| Starting Compound | Product Compound | Analytical Data |
|---|---|---|
| BOC-glycine and Example 428 | 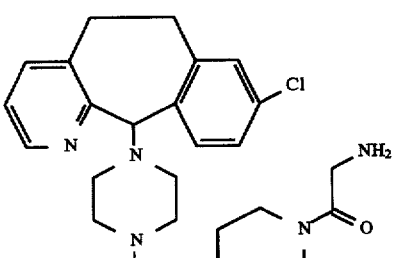 Example 433-C | Mass Spec.: MH+ = 496.35 |

EXAMPLE 434

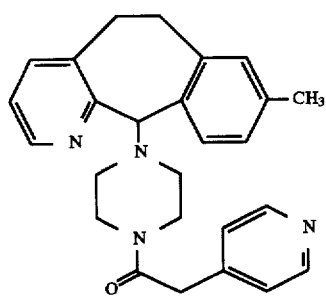

React the product of Preparative Example 67 with 4-pyridylacetic acid via essentially the same procedure as described for Example 411 to give the title compound. Mass Spec.: MH+=410

Using the appropriate carboxylic acid and the starting compound indicated, the following compounds were prepared via substantially the same procedure as described for Example 434:

EXAMPLE 435

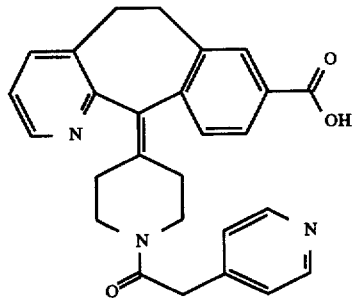

Dissolve 3.04 g (6.7 mmol) of the compound of Example 434-A in 100 mL of MeOH. Add 100 mL of a 12% KOH (aqueous) and stir for one hour at 25° C. Remove the MeOH under vacuum, neutralize to pH 7 with 12N HCl and concentrate in vacuo to a residue. Dry under vacuum and triturate with 10 mL of EtOH, then filter, concentrate the filtrate in vacuo to give the title compound. m.p.=238°–240° C.; Mass Spec.: MH+=440

| Starting Compound | Product Compound | Analytical Data |
|---|---|---|
| Preparative Example 68 | 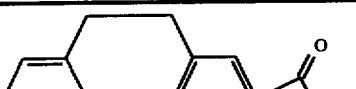 Example 434-A | m.p.p = 68.6°–70.3° C. Mass Spec.: MH+ = 454 |

EXAMPLE 436

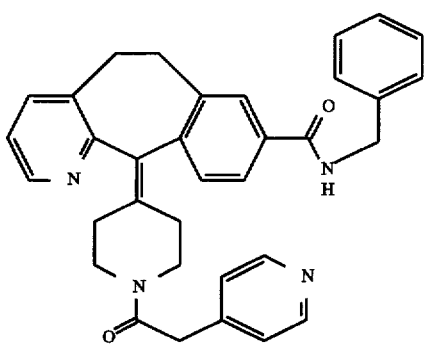

Dissolve 0.5 g (1.14 mmol) of the product of Example 435 in 25 mL of DMF, add 0.122 g (1.14 mmol) of benzylamine, 0.33 g (1.7 mmol) of DEC, 0.15 g (1.1 mmol) of HOBT, and 0.23 g (2.27 mmol) of N-methylmorpholine, and stir at 25° C., under nitrogen for 18 hours. Concentrate in vacuo to a residue, add 20 mL of water and extract with 50 mL of EtOAc. Dry the organic layer over $MgSO_4$ and concentrate in vacuo to a residue. Chromatograph (silica gel, 98% $CH_2Cl_2$/MeOH+$NH_4OH$) to give the product compound. m.p.=118°–120° C.; Mass Spec.: $MH^+$=529

Using the appropriate amine and the starting compound indicated, the following compounds were prepared via substantially the same procedure as described for Example 436:

| Starting Compound | Product Compound | Analytical Data |
|---|---|---|
| S-phenyl-alanine methyl ester and Example 435 | Example 436-A | m.p. = 116.9° – 118.4° C. Mass Spec.: $MH^+$ = 622 |
| alanine and Example 435 | Example 436-B | m.p. = 137.8° – 139.9° C. Mass Spec.: $MH^+$ = 516 |

-continued

| Starting Compound | Product Compound | Analytical Data |
|---|---|---|
| ethanolamine and Example 435 | 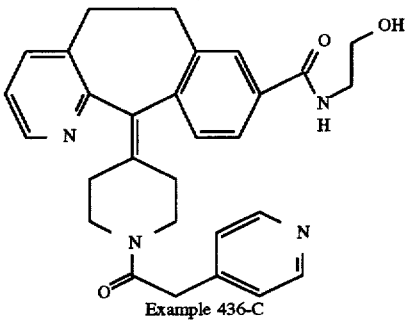 Example 436-C | m.p. = 130.9° – 132.5° C. Mass Spec.: MH⁺ = 482 |
| NH₄Cl and Example 435 | 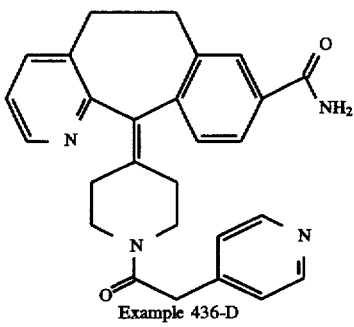 Example 436-D | m.p. = 133.2° – 133.5° C. Mass Spec.: MH⁺ = 439 |

EXAMPLE 437

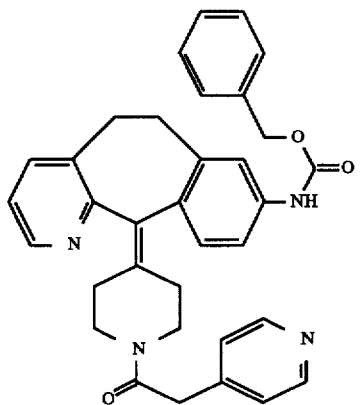

Dissolve 0.18 g (0.41 mmol) of the product of Example 435 in 2 mL of toluene, add 0.12 g (0.43 mmol) of diphenylphosphoryl azide, 0.041 g (0.41 mmol) of Et₃N, and 0.092 g (0.44 mmol) of benzyl alcohol and heat at reflux under nitrogen for 18 hours. Concentrate in vacuo to a residue and chromatograph (silica gel 95% CH₂Cl₂/MeOH) to obtain the title compound. m.p.=132.8°–133.7° C.; MH⁺= 545

EXAMPLE 438

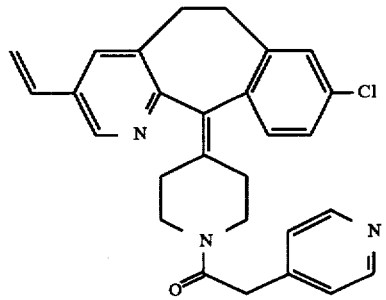

React the product of Preparative Example 70 with 4-pyridylacetic acid via essentially the same procedure as described for Example 411 to give the title compound. Mass Spec.: (FAB) MH⁺=456

Using the appropriate carboxylic acid and the starting compound indicated, the following compounds were prepared via substantially the same procedure as described for Example 438:

| Starting Compound | Product Compound | Analytical Data |
|---|---|---|
| Preparative Example 70 | Example 438-A | Mass Spec.: (FAB) MH⁺ = 476 |
| Preparative Example 70 | Example 439-B | Mass Spec.: (FAB) MH⁺ = 472 |

EXAMPLE 439

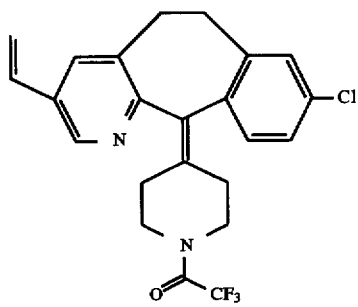

EXAMPLE 440

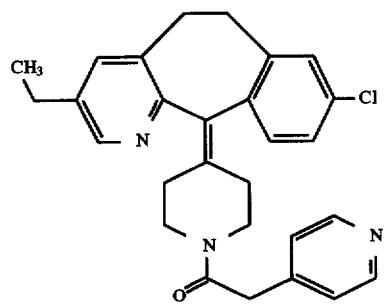

Combine 1.7 g (5 mmol) of the product of Preparative Example 70, Step D, and 10 mL of anhydrous pyridine at 0° C. under N₂ atmosphere, then slowly add (dropwise) 1 mL (7 mmol) of TFAA and stir at 25° C. overnight. Dilute with 100 ml of cold water, extract with CH₂Cl₂ (2×75 mL), wash the extracts successfully with 10% CuSO₄ (aqueous) and brine, then dry over MgSO₄. Concentrate in vacuo to a residue and chromatograph (silica gel 30%40% EtOAc/hexane) to give 1.75 g of the title compound. Mass Spec.: (FAB) MH⁺=433

Combine 0.07 g (0.154 mmol) of the product of Example 438, 7 mL of EtOH and 12 mg of PtO₂, and hydrogenate at 25° C. and atmospheric pressure for 1 hour. Filter, wash with EtOH and concentrate in vacuo to give 0.066 g of the title compound. Mass Spec.: (FAB) MH⁺=458

Using the starting compound indicated, the following compounds were prepared via substantially the same procedure as described for Example 440:

| Starting Compound | Product Compound | Analytical Data |
|---|---|---|
| Example 438-B | 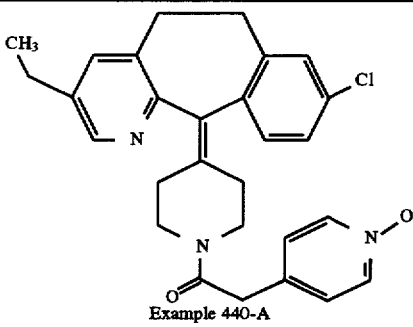 Example 440-A | Mass Spec.: (FAB) MH+ = 474 |

EXAMPLE 441

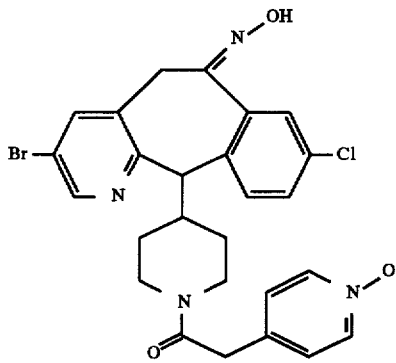

Combine 0.07 g of the compound of Example 410-R, 2 mL of THF, 0.5 mL of water, 10 drops of glacial HOAc, and 0.1 g of powdered Zn, and stir the mixture for 0.5 hours at 25° C. Purify the mixture by preparative thin layer chromatography (Prep TLC), (silica gel, 10% (10% NH$_4$OH in MeOH)/CH$_2$Cl$_2$), to give a total of 68 mg of the crude product. Purify again by Prep TLC), (silica gel, 13% (10% NH$_4$OH in MeOH)/CH$_2$Cl$_2$), to give 33 mg of the product compound. Mass Spec.: MH+=555

ASSAYS

1. In vitro enzyme assays: Inhibition of farnesyl protein transferase and geranylgeranyl protein transferase.

Both farnesyl protein transferase (FPT) and geranylgeranyl protein transferase (GGPT) I were partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyl-transferase from bovine brain: Implications for protein prenylation specificity, Proc. Natl. Acad. Sci U.S.A. 88: 5302–5306, the disclosure of which is incorporated herein by reference thereto). Human farnesyl protein transferase was also expressed in E. coli, using cDNA clones encoding both the α and β subunits. The methods used were similar to those published (Omer, C. et al., (1993), Characterization of recombinant human farnesyl protein transferase: Cloning, expression, farnesyl diphosphate binding, and functional homology with yeast prenyl-protein transferases, Biochemistry 32:5167–5176). Human farnesyl protein transferase was partially-purified from the soluble protein fraction of E. coli as described above. The tricyclic farnesyl protein transferase inhibitors disclosed herein inhibited both human and rat enzyme with similar potencies. Two forms of val[12]-Ha-Ras protein were prepared as substrates for these enzymes, differing in their carboxy terminal sequence. One form terminated in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins were constructed so that the proteins contain an amino-terminal extension of 6 histidine residues. Both proteins were expressed in Escherichia coli and purified using metal chelate affinity chromatography. The radiolabelled isoprenyl pyrophosphate substrates, [$^3$H]farnesyl pyrophosphate and [$^3$H]geranylgeranyl pyrophosphate, were purchased from DuPont/New England Nuclear.

Several methods for measuring farnesyl protein transferase activity have been described (Reiss et al 1990, Cell 62: 81; Schaber et al 1990, J. Biol. Chem. 265: 14701; Manne et al 1990, PNAS 87: 7541; and Barbacid & Manne 1993, U.S. Pat. No. 5,185,248). The activity was assayed by measuring the transfer of [$^3$H]farnesyl from [$^3$H]farnesyl pyrophosphate to Ras-CVLS using conditions similar to those described by Reiss et al. 1990 (Cell 62: 81) The reaction mixture contained 40 mM Hepes, pH 7.5; 20 mM magnesium chloride; 5 mM dithiothreitol; 0.25 µM [$^3$H] farnesyl pyrophosphate; 10 µl Q-Sepharose-purified farnesyl protein transferase; the indicated concentration of tricyclic compound or dimethylsulfoxide (DMSO) vehicle control (5% DMSO final); and 5 µM Ras-CVLS in a total volume of 100 µl. The reaction was allowed to proceed for 30 minutes at room temperature and then stopped with 0.5 ml of 4% sodium dodecyl sulfate (SDS) followed by 0.5 ml of cold 30% trichloracetic acid (TCA). Samples were allowed to sit on ice for 45 minutes and precipitated Ras protein was then collected on GF/C filter paper mats using a Brandel cell harvester. Filter mats were washed once with 6% TCA, 2% SDS and radioactivity was measured in a Wallac 1204 Betaplate BS liquid scintillation counter. Percent inhibition was calculated relative to the DMSO vehicle control.

The geranylgeranyl protein transferase I assay was essentially identical to the farnesyl protein transferase assay described above, with two exceptions: [$^3$H] geranylgeranylpyrophosphate replaced farnesyl pyrophosphate as the isoprenoid donor and Ras-CVLL was the protein acceptor. This is similar to the assay reported by Casey et al (Casey, P. J., et al., (1991), Enzymatic modification of proteins with a geranylgeranyl isoprenoid, Proc. Natl. Acad. Sci, U.S.A. 88: 8631–8635, the disclosure of which is incorporated herein by reference thereto).

2. Cell-Based Assay: Transient expression of val$^{12}$-Ha-Ras-CVLS and val$^{12}$-Ha-Ras-CVLL in COS monkey kidney cells: Effect of farnesyl protein transferase inhibitors on Ras processing and on disordered cell growth induced by transforming Ras.

COS monkey kidney cells were transfected by electroporation with the plasmid pSV-SPORT (Gibco/BRL) containing a cDNA insert encoding either Ras-CVLS or Ras-CVLL, leading to transient overexpression of a Ras substrate for either farnesyl protein transferase or geranylgeranyl protein transferase I, respectively (see above).

Following electroporation, cells were plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media was removed and fresh media containing the appropriate drugs was re-added.

48 hours after electroporation cells were examined under the microscope to monitor disordered cell growth induced by transforming Ras. Cells expressing transforming Ras become more rounded and refractile and overgrow the monolayer, reminiscent of the transformed phenotype. Cells were then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 µM leupeptin; and 0.1 µM pepstatin. Cells were lysed by homogenization and cell debris was removed by centrifugation at 2000×g for 10 min.

Cellular protein was precipitated by addition of ice-cold trichloroacetic acid and redissolved in 100 µl of SDS-electrophoresis sample buffer. Samples (5-10 µl) were loaded onto 14% polyacrylamide minigels (Novex, Inc.) and electrophoresed until the tracking dye neared the bottom of the gel. Proteins resolved on the gels were electroblotted onto nitrocellulose membranes for immunodetection.

Membranes were blocked by incubation overnight at 4° C. in PBS containing 2.5% dried milk and 0.5% Tween-20 and then incubated with a Ras-specific monoclonal antibody, Y13-259 (Furth, M. E., et al., (1982), Monoclonal antibodies to the p21 products of the transforming gene of Harvey murine sarcoma virus and of the cellular ras gene family. J. Virol. 43: 294–304), in PBS containing 1% fetal calf serum for one hour at room temperature. After washing, membranes were incubated for one hour at room temperature with a 1:5000 dilution of secondary antibody, rabbit anti-rat IgG conjugated to horseradish peroxidase, in PBS containing 1% fetal calf serum. The presence of processed and unprocessed Ras-CVLS or Ras-CVLL was detected using a colorimetric peroxidase reagent (4-chloro-1-naphthol) as described by the manufacturer (Bio-Rad).

3. Cell Mat Assay:

Normal human HEPM fibroblasts were planted in 3.5 cm dishes at a density of 5×10$^4$ cells/dish in 2 ml growth medium, and incubated for 3–5 d to achieve confluence. Medium was aspirated from each dish and the indicator tumor cells, T24-BAG4 human bladder carcinoma cells expressing an activated H-ras gene, were planted on top of the fibroblast monolayer at a density of 2×10$^3$ cells/dish in 2 ml growth medium, and allowed to attach overnight. Compound-induced colony inhibition was assayed by addition of serial dilutions of compound directly to the growth medium 24 h after tumor cell planting, and incubating cells for an additional 14 d to allow colony formation. Assays were terminated by rinsing monolayers twice with phosphate-buffered saline (PBS), fixing the monolayers with a 1% glutaraldehyde solution in PBS, then visualizing tumor cells by staining with X-Gal (Price, J., et al., Lineage analysis in the vertebrate nervous system by retrovirus-mediated gene transfer, Proc. Natl. Acad. Sci. 84, 156–160 (1987)). In the colony inhibition assay, compounds were evaluated on the basis of two IC$_{50}$ values: the concentration of drug required to prevent the increase in tumor cell number by 50% (tIC$_{50}$) and the concentration of drug required to reduce the density of cells comprising the cell mat by 50% (mIC$_{50}$). Both IC$_{50}$ values were obtained by determining the density of tumor cells and mat cells by visual inspection and enumeration of cells per colony and the number of colonies under the microscope. The therapeutic index of the compound was quantitatively expressed as the ratio of mIC$_{50}$/tIC$_{50}$, with values greater than one indicative of tumor target specificity.

RESULTS OF ASSAYS—TABLES 7 TO 28

The compounds listed in Table 7 refer to compounds of Formula 500.00:

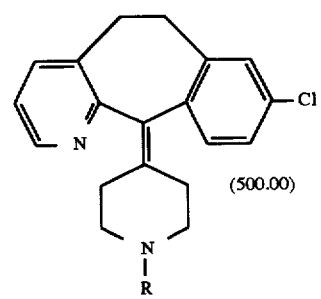

(500.00)

TABLE 7

| EXAMPLE | R | FPT IC$_{50}$ (µM) |
| --- | --- | --- |
| 1 | ![pyridylmethyl carbonyl] | 0.25 |
| 2 | ![pyridylmethyl carbonyl] | 0.47 |
| 3 | ![phthalimidomethyl carbonyl] | 0.66 |

TABLE 7-continued
| EXAMPLE | R | FPT IC$_{50}$ (μM) |
|---|---|---|
| 88 | 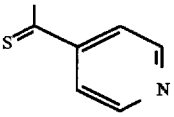 | 1.0 |
| 4 | 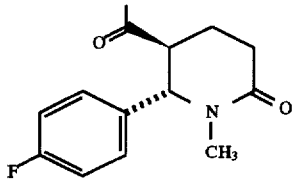 | 1.0<br>0.8 |
| 53 | 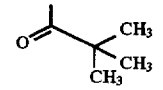 | 1.5 |
| 5 | 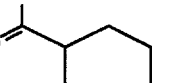 | 1.7 |
| 89 | 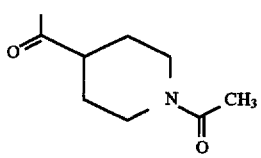 | 1.8 |
| 6 | 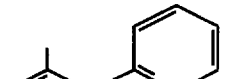 | 2.0 |
| 7 | 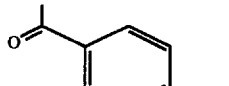 | 2.3 |
| 8 | 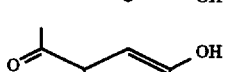 | 2.3 |
| 90 | 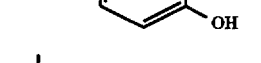 | 3.4 |
| 91 | 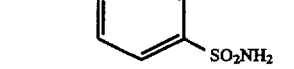 | 3.9 |
| 92 | 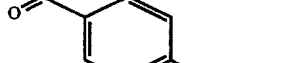 | 3.9 |
| 93 | 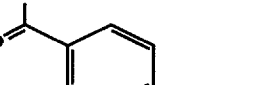 | 3.9 |
TABLE 7-continued
| EXAMPLE | R | FPT IC$_{50}$ (μM) |
|---|---|---|
| 94 | 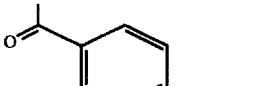 | 4.0 |
| 9 | 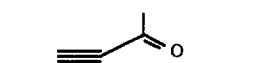 | 4.0 |
| 95 | 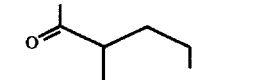 | 4.2 |
| 10 | 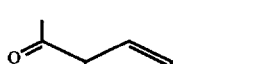 | 4.3 |
| 11 | 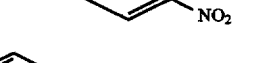 | 4.3 |
| 12 | 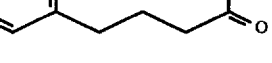 | 4.3 |
| 96 | 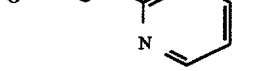 | 4.3 |
| 97 | 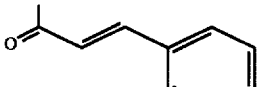 | 4.4 |
| 98 |  | 4.4 |
| 99 |  | 4.4 |
| 13 |  | 4.5 |
| 100 | 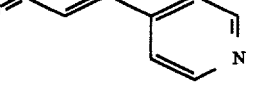 | 4.5 |

TABLE 7-continued

| EXAMPLE | R | FPT IC$_{50}$ (μM) |
|---|---|---|
| 101 | *N-acetyl-2-phenylcyclopropylamine* | 4.6 |
| 102 | *1-(thiophen-2-yl)propan-2-one* | 4.6 |
| 14 | *1-(pyridazin-4-yl)ethanone* | 4.6 |
| 103 | *1-(tetrahydrothiopyran-4-yl)ethanone* | 4.6 |
| 104 | *1-(4-(hydroxyimino)cyclohexyl)ethanone* | 4.7 |
| 15 | *1-(pyridin-4-yl)ethanone* | 4.7 |
| 16 | *1-(1H-pyrrol-3-yl)ethanone* | 4.8 |
| 17 | *1-(4-(dimethylamino)phenyl)ethanone* | 4.8 |
| 52 | *1-(furan-2-yl)ethanone* | 4.9 |
| 18 | *1-(1H-pyrazol-4-yl)ethanone* | 4.9 |
| 105 | *1-(4-aminocyclohexyl)ethanone* | 5.0 |
| 19A | *1-(tetrahydrofuran-2-yl)ethanone* | 5.1 |
| 20 | *1-(4-hydroxy-7-methyl-1,8-naphthyridin-3-yl)ethanone* | 5.2 |
| 54 | *acetophenone* | 5.3 |
| 106 | *4-acetylbenzoic acid* | 5.3 |
| 21 | *1-(4-aminophenyl)ethanone* | 5.9 |
| 55 | *1-(furan-3-yl)ethanone* | 5.9 |
| 22 | *1-(1-oxidopyridin-4-yl)ethanone* | 6.0 |
| 23 | *1-(1-methyl-5-oxo-2-thioxoimidazolidin-4-yl)propan-2-one* | 6.0 |
| 24 | *1-(4-hydroxy-3,5-dimethoxyphenyl)ethanone* | 6.2 |
| 25 | *1-(2-oxo-1,2-dihydropyridin-4-yl)ethanone* | 6.25 |
| 26 | *1-(pyridin-3-yl)ethanone* | 6.3 |
| 108 | *1-(4-(methylthio)phenyl)ethanone* | 6.9 |

TABLE 7-continued

| EXAMPLE | R | FPT IC$_{50}$ (µM) |
|---|---|---|
| 109 | 5-acetyl-2-(methylamino)pyridine | 7.2 |
| 27 | 2-acetylpyrazine | 7.3 |
| 28 | 4-acetyl-2-chloropyridine | 7.3 |
| 56 | ethyl pyruvate | 7.9 |
| 29 | 2-acetylpyridine | 8.0 |
| 30 | 3-acetylindole | 5.7 |
| 31 | 1-(4-hydroxy-3,5-dinitrophenyl)ethanone | 8.3 |
| 110 | 4-acetyl-2-(dimethylamino)pyridine | 8.3 |
| 111 | 1-(4-(trifluoromethylsulfonylamino)phenyl)ethanone | 8.5 |
| 32 | 4-acetylisoquinoline | 8.7 |
| 33 | dihydroxy pyrimidinyl acetyl | 8.7 |
| 112 | tert-butyl (2-oxopropyl)carbamate | 8.8 |
| 34 | 1-(8-nitrosonaphthalen-1-yl)ethanone derivative | 9.8 |
| 57 | 4,4-dimethylpentan-2-one | 9.8 |
| 35 | acetyl pyridazinone | 9.9 |
| 113 | N-methyl-N-(3-oxobutyl)acetamide | 10.3 |
| 114 | 3-acetyl-2(1H)-pyridinone | 11.1 |
| 36 | 5-acetyl-1-methyl-2(1H)-pyridinone | 11.2 |
| 37 | acetyl methyl chloro pyridine N-oxide | 11.4 |
| 38 | 4-acetylquinoline | 12.1 |
| 39 | methyl lactone ketone | 13.4 |
| 115 | methyl vinyl ketone | 14.2 |
| 58 | 1-methoxypropan-2-one | 14.4 |

TABLE 7-continued

| EXAMPLE | R | FPT IC$_{50}$ (μM) |
|---|---|---|
| 116 | (1-hydroxyethyl ketone, CH$_3$, OH) | 15.7 |
| 117 | (N-methyl acetamide) | 16.2 |
| 118 | (aminomethyl ketone, NH$_2$) | 22.3 |
| 59 | (acetyl, CH$_3$) | 26.9 |
| 119 | (3,4,5-trimethoxyphenyl ketone, OMe) | 41% at 11 μM |
| 120 | (N-acetyl tosylsulfonamide) | 4% at 39 μM |
| 121 | (phenyl thioketone) | 1.4 |
| 40 | (indol-2-yl ketone) | 44% at 13 μM |
| 122 | (hydantoin-substituted ketone) | 23% at 12.5 μM |
| 123 | (pyrrolidinone-substituted ketone) | 23% at 12.6 μM |
| 124 | (2-chloro-6-methylpyridin-4-yl ketone) | 37% at 12.8 μM |
| 125 | (2,6-dihydroxyphenyl acetone, HO, HO) | 10.3 |
| 126 | (2-nitrophenyl acetone, NO$_2$) | 2.9 |
| 127 | (3,4-dihydroxyphenyl acetone, OH, OH) | 3.5 / 2.7 |
| 128 | (4-hydroxyphenyl acetone, OH) | 3.0 |
| 129 | (indol-3-yl acetone, NH) | 32% at 11.8 μM |
| 41 | (2-phenyl-3-hydroxypropyl ketone, OH) | 6.1 (5.4) |
| 42 | (2,2-diphenyl ketone) | 0.6 (5.7) |
| 43 | (4-bromophenyl acetone, Br) | 0.6 (5.8) |
| 44 | (phenyl acetone) | 0.8 (5.9) |
| 45 | (3-nitrophenyl acetone, NO$_2$) | 1.2 / 0.87 (5.11) |
| 46 | (N-BOC-tyrosine derivative, NHBOC, OH) | 1.2 (5.12) |

TABLE 7-continued
| EXAMPLE | R | FPT IC$_{50}$ (μM) |
|---|---|---|
| 47 | 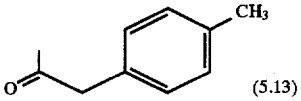 (5.13) | 1.3 1.01 |
| 48 | 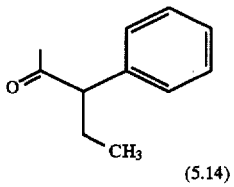 (5.14) | 1.3 |
| 49 | 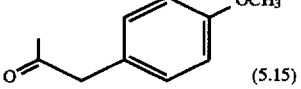 (5.15) | 1.4 |
| 84 |  (5.5) | 0.29 |
| 83 | 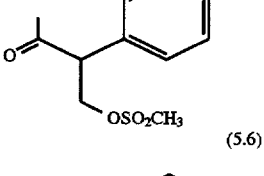 (5.6) | 0.59 |
| 19 | 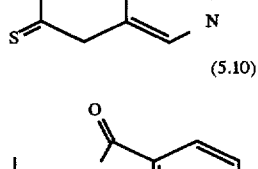 (5.10) | 1.0 |
| 85 | 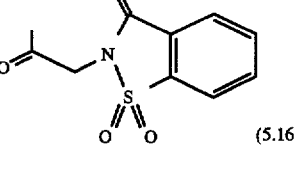 (5.16) | 2.0 |
| 219 | 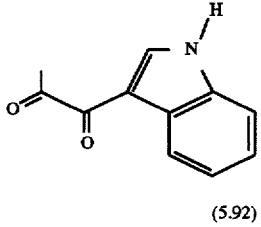 (5.92) | 6.64 |
| 220 | 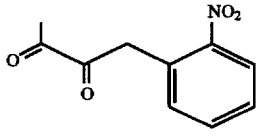 (5.93) | 2.49 |
| 221 | 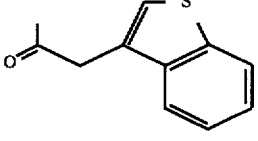 (5.94) | 3.71 |
| 222 | 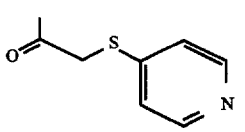 (5.95) | 0.38 |
| 227 | 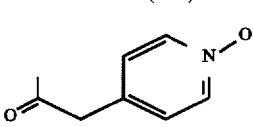 (5.102) | 0.53 |
| 228 | 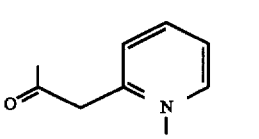 (5.103) | 7.5 |
| 287 | 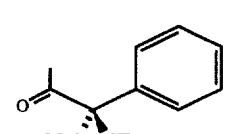 | 0.72 5.02 |
| 288 | 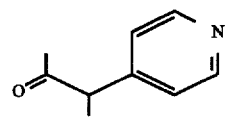 | 1.11 |
| 289 | 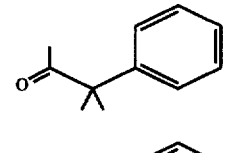 | 1.44 1.4 |
| 290 | 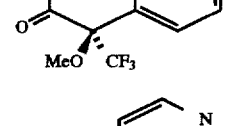 | 3.8 2.55 |
| 291 | 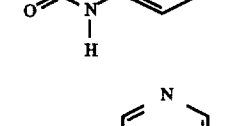 | 0.87 |
| 292 | 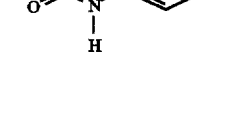 | 0.99 |

TABLE 7-continued
| EXAMPLE | R | FPT IC$_{50}$ (µM) |
|---|---|---|
| 293 | 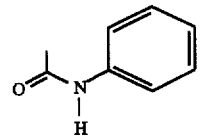 | 1.76 0.47 |
| 294 | 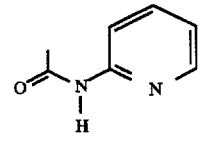 | 2.11 |
| 295 | 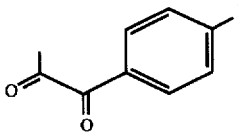 | 2.4 |
| 296 | 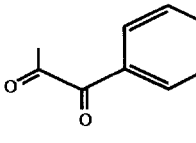 | 4.1 |
| 297 | 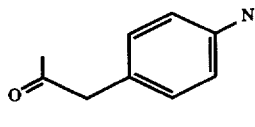 | 2.71 |
| 298 | 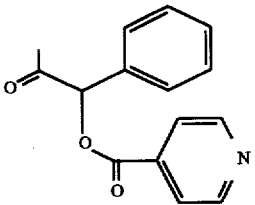 | 4.58 |
| 299 | 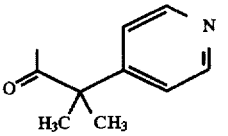 | 1.34 |
| 300 | 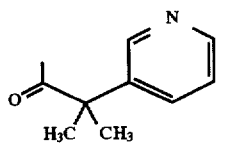 | 0.96 |
The compounds listed in Table 8 refer to compounds of Formula 505.00:
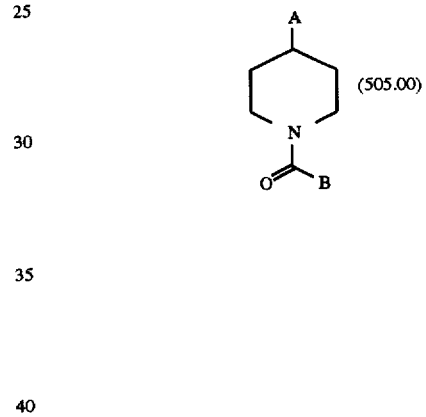
TABLE 8
| EXAMPLE | A | B | FPT IC$_{50}$ (µM) |
|---|---|---|---|
| 74B | 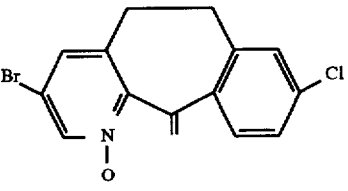 | CH$_3$ | 4.0 |
| 74C | 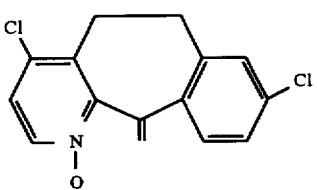 | CH$_3$ | 11.6 |

TABLE 8-continued

| EXAMPLE | A | B | FPT IC$_{50}$ (μM) |
|---|---|---|---|
| 74A | (structure with OCH$_3$, Cl, N-O) | CH$_3$ | 25% at 142 μM |
| 130 | (structure with Cl, N-Me) | CH$_3$ | 7% at 12.1 μM |
| 131 | (structure with Cl, N-O) | (4-methyl pyridine N-oxide) | 16% at 13.4 μM |
| 73 | (structure with Cl, N-O) | CH$_3$ | 27% at 15.6 μM |
| 132 | (structure with CH$_3$, Cl, N-O) | CH$_3$ | 22% at 15 μM |
| 133 | (structure with t-Bu, Cl, N-O) | CH$_3$ | 16% at 14.1 μM |
| 134 | (structure with Cl, N$^+$-O$^-$) | (2-Cl-6-methyl-4-methylpyridine) | 7% at 12.2 μM |
| 135 | (structure with Cl, Cl, N) | CH$_3$ | 7.7 |

TABLE 8-continued

| EXAMPLE | A | B | FPT IC$_{50}$ (μM) |
|---|---|---|---|
| 62 | (structure: Cl, Cl-substituted tricyclic with N) | CH$_3$ | 7.8 |
| 64 | (structure: H$_3$C, Cl-substituted tricyclic with N) | CH$_3$ | 10.6 |
| 136 | (structure: OCH$_3$, Cl-substituted tricyclic with N) | CH$_3$ | 11.5 |
| 66 | (structure: t-Bu, Cl-substituted tricyclic with N) | CH$_3$ | 22% at 50 μM |
| 137 | (structure: CH$_3$, Cl-substituted tricyclic with N) | CH$_3$ | 15% at 163 μM |
| 63 | (structure: H$_3$C, Cl-substituted tricyclic with N) | CH$_3$ | 1% at 16.4 μM |
| 139 | (structure: H$_3$C-C(=O), Cl-substituted tricyclic with N) | CH$_3$ | 37% at 15.2 μM |
| 140 | (structure: tricyclic with NH) | CH$_3$ | 15.7 |
| 71A | (structure: tricyclic with N, fused naphthalene) | CH$_3$ | 17.6 |

TABLE 8-continued

| EXAMPLE | A | B | FPT IC$_{50}$ (μM) |
|---|---|---|---|
| 141 | (structure: pyridine N-oxide fused cycloheptane with naphthalene, CH substituent) | CH$_3$ | 29% at 50 μM |
| 143 | (structure: pyridine fused cycloheptene with chlorobenzene, =CH$_2$) | CH$_3$ | 35.4 |
| 71B | (structure: pyridine fused cycloheptene with methoxybenzene, =CH$_2$) | CH$_3$ | 56.0 |
| 144 | (structure: pyridine fused cycloheptene with chlorobenzene, =CH$_2$) | CH$_3$ | 30% at 50 μM |
| 144a | (structure: pyridine fused cycloheptene with chlorobenzene, =CH$_2$) | (4-pyridyl N-oxide) | 47% at 46 μM |
| 71C | (structure: pyridine fused cycloheptene with dichlorobenzene, =CH$_2$) | CH$_3$ | 38% at 15.5 μM |
| 145 | (structure: pyridine fused cycloheptene with fluorobenzene, =CH$_2$) | CH$_2$-O-CH$_3$ | >10 |
| 146 | (structure: benzene fused cycloheptene with chlorobenzene, =CH$_2$) | (4-pyridyl N-oxide) | 45% at 12 μM |
| 147 | (structure: pyridine fused cycloheptene with benzene, =CH$_2$) | CH$_3$ | 0% at 18.8 μM |

TABLE 8-continued

| EXAMPLE | A | B | FPT IC$_{50}$ (μM) |
|---|---|---|---|
| 301 | (structure with H$_3$C, Cl) | 4-ethylpyridine | 0.04 / 0.075 |
| 180 | (structure with Cl, Cl) | 4-ethylpyridine | 0.072 / 0.04 |
| 303 | (structure with H$_3$C, Cl) | 3-ethylpyridine | 0.55 |
| 304 | (structure with (H$_3$C)$_3$C, Cl) | 3-ethylpyridine | 2.63 |
| 305 | (structure with (H$_3$C)$_3$C, Cl) | 4-ethylpyridine | 40% @ 4 μM |
| 230 | (structure with Cl, N-O) | 4-ethylpyridine | 2.06 |
| 307 | (structure with Cl) | 4-ethylpyridine | 0.22 / 0.14 |
| 235 | (structure with Cl, N-O, H) | 3-ethylpyridine | 3.57 |
| 309 | (structure with H$_3$C, Cl) | 4-ethylpyridine | 0.93 |

TABLE 8-continued
| EXAMPLE | A | B | FPT IC$_{50}$ (µM) |
|---|---|---|---|
| 310 | 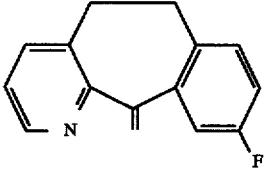 | 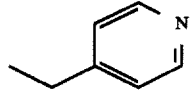 | 3.6 |
| 311 | 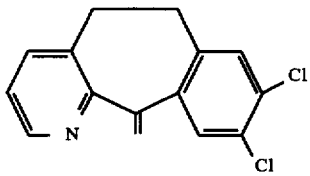 | 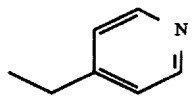 | 0.61 |
| 323 | 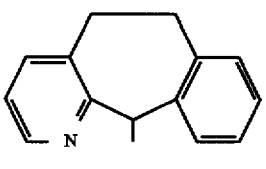 | 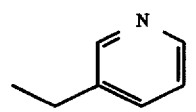 | 4.9 |
| 5.39 | 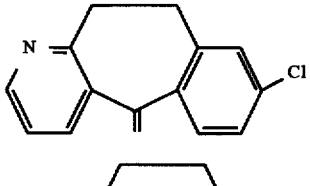 | 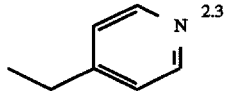 | 2.3 |
| 358 | 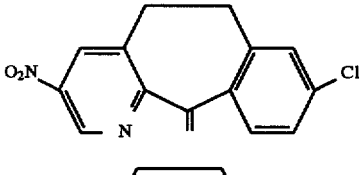 | 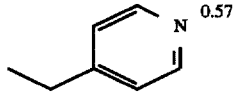 | 0.57 |
| 360 | 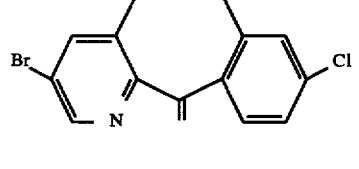 | 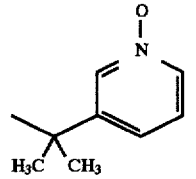 | 0.59 |
| 361 | 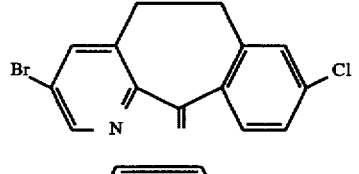 | 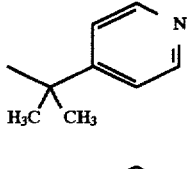 | 0.32 |
| 362 | 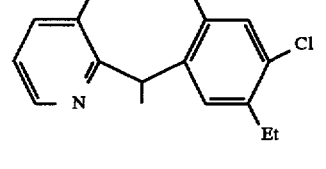 | 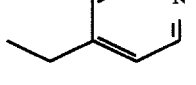 | 1.16 |
| 365 | 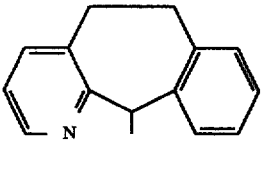 | 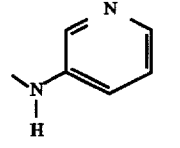 | 5.0 |

TABLE 8-continued
| EXAMPLE | A | B | FPT IC$_{50}$ (μM) |
|---|---|---|---|
| 366 |  |  | 4.0 |
| 367 | 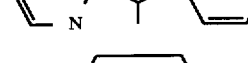 | 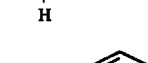 | 3.3 |
Table 9 lists FPT IC$_{50}$ results for additional compounds.
TABLE 9
| EXAMPLE | FPT IC$_{50}$ (μM) | EXAMPLE | FPT IC$_{50}$ (μM) | EXAMPLE | FPT IC$_{50}$ (μM) |
|---|---|---|---|---|---|
| 229 (5.104) | 4.38 | 231 (5.106) | 44% @ 12 μM | 232 (5.107) | 6.0 |
| 236 (5.111) | 1.48 | 237 (5.112) | 18% @ 4 μM | 238 (5.113) | 26% @ 4 μM |
| 239 (5.114) | 1.75 | 240 (5.115) | 3.12 | 246 (5.121) | 0.06 |
| 247 (5.122) | 0.16 | 248 (5.124) | 1.2 | 248 (5.123) | 0.19 |
| 249 (5.125) | 0.64 | 250 (5.126) | 0.95 | 256 (5.132) | 4.9 |
| 257 (5.133) | 2.3 | 258 (5.134) | 10.8 | 259 (5.135) | 2.2 |
| 260 (5.136) | 9.9 | 266 (5.138) | 0.46 | 2.69 (5.140) | 0.72 0.46 |
| 276 (5.145) | 1.77 | 279 (5.147) | 7.7 | 280 (5.148) | 23 |
| 281 (5.149) | 2.9 | 282 (5.150) | 4.5 | 283 (5.151) | 0.48 0.55 |
| 284 (5.152) | 4.3 | 285 (5.153) | 0.76 | 286 (5.154) | 1.5 |
| 278 | 0.8 | 274 | 0.91 1.38 | 270 | 2.8 |
The compounds listed in Table 10 refer to compounds of Formula 510.00:
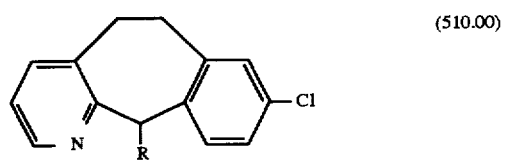
(510.00)
TABLE 10
| EXAMPLE | R | FPT IC$_{50}$ (μM) |
|---|---|---|
| 149 | 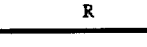 | 10.8 |
| 150 | 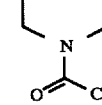 | 38% at 16.9 μM |
| 75 | 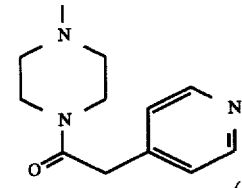 (5.17) | 0.36 0.16 |
| 76 | 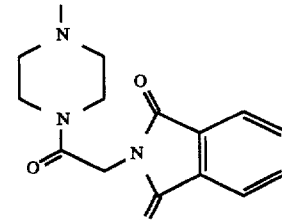 (5.18) | 0.82 |
| 77 | 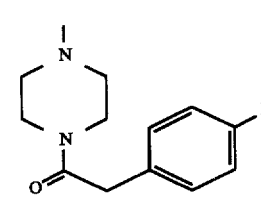 (5.19) | 2.04 |
| 78 | 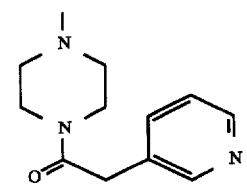 (5.20) | 1.0 0.42 |

TABLE 10-continued
| EXAMPLE | R | FPT IC$_{50}$ (µM) |
|---|---|---|
| 79 | 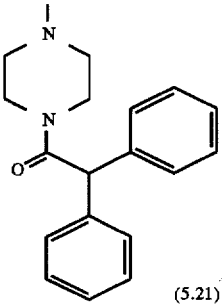 (5.21) | 2.5 |
| 80 | 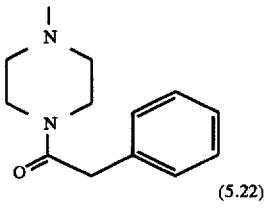 (5.22) | 2.73 |
| 81 | 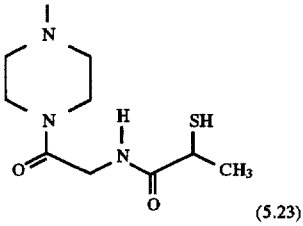 (5.23) | 2.78 |
| 82 | 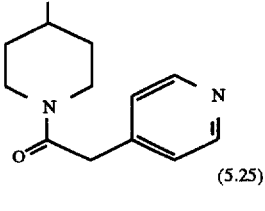 (5.25) | 0.16 0.36 |
| 312 | 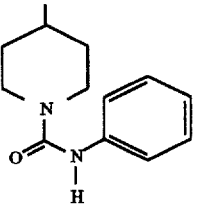 | 0.9 |
| 313 | 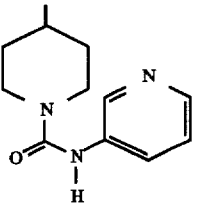 | 0.97 |
| 314 | 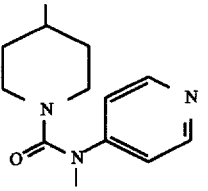 | 0.83 |
| 234 | 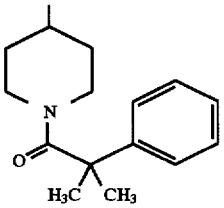 | 0.33 |
| 316 | 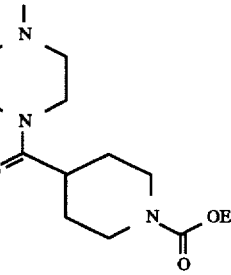 | 1.26 |
| 317 | 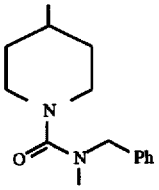 | 13.3 |
| 318 | 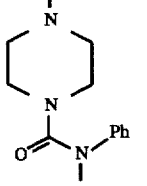 | 4.1 |
| 182 | 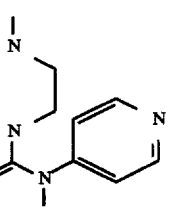 | 1.09 |
| 183 | | 0.97 0.90 |

TABLE 10-continued

| EXAMPLE | R | FPT IC$_{50}$ (μM) |
|---|---|---|
| 321 | (structure: piperidine-N-C(O)-CH2-phenyl-3,4-diOH attached at R position) | 6 |
| 368 | (structure: piperazine-N-C(O)-indole) | 14 @ 12 μM |

Table 11 lists FPT IC$_{50}$ results for additional compounds.

TABLE 11

| EXAMPLE | FPT IC$_{50}$ (μM) | EXAMPLE | FPT IC$_{50}$ (μM) | EXAMPLE | FPT IC$_{50}$ (μM) |
|---|---|---|---|---|---|
| 187 (6.7) | 1.34 | 187 (6.8) | 0.95 | 188 (6.9) | 4.6 |
| 189 (5.62) | 2.44 | 190 (5.63) | 3.3 | 191 (5.64) | 4.9 |
| 192 (5.65) | 1.24 | 194 (5.67) | 4.3 | 195 (5.68) | 6.8 |
| 196 (5.69) | 0.36 | 197 (5.70) | 1.17 | 198 (5.71) | 0.85 |
| 199 (5.72A) | 10.8 | 199 (5.72B) | 10.2 | 200 (5.73) | 0.87 |
| 201 (5.74) | 1.4 | 202 (5.75) | 20% @ 11 μM | 203 (5.76) | 11.3 |
| 205 (5.78) | 3.1 | 206 (5.79) | 1.19 | 207 (5.80) | 40% @ 12 μM |
| 208 (5.81) | 4.80 | 209 (5.82) | 7.92 | 210 (5.83) | 7.93 |
| 211 (5.84) | 8.17 | 212 (5.85) | 7.92 | 213 (5.86) | 23% @ 10 μM |
| 214 (5.87) | 0% @ 10 μM | 215 (5.88) | 30% @ 13 μM | 216 (5.89) | 34% @ 10 μM |
| 217 (5.90) | 6.75 | 218 (5.91) | 9.92 | 233 (5.108) | 0.67 |
| 251 (5.127) | 0.76 | 261 (6.12) | 1.3 | 351 | 0.7 |
| 352 | 0.74 | 353 | 0.76 | 354 (6.17) | 0.21 |
| 355 | 0.88 | 273 (5.143) | | | |
| 356 | 0.062 0.073 | 264 (6.15) | 26% @ 3.8 μM | 262 (6.13) | 0.82 |
| 263 (6.14) | 9.8 | 253 (5.129) | 4.3 | 350 | 2.1 |
| 252 (5.128) | 7.2 | 182 (6.4) | 1.09 | 268 (5.139) | 1.22 |
| 277 (6.20) | 2.3 | 193 | 7.4 | 204 | 13.3 |
| 355 | 0.88 | 352 | 0.74 0.38 | 353 | 0.76 0.30 |

The compounds listed in Table 12 refer to compounds of Formula 525.00:

(525.00)

TABLE 12

| EXAMPLE | A | B | FPT IC$_{50}$ (μM) |
|---|---|---|---|
| 184 (5.60) | (tricyclic benzocycloheptapyridine N-oxide with Cl) | (3-ethylpyridine) | 0.91 |
| 185 (5.61) | (tricyclic benzocycloheptapyridine N-oxide with Cl) | (3-ethylpyridine N-oxide) | 3.8 |

TABLE 12-continued

| EXAMPLE | A | B | FPT IC$_{50}$ (μM) |
|---|---|---|---|
| 223 (5.96) | (R isomer, Cl-substituted tricyclic) | 3-ethylpyridine | 2.1 |
| 223 (5.97) | (S isomer, Cl-substituted tricyclic) | 3-ethylpyridine | 0.19<br>0.72<br>0.61 |
| 224 (6.10) | (R isomer, Cl-substituted tricyclic) | N-methyl-3-aminopyridine | 3.2 |
| 224 (6.11) | (S isomer, Cl-substituted tricyclic) | N-methyl-3-aminopyridine | 0.46 |
| 225 (5.98) | (R isomer, Cl-substituted tricyclic) | 4-ethyl-1-acetylpiperidine | 3.5 |
| 225 (5.99) | (S isomer, Cl-substituted tricyclic) | 4-ethyl-1-acetylpiperidine | 1.6 |
| 226 (5.100) | (R isomer, Cl-substituted tricyclic) | 4-methyl-1-acetylpiperidine | 4.1 |
| 226 (5.101) | (S isomer, Cl-substituted tricyclic) | 4-methyl-1-acetylpiperidine | 1.8 |
| 351 | (Br, Cl-substituted tricyclic) | 3-ethylpyridine | 0.17 |

TABLE 12-continued

| EXAMPLE | A | B | FPT IC$_{50}$ (µM) |
|---|---|---|---|
| 354 | | | 0.21 |

The compounds listed in Table 13 refer to compounds of Formula 515.00:

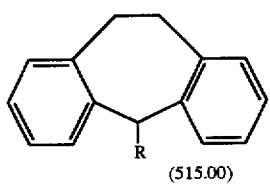

(515.00)

TABLE 13

| EXAMPLE | R | FPT IC$_{50}$ (µM) |
|---|---|---|
| 151 | | 15.0 |
| 152 | | 15.0 |
| 153 | | 29.6 |
| 87 | 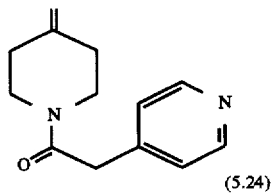 (5.24) | 1.14 |

Additional FPT IC$_{50}$ results were: (1) Example 180, compound 5.47, 0.072 µM; (2) Example 181, compound 5.48, 0.23 µM; (3) Example 182, compound 6.4, 1.09 µM; and (4) Example 183, compound 6.5, 0.97 µM.

Tables 20–22 disclose FPT Inhibition data for additional compounds.

TABLE 20

| EXAMPLE | FPT IC$_{50}$ (µM) | EXAMPLE | FPT IC$_{50}$ (µM) |
|---|---|---|---|
| 400 (5.210) | 0.068 | 401 (5.209) | 0.063 |
| | | | 0.08 |
| 400-B (5.203) | 0.068 | 400-C (5.200) | 0.030 |
| 400-D (5.217) | 0.21 | 400-E (5.208) | 0.04 |
| 400-F (5.201) | 0.036 | 400-G (5.204) | 0.024 |
| 400-H (5.220) | 0.24 | 400-J (5.212) | 0.14 |
| 400-K (5.218) | 0.21 | 400-L (5.206) | 0.095 |
| | | | 0.09 |

TABLE 21

| EXAMPLE | FPT IC$_{50}$ (µM) | EXAMPLE | FPT IC$_{50}$ (µM) |
|---|---|---|---|
| 411 | 0.32 | 411-A | 0.59 |
| 411-B | 0.32 | 402-A | 0.45 |
| | | | 0.56 |
| 411-D | 0.62 | 411-E | 11.4 |
| 411-F | 1.28 | 411-G | 0.7 |
| 411-L | 0.82 | 402 | 1.0 |
| 405 | 1.3 | 406 | 1.4 |
| 413 | 0.103 | 414-A | 1.90 |
| 414 | 0.90 | 417 | 1.16 |
| 418 | 1.85 | 417-A | 0.85 |
| 417-B | 0.14 | 419 | <0.12 |
| 420 | 0.23 | 422 | 0.60 |
| 423 | >4.3 | 422-A | >1.2 |
| | 35(4.3) | | 22(1.2) |
| 411-N | ~2 | 411-M | 0.65 |
| | 44(1.3) | | |
| 411-R | ~4 | 411-S | 2.1 |
| | 29(1.30) | | |
| 411-P | 3.8 | 411-Q | ~10 |
| | | | 33(4.3) |
| 411-O | ~5 | 411-X | 0.45 |
| | 39 (4) | | |
| 411-V | 0.27 | 411-T | 0.58 |
| 411-W | 0.16 | 411-U | 1.12 |
| | 0.17 | | |
| 425 | 1.74 | 425-B | 0.74 |
| 425-A | 2.2 | 425-C | 1.26 |
| 425-E | 0.49 | 425-D | 1.2 |
| 425-G | 2.3 | 425-F | 7 |
| 426 (5.207) | 0.012 | 425-H (5.202) | 0.059 |
| | | | 0.059 |
| | | | 0.049 |
| | | | 0.075 bv |
| 425-J | 0.39 | 425-K | 0.40 |
| | | | 0.41 |
| 425-L | 4.5 | 426-A | 0.33 |
| 427 | 1.8 | 427-A | 2.2 |
| 425-N | 0.64 | 428 | 1.25 |
| 429 | 1.27 | 425-M | 1.8 |
| 431 | 0.82 | 431-C | 0.88 |

TABLE 21-continued

| EXAMPLE | FPT IC$_{50}$ (µM) | EXAMPLE | FPT IC$_{50}$ (µM) |
|---|---|---|---|
| 431-B | 0.92 | 431-D | 1.0 |
| 431-A | 1.05 | 430 | 1.3 |
| 431-E | 0.88 | 425-O (5.126) | 0.17 |
|  |  |  | 0.14 |
|  |  |  | 0.122 |
|  |  |  | 0.118 |
|  |  |  | 0.178 bv |
| 425-P | 0.45 | 425-Q | 1.37 |
| 425-S | 0.6 | 425-R | 1.7 |
| 428-A | 1.1 | 431-F | 1.75 |
| 430-A | 7 | 431-G | 7 |
| 425-T | 12.2 | 425-U (5.211) | 0.10 |
|  |  |  | 0.14 |
| 425-V | 1.66 | 434 | 0.26 |
|  |  |  | 70(0.48) |
| 434-A | 3.5 | 435 | 7.0 |
| 437 | 1000 | 411-Z | 1.5 |
|  | 36 (11) |  |  |
| 427-B | 0.21 | 427-C | 0.24 |
| 432 | 0.66 | 415 | >3.8 |
| 411-C | 6.0 | 400-M | 0.9 |
| 411-DD | 3.1 | 411-EE | 10(3.3) |
| 411-FF | 1.8 |  |  |

TABLE 22

| EXAMPLE | FPT IC$_{50}$ (µM) | EXAMPLE | FPT IC$_{50}$ (µM) |
|---|---|---|---|
| 410 | 0.70 | 410-A | 0.086 |
| 410-B | 0.084 | 410-C | 0.052 |
| 410-D |  | 410-E | 1000 |
|  |  |  | 31(4.5) |
| 410-F | 2.2 | 410-G | 0.21 |
| 410-H | 7 | 410-J | 1.9 |
| 412 | 0.52 | 410-L | 2.9 |
| 403 | 1000 | 404 | 4.6 |
|  |  |  | 15 (12) |
| 401-A | 1.7 | 400-A | 2.6 |
| 412 | 0.52 | 416 | 3.7 |
| 410-M | ~12 | 424 | 1.3 |
|  | 27(3.6) |  |  |
| 424-A | 1000 | 433 | 2.5 |
|  | 22 (4) |  |  |
| 433-A | 1.1 | 433-B | 1.89 |
| 433-C | 2.5 | 436 | 17 |
| 436-A | 1000 | 436-B | 1000 |
|  | 17(9.6) |  | 2(10.6) |
| 436-C | 1000 | 436-D | 0.75 |
|  | 36 (10) |  |  |
| 410-S | 1000 | 410-T | 1.8 |
|  | 32(3.4) |  |  |
| 410-U | 5 | 410-V | 1.17 |
|  | 40(3.3) |  |  |
| 410-W | 1.16 |  |  |

TABLE 14

COMPARISON OF FPT INHIBITION AND GGPT INHIBITION

| EXAMPLE | ENZYME INHIBITION FPT IC$_{50}$ µM | ENZYME INHIBITION GGPT IC$_{50}$ µM |
|---|---|---|
| 1 | 0.25 | >46 |
| 2 | 0.47 | >46 |
| 3 | 0.66 | >39 |
| 5 | 1.7 | >46 |
| 7 | 2.3 | >45 |
| 8 | 2.3 | 42 |
| 181 | 0.23 | >42 |
| 78 | 2.19 | >46 |
|  | 0.53 |  |
|  | 0.74 |  |

TABLE 14-continued

COMPARISON OF FPT INHIBITION AND GGPT INHIBITION

| EXAMPLE | ENZYME INHIBITION FPT IC$_{50}$ µM | ENZYME INHIBITION GGPT IC$_{50}$ µM |
|---|---|---|
|  | 0.76 |  |
|  | 0.97 |  |
| 77 | 2.04 | >39 |
| 79 | 2.5 | >50 |
| 76 | 0.82 | >40 |

TABLE 23

COMPARISON OF FPT INHIBITION AND GGPT INHIBITION

| EXAMPLE | ENZYME INHIBITION FPT IC$_{50}$ µM | ENZYME INHIBITION GGPT IC$_{50}$ µM |
|---|---|---|
| 400-D | 0.21 | >38 |
| 400-C | 0.030 | >38 |
| 400-B | 0.068 | >38 |
| 400-E | 0.04 | 1000 |
|  |  | 30 (38) |
| 400-F | 0.036 | 1000 |
|  |  | 0 (36) |
| 400-G | 0.024 | >39 |
| 400-H | 0.24 | 1000 |
|  |  | 0 (36) |
| 400-J | 0.14 | 1000 |
|  |  | 6 (36) |
| 400-K | 0.21 | 1000 |
|  |  | 6 (37) |
| 400 | 0.068 | 1000 |
|  |  | 29 (36) |
| 401 | 0.063 | 1000 |
|  | 0.08 | 7 (34) |
| 413 | 0.103 | >35 |
| 417-B | 0.14 | 1000 |
|  |  | 15 (32) |
| 419 | <0.12 | 1000 |
|  |  | 0 (41) |
| 411-W | 0.16 | 1000 |
|  | 0.17 | 3 (42) |
| 426 | 0.012 | >39 |
| 425-H | 0.059 | >38 |
|  | 0.059 |  |
|  | 0.049 |  |
|  | 0.075bv |  |
| 425-O | 0.17 | >38 |
|  | 0.14 |  |
|  | 0.122 |  |
|  | 0.118 |  |
|  | 0.178bv |  |
| 425-U | 0.10 | >38 |
|  | 0.14 |  |
| 400-L | 0.095 | 38 |
|  | 0.09 |  |

TABLE 24

COMPARISON OF FPT INHIBITION AND GGPT INHIBITION

| EXAMPLE | ENZYME INHIBITION FPT IC$_{50}$ µM | ENZYME INHIBITION GGPT IC$_{50}$ µM |
|---|---|---|
| 410-G | 0.21 | 1000 |
|  |  | 32 (33) |
| 410-A | 0.086 | ~40 |
|  |  | 47 (35) |
| 410-B | 0.084 | 1000 |
|  |  | 21 (35) |

TABLE 15

ACTIVITY IN COS CELLS

| Example | Inhibition of Ras Processing IC$_{50}$ (μM) | Example | Inhibition of Ras Processing IC$_{50}$ (μM) |
|---|---|---|---|
| 1 | 1.0 | — | — |
| 82 | 1.2 | 156 (5.46) | 2.7 |
| 75 | 3.7 | 2 | 3.7 |
| 45 | 4.2 | 157 | 4.5 |
| 78 | <4.6 | 42 | 5.8 |
| 19 | 6.2 | 89. | 6.3 |
| 83 | 7.4 | 5 | 9.2 |
| 77 | 9.2 | 43 | 9.7 |
| 6 | 10.0 | 49 | 10.7 |
| 47 | 11.1 | 44 | 11.6 |
| 87 | 12.7 | 46 | >8.0 |
| 85 | >37.4 | 84 | >9.7 |
| 3 | >10 | 76 | 39.9 |
| 154 (5.28) | >10.0 | 48 | 10.7 |
| 5 | >12 | 88 | >12 |
| 53 | >13 | 181 (5.48) | 1.1 |
| 278 | 2.6 | 274 | 8.0 |

In Table 15, the numbers in parenthesis in the Example column refer to the formula number for the compound used in the indicated example. Also, the compound of Example 157 is:

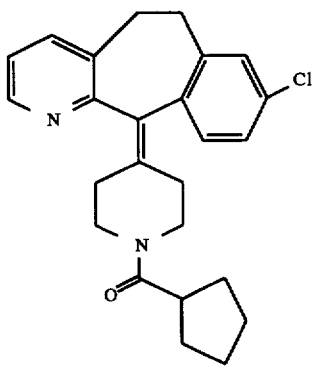

(1.1)

TABLE 25

ACTIVITY IN COS CELLS

| Example | Inhibition of Ras Processing IC$_{50}$ (μM) | Example | Inhibition of Ras Processing IC$_{50}$ (μM) |
|---|---|---|---|
| 411 | ~1 93 (5) | 411-A | 0.7 |
| 411-B | 1.8 | 441-D | 1.6 |
| 400-D | 2.0 | 400-C | 0.7 |
| 402 | >10 | 411-G | 5.1 |
| 400-G | 0.58 | 400-H | 2.5 100 (5) |
| 400-K | 2.2 100 (5) | 411-B | 1.8 |
| 400-D | 2.0 | 400-C | 0.7 |
| 400-G | 0.58 | 413 | 1.5 |
| 417 | 4.0 | 418 | >10 |
| 425-E | 5.0 | 426 | 0.38 |
| 425-H | 0.63 0.45 | 425-J | 5.0 |
| 425-K | 0.45 | 426-A | >5.0 |
| 425-O | 0.10 tox (10) 0.4 | 425-P | 5.7 |

TABLE 25-continued

ACTIVITY IN COS CELLS

| Example | Inhibition of Ras Processing IC$_{50}$ (μM) | Example | Inhibition of Ras Processing IC$_{50}$ (μM) |
|---|---|---|---|
| 425-U | 0.45 tox (10) | 434 | <<5 |
| 400-L | 0.6 | | |
| | 0.65 | | |

TABLE 26

ACTIVITY IN COS CELLS

| Example | Inhibition of Ras Processing IC$_{50}$ (μM) | Example | Inhibition of Ras Processing IC$_{50}$ (μM) |
|---|---|---|---|
| 410-G | 4.0 | 410-D | 18.5 |

TABLE 16

INHIBITION OF TUMOR CELL GROWTH MAT ASSAY

| Example | Tumor IC$_{50}$ (μM) | Normal IC$_{50}$ (μM) | Example | Tumor IC$_{50}$ (μM) | Normal IC$_{50}$ (μM) |
|---|---|---|---|---|---|
| 75 | 2.5 | >50.0 | — | — | — |
| 1 | 3.1 | 25.0 | 82 | 3.1 | 40.0 |
| 5 | 6.3 | >50.0 | 89 | 6.3 | >25.0 |
| 127 | 6.3 | >50.0 | 45 | 6.3 | >50.0 |
| 88 | 8.0 | >50.0 | 6 | 12.5 | 50.0 |
| 49 | 12.5 | >50.0 | 47 | 12.5 | >50.0 |
| 48 | 12.5 | 25.0 | 79 | 12.5 | >50.0 |
| 158 (5.36) | 12.5 | 18.0 | 2 | 25.0 | >50.0 |
| 10 | 25.0 | >50.0 | 128 | 25.0 | >50.0 |
| 44 | 25.0 | 25.0 | 164 (5.30) | 25.0 | >50.0 |
| 43 | 25.0 | 50.0 | 165 (5.34) | 25.0 | 50.0 |
| 53 | 25.0 | >50.0 | 166 (5.26) | 37.0 | >50.0 |
| 159 (5.31) | 37.0 | >50.0 | 167 (5.32) | 37.0 | 50.0 |
| 160 (5.39) | 37.0 | 50.0 | 168 (5.44) | 37.0 | >50.0 |
| 161 (5.45) | 37.0 | >50.0 | 5 | 37.5 | 100.0 |
| 162 (5.29) | 37.0 | >50.0 | 93 | 40.0 | >50.0 |
| 94 | 40.0 | 80.0 | 88 | >50.0 | >50.0 |
| 3 | >50.0 | >50.0 | 7 | 50.0 | 100.0 |
| 90 | 50.0 | >50.0 | 91 | 50.0 | 80.0 |
| 95 | >50.0 | >50.0 | 11 | >50.0 | >50.0 |
| 12 | 50.0 | >50.0 | 96 | 50.0 | >50.0 |
| 97 | >50.0 | >50.0 | 98 | 50.0 | >50.0 |
| 121 | 50.0 | >50.0 | 126 | 50.0 | >50.0 |
| 163 (5.27) | 50.0 | >50.0 | 42 | 50.0 | >50.0 |
| 154 (5.28) | >50.0 | >50.0 | 169 (5.33) | >50.0 | >50.0 |
| 46 | 50.0 | >50.0 | 80 | >50.0 | >50.0 |
| 77 | >50.0 | >50.0 | 76 | >50.0 | >50.0 |
| 81 | >50.0 | >50.0 | 173 (5.35) | >50.0 | >50.0 |
| 170 (5.37) | 50.0 | >50.0 | 174 (5.38) | 50.0 | 50.0 |
| 171 (5.40) | 50.0 | >50.0 | 87 | 50.0 | >50.0 |
| 172 (5.42) | >50.0 | >50.0 | 175 (5.43) | >50.0 | >50.0 |
| 180 (5.47) | 18 | >50.0 | 181 (5.48) | <3.1 | >50.0 |

In Table 16, the numbers in parenthesis in the Example column refer to the formula number for the compound used in the indicated example.

TABLE 27

INHIBITION OF TUMOR CELL GROWTH MAT ASSAY

| Example | Tumor IC$_{50}$ (µM) | Normal IC$_{50}$ (µM) | Example | Tumor IC$_{50}$ (µM) | Normal IC$_{50}$ (µM) |
|---|---|---|---|---|---|
| 411-A | 1.6 | >25 | 411 | 18 | >25 |
| 411-B | 6.25 | >25 | 402-A | 3.1 | >25 |
| 411-D | 8 | >25 | 411-E | >25 | >25 |
| 400-D | 4 | >25 | 400-C | <1.6 | >25 |
| 402 | 18 | >25 | 400-B | <1.6 | 6.25 |
| 411-G | 6.25 | >25 | 400-E | <1.6 | 18 |
|  | 4 | >12.5 |  |  |  |
| 400-F | <1.6 | >25 | 405 | 12.5 | >25 |
| 400-G | 1.6 | >25 | 400 | 1.6 | >25 |
| 401 | <1.6 | >25 | 411-B | 6.25 | >25 |
| 402-A | 3.1 | >25 | 400-D | 4 | >25 |
| 400-C | <1.6 | >25 | 400-B | <1.6 | >25 |
| 400-G | 1.6 | >25 | 413 | >6.25 | 10 |
| 417 | 10 | 18 | 418 | 25 | >25 |
| 417-B | <1.6 | >25 | 425 | 12.5 | >25 |
| 425-B | 12.5 | >25 | 425-E | 1.6 | >25 |
| 426 | 3.1 | 25 | 425-H | <1.6 | >25 |
|  | <0.8 | >12.5 |  |  |  |
| 425-J | 3.1 | >25 | 425-K | 6.25 | >25 |
| 426-A | 6.25 | >25 | 428 | 12.5 | 18 |
| 425-O | 3.1 | 6.25 | 425-P | >3.1 | 3.1 |
|  | <0.8 | 6.25 |  |  |  |
| 425-U | 6.25 | 10 | 400-L | <1.6 | >25 |
|  |  |  |  | <0.8 | >12.5 |

TABLE 28

INHIBITION OF TUMOR CELL GROWTH MAT ASSAY

| Example | Tumor IC$_{50}$ (µM) | Normal IC$_{50}$ (µM) | Example | Tumor IC$_{50}$ (µM) | Normal IC$_{50}$ (µM) |
|---|---|---|---|---|---|
| 410-D | 10 | >50.0 |  |  |  |

TABLE 17

| Example | Enzyme Inhibition GGPT IC$_{50}$ (µM) | COS CELLS Activity Inhibition of Ras Processing IC$_{50}$ (µM) | Inhibition of Tumor Cell Growth MAT Assay IC$_{50}$ (µM) Tumor | Normal |
|---|---|---|---|---|
| 180 | >42 | 1.0 | 18 | >50 |
|  |  | 6.3 | 12.5 | 50 |
|  |  | 2.4 | 12.5 | >50 |
| 182 (6.4) | >40 | 12.0 | 37 | >50 |
| 183 (6.5) | >40 | 10.5 | 5 | 18 |
| 184 (5.60) | — | 11.5 | 12.5 | >50 |
| 185 (5.61) | — | >20 | — | — |
| 187 (6.7) | >46 | 4.8 | 37 | >50 |
|  |  |  | 25 | >50 |
| 187 (6.8) | >46 | 1.3 | 9 | >50 |
|  |  |  | 4 | 50 |
| 189 (5.62) | 42 | 7.0 | 37 | >50 |
| 190 (5.63) | — | — | >50 | >50 |
| 191 (5.64) | — | — | <3.1 | 50 |
| 192 (5.65) | >43 | 4.9 | 25 | >50 |
|  |  |  | 37 | >50 |
| 196 (5.69) | >46 | 5.0 | 37 | >50 |
|  |  |  | 25 | >50 |
| 197 (5.70) | — | 11.1 | 25 | >50 |
| 198 (5.71) | — | 6.1 | 12.5 | >50 |
| 200 (5.73) | — | 2.7 | 18 | >50 |
| 201 (5.74) | — | 0.93 | 31 | 12.5 |
| 206 | — | 2.4 | <3.1 | 16 |
| 208 (5.81) | — | — | >50 | >50 |
| 209 (5.82) | — | — | 25 | >50 |
| 211 (5.84) | — | — | 37 | >50 |
| 212 (5.85) | — | — | 25 | 37 |
| 217 (5.90) | — | — | 37 | 50 |
| 218 (5.91) | — | — | 37 | 50 |
| 219 (5.92) | — | — | 25 | >50 |
| 220 (5.93) | — | — | 25 | >50 |
| 221 (5.94) | — | — | 6.25 | >50 |
| 222 (5.95) | — | 4.7 | 18 | 37 |
| 223 (5.96) | — | 10.5 | 25 | >50 |
| 223 (5.97) | — | 1.3 | 8 | >50 |
| 224 (61.1) | — | 7.3 | 37 | >50 |
| 225 (5.98) | — | — | 12.5 | 50 |
| 225 (5.99) | — | 6.2 | 12.5 | >50 |
| 226 (5.100) | — | — | 25 | >50 |
| 226 (5.101) | — | 6.5 | 12.5 | >50 |
| 227 (5.102) | >41 | 1.0 | 4 | µ50 |
| 229 (5.104) | — | — | 37 | >50 |
| 230 (5.105) | — | >20 | 37 | >50 |
| 233 (5.108) | — | 10 | 18 | >50 |
| 235 | — | 9.1 | 12.5 | >50 |
| 236 (5.111) | >45 | 3.5 | 4 | >50 |
| 237 (5.112) | — | — | >50 | >50 |
| 238 (5.113) | — | — | >50 | >50 |
| 239 (5.114) | — | 4.6 | 37 | >50 |
| 246 (5.121) | >40 | µ3.9 | 12.5 | 50 |
|  |  | 3.1 | µ3.1 | >50 |
|  |  | 0.91 |  |  |
| 247 (5.122) | >40 | >3.9 | 25 | >50 |
|  |  | 3.5 | 8 | >50 |
| 248 (5.124) | — | 2.05 | µ8 | >50 |
| 248 (5.123) | — | 4.6 | 18 | >50 |
| 250 (5.126) | — | 8.6 | 18 | >50 |
| 251 (5.127) | — | 8.1 | — | — |
| 261 (6.12) | — | 9.1 | — | — |
| 266 (5.138) | — | 0.77 | 3.1 | 6.25 |
|  |  | 0.89 |  |  |
| 267 (6.17) | — | 12.5 | — | — |
| 269 (5.140) | — | 0.69 | 6.25 | 12.5 |
| 276 (5.145) | — | 2.9 | 12.5 | 50 |
| 281 (5.149) | — | 7.0 | 4 | >50 |
| 283 (5.151) | — | 5.6 | 10 | >50 |
| 285 (5.153) | — | 5.2 | 12.5 | >50 |
|  |  | 10.1 |  |  |
| 286 (5.154) | — | 8.3 | 25 | >50 |
| 287 | >40 | >10 | 3.1 | >50 |
|  |  | >10 | 50 | >50 |
|  |  |  | 25 |  |
| 288 | — | 2.8 | 8 | >50 |
| 289 | >40 | >10 | 12.5 | >50 |
|  |  |  | 18 | 50 |
|  |  |  | 12.5 | >50 |
| 290 | >38 | — | 12.5 | >50 |
|  |  |  | 6.25 | >50 |
|  |  |  | 8 | >50 |
| 291 | >46 | 3.6 | 18 | >50 |
| 292 | >44 | 6.8 | 6.25 | >50 |
| 293 | >40 | >11.1 | 12.5 | >50 |
|  |  | 6.5 | 12.5 | >50 |
|  |  |  | 12.5 | >50 |
| 294 | — | 5.2 | 18 | >50 |
|  |  | 2.8 |  |  |
| *295 | — | 20.8 | — | — |
| 297 | 41 | — | >50 | >50 |
| 298 | >35 | >9 | >50 | >50 |
| 299 | 1000 | — | — | — |
| 300 | — | 2.6 | <3.1 | >50 |
| 301 | 40 | 4.4 | 12.5 | >50 |

TABLE 17-continued

| Example | Enzyme Inhibition GGPT IC$_{50}$ (µM) | COS CELLS Activity Inhibition of Ras Processing IC$_{50}$ (µM) | Inhibition of Tumor Cell Growth MAT Assay IC$_{50}$ (µM) | |
|---|---|---|---|---|
| | | | Tumor | Normal |
| | | 1.0 | <3.1 | >50 |
| | | | <3.1 | >50 |
| 303 | >43 | 3.4 | 8 | >50 |
| 304 | >40 | — | 50 | >50 |
| 305 | — | — | 25 | >50 |
| 307 | — | 4.6 | 12.5 | 50 |
| | | 0.85 | | |
| 309 | 35.1 | >10 | — | — |
| 310 | — | — | 25 | >50 |
| 311 | 41.3 | 9.5 | 10 | >50 |
| 312 | >46 | 3.8 | 12.5 | >50 |
| 313 | >46 | 1.5 | 6.25 | >50 |
| 314 | >46 | 3.0 | 4 | >50 |
| 234 | >43 | 2.2 | 3.1 | >50 |
| 316 | >43 | 18.4 | 25 | >50 |
| 318 | — | — | 37 | 37 |
| 321 | — | — | 6.25 | >50 |
| 322 | — | 2.8 | 8 | >50 |
| 351 | 1000 | 2.8 | 6.25 | 25 |
| 354 | 1000 | — | 6.25 | ≧25 |
| 365 | — | 3.1 | 6.25 | >50 |
| 366 | — | 3.3 | 3.1 | >50 |
| 367 | — | 6.2 | 6.25 | >50 |
| 78 | >46 | — | — | — |
| 77 | >39 | — | — | — |
| 79 | >50 | 5.1 | — | — |
| 76 | >50 | — | — | — |
| 350 | — | 3.7 | — | — |
| 355 | — | 0.89 | 8 | >25 |
| 352 | — | 2.2 | 1.6 | >25 |
| 353 | — | 0.9 | 6.25 | >25 |

RESULTS:

1. Enzymology:

The data demonstrate that the compounds of the invention are inhibitors of Ras-CVLS farnesylation by partially purified rat brain farnesyl protein transferase (FPT). The data also show that there are compounds of the invention which can be considered as potent (IC$_{50}$<10 µM) inhibitors of Ras-CVLS farnesylation by partially purified rat brain FPT.

The data also demonstrate that compounds of the invention are poorer inhibitors of geranylgeranyl protein transferase (GGPT) assayed using Ras-CVLL as isoprenoid acceptor. Generally, the compounds of the invention are inactive or weakly active as geranylgeranyl transferase inhibitors at 20 µg/mL. For example, with reference to Table 14, the compound of Example 1 inhibits GGPT 24% at 46 µM and is at least 184-fold selective for FPT inhibition. The compound of Example 2, for example, inhibits GGPT 25% at 46 µM and is at least 98-fold selective for FPT inhibition. For another example, the compound of Example 3 inhibits GPPT 3% at 39 µM and is at least 59-fold selective for FPT. This selectivity is important for the therapeutic potential of the compounds used in the methods of this invention, and increases the potential that the compounds will have selective growth inhibitory properties against Ras-transformed cells.

2. Cell-Based:

COS Cell Assay

Western blot analysis of the Ras protein expressed in Ras-transfected COS cells following treatment with the tricyclic farnesyl protein transferase inhibitors of this invention indicated that they inhibit Ras-CVLS processing, causing accumulation of unprocessed Ras (see Table 15). The compound of Example 1, for example, inhibited Ras-CVLS processing with an IC$_{50}$ value of 1 µM (0.44 µg/mL), but did not block the geranylgeranylation of Ras-CVLL at concentrations up to 20 µg/mL. Microscopic and photographic examination of the Ras-transfected COS cells following treatment with two of the tricyclic farnesyl transferase inhibitors of this invention indicated that they also blocked phenotypic changes induced by expression of oncogenic Ras. Cells expressing oncogenicRas-CVLS or Ras-CVLL overgrew the monolayer and formed dense foci of cells. The compound of Example 1 inhibited the morphological changes induced by Ras-CVLS in a dose-dependent manner over the concentration range of 2 to 20 µg/mL. The compound of Example 1 had little effect at 0.2 or 0.5 µg/mL. Importantly, 20 µg/mL of the compound of Example 1 did not prevent the morphological changes induced by Ras-CVLL.

These results provide evidence for specific inhibition of farnesyl protein transferase, but not geranylgeranyl transferase I, by compounds of this invention in intact cells and indicate their potential to block cellular transformation by activated Ras oncogenes.

3. Cell-Based:

Cell Mat Assay

Tricyclic farnesyl protein transferase inhibitors of this invention also inhibited the growth of Ras-transformed tumor cells in the Mat assay without displaying cytotoxic activity against the normal monolayer.

In Vivo Anti-Tumor Studies:

Tumor cells (5×10$^5$ to 8×10$^6$ of M27 (mouse Lewis lung carcinoma), A431 (human epidermal carcinoma) or SW620 (human colon adenocarcinoma [lymph node metastasis])) are innoculated subcutaneously into the flank of 5–6 week old athymic nu/nu female mice. For the C-f-1 (mouse fibroblast transformed with c-fos oncogene) tumor model, 2 mm$^3$ tumor fragments are transplanted subcutaneously into the flank of 5–6 week old athymic nu/nu female mice. Tumor bearing animals are selected and randomized when the tumors are established. Animals are treated with vehicle (beta cyclodextran for i.p. or corn oil for p.o.) only or compounds in vehicle twice a day (BID) for 5 (1–5), 6 (1–6), or 7 (1–7) days per week for 2 (×2) or 4 (×4) weeks. The percent inhibition of tumor growth relative to vehicle controls are determined by tumor measurements. The results are reported in Table 18.

TABLE 18

In-Vivo Anti-Tumor Results

| s.c. Tumor | Route & Schedule | Ex 2 | Ex 1 | Ex 3 | Ex 7 | Ex 78 | Ex 79 | Ex 75 |
|---|---|---|---|---|---|---|---|---|
| M27 | po, BID, 1-7, x4 | 61.2 | — | 27.3 | 58.2 | — | — | — |
| A431 | ip, BID, 1-5, x4 | — | 20.5 | 0 | 0 | — | — | — |
| A431 | po, BID 1-5, x4 | 45.6 | — | 8 | 29.1 | — | — | — |
| A431 | po, BID, 1-5, x4 | 36.5 | — | 26 | — | — | — | — |
| A431 | po, BID, 1-6, x4 | — | — | — | — | 31 | 0 | 34.5 |
| C-f-1 | ip, BID, 1-5, x2 | 8 | 0 | 8 | 39.7 | — | — | — |
| C-f-1 | po, BID, 1-5, x4 | 9.6 | — | 0 | 39.3 | — | — | — |
| C-f-1 | po, BID, 1-5, x4 | — | — | — | — | 26.7 | 25 | 20 |
| SW- | ip, BID, | 0 | 0 | 27 | 19.6 | — | — | — |

TABLE 18-continued

In-Vivo Anti-Tumor Results

| s.c. Tumor | Route & Schedule | Ex 2 | Ex 1 | Ex 3 | Ex 7 | Ex 78 | Ex 79 | Ex 75 |
|---|---|---|---|---|---|---|---|---|
| 620 | 1-5, x4 | | | | | | | |
| SW-620 | po, BID, 1-5, x2 | 46.1 | 0 | 15.8 | 48.6 | — | — | — |
| SW-620 | po, BID, 1-5, x4 | 33.5 | — | — | 0 | — | — | — |
| SW-620 | po, BID, 1-5, x4 | — | — | — | — | 59.6 | 26.7 | 43.4 |

Additional in-vivo anti-tumor results are reported in Table 19. In Table 23, LOX is a human melanoma cell line, and the schedule "10/wk, ×4", for example, means 10 times per week (twice a day Monday to Friday) for 4 weeks.

TABLE 19

In-Vivo Anti-Tumor Results

| Example of Structure | Tumor | Dose (MPK) | Route & Schedule | Average % Tumor Inhibiton |
|---|---|---|---|---|
| Ex. 2 | SW620 | 100 | ip, 10/wk, x2 | 0 |
| | SW620 | 100 | po, 10/wk, x2 | 0 |
| | SW620 | 100 | po, 10/wk, x4 | 1 |
| | M27 | 100 | po, 14/wk, x4 | 45 |
| Ex. 4 | SW620 | 100 | po, 10/wk, x4 | 2 |
| Ex.7 | SW620 | 100 | po, 10wk, x2 | 13 |
| | SW620 | 100 | po, 10/wk, x4 | 0 |
| | M27 | 100 | po, 14/wk, x4 | 40 |
| Ex. 45 | SW620 | 100 | po, 10/wk, x4 | 0 |
| | SW620 | 100 | po, 10/wk, x4 | 19 |
| | M27 | 100 | po, 10/wk, x3 | 0 |
| Ex. 47 | SW820 | 100 | po, 10/wk, x4 | 0 |
| | SW620 | 100 | po, 10/wk, x4 | 30 |
| | M27 | 100 | po, 10/wk, x3 | 19 |
| Ex. 49 | SW620 | 100 | po, 10/wk, x4 | 0 |
| | SW620 | 100 | po, 10/wk, x4 | 27 |
| | M27 | 100 | po, 10/wk, x3 | 30 |
| Ex. 75 | SW620 | 100 | po, 10/wk, x4 | 26 |
| | SW620 | 100 | po, 10/wk, x4 | 4 |
| | SW620 | 100 | po, 10/wk, x4 | 54 |
| | SW620 | 100 | po, 10/wk, x4 | 7 |
| | M27 | 100 | po, 10/wk, x4 | 0 |
| Ex. 82 | SW620 | 100 | po, 10/wk, x4 | 25 |
| | SW620 | 100 | po, 10/wk, x4 | 32 |
| Ex. 88 | SW620 | 100 | po, 10/wk, x4 | 43.25* |
| | M27 | 100 | po, 10/wk, x4 | 19 |
| | SW620 | 100 | po, 10/wk, x4 | 38* |
| | LOX | 100 | po, 10/1k, x4 | 70 |
| | SW620 | 100 | po, 10/wk, x4 | 38 |
| | SW620 | 100 | po, 10/wk, x4 | 37 |
| | SW620 | 50 | po, 10/wk, x4 | 30 |
| | SW620 | 50 | po, 10/wk, x4 | 30 |
| | SW620 | 25 | po, 10/wk, x4 | 4 |
| | SW620 | 25 | po, 10/wk, x4 | 0 |
| | SW620 | 100 | po, 10/wk, x4 | 27.4* |
| | LOX | 100 | po, 10/wk, x4 | 33 |
| | SW620 | 100 | po, 10/wk, x4 | 28 |
| | SW620 | 100 | po, 10/wk, x4 | 38 |
| Ex. 127 | SW620 | 100 | po, 10/wk, x4 | 25 |
| | SW620 | 100 | po, 10/wk, x4 | 42 |
| | M27 | 100 | po, 10/wk, x3 | 22 |
| Ex. 187 (6.8) | SW620 | 100 | p6, 10/wk, x4 | 11 |
| | SW620 | 100 | po, 10/wk, x4 | 21 |
| Ex. 192 | SW620 | 100 | po, 10/wk, x4 | 29 |
| | SW620 | 100 | po, 10/wk, x4 | 40 |
| Ex. 287 | SW620 | 100 | po, 10/wk, x4 | 14 |
| | SW620 | 100 | po, 10/wk, x4 | 0 |
| Ex. 290 | SW620 | 100 | po, 10/wk, x4 | 41 |
| | SW620 | 100 | po, 10/wk, x4 | 16 |
| Ex. 293 | SW620 | 100 | po, 10/wk, x4 | 5 |

TABLE 19-continued

In-Vivo Anti-Tumor Results

| Example of Structure | Tumor | Dose (MPK) | Route & Schedule | Average % Tumor Inhibiton |
|---|---|---|---|---|
| | SW620 | 100 | po, 10/wk, x4 | 47 |
| Ex. 301 | SW620 | 100 | po, 10/wk, x4 | 16 |
| | SW620 | 100 | po, 10/wk, x4 | 0 |
| Ex. 82A | SW620 | 100 | po, 10/wk, x4 | 27 |
| | SW620 | 100 | po, 10/wk, x4 | 26 |
| Ex. 342 | SW620 | 100 | po, 10/wk, x4 | 39 |
| | SW620 | 100 | po, 10/wk, x4 | 31 |
| 5.21 | SW620 | 100 | po, 10/wk, x4 | 19 |
| | SW620 | 100 | po, 10/wk, x4 | 17 |
| | M27 | 100 | po, 10/wk, x4 | 0 |
| 5.25 | SW620 | 100 | po, 10/wk, x4 | 7 |
| | SW620 | 100 | po, 10/wk, x4 | 36 |

*Average of several results

The compound of Example 342 (Table 19) is:

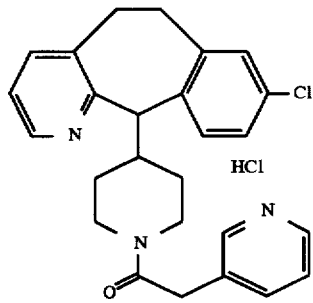

(Ex. 342)

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

In addition to the examples provided above, the following compounds were prepared using the product of Preparative Example 40 and following substantially the same procedures as described for Examples 193, 428, 431, 433-A, and 183, as appropriate:

| Example No. | Compound | Analytical Data |
|---|---|---|
| 500 | | Mass Spec.: MH⁺ = 619.15 |
| 501 | | Mass Spec.: MH⁺ = 517 |
| 502 | | Mass Spec.: MH⁺ = 560 |
| 503 | | Mass Spec.: MH⁺ = 604.2 |
| 504 | | Mass Spec.: MH⁺ = 532.15 |

EXAMPLE 505

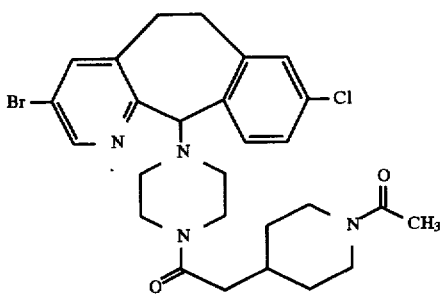

React the compound of Example 501 with an excess of acetic anhydride in MeOH via standard procedures to form the product compound in 91% yield. Mass Spec.: MH$^+$=559

EXAMPLE 506

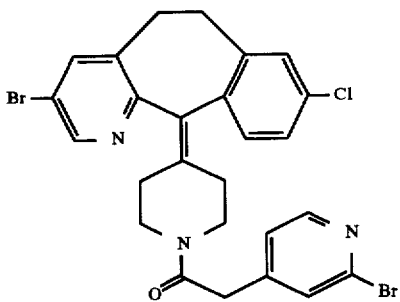

React the compound of Preparative Example 49 with 4-(2-bromopyridyl)acetic acid via the substantially the same procedure as described for Example 410 to give the product compound, m.p.=134°–136.1° C.; Mass Spec.: MH$^+$=588

What is claimed is:

1. A process for producting 3-nitro substituted compounds of Formula 1.0h:

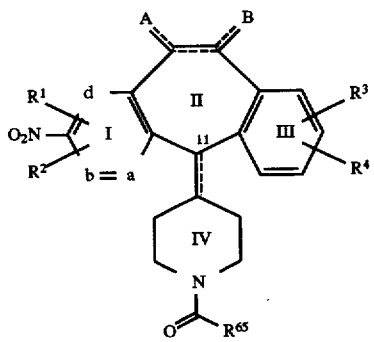
(1.0h)

comprising:

reacting one molar equivalent of a compound of Formula 1.0g:

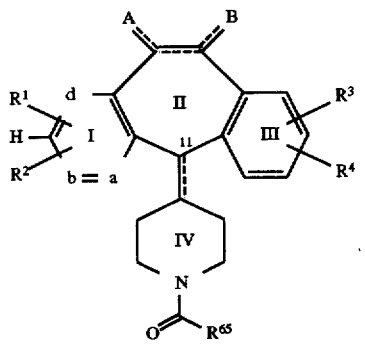
(1.0g)

with one molar equivalent of a nitrating reagent, said nitrating reagent being preformed by mixing, at cold temperature, equimolar amounts of tetrabutyl ammonium nitrate with trifluoroacetic anhydride;

the reaction of said nitrating reagent with said compound of Formula 1.0g taking place in a solvent selected from the group consisting of: $CH_2Cl_2$, $CHCl_3$, toluene and THF; and said reaction with said nitrating reagent being conducted at an initial temperature of 0° C., and said reaction temperature is thereafter allowed to rise to about 25° C. during the reaction time period to produce the 3-nitro compound of Formula 1.0h; and wherein:

a represents N, and the remaining a, b and d groups represent $CR^1$ or $CR^2$;

each $R^1$ and each $R^2$ is independently selected from H, halo, —$CF_3$, —$OR^{10}$, —$COR^{10}$, —$SR^{10}$, —$S(O)_t R^{11}$ (wherein t is 0, 1 or 2), —SCN, —$N(R^{10})_2$, —$NO_2$, —$OC(O)R^{10}$, —$CO_2R^{10}$, —$OCO_2R^{11}$, —CN, —$NHC(O)R^{10}$, —$NHSO_2R^{10}$, —$CONHR^{10}$, —$CONHCH_2CH_2OH$, $NR^{10}COOR^{11}$, —$SR^{11}C(O)OR^{11}$,

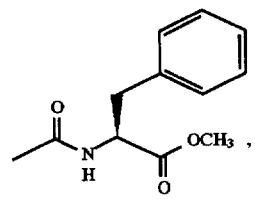

—$SR^{11}N(R^{75})_2$ (wherein each $R^{75}$ is independently selected from H and —$C(O)OR^{11}$), benzotriazol-1-yloxy, tetrazol-5-ylthio, or substituted tetrazol-5-ylthio, alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring;

$R^{10}$ represents H, alkyl, aryl, or aralkyl;

$R^{11}$ represents alkyl or aryl;

the dotted line between carbon atoms 5 and 6 represents an optional double bond, such that when a double bond is present, A and B independently represent —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$; H and halo, dihalo, alkyl and H, (alkyl)$_2$, —H and —$OC(O)R^{10}$, H and —$OR^{10}$, =O, aryl and H, =NOR¹⁰ or —O—(CH₂)ₚ—O— wherein p is 2, 3 or 4; and R⁶⁵ represents H or —OR⁶⁶ wherein R⁶⁶ represents alkyl.

2. The process of claim 1 wherein $R^1$ is Cl or H, $R^2$ is H, Cl, or Br; $R^3$ and $R^4$ are independently represent H or halo; when the optional bond between carbon atoms 5 and 6 is present, A and B represent H; and when no double bond is present between carbon atoms 5 and 6 A represents $H_2$ and B represents $H_2$ or =O.

3. The process of claim 2 wherein said aprotic solvent is $CH_2Cl_2$.

4. A process for producing 3-nitro compounds of the formula:

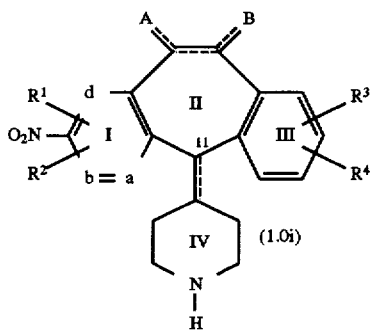

(1.0i)

comprising:

reacting one molar equivalent of a compound of Formula 1.0g:

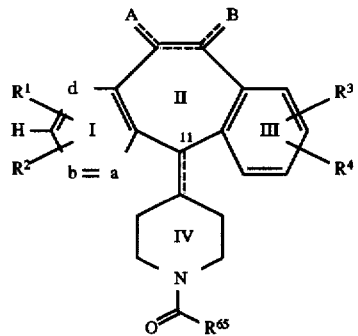

(1.0g)

with one molar equivalent of a nitrating reagent, said nitrating reagent being preformed by mixing, at cold temperature, equimolar amounts of tetrabutyl ammonium nitrate with trifluoroacetic anhydride;

the reaction of said nitrating reagent with said compound of Formula 1.0g taking place in a solvent selected from the group consisting of: $CH_2Cl_2$, $CHCl_3$, toluene and THF; and said reaction with said nitrating reagent being conducted at an initial temperature of 0° C., and said reaction temperature is thereafter allowed to rise to about 25° C. during the reaction time period to produce the 3-nitro compound of Formula 1.0h:

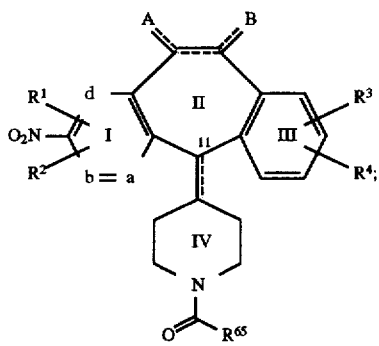

(1.0h)

hydrolyzing the compound of Formula 1.0h by dissolving the compound of Formula 1.0h in a sufficient amount of concentrated acid, and heating the resulting mixture to a temperature sufficient to remove the —C(O)R⁶⁵ substituent to produce the compound of Formula 1.0i; and wherein:

a represents N, and the remaining a, b and d groups represent $CR^1$ or $CR^2$;

each $R^1$ and each $R^2$ is independently selected from H, halo, —CF₃, —OR¹⁰, —COR¹⁰, —SR¹⁰, —S(O)ₜ R¹¹ (wherein t is 0, 1 or 2), —SCN, —N(R¹⁰)₂, —NO₂, —OC(O)R¹⁰, —CO₂R¹⁰, —OCO₂R¹¹, —CN, —NHC(O)R¹⁰, —NHSO₂R¹⁰, —CONHR¹⁰, —CONHCH₂CH₂OH, —NR¹⁰COOR¹¹, —SR¹¹C(O)OR¹¹,

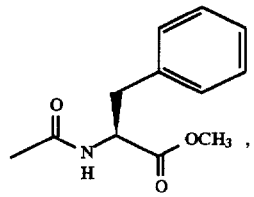

—SR¹¹N(R⁷⁵)₂ (wherein each R⁷⁵ is independently selected from H and —C(O)OR¹¹), benzotriazol-1-yloxy, tetrazol-5-ylthio, or substituted tetrazol-5-ylthio, alkynyl, alkenyl or alkyl, said alkyl or alkenyl group optionally being substituted with halo, —OR¹⁰ or —CO₂R¹⁰;

$R^3$ and $R^4$ are the same or different and each independently represents H, any of the substituents of $R^1$ and $R^2$, or $R^3$ and $R^4$ taken together represent a saturated or unsaturated $C_5$-$C_7$ fused ring to the benzene ring;

R¹⁰ represents H, alkyl, aryl, or aralkyl;

R¹¹ represents alkyl or aryl;

the dotted line between carbon atoms 5 and 6 represents an optional double bond, such that when a double bond is present, A and B independently represent —R¹⁰, halo, —OR¹¹, —OCO₂R¹¹ or —OC(O)R¹⁰, and when no double bond is present between carbon atoms 5 and 6, A and B each independently represent $H_2$, —(OR¹¹)₂; H and halo, dihalo, alkyl and H, (alkyl)₂, —H and —OC(O)R¹⁰, H and —OR¹⁰, =O, aryl and H, =NOR¹⁰ or —O—(CH₂)ₚ—O— wherein p is 2, 3 or 4; and R⁶⁵ represents H or —OR⁶⁶ wherein R⁶⁶ represents alkyl.

5. The process of claim 4 wherein $R^1$ is Cl or H; $R^2$ is H, Cl or Br; $R^3$ and $R^4$ are independently represent H or halo; when the optional bond between carbon atoms 5 and 6 is present, A and B represent H; and when no double bond is present between carbon atoms 5 and 6 A represents H₂ and B represents H₂ or =O.

6. The process of claim 5 wherein said aprotic solvent is CH₂Cl₂.

7. The process of claim 6 wherein: in hydrolyzing the compound of Formula 1.0h said concentrated acid is selected from the group consisting of: concentrated HCl or aqueous sulfuric acid, and said —C(O)R⁶⁵ substituent is removed by heating to reflux or by heating to a temperature of about 100° C.

8. A process for producing a compound of Formula 1.0m:

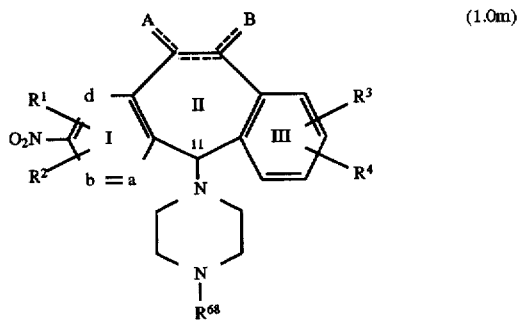

(1.0m)

comprising:

reacting one molar equivalent a compound of formula:

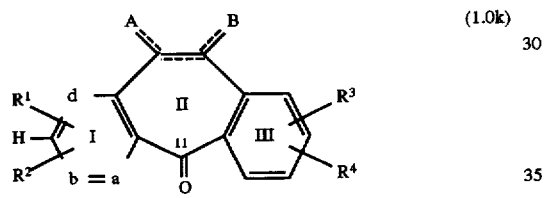

(1.0k)

with one molar equivalent of a nitrating reagent;

said nitrating reagent being preformed, by mixing at a cold temperature, equimolar amounts of tetrabutyl ammonium nitrate with trifluoroacetic anhydride;

the reaction of said nitrating reagent with the compound of Formula 1.0k taking place in a solvent selected from the group consisting of: CH₂Cl₂, CHCl₃, toluene and THF;

said reaction with said nitrating reagent being conducted at an initial temperature of 0° C., said reaction temperature is thereafter allowed to rise to about 25° C. during the reaction time period to produce the 3-nitro compound of Formula 1.0j:

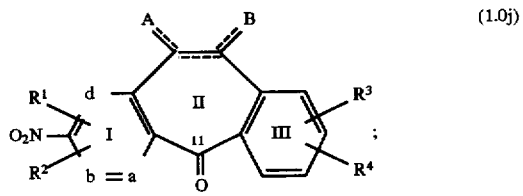

(1.0j)

reducing said compound of Formula 1.0j with a suitable reducing agent in a suitable solvent at a suitable temperature to allow the reaction to proceed at a reasonable rate;

reacting the resulting hydroxy product with a chlorinating agent in a suitable organic solvent at a suitable temperature to allow the reaction to proceed at a reasonable rate to produce a compound of Formula 1.0n:

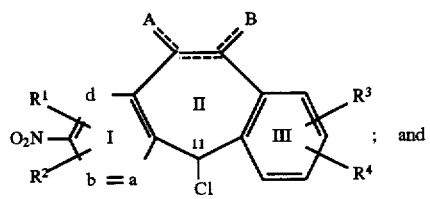

(1.0n)

; and reacting said compound of Formula 1.0n with a compound of the formula:

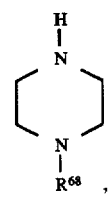

in a suitable organic solvent containing a suitable base at a suitable temperature to allow the reaction to proceed at a reasonable rate to produce the compounds of Formula 1.0m; wherein:

a, and the remaining a, b and d groups represent CR¹ or CR²; or each R¹ and each R² is independently selected from H, halo, —CF₃, —OR¹⁰, —COR¹⁰, —SR¹⁰, —S(O)ₜR¹¹ (wherein t is 0, 1 or 2), —SCN, —N(R¹⁰)₂, —NO₂, —OC(O)R¹⁰, —CO₂R¹⁰, —OCO₂R¹¹, —CN, —NHC(O)R¹⁰, —NHSO₂R¹⁰, —CONHR¹⁰, —CONHCH₂CH₂OH, —NR¹⁰COOR¹¹, —SR¹¹C(O)OR¹¹,

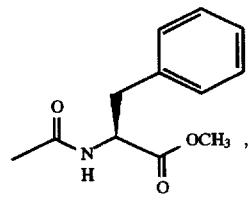

—SR¹¹N(R⁷⁵)₂ (wherein each R⁷⁵ is independently selected from H and —C(O)OR¹¹), benzotriazol-1-yloxy, tetrazol-5-ylthio, or substituted tetrazol-5-ylthio, alkynyl, alkenyl or alkyl, said alkyl or alkenyl group optionally being substituted with halo, —OR¹⁰ or —CO₂R¹⁰;

R³ and R⁴ are the same or different and each independently represents H, any of the substituents of R¹ and R², or R³ and R⁴ taken together represent a saturated or unsaturated C₅-C₇ fused ring to the benzene ring;

R¹⁰ represents H, alkyl, aryl, or aralkyl;

R¹¹ represents alkyl or aryl;

the dotted line between carbon atoms 5 and 6 represents an optional double bond, such that when a double bond is present, A and B independently represent —R¹⁰, halo, —OR¹¹, —OCO₂R¹¹ or —OC(O)R¹⁰, and when no double bond is present between carbon atoms 5 and 6, A and B each indendently represent H₂, —(OR¹¹)₂, H and halo, dihalo, alkyl and H, (alkyl)₂, —H and —OC(O)R¹⁰, H and —OR¹⁰, =O, aryl and H, =NOR¹⁰ or —O—(CH₂)ₚ—O— wherein p is 2, 3 or 4; and R⁶⁸ is H or —COORᵃ wherein Rₐ is a C₁ to C₃ alkyl group.

9. The process of claim 8 wherein R¹ is Cl or H; R² is H, Cl or Br; R³ and R⁴ are independently represent H or halo; when the optional bond between carbon atoms 5 and 6 is present, A and B represent H; and when no double bond is present between carbon atoms 5 and 6 A represents H₂ and B represents H₂ or ═O.

10. The process of claim 8 wherein for reducing said compound of Formula 1.0j said reducing agent is sodium borohydride, said solvent is selected from the group consisting of: ethanol and methanol, and said temperature is 0° to about 25° C.

11. The process of claim 8 wherein in the reaction to produce the compound of Formula 1.0n, said chlorinating agent is thionyl chloride, said organic solvent is selected from the group consisting of benzene, toluene and pyridine, and said temperature is about −20° to about 20° C.

12. The process of claim 8 wherein in the reaction of the compound of Formula 1.0n with

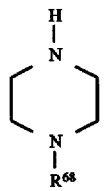

said organic solvent is selected from the group consisting of: THF and toluene, said base is selected from the group consisting of: triethylamine and N-methylmorpholine, and said temperature is 25° to about 120° C.

13. The process of claim 8 wherein said aprotic solvent is CH₂Cl₂ in the reaction of the compound of Formula 1.0k with said nitrating reagent.

14. The process of claim 8 wherein: (a) in the reaction of said nitrating agent said aprotic solvent is CH₂Cl₂; (b) for reducing said compound of Formula 1.0j said reducing agent is sodium borohydride, said solvent is selected from the group consisting of: ethanol and methanol, and said temperature is 0° to about 25° C.; (c) in the reaction to produce the compound of Formula 1.0n, said chlorinating agent is thionyl chloride, said organic solvent is selected from the group consisting of benzene, toluene and pyridine, and said temperature is about −20° to about 20° C.; (d) in the reaction of the compound of Formula 1.0n with

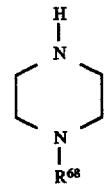

said organic solvent is selected from the group consisting of: THF and toluene, said base is selected from the group consisting of: triethylamine and N-methylmorpholine, and said temperature is 25° to about 120° C.; and (e) R¹ is Cl or H, R² is H, Cl or Br; R³ and R⁴ are independently represent H or halo; when the optional bond between carbon atoms 5 and 6 is present A and B represent H; and when no double bond is present between carbon atoms 5 and 6 A represents H₂ and B represents H₂ or ═O.

15. A process for producing 3-nitro substituted compounds of the formula:

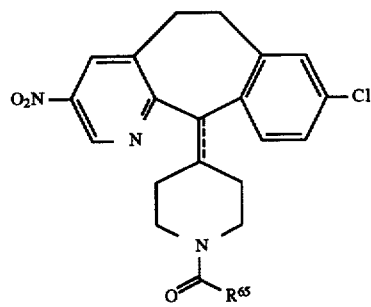

comprising:

reacting one molar equivalent of a compound of Formula 1.0g:

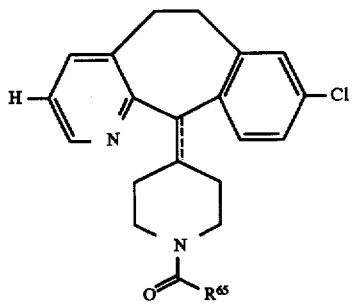

with one molar equivalent of a nitrating reagent, said nitrating reagent being preformed by mixing, at cold temperature, equimolar amounts of tetrabutyl ammonium nitrate with trifluoroacetic anhydride;

the reaction of said nitrating reagent with said compound of Formula 1.0g taking place in CH₂Cl₂; and said reaction with said nitrating reagent being conducted at an initial temperature of 0° C., and said reaction temperature is thereafter allowed to rise to about 25° C. during the reaction time period to produce the 3-nitro compound of Formula 1.0h; and wherein:
R⁶⁵ represents H or —OR⁶⁶ wherein R⁶⁶ represents alkyl.

16. The process of claim 15 wherein R⁶⁵ represents —OR⁶⁶ and R⁶⁶ represents —C₂H₅.

17. The process of claim 16 wherein the compound

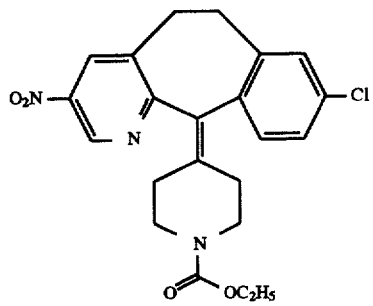

is produced from the compound

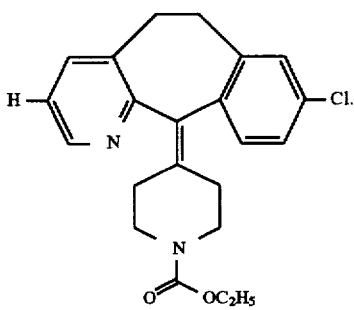

18. The process of claim 16 wherein the compound

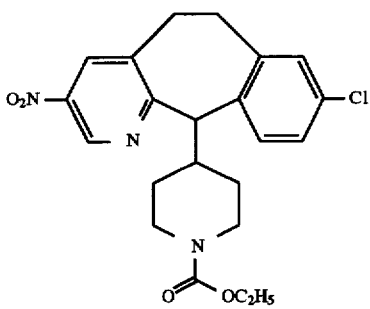

is produced from the compound

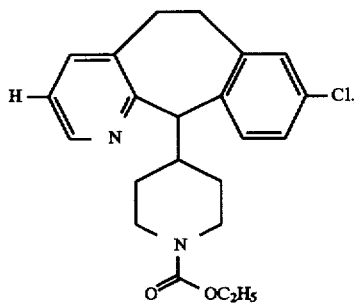

19. A process for producing 3-nitro substituted compounds of Formula 1.0h:

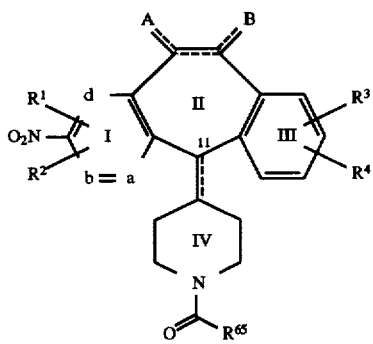
(1.0h)

comprising:

reacting one molar equivalent of a compound of Formula 1.0g:

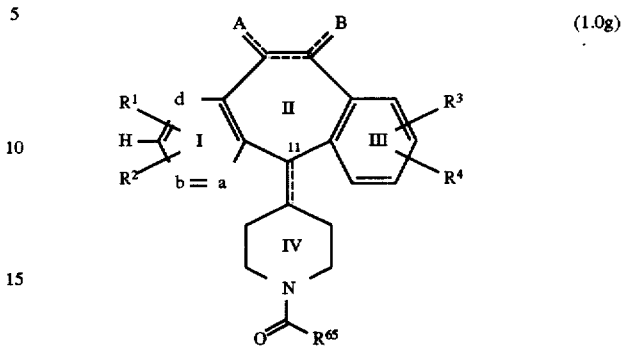
(1.0g)

with one molar equivalent of a nitrating reagent, said nitrating reagent being preformed by mixing, at cold temperature, equimolar amounts of tetrabutyl ammonium nitrate with trifluoroacetic anhydride;

the reaction of said nitrating reagent with said compound of Formula 1.0g taking place in a solvent selected from the group consisting of: $CH_2Cl_2$, $CHCl_3$, toluene and THF; and said reaction with said nitrating reagent being conducted at an initial temperature of 0° C., and said reaction temperature is thereafter allowed to rise to about 25° C. during the reaction time period to produce the 3-nitro compound of Formula 1.0h; and wherein:

a represents N, and the remaining a, b and d groups represent $CR^1$ or $CR^2$;

each $R^1$ and each $R^2$ is independently selected from H, halo, —$CF_3$, lower alkyl or benzotriazol-1-yloxy;

$R^3$ and $R^4$ are the same or different and each independently represents H, halo, —$CF_3$, —$OR^{10}$ or alkyl;

$R^{10}$ represents H, alkyl, aryl, or aralkyl;

the dotted line between carbon atoms 5 and 6 represents an optional double bond, such that when a double bond is present, A and B independently represent H, lower alkyl, or alkyloxy; and when no double bond is present between carbon atoms 5 and 6, A and B each independently represent $H_2$, —H and —OH, or =O; and $R^{65}$ represents H or —$OR^{66}$ wherein $R^{66}$ represents alkyl.

20. The process of claim 19 wherein when the optional bond between carbon atoms 5 and 6 is present, A and B represent H; and when no double bond is present between carbon atoms 5 and 6 A represents $H_2$ and B represents $H_2$ or =O.

21. The process of claim 20 wherein the solvent is $CH_2Cl_2$.

22. The process of claim 21 wherein $R^1$ is Cl or H; $R^2$ is H, Cl or Br; $R^3$ and $R^4$ are independently represent H or halo.

* * * * *